US012774465B2

(12) United States Patent
Naldini et al.

(10) Patent No.: US 12,774,465 B2
(45) **Date of Patent: *Oct. 27, 2026**

(54) PERMANENT EPIGENETIC GENE SILENCING

(71) Applicants: Ospedale San Raffaele S.R.L., Milan (IT); Fondazione Telethon, Rome (IT)

(72) Inventors: Luigi Naldini, Milan (IT); Angelo Leone Lombardo, Milan (IT); Angelo Amabile, Milan (IT); Alessandro Migliara, Milan (IT)

(73) Assignees: Ospedale San Raffaele S.R.L., Milan (IT); Fondazione Telethon, Rome (IT)

( * ) Notice: Subject to any disclaimer, the term of this patent is extended or adjusted under 35 U.S.C. 154(b) by 928 days.

This patent is subject to a terminal disclaimer.

(21) Appl. No.: 17/963,631

(22) Filed: Oct. 11, 2022

(65) Prior Publication Data

US 2023/0340471 A1 Oct. 26, 2023

Related U.S. Application Data

(63) Continuation of application No. 15/521,294, filed on Apr. 23, 2017, now Pat. No. 12,152,240.

(51) Int. Cl.

| | |
|---|---|
| ***C12N 15/113*** | (2010.01) |
| ***A61K 35/12*** | (2015.01) |
| ***A61K 38/00*** | (2006.01) |
| ***A61K 38/17*** | (2006.01) |
| ***A61K 38/45*** | (2006.01) |
| ***A61K 48/00*** | (2006.01) |
| ***C07K 14/47*** | (2006.01) |
| ***C12N 9/10*** | (2006.01) |
| ***C12N 9/22*** | (2006.01) |

(52) U.S. Cl.

CPC ............ *C12N 15/113* (2013.01); *A61K 35/12* (2013.01); *A61K 38/1709* (2013.01); *A61K 38/45* (2013.01); *A61K 48/005* (2013.01); *C07K 14/4703* (2013.01); *C12N 9/1007* (2013.01); *C12N 9/22* (2013.01); *C12Y 201/01037* (2013.01); *C12Y 201/01043* (2013.01); *A61K 38/00* (2013.01); *C07K 2319/80* (2013.01); *C12N 2310/20* (2017.05); *C12N 2740/16043* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 6,919,204 | B2 | 7/2005 | Wolffe et al. |
| 8,450,107 | B1 | 5/2013 | Zhang et al. |
| 8,658,393 | B2 | 2/2014 | Reik et al. |
| 8,697,359 | B1 | 4/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,993,233 | B2 | 3/2015 | Zhang et al. |
| 8,999,641 | B2 | 4/2015 | Zhang et al. |
| 9,139,628 | B2 | 9/2015 | Minczuk et al. |
| 9,267,135 | B2 | 2/2016 | Church et al. |
| 9,322,006 | B2 | 4/2016 | Liu et al. |
| 9,526,784 | B2 | 12/2016 | Liu et al. |
| 9,771,601 | B2 | 9/2017 | May et al. |
| 9,840,713 | B2 | 12/2017 | Zhang |
| 9,850,500 | B2 | 12/2017 | Yun et al. |
| 10,266,850 | B2 | 4/2019 | Doudna et al. |
| 10,323,073 | B2 | 6/2019 | Tremblay et al. |
| 10,329,587 | B2 | 6/2019 | Church et al. |
| 10,378,027 | B2 | 8/2019 | Joung et al. |
| 10,443,076 | B2 | 10/2019 | Doudna et al. |
| 10,525,082 | B2 | 1/2020 | Crane et al. |

(Continued)

FOREIGN PATENT DOCUMENTS

| | | | |
|---|---|---|---|
| EP | 3209783 | B1 | 11/2021 |
| JP | 2010-515448 | A | 5/2010 |

(Continued)

OTHER PUBLICATIONS

[No Author Listed], Cell lines in the In Vitro Screen. NIH Division of Cancer Treatment & Diagnosis Aug. 5, 2015. 5 pages. D16, submitted in Opposition of European Patent No. EP 3209783 on Nov. 4, 2022.

(Continued)

*Primary Examiner* — Christopher M Babic

*Assistant Examiner* — Kimberly A Aron

(74) *Attorney, Agent, or Firm* — Wolf, Greenfield & Sacks, P.C.

(57) ABSTRACT

A product comprising two or more artificial transcription repressors (ATRs), or polynucleotides encoding therefor, selected from groups (a), (b), (c) or (d): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; (c) an ATR comprising a DNA-binding domain operably linked to a DNMT3L domain or homologue thereof; and (d) an ATR comprising a DNA-binding domain operably linked to a SETDB1 domain or homologue thereof, wherein at least two of the ATRs are selected from different groups (a), (b), (c) or (d).

20 Claims, 46 Drawing Sheets

Specification includes a Sequence Listing.

(56) References Cited

U.S. PATENT DOCUMENTS

| | | | |
|---|---|---|---|
| 10,570,378 | B2 | 2/2020 | Ji et al. |
| 10,583,201 | B2 | 3/2020 | Chen et al. |
| 10,612,044 | B2 | 4/2020 | Hatada et al. |
| 10,676,726 | B2 | 6/2020 | Gersbach et al. |
| 10,676,735 | B2 | 6/2020 | Gersbach et al. |
| 10,704,060 | B2 | 7/2020 | Gersbach et al. |
| 12,152,240 | B2 | 11/2024 | Naldini et al. |
| 2002/0160940 | A1 | 10/2002 | Case et al. |
| 2002/0188103 | A1 | 12/2002 | Bestor |
| 2004/0204345 | A1 | 10/2004 | Case et al. |
| 2007/0059795 | A1 | 3/2007 | Moore et al. |
| 2007/0192880 | A1 | 8/2007 | Muyan et al. |
| 2009/0023153 | A1 | 1/2009 | Wolffe et al. |
| 2011/0306559 | A1 | 12/2011 | Forsayeth et al. |
| 2012/0207744 | A1 | 8/2012 | Mendlein et al. |
| 2014/0377868 | A1 | 12/2014 | Joung et al. |
| 2015/0191744 | A1 | 7/2015 | Wolfe et al. |
| 2015/0247150 | A1 | 9/2015 | Zhang et al. |
| 2016/0201089 | A1 | 7/2016 | Gersbach et al. |
| 2016/0298135 | A1 | 10/2016 | Chen et al. |
| 2017/0191082 | A1 | 7/2017 | Chen et al. |
| 2017/0204407 | A1 | 7/2017 | Gilbert et al. |
| 2017/0219596 | A1 | 8/2017 | Tanenbaum et al. |
| 2017/0233762 | A1 | 8/2017 | Zalatan et al. |
| 2018/0273976 | A1 | 9/2018 | Ümit et al. |
| 2019/0032049 | A1 | 1/2019 | Naldini et al. |
| 2019/0376090 | A1 | 12/2019 | Joung et al. |
| 2020/0071730 | A1 | 3/2020 | Joung et al. |
| 2025/0236870 | A1 | 7/2025 | Naldini et al. |

FOREIGN PATENT DOCUMENTS

| | | | |
|---|---|---|---|
| JP | 2013-543381 | A | 12/2013 |
| JP | 2017-537611 | A | 12/2017 |
| JP | 7002936 | B2 | 2/2022 |
| WO | WO 1998/005635 | A1 | 2/1998 |
| WO | WO 1998/007859 | A2 | 2/1998 |
| WO | WO 1998/009985 | A2 | 3/1998 |
| WO | WO 1999/041397 | A1 | 8/1999 |
| WO | WO 2001/079518 | A2 | 10/2001 |
| WO | WO 2003/072788 | A1 | 9/2003 |
| WO | WO 2008/084219 | A1 | 7/2008 |
| WO | WO 2011/016840 | A2 | 2/2011 |
| WO | WO 2012/045082 | A2 | 4/2012 |
| WO | WO 2013/093489 | A2 | 6/2013 |
| WO | WO 2013/130824 | A1 | 9/2013 |
| WO | WO 2013/138650 | A1 | 9/2013 |
| WO | WO 2013/141680 | A1 | 9/2013 |
| WO | WO 2013/176772 | A1 | 11/2013 |
| WO | WO 2014/065596 | A1 | 5/2014 |
| WO | WO 2014/089290 | A1 | 6/2014 |
| WO | WO 2014/099744 | A1 | 6/2014 |
| WO | WO 2023/250148 | A1 | 12/2023 |

OTHER PUBLICATIONS

[No Author Listed], SEQ ID No. 8 of the Patent and the DNMT3A sequence disclosed in Li et al., Nucleic Acids Res. 2007;35(1):100-12. Retrieved from www.ebi.ac.uk on Jul. 14, 2022. 2 pages. D17, submitted in Opposition of European Patent No. EP 3209783 on Nov. 4, 2022.

[No Author Listed], Two bright new faces in gene therapy. Nat Biotechnol. May 1996;14(5):556. doi: 10.1038/nbt0596-556.

Aiuti et al., Gene therapy for immunodeficiency due to adenosine deaminase deficiency. N Engl J Med. Jan. 29, 2009;360(5):447-58. doi: 10.1056/NEJMoa0805817.

Aiuti et al., Lentiviral hematopoietic stem cell gene therapy in patients with Wiskott-Aldrich syndrome. Science. Aug. 23, 2013;341(6148):1233151. doi: 10.1126/science.1233151. Epub Jul. 11, 2013.

Altschul et al., Basic local alignment search tool. J Mol Biol. Oct. 5, 1990;215(3):403-10. doi: 10.1016/S0022-2836(05)80360-2.

Amabile et al., 690. Permanent Epigenetic Silencing of Human Genes With Artificial Transcriptional Repressors. 18th ASGCT Annual Meeting. May 16, 2015. Published in Mol Ther. May 2015;23(Suppl 1): S275. 1 page.

Amabile et al., Inheritable Silencing of Endogenous Genes by Hit-and-Run Targeted Epigenetic Editing. Cell. Sep. 22, 2016;167(1):219-232.e14. doi: 10.1016/j.cell.2016.09.006.

Amabile et al., Inheritable Silencing of Endogenous Genes by Hit-and-Run Targeted Epigenetic Editing. Cell. Sep. 22, 2016;167(1):219-232.e14. doi: 10.1016/j.cell.2016.09.006. D15, submitted in Opposition of European Patent No. EP 3209783 on Nov. 4, 2022.

Andreani et al., Quantitatively different red cell/nucleated cell chimerism in patients with long-term, persistent hematopoietic mixed chimerism after bone marrow transplantation for thalassemia major or sickle cell disease. Haematologica. Jan. 2011;96(1):128-33. doi: 10.3324/haematol.2010.031013. Epub Oct. 7, 2010.

Ausubel et al., Current Protocols in Molecular Biology. Chapters 9, 13, 16. John Wiley & Sons. 1995.

Ausubel et al., Short Protocols in Molecular Biology. Current Protocols. 4th Ed. 1999. pp. 7-58 to 7-60.

Ausubel et al., Short Protocols in Molecular Biology: Chapter 18. Current Protocols. 4th Ed. 1999.

Ayyanathan et al., Regulated recruitment of HP1 to a euchromatic gene induces mitotically heritable, epigenetic gene silencing: a mammalian cell culture model of gene variegation. Genes Dev. Aug. 1, 2003;17(15):1855-69. doi: 10.1101/gad.1102803. Epub Jul. 17, 2003.

Ayyanathan et al., Regulated recruitment of HP1 to a euchromatic gene induces mitotically heritable, epigenetic gene silencing: a mammalian cell culture model of gene variegation. Genes Dev. Aug. 1, 2003;17(15):1855-69. doi: 10.1101/gad.1102803. Epub Jul. 17, 2003. D3, submitted in Opposition of European Patent No. EP 3209783 on Nov. 4, 2022.

Bauer et al., An erythroid enhancer of BCL11A subject to genetic variation determines fetal hemoglobin level. Science. Oct. 11, 2013;342(6155):253-7. doi: 10.1126/science.1242088.

Biffi et al., Lentiviral hematopoietic stem cell gene therapy benefits metachromatic leukodystrophy. Science. Aug. 23, 2013;341(6148):1233158. doi: 10.1126/science.1233158. Epub Jul. 11, 2013.

Broude et al., p21 (CDKN1A) is a negative regulator of p53 stability. Cell Cycle. Jun. 15, 2007;6(12):1468-71. Epub Apr. 12, 2007.

Broude et al., p21 (CDKNIA) is a negative regulator of p53 stability. Cell Cycle. Jun. 15, 2007;6(12):1468-71. Epub Apr. 12, 2007. D5, submitted in Opposition of European Patent No. EP 3209783 on Nov. 4, 2022.

Cai et al., Targeted genome editing by lentiviral protein transduction of zinc-finger and TAL-effector nucleases. Elife. Apr. 24, 2014;3:e01911. doi: 10.7554/eLife.01911.

Carroll, Genome engineering with targetable nucleases. Annu Rev Biochem. 2014;83:409-39. doi: 10.1146/annurev-biochem-060713-035418. Epub Mar. 3, 2014.

Cartier et al., Hematopoietic stem cell gene therapy with a lentiviral vector in X-linked adrenoleukodystrophy. Science. Nov. 6, 2009;326(5954):818-23. doi: 10.1126/science.1171242.

Cavazzana-Calvo et al., Transfusion independence and HMGA2 activation after gene therapy of human ß-thalassaemia. Nature. Sep. 16, 2010;467(7313):318-22. doi: 10.1038/nature09328.

Chen et al., Chromatin modifiers and remodellers: regulators of cellular differentiation. Nat Rev Genet. Feb. 2014;15(2):93-106. doi: 10.1038/nrg3607. Epub Dec. 24, 2013.

Ciccia et al., The DNA damage response: making it safe to play with knives. Mol Cell. Oct. 22, 2010;40(2):179-204. doi: 10.1016/j.molcel.2010.09.019.

Davidson et al., Current prospects for RNA interference-based therapies. Nat Rev Genet. May 2011;12(5):329-40. doi: 10.1038/nrg2968.

De Groote et al., Epigenetic Editing: targeted rewriting of epigenetic marks to modulate expression of selected target genes. Nucleic Acids Res. Nov. 2012;40(21):10596-613. doi: 10.1093/nar/gks863. Epub Sep. 21, 2012.

(56) References Cited

OTHER PUBLICATIONS

Deuschle et al., Tetracycline-reversible silencing of eukaryotic promoters. Mol Cell Biol. Apr. 1995;15(4):1907-14. doi: 10.1128/MCB.15.4.1907.
Devereux et al., A comprehensive set of sequence analysis programs for the VAX. Nucleic Acids Res. Jan. 11, 1984;12(1 Pt 1):387-95. doi: 10.1093/nar/12.1part1.387.
Digiusto et al., Development of hematopoietic stem cell based gene therapy for HIV-1 infection: considerations for proof of concept studies and translation to standard medical practice. Viruses. Nov. 22, 2013;5(11):2898-919. doi: 10.3390/v5112898.
Digiusto et al., RNA-based gene therapy for HIV with lentiviral vector-modified CD34(+) cells in patients undergoing transplantation for AIDS-related lymphoma. Sci Transl Med. Jun. 16, 2010;2(36):36ra43. doi: 10.1126/scitranslmed.3000931.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Feschotte et al., Endogenous viruses: insights into viral evolution and impact on host biology. Nat Rev Genet. Mar. 16, 2012;13(4):283-96. doi: 10.1038/nrg3199.
Gait, Oligonucleotide Synthesis: A Practical Approach. Oxford. IRL Press. 1984.
Gaj et al., Targeted gene knockout by direct delivery of zinc-finger nuclease proteins. Nat Methods. Jul. 1, 2012;9(8):805-7. doi: 10.1038/nmeth.2030.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Galarneau et al., Fine-mapping at three loci known to affect fetal hemoglobin levels explains additional genetic variation. Nat Genet. Dec. 2010;42(12):1049-51. doi: 10.1038/ng.707. Epub Nov. 7, 2010.
Gilbert et al., CRISPR-mediated modular RNA-guided regulation of transcription in eukaryotes. Cell. Jul. 18, 2013;154(2):442-51. doi: 10.1016/j.cell.2013.06.044. Epub Jul. 11, 2013.
Gilbert et al., Genome-Scale CRISPR-Mediated Control of Gene Repression and Activation. Cell. Oct. 23, 2014;159(3):647-61. doi: 10.1016/j.cell.2014.09.029. Epub Oct. 9, 2014.
Gossen et al., Tight control of gene expression in mammalian cells by tetracycline-responsive promoters. Proc Natl Acad Sci U S A. Jun. 15, 1992;89(12):5547-51. doi: 10.1073/pnas.89.12.5547.
Gowher et al., Mechanism of stimulation of catalytic activity of Dnmt3A and Dnmt3B DNA-(cytosine-C5)-methyltransferases by Dnmt3L. J Biol Chem. Apr. 8, 2005;280(14):13341-8. doi: 10.1074/jbc.M413412200. Epub Jan. 24, 2005.
Groner et al., KRAB-zinc finger proteins and KAP1 can mediate long-range transcriptional repression through heterochromatin spreading. PLoS Genet. Mar. 5, 2010;6(3):e1000869. doi: 10.1371/journal.pgen.1000869.
Hacein-Bey-Abina et al., Efficacy of gene therapy for X-linked severe combined immunodeficiency. N Engl J Med. Jul. 22, 2010;363(4):355-64. doi: 10.1056/NEJMoa1000164.
Hathaway et al., Dynamics and memory of heterochromatin in living cells. Cell. Jun. 22, 2012;149(7):1447-60. doi: 10.1016/j.cell.2012.03.052. Epub Jun. 14, 2012.
Huntley et al., A comprehensive catalog of human KRAB-associated zinc finger genes: insights into the evolutionary history of a large family of transcriptional repressors. Genome Res. May 2006;16(5):669-77. doi: 10.1101/gr.4842106. Epub Apr. 10, 2006.
Hütter et al., Long-term control of HIV by CCR5 Delta32/Delta32 stem-cell transplantation. N Engl J Med. Feb. 12, 2009;360(7):692-8. doi: 10.1056/NEJMoa0802905.
Issa et al., Azacitidine. Nat Rev Drug Discov. Apr. 2005;4:275-6. Supplemental Info. S6-7.
Iyengar et al., KAP1 protein: an enigmatic master regulator of the genome. J Biol Chem. Jul. 29, 2011;286(30):26267-76. doi: 10.1074/jbc.R111.252569. Epub Jun. 7, 2011.
Jeltsch et al., Application of DNA methyltransferases in targeted DNA methylation. Appl Microbiol Biotechnol. Jul. 2007;75(6):1233-40. doi: 10.1007/s00253-007-0966-0. Epub Apr. 13, 2007.
Jones, Functions of DNA methylation: islands, start sites, gene bodies and beyond. Nat Rev Genet. May 29, 2012;13(7):484-92. doi: 10.1038/nrg3230.
Kabadi et al., Engineering synthetic TALE and CRISPR/Cas9 transcription factors for regulating gene expression. Methods. Sep. 2014;69(2):188-97. doi: 10.1016/j.ymeth.2014.06.014. Epub Jul. 8, 2014. D21, submitted in Opposition of European Patent No. EP 3209783 on Nov. 4, 2022.
Kay, State-of-the-art gene-based therapies: the road ahead. Nat Rev Genet. May 2011;12(5):316-28. doi: 10.1038/nrg2971. Epub Apr. 6, 2011.
Kearns et al., Cas9 effector-mediated regulation of transcription and differentiation in human pluripotent stem cells. Development. Jan. 2014;141(1):219-23. doi: 10.1242/dev.103341.
Kim et al., Zinc-fingers and homeoboxes 1 (ZHX1) binds DNA methyltransferase (DNMT) 3B to enhance DNMT3B-mediated transcriptional repression. Biochem Biophys Res Commun. Apr. 6, 2007;355(2):318-23. doi: 10.1016/j.bbrc.2007.01.187. Epub Feb. 8, 2007.
Kim et al., Zinc-fingers and homeoboxes 1 (ZHX1) binds DNA methyltransferase (DNMT) 3B to enhance DNMT3B-mediated transcriptional repression. Biochem Biophys Res Commun. Apr. 6, 2007;355(2):318-23. doi: 10.1016/j.bbrc.2007.01.187. Epub Feb. 8, 2007. D8, submitted in Opposition of European Patent No. EP 3209783 on Nov. 4, 2022.
Kocak, Synthetic Transcription Factors and their Effects on Endogenous DNA Methylation in Human Cells. Duke University Thesis. Submitted 2013. 35 pages.
Kocak, Synthetic Transcription Factors and their Effects on Endogenous DNA Methylation in Human Cells. Duke University Thesis. Submitted 2013. 35 pages. D18, submitted in Opposition of European Patent No. EP 3209783 on Nov. 4, 2022.
Konermann et al., Optical control of mammalian endogenous transcription and epigenetic states. Nature. Aug. 22, 2013;500(7463):472-476. doi: 10.1038/nature12466. Epub Aug. 23, 2013.
Kühnel et al., Tumor-specific adenoviral gene therapy: transcriptional repression of gene expression by utilizing p53-signal transduction pathways. Cancer Gene Ther. Jan. 2004;11(1):28-40. doi: 10.1038/sj.cgt.7700632.
Kühnel et al., Tumor-specific adenoviral gene therapy: transcriptional repression of gene expression by utilizing p53-signal transduction pathways. Cancer Gene Ther. Jan. 2004;11(1):28-40. doi: 10.1038/sj.cgt.7700632. D6, submitted in Opposition of European Patent No. EP 3209783 on Nov. 4, 2022.
Kungulovski et al., Targeted epigenome editing of an endogenous locus with chromatin modifiers is not stably maintained. Epigenetics Chromatin. Mar. 18, 2015;8:12. doi: 10.1186/s13072-015-0002-z.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Law et al., Establishing, maintaining and modifying DNA methylation patterns in plants and animals. Nat Rev Genet. Mar. 2010;11(3):204-20. doi: 10.1038/nrg2719.
Leung et al., Silencing of endogenous retroviruses: when and why do histone marks predominate? Trends Biochem Sci. Apr. 2012;37(4):127-33. doi: 10.1016/j.tibs.2011.11.006. Epub Dec. 15, 2011.
Li et al., Chimeric DNA methyltransferases target DNA methylation to specific DNA sequences and repress expression of target genes. Nucleic Acids Res. 2007;35(1):100-12. doi: 10.1093/nar/gkl1035. Epub Dec. 6, 2006.
Li et al., Chimeric DNA methyltransferases target DNA methylation to specific DNA sequences and repress expression of target genes. Nucleic Acids Res. 2007;35(1):100-12. doi: 10.1093/nar/gkl1035. Epub Dec. 6, 2006. D7, submitted in Opposition of European Patent No. EP 3209783 on Nov. 4, 2022.
Li et al., The histone methyltransferase SETDB1 and the DNA methyltransferase DNMT3A interact directly and localize to pro-

(56) References Cited

OTHER PUBLICATIONS moters silenced in cancer cells. J Biol Chem. Jul. 14, 2006;281(28):19489-500. doi: 10.1074/jbc.M513249200. Epub May 8, 2006.
Li et al., The histone methyltransferase SETDB1 and the DNA methyltransferase DNMT3A interact directly and localize to promoters silenced in cancer cells. J Biol Chem. Jul. 14, 2006;281(28):19489-500. doi: 10.1074/jbc.M513249200. Epub May 8, 2006. D1, submitted in Opposition of European Patent No. EP 3209783 on Nov. 4, 2022.
Lilley et al., Methods in Enzymology. DNA Structures, Part A, Synthesis and Physical Analysis of DNA. Academic Press. 1992.
Liu et al., Homozygous defect in HIV-1 coreceptor accounts for resistance of some multiply- exposed individuals to HIV-1 infection. Cell. Aug. 9, 1996;86(3):367-77. doi: 10.1016/s0092-8674(00)80110-5.
Lombardo et al., Site-specific integration and tailoring of cassette design for sustainable gene transfer. Nat Methods. Aug. 21, 2011;8(10):861-9. doi: 10.1038/nmeth.1674.
Lupo et al., KRAB-Zinc Finger Proteins: A Repressor Family Displaying Multiple Biological Functions. Curr Genomics. Jun. 2013;14(4):268-78. doi: 10.2174/1389202911314999000 2.
Ma et al., Targeted gene suppression by inducing de novo DNA methylation in the gene promoter. Epigenetics Chromatin. Aug. 18, 2014;7:20. doi: 10.1186/1756-8935-7-20. D12, submitted in Opposition of European Patent No. EP 3209783 on Nov. 4, 2022.
Maetzig et al., Retroviral protein transfer: falling apart to make an impact. Curr Gene Ther. Oct. 2012;12(5):389-409. doi: 10.2174/156652312802762581.
Mandegar et al., CRISPR Interference Efficiently Induces Specific and Reversible Gene Silencing in Human iPSCs. Cell Stem Cell. Apr. 7, 2016;18(4):541-53. doi: 10.1016/j.stem.2016.01.022. Epub Mar. 10, 2016.
Mcbride et al., Preclinical safety of RNAi-mediated HTT suppression in the rhesus macaque as a potential therapy for Huntington's disease. Mol Ther. Dec. 2011;19(12):2152-62. doi: 10.1038/mt.2011.219. Epub Oct. 25, 2011.
Mendenhall et al., Locus-specific editing of histone modifications at endogenous enhancers. Nat Biotechnol. Dec. 2013;31(12):1133-6. doi: 10.1038/nbt.2701. Epub Sep. 8, 2013.
Murphy et al., The Transcriptional Repressive Activity of KRAB Zinc Finger Proteins Does Not Correlate with Their Ability to Recruit TRIM28. PLoS One. Sep. 22, 2016;11(9):e0163555. doi: 10.1371/journal.pone.0163555. D23, submitted in Opposition of European Patent No. EP 3209783 on Nov. 4, 2022.
Nakamura et al., Durable CRISPR-Based Epigenetic Silencing. Biodesign Research. Jul. 1, 2021;2021:9815820. doi: 10.34133/2021/9815820. 8 pages.
Naldini et al., Ex vivo gene transfer and correction for cell-based therapies. Nat Rev Genet. May 2011;12(5):301-15. doi: 10.1038/nrg2985. Epub Mar. 29, 2011.
Ooi et al., DNMT3L connects unmethylated lysine 4 of histone H3 to de novo methylation of DNA. Nature. Aug. 9, 2007;448(7154):714-7. doi: 10.1038/nature05987.
Opposition filed by James Poole Limited against European Patent No. EP 3209783, mailed Aug. 30, 2022. 29 pages.
Opposition filed by Mr. H. Ulrich Dorries against European Patent No. EP 3209783, mailed Aug. 29, 2022. 28 pages.
Patentee's Letter dated Aug. 12, 2019. 4 pages. D24, submitted in Opposition of European Patent No. EP 3209783 on Nov. 4, 2022.
Patentee's Letter dated Dec. 18, 2017. 5 pages. D20, submitted in Opposition of European Patent No. EP 3209783 on Nov. 4, 2022.
Platt et al., Mortality in sickle cell disease. Life expectancy and risk factors for early death. N Engl J Med. Jun. 9, 1994;330(23):1639-44. doi: 10.1056/NEJM199406093302303.
Polak et al., In Situ Hybridization: Principles and Practice. Oxford University Press. 1990.
Probst et al., Epigenetic inheritance during the cell cycle. Nat Rev Mol Cell Biol. Mar. 2009;10(3):192-206. doi: 10.1038/nrm2640.
Qi et al., Repurposing CRISPR as an RNA-guided platform for sequence-specific control of gene expression. Cell. Feb. 28, 2013;152(5):1173-83. doi: 10.1016/j.cell.2013.02.022. Erratum in: Cell. Feb. 4, 2021;184(3):844.
Quenneville et al., In embryonic stem cells, ZFP57/KAP1 recognize a methylated hexanucleotide to affect chromatin and DNA methylation of imprinting control regions. Mol Cell. Nov. 4, 2011;44(3):361-72. doi: 10.1016/j.molcel.2011.08.032.
Ramachandran et al., Recent advances in RNA interference therapeutics for CNS diseases. Neurotherapeutics. Jul. 2013;10(3):473-85. doi: 10.1007/s13311-013-0183-8.
Reik et al., Stability and flexibility of epigenetic gene regulation in mammalian development. Nature. May 24, 2007;447(7143):425-32. doi: 10.1038/nature05918.
Rivenbark et al., Epigenetic reprogramming of cancer cells via targeted DNA methylation. Epigenetics. Apr. 2012;7(4):350-60. doi: 10.4161/epi.19507. Epub Apr. 1, 2012.
Rivenbark et al., Epigenetic reprogramming of cancer cells via targeted DNA methylation. Epigenetics. Apr. 2012;7(4):350-60. doi: 10.4161/epi.19507. Epub Apr. 1, 2012. D11, submitted in Opposition of European Patent No. EP 3209783 on Nov. 4, 2022.
Roe et al., DNA Isolation and Sequencing: Essential Techniques. John Wiley & Sons. 1996.
Sambrook et al., Molecular Cloning: A Laboratory Manual. Cold Spring Harbor Laboratory Press. 1989.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sankaran et al., Human fetal hemoglobin expression is regulated by the developmental stage-specific repressor BCL11A. Science. Dec. 19, 2008;322(5909):1839-42. doi: 10.1126/science.1165409. Epub Dec. 4, 2008.
Schultz et al., SETDB1: a novel KAP-1-associated histone H3, lysine 9-specific methyltransferase that contributes to HP1-mediated silencing of euchromatic genes by KRAB zinc-finger proteins. Genes Dev. Apr. 15, 2002;16(8):919-32. doi: 10.1101/gad.973302.
Schultz et al., SETDB1: a novel KAP-1-associated histone H3, lysine 9-specific methyltransferase that contributes to HP1-mediated silencing of euchromatic genes by KRAB zinc-finger proteins. Genes Dev. Apr. 15, 2002;16(8):919-32. doi: 10.1101/gad.973302. D22, submitted in Opposition of European Patent No. EP 3209783 on Nov. 4, 2022.
Schwartz et al., A new world of Polycombs: unexpected partnerships and emerging functions. Nat Rev Genet. Dec. 2013;14(12):853-64. doi: 10.1038/nrg3603. Epub Nov. 12, 2013.
Sera, Zinc-finger-based artificial transcription factors and their applications. Adv Drug Deliv Rev. Jul. 2, 2009;61(7-8):513-26. doi: 10.1016/j.addr.2009.03.012. Epub Apr. 23, 2009.
Siddique et al., Targeted methylation and gene silencing of VEGF-A in human cells by using a designed Dnmt3a-Dnmt3L single-chain fusion protein with increased DNA methylation activity. J Mol Biol. Feb. 8, 2013;425(3):479-91 and Supplemental Information. doi: 10.1016/j.jmb.2012.11.038. Epub Dec. 4, 2012. D10, submitted in Opposition of European Patent No. EP 3209783 on Nov. 4, 2022.
Siddique et al., Targeted methylation and gene silencing of VEGF-A in human cells by using a designed Dnmt3a-Dnmt3L single-chain fusion protein with increased DNA methylation activity. J Mol Biol. Feb. 8, 2013;425(3):479-91. doi: 10.1016/j.jmb.2012.11.038. Epub Dec. 4, 2012.
Silva et al., Meganucleases and other tools for targeted genome engineering: perspectives and challenges for gene therapy. Curr Gene Ther. Feb. 2011;11(1):11-27. doi: 10.2174/156652311794520111.
Smith et al., DNA methylation: roles in mammalian development. Nat Rev Genet. Mar. 2013;14(3):204-20. doi: 10.1038/nrg3354. Epub Feb. 12, 2013.
Stamatoyannopoulos, Control of globin gene expression during development and erythroid differentiation. Exp Hematol. Mar. 2005;33(3):259-71. doi: 10.1016/j.exphem.2004.11.007.
Szulc et al., A versatile tool for conditional gene expression and knockdown. Nat Methods. Feb. 2006;3(2):109-16. doi: 10.1038/nmeth846.

(56) References Cited

OTHER PUBLICATIONS

Tatusova et al., BLAST 2 Sequences, a new tool for comparing protein and nucleotide sequences. FEMS Microbiol Lett. May 15, 1999;174(2):247-50. doi: 10.1111/j.1574-6968.1999.tb13575.x. Erratum in: FEMS Microbiol Lett Aug. 1, 1999;177(1):187-8.
Uda et al., Genome-wide association study shows BCL11A associated with persistent fetal hemoglobin and amelioration of the phenotype of beta-thalassemia. Proc Natl Acad Sci U S A. Feb. 5, 2008;105(5):1620-5. doi: 10.1073/pnas.0711566105. Epub Feb. 1, 2008.
Urrutia, KRAB-containing zinc-finger repressor proteins. Genome Biol. 2003;4(10):231. doi: 10.1186/GB-2003-4-10-231. Epub Sep. 23, 2003.
Van Der Oost et al., Unravelling the structural and mechanistic basis of CRISPR-Cas systems. Nat Rev Microbiol. Jul. 2014;12(7):479-92. doi: 10.1038/nrmicro3279. Epub Jun. 9, 2014.
Wang et al., Tightly regulated gene expression in human hematopoietic stem cells after transduction with helper-dependent Ad5/35 vectors. Exp Hematol. Jul. 2008;36(7):823-31. doi: 10.1016/j.exphem.2008.01.014. Epub Apr. 18, 2008.
Weatherall, The role of the inherited disorders of hemoglobin, the first "molecular diseases," in the future of human genetics. Annu Rev Genomics Hum Genet. 2013;14:1-24. doi: 10.1146/annurev-genom-091212-153500. Epub Jul. 3, 2013.
Wilber et al., Therapeutic levels of fetal hemoglobin in erythroid progeny of ß-thalassemic CD34+ cells after lentiviral vector-mediated gene transfer. Blood. Mar. 10, 2011;117(10):2817-26. doi: 10.1182/blood-2010-08-300723. Epub Dec. 14, 2010.
Wiznerowicz et al., The Kruppel-associated box repressor domain can trigger de novo promoter methylation during mouse early embryogenesis. J Biol Chem. Nov. 23, 2007;282(47):34535-41. doi: 10.1074/jbc.M705898200. Epub Sep. 24, 2007.
Xu et al., Correction of sickle cell disease in adult mice by interference with fetal hemoglobin silencing. Science. Nov. 18, 2011;334(6058):993-6. doi: 10.1126/science.1211053. Epub Oct. 13, 2011.
Younan et al., Genetically modified hematopoietic stem cell transplantation for HIV-1-infected patients: can we achieve a cure? Mol Ther. Feb. 2014;22(2):257-264. doi: 10.1038/mt.2013.264. Epub Nov. 13, 2013.
Zhang et al., Dissecting the roles of miR-302/367 cluster in cellular reprogramming using TALE-based repressor and TALEN. Stem Cell Reports. Aug. 15, 2013;1(3):218-25. doi: 10.1016/j.stemcr.2013.07.002.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zhao et al., Intracellular delivery of artificial transcription factors fused to the protein transduction domain of HIV-1 Tat. Protein Expr Purif. Jul. 2013;90(1):27-33. doi: 10.1016/j.pep.2013.04.007. Epub May 3, 2013.
Zhao et al., Intracellular delivery of artificial transcription factors fused to the protein transduction domain of HIV-1 Tat. Protein Expr Purif. Jul. 2013;90(1):27-33. doi: 10.1016/j.pep.2013.04.007. Epub May 3, 2013. D4, submitted in Opposition of European Patent No. EP 3209783 on Nov. 4, 2022.
[No Author Listed], Appendix—Bioinformatic Analysis of KRAB Domain. 4 pages. D46, submitted in Opposition of European Patent No. EP 3209783 on Nov. 15, 2024.
[No Author Listed], Figures 1-20 in color from EP Patent No. 3209783. D25, submitted in Opposition of European Patent No. EP 3209783 on May 28, 2024. 20 pages.
[No Author Listed], Sequence Alignment of the Amino Acid Sequence of DNMT3L Used in D45 with SEQ ID No. 11 of the Patent. D56, submitted in Opposition of European Patent No. EP 3209783 on Nov. 15, 2024. 1 page.
[No Author Listed], Uniprot Acc No. P15840. 5 pages. D63, submitted in Opposition of European Patent No. EP 3209783 on Jan. 13, 2025.
Abaandou et al., Affecting HEK293 Cell Growth and Production Performance by Modifying the Expression of Specific Genes. Cells. Jul. 2, 2021;10(7):1667. doi: 10.3390/cells10071667. D40, submitted in Opposition of European Patent No. EP 3209783 on May 28, 2024.
Alerasool et al., An efficient KRAB domain for CRISPRi applications in human cells. Nat Methods. Nov. 2020;17(11):1093-1096. doi: 10.1038/s41592-020-0966-x. Epub Oct. 5, 2020. D30, submitted in Opposition of European Patent No. EP 3209783 on May 28, 2024.
Amabile et al., 690. Permanent Epigenetic Silencing of Human Genes With Artificial Transcriptional Repressors. 18th ASGCT Annual Meeting. May 16, 2015. Published in Mol Ther. May 2015;23(Suppl 1): S275. 1 page. D57, submitted in Opposition of European Patent No. EP 3209783 on Nov. 15, 2024.
Braliou et al., The v-ErbA oncoprotein quenches the activity of an erythroid-specific enhancer. Oncogene. Feb. 15, 2001;20(7):775-87. doi: 10.1038/sj.onc.1204159. D28, submitted in Opposition of European Patent No. EP 3209783 on May 28, 2024.
Cano-Rodriguez et al., Epigenetic Editing: On the Verge of Reprogramming Gene Expression at Will. Curr Genet Med Rep. 2016;4(4):170-179. doi: 10.1007/s40142-016-0104-3. Epub Oct. 1, 2016. D41, submitted in Opposition of European Patent No. EP 3209783 on May 28, 2024.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012. D60, submitted in Opposition of European Patent No. EP 3209783 on Jan. 7, 2025.
Cortés-Mancera et al., Gene-Targeted DNA Methylation: Towards Long-Lasting Reprogramming of Gene Expression? Adv Exp Med Biol. 2022;1389:515-533. doi: 10.1007/978-3-031-11454-0_18. D27, submitted in Opposition of European Patent No. EP 3209783 on May 28, 2024.
CV of Dana Carroll, revised Nov. 2024. D47a, submitted in Opposition of European Patent No. EP 3209783 on Nov. 15, 2024. 19 pages.
CV of Professor Dr. A. Jeltsch. D37a, submitted in Opposition of European Patent No. EP 3209783 on May 28, 2024. 4 pages.
Das et al., Tet-On Systems For Doxycycline-inducible Gene Expression. Curr Gene Ther. 2016;16(3):156-67. doi: 10.2174/1566523216666160524144041. D43, submitted in Opposition of European Patent No. EP 3209783 on May 28, 2024.
De Groote et al., Epigenetic Editing: targeted rewriting of epigenetic marks to modulate expression of selected target genes. Nucleic Acids Res. Nov. 2012;40(21):10596-613. doi: 10.1093/nar/gks863. Epub Sep. 21, 2012. D58, submitted in Opposition of European Patent No. EP 3209783 on Nov. 15, 2024.
Evidence that Luo et al., Nucleic Acids Res. 2015;43(1):674-81 was published online on Oct. 17, 2014. D39a, submitted in Opposition of European Patent No. EP 3209783 on May 28, 2024. 2 pages.
Expert Declaration of Dana Carroll dated Nov. 13, 2024. D47, submitted in Opposition of European Patent No. EP 3209783 on Nov. 15, 2024. 4 pages.
Expert Declaration of Professor Dr. Albert Jeltsch dated Oct. 2, 2023. D37, submitted in Opposition of European Patent No. EP 3209783 on May 28, 2024. 3 pages.
Fuks, DNA methylation and histone modifications: teaming up to silence genes. Curr Opin Genet Dev. Oct. 2005;15(5):490-5. doi: 10.1016/j.gde.2005.08.002. D34, submitted in Opposition of European Patent No. EP 3209783 on May 28, 2024.
Hathaway et al., Dynamics and memory of heterochromatin in living cells. Cell. Jun. 22, 2012;149(7):1447-60 and Supplemental Information. doi: 10.1016/j.cell.2012.03.052. Epub Jun. 14, 2012.
Hochstrasser et al., CasA mediates Cas3-catalyzed target degradation during CRISPR RNA-guided interference. Proc Natl Acad Sci U S A. May 6, 2014;111(18):6618-23. doi: 10.1073/pnas.1405079111. Epub Apr. 18, 2014. D36, submitted in Opposition of European Patent No. EP 3209783 on May 28, 2024.
Kao et al., Ectopic DNMT3L triggers assembly of a repressive complex for retroviral silencing in somatic cells. J Virol. Sep. 2014;88(18):10680-95. doi: 10.1128/JVI.01176-14. Epub Jul. 2, 2014. D33, submitted in Opposition of European Patent No. EP 3209783 on May 28, 2024.

(56) References Cited

OTHER PUBLICATIONS

Letter in Reply to the Preliminary Opinion and in Preparation of the Oral Proceedings Scheduled for Jan. 16 and 17, 2025, dated Nov. 15, 2024, from Opponent Dr. Hans Ulrich Dorries. D74, submitted in Opposition of European Patent No. EP 3209783 on Oct. 23, 2025. 29 pages.
Letter in Reply to the Preliminary Opinion and in Preparation of the Oral Proceedings Scheduled for Jan. 16 and 17, 2025, dated Nov. 15, 2024, from Opponent James Poole Limited. D80, submitted in Opposition of European Patent No. EP 3209783 on Oct. 23, 2025. 33 pages.
Letter in Reply to the Submissions of the Patentee of Dec. 15, 2023, from Opponent James Poole Limited. D79, submitted in Opposition of European Patent No. EP 3209783 on Oct. 23, 2025. 11 pages.
Letter in Reply to the Submissions of the Patentee of May 25, 2023, dated Nov. 3, 2023, from Opponent Dr. Dr. Hans Ulrich Dörries. D73, submitted in Opposition of European Patent No. EP 3209783 on Oct. 23, 2025. 13 pages.
Letter in Reply to the Submissions of the Patentee of May 25, 2023, from Opponent James Poole Limited. D78, submitted in Opposition of European Patent No. EP 3209783 on Oct. 23, 2025. 24 pages.
Letter regarding Opposition of European Patent EP 3209783 B1 by James Poole Limited. D77, submitted in Opposition of European Patent No. EP 3209783 on Oct. 23, 2025. 23 pages.
Letter to EPO re: Third Set of Written Submissions filed by Patentee, dated Jan. 14, 2025. D76, submitted in Opposition of European Patent No. EP 3209783 on Oct. 23, 2025. 1 page.
Letter to the EPO re: Second Set of Written Submissions filed by Patentee, dated Jan. 10, 2025. D75, submitted in Opposition of European Patent No. EP 3209783 on Oct. 23, 2025. 2 pages.
List of Publication of Professor Dr. Jeltsch. Aug. 2023. D37b, submitted in Opposition of European Patent No. EP 3209783 on May 28, 2024. 17 pages.
Liu et al., Engineering cell signaling using tunable CRISPR-Cpf1-based transcription factors. Nat Commun. Dec. 13, 2017;8(1):2095. doi: 10.1038/s41467-017-02265-x. D53, submitted in Opposition of European Patent No. EP 3209783 on Nov. 15, 2024.
Luo Repurposing endogenous type I CRISPR-Cas systems for programmable gene repression. Nucleic Acids Res. Jan. 2015;43(1):674-81. doi: 10.1093/nar/gku971. Epub Oct. 17, 2014. D39, submitted in Opposition of European Patent No. EP 3209783 on May 28, 2024.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015. Author Manuscript. 31 pages. D48, submitted in Opposition of European Patent No. EP 3209783 on Nov. 15, 2024.
Mlambo et al., Designer epigenome modifiers enable robust and sustained gene silencing in clinically relevant human cells. Nucleic Acids Res. May 18, 2018;46(9):4456-4468. doi: 10.1093/nar/gky171. D61, submitted in Opposition of European Patent No. EP 3209783 on Jan. 7, 2025.
Moussa et al., Here to stay: Writing lasting epigenetic memories. Cell. Apr. 29, 2021;184(9):2281-2283. doi: 10.1016/j.cell.2021.04.007. D29, submitted in Opposition of European Patent No. EP 3209783 on May 28, 2024.
Nakamura et al., Durable CRISPR-Based Epigenetic Silencing. Biodesign Research. Jul. 1, 2021;2021:9815820. doi: 10.34133/2021/9815820. 8 pages. D45, submitted in Opposition of European Patent No. EP 3209783 on Nov. 15, 2024.
Nuñez et al., Genome-wide programmable transcriptional memory by CRISPR-based epigenome editing. Cell. Apr. 29, 2021;184(9):2503-2519.e17. doi: 10.1016/j.cell.2021.03.025. Epub Apr. 9, 2021.
Nuñez et al., Genome-wide programmable transcriptional memory by CRISPR-based epigenome editing. Cell. Apr. 29, 2021;184(9):2503-2519.e17. doi: 10.1016/j.cell.2021.03.025. Epub Apr. 9, 2021. D55, submitted in Opposition of European Patent No. EP 3209783 on Nov. 15, 2024.
O'Geen et al., Determinants of heritable gene silencing for KRAB-dCas9 + DNMT3 and Ezh2-dCas9 + DNMT3 hit-and-run epigenome editing. Nucleic Acids Res. Apr. 8, 2022;50(6):3239-3253. doi: 10.1093/nar/gkac123. D32, submitted in Opposition of European Patent No. EP 3209783 on May 28, 2024.
O'Green et al., dCas9-based epigenome editing suggests acquisition of histone methylation is not sufficient for target gene repression. Nucleic Acids Res. Sep. 29, 2017;45(17):9901-9916. doi: 10.1093/nar/gkx578. D54, submitted in Opposition of European Patent No. EP 3209783 on Nov. 15, 2024.
Opposition Communication from Opponent 1 dated Oct. 23, 2025, issued against Patent No. EP 3209783, mailed Oct. 28, 2025. 46 pages.
Opposition Communication from Opponent 2 dated Oct. 23, 2025, issued against Patent No. EP 3209783, mailed Oct. 28, 2025. 68 pages.
Opposition Communication issued against Patent No. EP 3209783 mailed Apr. 24, 2025. 11 pages.
Orth et al., Structural basis of gene regulation by the tetracycline inducible Tet repressor-operator system. Nat Struct Biol. Mar. 2000;7(3):215-9. doi: 10.1038/73324. D42, submitted in Opposition of European Patent No. EP 3209783 on May 28, 2024.
Policarpi et al., Epigenetic editing: Dissecting chromatin function in context. Bioessays. May 2021;43(5):e2000316. doi: 10.1002/bies.202000316. Epub Mar. 16, 2021. D26, submitted in Opposition of European Patent No. EP 3209783 on May 28, 2024.
Quenneville et al., The KRAB-ZFP/KAP1 system contributes to the early embryonic establishment of site-specific DNA methylation patterns maintained during development. Cell Rep. Oct. 25, 2012;2(4):766-73 with Supplemental Info. doi: 10.1016/j.celrep.2012.08.043. Epub Oct. 4, 2012. 12 pages.
Quenneville et al., The KRAB-ZFP/KAP1 system contributes to the early embryonic establishment of site-specific DNA methylation patterns maintained during development. Cell Rep. Oct. 25, 2012;2(4):766-73. doi: 10.1016/j.celrep.2012.08.043. Epub Oct. 4, 2012. D59, submitted in Opposition of European Patent No. EP 3209783 on Nov. 15, 2024.
Schunder et al., First indication for a functional CRISPR/Cas system in Francisella tularensis. Int J Med Microbiol. Mar. 2013;303(2):51-60. doi: 10.1016/j.ijmm.2012.11.004. Epub Jan. 18, 2013. D50, submitted in Opposition of European Patent No. EP 3209783 on Nov. 15, 2024.
Second Expert Declaration of Professor Dr. Albert Jeltsch dated Dec. 13, 2023. D38, submitted in Opposition of European Patent No. EP 3209783 on May 28, 2024. 6 pages.
Statement of Grounds of Opposition, dated Aug. 24, 2022, from Opponent Dr. Hans Ulrich Dörries. D72, submitted in Opposition of European Patent No. EP 3209783 on Oct. 23, 2025. 22 pages.
Stepper, CRISPR-Cas9 fusions for synthetic epigenetics. Thesis. 2020. Institut für Biochemie und Technische Biochemie der Universität Stuttgart. D44, submitted in Opposition of European Patent No. EP 3209783 on May 28, 2024. 152 pages.
Summons to Attend Oral Proceeding in Opposition against European Patent No. EP 3209783, Preliminary Opinion of Opposition Division, and Consolidated List of Cited Documents, mailed May 28, 2024. 17 pages.
Tak et al., Inducible and multiplex gene regulation using CRISPR-Cpf1-based transcription factors. Nat Methods. Dec. 2017;14(12):1163-1166. doi: 10.1038/nmeth.4483. Epub Oct. 30, 2017. D52, submitted in Opposition of European Patent No. EP 3209783 on Nov. 15, 2024.
Tang et al., A CRISPR-Cpf1 system for efficient genome editing and transcriptional repression in plants. Nat Plants. Feb. 17, 2017;3:17018. doi: 10.1038/nplants.2017.18. Erratum in: Nat Plants. Jun. 19, 2017;3:17103. doi: 10.1038/nplants.2017.103. D51, submitted in Opposition of European Patent No. EP 3209783 on Nov. 15, 2024.
Third Party Observations issued in Application No. EP 15794644.3 mailed Nov. 21, 2024. 34 pages.
Third Party Observations issued in Application No. EP 21197502.4 mailed Feb. 19, 2025. 4 pages.
Third Party Observations issued in Application No. EP 21197502.4 mailed Mar. 18, 2026. 10 pages.
Third Party Observations issued in Application No. EP 21197502.4 mailed Aug. 13, 2025. 8 pages.

(56) References Cited

OTHER PUBLICATIONS

Tycko et al., High-Throughput Discovery and Characterization of Human Transcriptional Effectors. Cell. Dec. 23, 2020;183(7):2020-2035.e16. doi: 10.1016/j.cell.2020.11.024. Epub Dec. 15, 2020. D31, submitted in Opposition of European Patent No. EP 3209783 on May 28, 2024.
Yamazaki et al., Targeted DNA methylation in pericentromeres with genome editing-based artificial DNA methyltransferase. PLoS One. May 18, 2017;12(5):e0177764. doi: 10.1371/journal.pone.0177764. D64, submitted in Opposition of European Patent No. EP 3209783 on Jan. 13, 2025.
Yamazaki et al., Time-lapse and retrospective analysis of DNA methylation in mouse preimplantation embryos by live cell imaging. Dev Biol. Apr. 1, 2007;304(1):409-19. doi: 10.1016/j.ydbio.2006.12.046. Epub Dec. 24, 2006. D65, submitted in Opposition of European Patent No. EP 3209783 on Jan. 13, 2025.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015. D49, submitted in Opposition of European Patent No. EP 3209783 on Nov. 15, 2024.
Communication of the Board of Appeals in Opposition against European Patent No. EP 3209783, mailed Jul. 9, 2026. 12 pages.

A

B

PERMANENT EPIGENETIC GENE SILENCING

RELATED APPLICATIONS

This application is a continuation of U.S. application Ser. No. 15/521,294, filed Apr. 23, 2017, which is a national stage filing under 35 U.S.C. § 371 of international application PCT/IB2015/058202, filed Oct. 23, 2015, the entire contents of each of which is incorporated herein by reference in its entirety.

REFERENCE TO AN ELECTRONIC SEQUENCE LISTING

The contents of the electronic sequence listing (C169870002US01-SUBSEQ-JRV.xml; Size: 210,844 bytes; and Date of Creation: Jun. 13, 2023) is herein incorporated by reference in its entirety.

FIELD OF THE INVENTION

The present invention relates to gene silencing and/or epigenetic editing. More specifically, the present invention relates to improved methods for silencing a gene of interest or for editing the epigenetic state of a genetic element of interest, including during gene therapy applications.

BACKGROUND TO THE INVENTION

Gene therapy involves the incorporation of genetic material into a cell to treat or prevent disease. The genetic material may supplement defective genes with functional copies of those genes, inactivate improperly functioning genes or introduce new therapeutic genes to a cell.

A classic example of gene therapy is gene replacement, where a DNA sequence that encodes a functional, therapeutic gene is used to replace a dysfunctional gene (Naldini, L. (2011) *Nat. Rev. Genet.* 12: 301-15; Kay, M. A. (2011) *Nat. Rev. Genet.* 12: 316-28; Biffi, A. et al. (2013) *Science* 341: 1233158; Aiuti, A. et al. (2013) *Science* 341: 1233151; Aiuti, A. et al. (2009) *N. Engl. J. Med.* 360: 447-58). However, there are several inherited diseases where the goal of gene therapy is to silence rather than replace gene function. Paradigmatic examples include Huntington's disease, most types of Spinocerebellar ataxias and some collagenopathies. Furthermore, gene silencing is emerging as a promising strategy to treat certain infectious diseases (Younan, P. et al. (2014) *Mol. Ther.* 22: 257-64), by inactivating either pathogen-associated gene products or host genes that are necessary for the pathogen life cycle.

For example, silencing of the chemokine (C—C motif) receptor type 5 (CCR5) gene, one of two cellular co-receptors required for HIV entry into T cells, has received significant attention. This is because a natural deletion in CCR5 confers resistance to infection by CCR5-tropic HIV strains without causing overt pathological effects (Liu, R. et al. (1996) *Cell* 86: 367-77; Hutter, G. et al. (2009) *N. Engl. J. Med.* 360: 692-8).

In addition, it has recently been proposed that the haemoglobinopathies (Weatherall, D. J. (2013) *Annu. Rev. Genomics Hum. Genet.* 14: 1-24), the most common inherited recessive disorders of the haematopoietic system and major targets for therapeutic gene replacement, can also be amenable to therapeutic gene silencing. This intriguing concept stems from our increasing understanding of the mechanisms that orchestrate the foetal to adult haemoglobin switch during development (Stamatoyannopoulos, G. (2005) *Exp. Hematol.* 33: 259-71; Bauer, D. E. et al. (2011) *Curr. Opin. Pediatr.* 23: 1-8) and by extensive clinical evidence showing that persistent expression of the foetal haemoglobin (HbF) significantly ameliorates morbidity and mortality of Sickle Cell Disease (SCD; Platt, O. S. et al. (1994) *N. Engl. J. Med.* 330: 1639-44) and β-thalassemia (β-Thal; Andreani, M. et al. (2011) *Haematologica* 96: 128-33) patients. In particular, genome-wide association studies performed on patients affected by the hereditary persistence of HbF revealed that the transcription factor B-cell lymphoma/leukaemia 11A (BCL11A) is a major regulator of the haemoglobin switch (Sankaran, V. G. et al. (2008) *Science* 322: 1839-42; Uda, M. et al. (2008) *Proc. Natl. Acad. Sci. USA* 105: 1620-5; Galarneau, G. et al. (2010) *Nat. Genet.* 42: 1049-51) and that inactivating mutations in this gene result in increased HbF expression (Wilber, A. et al. (2011) *Blood* 117: 2817-26; Xu, J. et al. (2011) *Science* 334: 993-6). Moreover, an erythroid-specific enhancer within the second intron of BCL11A has recently been identified (Bauer, D. E. et al. (2013) *Science* 342: 253-7). Genetic inactivation of this regulatory element impairs BCL11A expression specifically in erythroid precursors, resulting in HbF reactivation, while it preserves the activity of this protein necessary for proper B-cell ontogeny (Canver, M. C. et al. (2015) Nature September 16 doi: 10.1038/nature15521 [Epub ahead of print]; Vierstra, J. et al. (2015) Nat. Methods 12: 927-30).

To date, two main targeting technologies have been used to silence gene expression: RNA interference (RNAi; Davidson, B. L. et al. (2011) *Nat. Rev. Genet.* 12: 329-40) with single short hairpin RNA (shRNA); and gene targeting with artificial nucleases (AN; Carroll, D. (2014) *Annu. Rev. Biochem.* 83: 409-39). RNAi exploits the endogenous microRNA (miRNA) pathway to downregulate expression of the target transcript that is complementary to the shRNA (Davidson, B. L. et al. (2011) *Nat. Rev. Genet.* 12: 329-40). The AN approach exploits the error-prone nature of the non-homologous end joining DNA repair process to permanently disrupt the coding frame of the AN-target gene (Ciccia, A. et al. (2010) *Mol. Cell* 40: 179-204).

Although promising pre-clinical and clinical data have been obtained using these technologies (DiGiusto, D. L. et al. (2013) *Viruses* 5: 2898-919; DiGiusto, D. L. et al. (2010) *Sci. Transl. Med.* 2: 36ra43; Ramachandran, P. S. et al. (2013) *Neurotherapeutics* 10: 473-85; McBride, J. L. et al. (2011) *Mol. Ther.* 19: 2152-62), partial depletion of gene expression with shRNA and the low efficiency by which homozygous disruption occurs in diploid mammalian cells may jeopardise efficacy of these treatments. These disadvantages are particularly relevant in those applications where residual levels of gene activity are sufficient for biological function.

Furthermore, safe exploitation of these technologies requires solving issues with: a) off-target gene silencing; b) altering the transcriptional profile of the cell by interfering with the endogenous miRNA pathway; and c) altering the cell cycle progression or triggering apoptosis by over-activating the DNA damage response (Ciccia, A. et al. (2010) *Mol. Cell* 40: 179-204). In addition, RNAi and AN are not suitable for inactivation of wide non-transcribed regulatory elements, such as promoters or enhancers.

In addition, epigenetic mechanisms have been exploited to silence gene expression. Epigenetics refers to mechanisms that convey heritable changes in the function of the genome without altering the primary DNA sequence. These changes can mediate short-term instructions that can be quickly reverted in response to exogenous stimuli (e.g.

histone post-transcriptional modifications; HPTMs). Alternatively, they can constitute long-term instructions that stably contribute to cellular identity and memory (e.g. DNA methylation; Smith, Z. D. et al. (2013) *Nat. Rev. Genet.* 14: 204-20). Current studies are unravelling the composition and function of the molecular complexes recruited to chromatin to induce epigenetic repressive states, and the mechanisms by which these states are indefinitely propagated throughout cell division (Cedar, H. et al. (2009) *Nat. Rev. Genet.* 10: 295-304; Chen, T. et al. (2014) *Nat. Rev. Genet.* 15: 93-106; Probst, A. V. et al. (2009) *Nat. Rev. Mol. Cell Biol.* 10: 192-206).

A number of studies have established gene silencing using stably expressed artificial transcription repressors (ATRs) created from DNA-binding domains fused to the effector domains of chromatin remodelling enzymes (de Groote, M. L. et al. (2012) *Nucleic Acids Res.* 40: 10596-613; Mendenhall, E. M. et al. (2013) *Nat. Biotechnol.* 31: 1133-6; Zhang, F. et al. (2011) *Nat. Biotechnol.* 29: 149-53; Konermann, S. et al. (2013) *Nature* 500: 472-6; Sera, T. (2009) *Adv. Drug Deliv. Rev.* 61: 513-26; Qi, L. S. et al. (2013) *Cell* 152: 1173-83). However, these studies failed to demonstrate permanent epigenetic silencing in the absence of continuous expression of the ATRs, likely because of the intrinsic inability of the chosen effector domains to recreate self-propagating chromatin repressive states at the ATR-target loci.

In addition, silencing induced by artificial Krüppel-associated box (KRAB)-based repressors has been shown to be erased in somatic cells once the repressor proteins are not expressed or no longer bind to their target locus (Szulc, J. et al. (2006) *Nat. Methods* 3: 109-16).

Accordingly, there remains a significant need for the development of more powerful and safer gene silencing technologies.

SUMMARY OF THE INVENTION

We have developed a novel approach for gene silencing that exploits endogenous epigenetic mechanisms. Unexpectedly, our approach conveys robust and heritable states of transcriptional repression of the desired target gene. Importantly, this allows permanent inactivation of genes of therapeutic (e.g. disease-causing) or biotechnological interest.

Because of the previous difficulties with sustaining robust gene silencing, and because long-lasting expression of artificial transcription repressors (ATRs) from integrating vectors may represent a major safety threat to the cells, we selected to use only ATRs that satisfy all of the following criteria:

1. work by combinatorial assembly of two or more different effector modules;
2. establish robust and permanent states of epigenetic repression; and
3. exert this biological function when transiently expressed in the cell.

This approach has allowed us to improve both the efficiency and safety of gene silencing, as activity of each individual ATR at off-target sites will be transient if not absent.

In one aspect, the present invention provides a product comprising two or more artificial transcription repressors (ATRs), or polynucleotides encoding therefor, selected from groups (a), (b), (c) or (d):

(a) an ATR comprising a DNA-binding domain operably linked to a KRAB domain or homologue thereof;

(b) an ATR comprising a DNA-binding domain operably linked to a DNMT3A, DNMT3B or DNMT1 domain or homologue thereof;

(c) an ATR comprising a DNA-binding domain operably linked to a DNMT3L domain or homologue thereof; and (d) an ATR comprising a DNA-binding domain operably linked to a SETDB1 domain or homologue thereof wherein at least two of the ATRs are selected from different groups (a), (b), (c) or (d).

In another aspect, the present invention provides a product comprising two or more artificial transcription repressors (ATRs), or polynucleotides encoding therefor, selected from groups (a), (b) or (c):

(a) an ATR comprising a DNA-binding domain operably linked to a KRAB domain or homologue thereof;

(b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof wherein at least two of the ATRs are selected from different groups (a), (b) or (c).

In one embodiment, the product of the invention comprises the ATRs (a) and (b), or polynucleotides encoding therefor. In another embodiment, the product of the invention comprises the ATRs (a) and (c), or polynucleotides encoding therefor. In another embodiment, the product of the invention comprises the ATRs (b) and (c), or polynucleotides encoding therefor. In a preferred embodiment, the product of the invention comprises the ATRs (a), (b) and (c), or polynucleotides encoding therefor. In another embodiment, the product of the invention comprises the ATRs (a), (b) and (d), or polynucleotides encoding therefor. In another embodiment, the product of the invention comprises the ATRs (b) and (d), or polynucleotides encoding therefor. In another embodiment, the product of the invention comprises the ATRs (c) and (d), or polynucleotides encoding therefor. In another preferred embodiment, the product of the invention comprises the ATRs (b), (c) and (d), or polynucleotides encoding therefor.

The KRAB domain or homologue thereof may comprise an amino acid sequence that has at least 50%, 60%, 70%, 80%, 90%, 95%, 99% or 100% identity to SEQ ID NO: 1, 2, 3, 4, 5, 6 or 7 wherein the amino acid sequence substantially retains the natural function of the protein represented by SEQ ID NO: 1, 2, 3, 4, 5, 6, or 7.

The DNMT3A domain or homologue thereof may comprise an amino acid sequence that has at least 50%, 60%, 70%, 80%, 90%, 95%, 99% or 100% identity to SEQ ID NO: 8 wherein the amino acid sequence substantially retains the natural function of the protein represented by SEQ ID NO: 8.

The DNMT3B domain or homologue thereof may comprise an amino acid sequence that has at least 50%, 60%, 70%, 80%, 90%, 95%, 99% or 100% identity to SEQ ID NO: 9 or 36 wherein the amino acid sequence substantially retains the natural function of the protein represented by SEQ ID NO: 9 or 36.

The DNMT1 domain or homologue thereof may comprise an amino acid sequence that has at least 50%, 60%, 70%, 80%, 90%, 95%, 99% or 100% identity to SEQ ID NO: 10 wherein the amino acid sequence substantially retains the natural function of the protein represented by SEQ ID NO: 10.

The DNMT3L domain or homologue thereof may comprise an amino acid sequence that has at least 50%, 60%, 70%, 80%, 90%, 95%, 99% or 100% identity to SEQ ID NO: 11 wherein the amino acid sequence substantially retains the natural function of the protein represented by SEQ ID NO: 11.

The SETDB1 domain or homologue thereof may comprise an amino acid sequence that has at least 50%, 60%, 70%, 80%, 90%, 95%, 99% or 100% identity to SEQ ID NO: 12 or 13 wherein the amino acid sequence substantially retains the natural function of the protein represented by SEQ ID NO: 12 or 13.

In one embodiment, the DNA-binding domain of (a), (b), (c) or (d) comprises a domain independently selected from a TALE DNA-binding domain, a zinc finger domain, a tetR DNA-binding domain, a meganuclease or a CRISPR/Cas system. In a preferred embodiment, the DNA-binding domain of (a), (b), (c) or (d) comprises a TALE DNA-binding domain or a CRISPR/Cas system.

The DNA-binding domains, for example the TALE DNA-binding domains or the CRISPR/Cas system, of (a), (b), (c) or (d) may be selected or engineered to bind to different binding sites.

The DNA-binding domains may bind to binding sites within a target gene or within regulatory sequences for the target gene, for example promoter or enhancer sequences.

The DNA-binding domains may bind to binding sites within splicing sites. Splicing variants of a given gene may be regulated by DNA methylation/demethylation at splicing sites. In turn, these modifications may cause exon exclusion/inclusion in the mature transcript. This exclusion/inclusion may have therapeutic relevance, such as in the case of Duchenne Muscular Dystrophy, in which exclusion (by genetic ablation or exon skipping) from the mature mRNA of an exon bearing the most frequent disease-causing mutation has been proposed for therapy (Ousterout, D. G. et al. (2015) Mol. Ther. 23: 523-32; Ousterout, D. G. et al. (2015) Nat. Commun. 6: 6244; Kole, R. et al. (2015) Adv. Drug Deliv. Rev. 87: 104-7; Touznik, A. et al. (2014) Expert Opin. Biol. Ther. 14: 809-19).

The ATRs of the present invention may also target genetic elements which may be actively transcribed or not (e.g. sequences that control the topological arrangement, stability and replication of the genome, such as insulators, laminin-associated domains, telomeric and centromeric regions), repetitive or mobile elements. Accordingly, the present invention may relate to epigenetic editing, such as silencing/editing of a genetic element. The invention may therefore encompass the use of the products and ATRs of the invention for epigenetic editing of regulatory DNA elements, such as those described herein. Epigenetic editing of a target gene or of a genetic element may also be associated with its transcription activation or activity, respectively. The invention may also encompass the use of the products and ATRs of the invention for simultaneous epigenetic silencing of multiple target genes or regulatory DNA elements, such as those described herein.

In one embodiment, the polynucleotides encoding the two or more ATRs are in the form of a single vector or are comprised within separate vectors.

In one embodiment where two ATRs are used, polynucleotides encoding (a) and (b) may be comprised within a single vector; polynucleotides encoding (a) and (c) may be comprised within a single vector; or polynucleotides encoding (b) and (c) may be comprised within a single vector.

In another embodiment where two ATRs are used, polynucleotides encoding (a) and (d) may be comprised within a single vector; polynucleotides encoding (b) and (d) may be comprised within a single vector; or polynucleotides encoding (c) and (d) may be comprised within a single vector.

In another embodiment where two ATRs are used, polynucleotides encoding (a) and (b) may be comprised within separate vectors; polynucleotides encoding (a) and (c) may be comprised within separate vectors; or polynucleotides encoding (b) and (c) may be comprised within separate vectors.

In another embodiment where two ATRs are used, polynucleotides encoding (a) and (d) may be comprised within separate vectors; polynucleotides encoding (b) and (d) may be comprised within separate vectors; or polynucleotides encoding (c) and (d) may be comprised within separate vectors.

In one embodiment where three ATRs are used, polynucleotides encoding (a), (b) and (c) may be comprised within a single vector; polynucleotides encoding (a), (b) and (c) may be comprised within separate vectors; polynucleotides encoding (a) and (b) may be comprised within a single vector and the polynucleotide encoding (c) may be comprised within a separate vector; polynucleotides encoding (a) and (c) may be comprised within a single vector and the polynucleotide encoding (b) may be comprised within a separate vector; or polynucleotides encoding (b) and (c) may be comprised within a single vector and the polynucleotide encoding (a) may be comprised within a separate vector.

In another embodiment where three ATRs are used, polynucleotides encoding (a), (b) and (d) may be comprised within a single vector; polynucleotides encoding (a), (b) and (d) may be comprised within separate vectors; polynucleotides encoding (a) and (b) may be comprised within a single vector and the polynucleotide encoding (d) may be comprised within a separate vector; polynucleotides encoding (a) and (d) may be comprised within a single vector and the polynucleotide encoding (b) may be comprised within a separate vector; or polynucleotides encoding (b) and (d) may be comprised within a single vector and the polynucleotide encoding (a) may be comprised within a separate vector.

In another embodiment where three ATRs are used, polynucleotides encoding (b), (c) and (d) may be comprised within a single vector; polynucleotides encoding (b), (c) and (d) may be comprised within separate vectors; polynucleotides encoding (b) and (c) may be comprised within a single vector and the polynucleotide encoding (d) may be comprised within a separate vector; polynucleotides encoding (b) and (d) may be comprised within a single vector and the polynucleotide encoding (c) may be comprised within a separate vector; or polynucleotides encoding (c) and (d) may be comprised within a single vector and the polynucleotide encoding (b) may be comprised within a separate vector.

The vectors may, for example, be plasmid vectors, mRNA vectors (e.g. in vitro transcribed mRNA vectors) or viral vectors. Preferably the vectors enable transient expression of the ATRs within a cell.

As an alternative to the delivery of polynucleotides encoding ATRs to cells, the ATRs of the present invention may be delivered to cells by protein transduction. The protein transduction may, for example, be via vector delivery or by direct protein delivery.

In one embodiment, the product of the invention is in the form of a pharmaceutical composition further comprising a pharmaceutically acceptable carrier, diluent or excipient.

In one embodiment, the product of the invention further comprises a KRAB domain or homologue thereof, or polynucleotide encoding therefor, wherein the KRAB domain or homologue thereof is not operably linked to a DNA-binding domain.

In one embodiment, the product of the invention further comprises a DNMT3A, DNMT3B or DNMT1 domain or homologue thereof, or polynucleotide encoding therefor, wherein the DNMT3A, DNMT3B or DNMT1 domain or homologue thereof is not operably linked to a DNA-binding domain.

In one embodiment, the product of the invention further comprises a DNMT3L domain or homologue thereof, or polynucleotide encoding therefor, wherein the DNMT3L domain or homologue thereof is not operably linked to a DNA-binding domain.

In one embodiment, the product of the invention further comprises a SETDB1 domain or homologue thereof, or polynucleotide encoding therefor, wherein the SETDB1 domain or homologue thereof is not operably linked to a DNA-binding domain.

In another aspect, the present invention provides the product of the invention for use in therapy.

In another aspect, the present invention provides the product of the invention for use in therapy, wherein the two or more artificial transcription repressors (ATRs), or polynucleotides encoding therefor, are a combined preparation for administration to a subject simultaneously, sequentially or separately.

Herein, administration to a subject may include administration to a cell, for example during ex vivo therapy.

In another aspect, the present invention provides the use of the product of the invention for silencing a target gene. The use may, for example, be in vitro or ex vivo use. For example, a target gene may be silenced in a population of cells (e.g. a cell line or primary cells) to enhance the production of an agent (e.g. a biotherapeutic agent) by the cells, or to impart a growth advantage to the cells. Alternatively, for example, a target gene may be silenced to generate a knockout animal model for the target gene. The epigenetic approach of the present invention provides an alternative to existing methods of knocking out a gene, such as those utilising homologous recombination. Alternatively, for example, a target gene may be silenced in a plant cell.

According to the above uses, including the uses in therapy, the delivery of the two or more ATRs of the invention to a cell may silence a target gene. The delivery may be transient delivery. The delivery may be via expression of the two or more ATRs in a cell, for example expression from polynucleotides encoding the ATRs. The delivery of the two or more ATRs of the invention to a cell may also cause exon exclusion/inclusion in a mature transcript, for example through an effect on a splicing site. The delivery of the two or more ATRs of the invention to a cell may also enable silencing and/or editing of a genetic element as described herein.

In one embodiment, expression of the two or more ATRs of the invention in a cell silences a target gene. The expression may be transient expression.

In one embodiment, delivery of the two or more ATRs of the invention to a cell (e.g. by expression in the cell) permanently silences a target gene. In another embodiment, delivery of the two or more ATRs of the invention to a cell (e.g. by expression in the cell) permanently silences a target gene in the cell's progeny. For example, the cell may be a stem cell and the target gene may be silenced in the stem cell's progeny (e.g. the target gene may be silenced in cells resulting from differentiation of the stem cells).

By way of example, the cells may be derived from animals (such as mammals, e.g. humans), fungi (such as yeast) or plants. For example, the cells may be haematopoietic stem and progenitor cells, T lymphocytes, mesenchymal stem cells, fibroblasts, monocytes, epidermal or neural stem cells.

The separation of the binding sites to which the DNA-binding domains of the different ATRs are selected to bind is not particularly limited in size. For example, the DNA-binding domains of the different ATRs may be selected to bind to binding sites that are separated by about 1-100 bp, 1-50 bp, 1-30 bp, 5-30 bp, 10-30 bp or 15-30 bp. In one embodiment, the DNA-binding domains of the different ATRs are selected to bind to binding sites that are separated by 1-30 bp. Preferably, the DNA-binding domains of the different ATRs are selected to bind to binding sites that are separated by about 15-25 bp. For example, the DNA-binding domains of the different ATRs may be selected to bind to binding sites that are separated by 1, 2, 3, 4, 5, 6, 7, 8, 9, 10, 11, 12, 13, 14, 15, 16, 17, 18, 19, 20, 21, 22, 23, 24, 25, 26, 27, 28, 29 or30 bp.

The DNA-binding domains of the different ATRs may also be selected to bind to the same binding site, for example the DNA-binding domains of the different ATRs may be selected to bind to binding sites that are separated by 0 bp. Thus, for example, the DNA-binding domains of the different ATRs may be selected to bind to binding sites that are separated by about 0-100 bp, 0-50 bp, 0-30 bp, 5-30 bp, 10-30 bp or 15-30 bp. The DNA-binding domains of the different ATRs may be selected to bind to binding sites that are separated by about 0-15 or 15-25 bp.

The directional order in which the different ATRs bind relative to the target gene is not particularly important. In one embodiment, the two or more ATRs comprise an ATR comprising a KRAB domain or homologue thereof and an ATR comprising a DNMT3A, DNMT3B or DNMT1 domain or homologue thereof, and the DNA-binding domains (e.g. TALE DNA-binding domains) of each ATR are selected such that the ATR comprising a DNMT3A, DNMT3B or DNMT1 domain or homologue thereof binds to DNA upstream of the ATR comprising a KRAB domain or homologue thereof.

In one embodiment, the DNA-binding domains are TALE DNA-binding domains or CRISPR/Cas systems.

The selection of the DNA-binding domains may comprise engineering DNA-binding domains to bind to specific, desired DNA sequences.

In another aspect, the present invention provides an artificial transcription repressor (ATR) comprising a DNA-binding domain operably linked to a KRAB domain or homologue thereof, or polynucleotide encoding therefor, for use in therapy wherein the ATR is administered to a subject simultaneously, sequentially or separately in combination with a second ATR comprising a DNA-binding domain operably linked to a DNMT3A, DNMT3B or DNMT1 domain or homologue thereof and/or a third ATR comprising a DNA-binding domain operably linked to a DNMT3L domain or homologue thereof, or polynucleotides encoding therefor.

In another aspect, the present invention provides an artificial transcription repressor (ATR) comprising a DNA-binding domain operably linked to a DNMT3A, DNMT3B or DNMT1 domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof and/or a third ATR comprising a DNA-binding domain operably linked to a DNMT3L domain or homologue thereof, or polynucleotides encoding therefor.

In another aspect, the present invention provides an artificial transcription repressor (ATR) comprising a DNA-binding domain operably linked to a DNMT3L domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof and/or a third ATR comprising a DNA-binding domain operably linked to a DNMT3A, DNMT3B or DNMT1 domain or homologue thereof, or polynucleotides encoding therefor.

In another aspect, the present invention provides an artificial transcription repressor (ATR) comprising a DNA-binding domain operably linked to a KRAB domain or homologue thereof, or polynucleotide encoding therefor, for use in therapy wherein the ATR is administered to a subject simultaneously, sequentially or separately in combination with a second ATR comprising a DNA-binding domain operably linked to a DNMT3A, DNMT3B or DNMT1 domain or homologue thereof, and/or a third ATR comprising a DNA-binding domain operably linked to a DNMT3L domain or homologue thereof, and/or a fourth ATR comprising a DNA-binding domain operably linked to a SETDB1 domain or homologue thereof, or polynucleotides encoding therefor.

In another aspect, the present invention provides an artificial transcription repressor (ATR) comprising a DNA-binding domain operably linked to a DNMT3A, DNMT3B or DNMT1 domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof, and/or a third ATR comprising a DNA-binding domain operably linked to a DNMT3L domain or homologue thereof, and/or a fourth ATR comprising a DNA-binding domain operably linked to a SETDB1 domain or homologue thereof, or polynucleotides encoding therefor.

In another aspect, the present invention provides an artificial transcription repressor (ATR) comprising a DNA-binding domain operably linked to a DNMT3L domain or homologue thereof, or polynucleotide encoding therefor, for use in therapy wherein the ATR is administered to a subject simultaneously, sequentially or separately in combination with a second ATR comprising a DNA-binding domain operably linked to a KRAB domain or homologue thereof, and/or a third ATR comprising a DNA-binding domain operably linked to a DNMT3A, DNMT3B or DNMT1 domain or homologue thereof, and/or a fourth ATR comprising a DNA-binding domain operably linked to a SETDB1 domain or homologue thereof, or polynucleotides encoding therefor.

In another aspect, the present invention provides an artificial transcription repressor (ATR) comprising a DNA-binding domain operably linked to a SETDB1 domain or homologue thereof, or polynucleotide encoding therefor, for use in therapy wherein the ATR is administered to a subject simultaneously, sequentially or separately in combination with a second ATR comprising a DNA-binding domain operably linked to a DNMT3A, DNMT3B or DNMT1 domain or homologue thereof, and/or a third ATR comprising a DNA-binding domain operably linked to a DNMT3L domain or homologue thereof, and/or a fourth ATR comprising a DNA-binding domain operably linked to a KRAB domain or homologue thereof, or polynucleotides encoding therefor.

In another aspect, the present invention provides a cell comprising the two or more artificial transcription repressors (ATRs) of the invention. The cell may be transfected by the polynucleotides encoding the two or more ATRs of the invention. The polynucleotides may be in the form of a single vector or may be comprised within separate vectors.

In another aspect, the present invention provides a cell wherein said cell is a descendant of a cell comprising the two or more artificial transcription repressors (ATRs) of the invention. In one embodiment, the descendant cell no longer comprises the two or more ATRs of the invention. In another aspect, the present invention provides the cell of the invention for use in therapy.

In another aspect, the present invention provides a method of gene therapy comprising transfecting a cell with the polynucleotides encoding the two or more artificial transcription repressors (ATRs) of the invention, wherein the polynucleotides are in the form of a single vector or are comprised within separate vectors.

In one embodiment, the transfection is carried out ex vivo.

In another aspect, the present invention provides a method of gene therapy comprising administering two or more artificial transcription repressors (ATRs), or polynucleotides encoding therefor, selected from groups (a), (b) or (c):

(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof; and
(c) an ATR comprising a DNA-binding domain operably linked to a DNMT3L domain or homologue thereof to a subject simultaneously, sequentially or separately wherein at least two of the ATRs are selected from different groups (a), (b) or (c). The present invention also provides a method of gene therapy comprising administering two or more artificial transcription repressors (ATRs), or polynucleotides encoding therefor, selected from groups (a), (b), (c) or (d):

(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof;
(c) an ATR comprising a DNA-binding domain operably linked to a DNMT3L domain or homologue thereof; and
(d) an ATR comprising a DNA-binding domain operably linked to a SETDB1 domain or homologue thereof to a subject simultaneously, sequentially or separately, wherein at least two of the ATRs are selected from different groups (a), (b), (c) or (d).

In another aspect, the present invention provides a kit comprising two or more artificial transcription repressors (ATRs), or polynucleotides encoding therefor, selected from groups (a), (b) or (c):

(a) an ATR comprising a DNA-binding domain operably linked to a KRAB domain or homologue thereof;
(b) an ATR comprising a DNA-binding domain operably linked to a DNMT3A, DNMT3B or DNMT1 domain or homologue thereof; and
(c) an ATR comprising a DNA-binding domain operably linked to a DNMT3L domain or homologue thereof wherein at least two of the ATRs are selected from different groups (a), (b) or (c). The present invention also provides a kit comprising two or more artificial transcription repressors (ATRs), or polynucleotides encoding therefor, selected from groups (a), (b), (c) or (d):

(a) an ATR comprising a DNA-binding domain operably linked to a KRAB domain or homologue thereof;

(b) an ATR comprising a DNA-binding domain operably linked to a DNMT3A, DNMT3B or DNMT1 domain or homologue thereof;

(c) an ATR comprising a DNA-binding domain operably linked to a DNMT3L domain or homologue thereof; and (d) an ATR comprising a DNA-binding domain operably linked to a SETDB1 domain or homologue thereof wherein at least two of the ATRs are selected from different groups (a), (b), (c) or (d).

In another aspect, the present invention provides a method of silencing a target gene comprising the step of administering the two or more ATRs, or polynucleotides encoding therefor, of the invention to a cell. The method may be an in vitro method.

In another aspect, the present invention provides a product comprising an artificial transcription repressor (ATR) comprising a DNA-binding domain operably linked to a DNMT3A, DNMT3B or DNMT1 domain or homologue thereof, preferably a DNMT3A domain or homologue thereof, and an ATR comprising a DNA-binding domain operably linked to a SETDB1 domain or homologue thereof, or polynucleotides encoding therefor. The present invention also provides uses of this product, uses of this product in therapy, cells comprising this product and their descendants, methods employing this product and kits comprising this product, as described herein. This product may also further comprise an ATR comprising a DNA-binding domain operably linked to a DNMT3L or KRAB domain or homologue thereof, or polynucleotide encoding therefor.

In one embodiment, the product comprises an artificial transcription repressor (ATR) comprising a DNA-binding domain operably linked to a DNMT3A, DNMT3B or DNMT1 domain or homologue thereof, preferably a DNMT3A domain or homologue thereof, an ATR comprising a DNA-binding domain operably linked to a SETDB1 domain or homologue thereof, and an ATR comprising a DNA-binding domain operably linked to a DNMT3L domain or homologue thereof, or polynucleotides encoding therefor.

In one embodiment, the product comprises an artificial transcription repressor (ATR) comprising a DNA-binding domain operably linked to a DNMT3A, DNMT3B or DNMT1 domain or homologue thereof, preferably a DNMT3A domain or homologue thereof, an ATR comprising a DNA-binding domain operably linked to a SETDB1 domain or homologue thereof, and an ATR comprising a DNA-binding domain operably linked to a KRAB domain or homologue thereof, or polynucleotides encoding therefor.

The SETDB1 domain or homologue thereof may comprise an amino acid sequence that has at least 50%, 60%, 70%, 80%, 90%, 95%, 99% or 100% identity to SEQ ID NO: 12 or 13 wherein the amino acid sequence substantially retains the natural function of the protein represented by SEQ ID NO: 12 or 13.

In another aspect, the present invention provides an artificial transcription repressor (ATR), or a polynucleotide encoding therefor, wherein the ATR comprises a DNA-binding domain operably linked to two or more domains selected from groups (a), (b) or (c):

(a) a KRAB domain or homologue thereof;

(b) a DNMT3A, DNMT3B or DNMT1 domain or homologue thereof; and (c) a DNMT3L domain or homologue thereof wherein at least two of the domains operably linked to the DNA-binding domain are selected from different groups (a), (b) or (c). The ATR may, for example, comprise a DNA-binding domain operably linked to a domain of group (a), a domain of group (b) and a domain of group (c). The present invention also provides an artificial transcription repressor (ATR) comprising a DNA-binding domain operably linked to two or more domains selected from groups (a), (b), (c) or (d):

(a) a KRAB domain or homologue thereof;

(b) a DNMT3A, DNMT3B or DNMT1 domain or homologue thereof;

(c) a DNMT3L domain or homologue thereof; and (d) a SETDB1 domain or homologue thereof wherein at least two of the domains operably linked to the DNA-binding domain are selected from different groups (a), (b), (c) or (d).

In one embodiment, the DNA-binding domain comprises a TALE DNA-binding domain, a zinc finger domain, a tetR DNA-binding domain, a meganuclease or a CRISPR/Cas system.

The present invention also provides uses of this ATR, uses of this ATR in therapy, cells comprising this ATR and their descendants, methods employing this ATR and kits comprising this ATR, as described herein.

In another aspect, the present invention provides a product comprising two or more different artificial transcription repressors (ATRs), or polynucleotides encoding therefor, wherein the two or more different ATRs individually comprise a DNA-binding domain operably linked to two or more domains selected from groups (a), (b) or (c):

(a) a KRAB domain or homologue thereof;

(b) a DNMT3A, DNMT3B or DNMT1 domain or homologue thereof; and (c) a DNMT3L domain or homologue thereof wherein at least two of the domains operably linked to each individual DNA-binding domain are selected from different groups (a), (b) or (c). Each ATR may, for example, comprise a DNA-binding domain operably linked to a domain of group (a), a domain of group (b) and a domain of group (c). The present invention also provides a product comprising two or more different artificial transcription repressors (ATRs), or polynucleotides encoding therefor, wherein the two or more different ATRs individually comprise a DNA-binding domain operably linked to two or more domains selected from groups (a), (b), (c) or (d):

(a) a KRAB domain or homologue thereof;

(b) a DNMT3A, DNMT3B or DNMT1 domain or homologue thereof;

(c) a DNMT3L domain or homologue thereof; and (d) a SETDB1 domain or homologue thereof wherein at least two of the domains operably linked to each individual DNA-binding domain are selected from different groups (a), (b), (c) or (d).

In one embodiment, the DNA-binding domains of the two or more different ATRs are individually selected from the group consisting of a TALE DNA-binding domain, a zinc finger domain, a tetR DNA-binding domain, a meganuclease or a CRISPR/Cas system.

The DNA-binding domains, for example the TALE DNA-binding domains or the CRISPR/Cas system, of the two or more different ATRs may be selected or engineered to bind to different binding sites.

The DNA-binding domains may bind to binding sites within a target gene or within regulatory sequences for the target gene, for example promoter or enhancer sequences. The DNA-binding domains may bind to binding sites within splicing sites.

The present invention also provides uses of this product, uses of this product in therapy, cells comprising this product and their descendants, methods employing this product and kits comprising this product, as described herein.

In another aspect, the present invention provides a product comprising only one ATR and a separate effector protein that is not operably linked to a DNA-binding domain, or polynucleotides encoding therefor. The ATR may comprise a DNA-binding domain operably linked to an effector domain selected from: (a) a KRAB domain or homologue thereof; (b) a DNMT3A, DNMT3B or DNMT1 domain or homologue thereof; or (c) a DNMT3L domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof. Preferably the separate effector protein is different to the effector domain of the ATR. Preferably the separate effector protein is of a different class to the effector domain of the ATR. Preferably the separate effector protein is selected such that it does not comprise a domain belonging to the same group (a), (b) or (c) as the effector domain that constitutes the ATR.

The separate effector protein that is not operably linked to a DNA-binding domain may also comprise a SETDB1 domain or homologue thereof.

In another aspect, the present invention provides a product comprising only one ATR and a separate effector protein that is not operably linked to a DNA-binding domain, or polynucleotides encoding therefor. The ATR may comprise a DNA-binding domain operably linked to a SETDB1 effector domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof.

In one embodiment, the DNA-binding domain of the ATR is selected from the group consisting of a TALE DNA-binding domain, a zinc finger domain, a tetR DNA-binding domain, a meganuclease or a CRISPR/Cas system.

The present invention also provides uses of this product, uses of this product in therapy, cells comprising this product and their descendants, methods employing this product and kits comprising this product, as described herein.

When the product of the invention comprises only one ATR and a separate effector protein that is not operably linked to a DNA-binding domain, the polynucleotides encoding the ATR and separate effector protein may be in the form of a single vector or comprised within separate vectors.

The vectors may, for example, be plasmid vectors, mRNA vectors (e.g. in vitro transcribed mRNA vectors) or viral vectors. Preferably the vectors enable transient expression of the ATR and/or separate effector protein within a cell.

The ATR and/or separate effector protein of the present invention may also be delivered to cells by protein transduction, as described herein.

The ATRs and/or separate effector proteins of the invention, or polynucleotides encoding therefor, may be in the form of a pharmaceutical composition further comprising a pharmaceutically acceptable carrier, diluent or excipient.

In another aspect, the present invention provides the ATR of the invention, or the ATR and separate effector protein of the invention, or polynucleotides encoding therefor, for use in therapy.

In another aspect, the present invention provides the ATR and separate effector protein of the invention, or polynucleotides encoding therefor, for use in therapy, wherein the ATR and separate effector protein, or polynucleotides encoding therefor, are a combined preparation for administration to a subject simultaneously, sequentially or separately.

In another aspect, the present invention provides the ATR of the invention, or the ATR and separate effector protein of the invention, or polynucleotides encoding therefor, for silencing a target gene. The use may, for example, be in vitro or ex vivo use.

According to the above uses, including the uses in therapy, the delivery of the ATR of the invention, or the ATR and separate effector protein of the invention to a cell may silence a target gene. The delivery may be transient delivery. The delivery may be via expression of the ATR of the invention, or the ATR and separate effector protein of the invention in a cell, for example expression from polynucleotides encoding the ATR of the invention, or the ATR and separate effector protein of the invention.

In one embodiment, expression of the ATR of the invention, or the ATR and separate effector protein of the invention in a cell silences a target gene. The expression may be transient expression.

In one embodiment, delivery of the ATR of the invention, or the ATR and separate effector protein of the invention to a cell (e.g. by expression in the cell) permanently silences a target gene. In another embodiment, delivery of the ATR of the invention, or the ATR and separate effector protein of the invention to a cell (e.g. by expression in the cell) permanently silences a target gene in the cell's progeny. For example, the cell may be a stem cell and the target gene may be silenced in the stem cell's progeny (e.g. the target gene may be silenced in cells resulting from differentiation of the stem cells).

By way of example, the cells may be derived from animals (such as mammals, e.g. humans), fungi (such as yeast) or plants. For example, the cells may be haematopoietic stem and progenitor cells, T lymphocytes, mesenchymal stem cells, fibroblasts, monocytes, epidermal or neural stem cells.

In another aspect, the present invention provides an artificial transcription repressor (ATR) comprising a DNA-binding domain operably linked to a KRAB domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a DNMT3A, DNMT3B or DNMT1 domain or homologue thereof and/or a second separate effector protein that is not operably linked to a DNA-binding domain comprising a DNMT3L domain or homologue thereof, or polynucleotides encoding therefor.

In another aspect, the present invention provides an artificial transcription repressor (ATR) comprising a DNA-binding domain operably linked to a DNMT3A, DNMT3B or DNMT1 domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a KRAB domain or homologue thereof and/or a second separate effector protein that is not operably linked to a DNA-binding domain comprising a DNMT3L domain or homologue thereof, or polynucleotides encoding therefor.

In another aspect, the present invention provides an artificial transcription repressor (ATR) comprising a DNA-binding domain operably linked to a DNMT3L domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a KRAB domain or homologue thereof and/or a second separate effector protein that is not operably linked to a DNA-binding domain comprising a DNMT3A, DNMT3B or DNMT1 domain or homologue thereof, or polynucleotides encoding therefor.

A third separate effector protein that is not operably linked to a DNA-binding domain comprising a SETDB1 domain or homologue thereof may also be used in these combinations.

In another aspect, the present invention provides an artificial transcription repressor (ATR) comprising a DNA-binding domain operably linked to a SETDB1 domain or homologue thereof, or polynucleotide encoding therefor, for use in therapy wherein the ATR is administered to a subject simultaneously, sequentially or separately in combination with a first separate effector protein that is not operably linked to a DNA-binding domain comprising a KRAB domain or homologue thereof and/or a second separate effector protein that is not operably linked to a DNA-binding domain comprising a DNMT3A, DNMT3B or DNMT1 domain or homologue thereof and/or a third separate effector protein that is not operably linked to a DNA-binding domain comprising a DNMT3L domain or homologue thereof, or polynucleotides encoding therefor.

In another aspect, the present invention provides a cell comprising the ATR of the invention, or the ATR and separate effector protein of the invention. The cell may be transfected by the polynucleotides encoding the ATR of the invention, or the ATR and separate effector protein of the invention. The polynucleotides encoding the ATR and separate effector protein of the invention may be in the form of a single vector or may be comprised within separate vectors.

In another aspect, the present invention provides a cell wherein said cell is a descendant of a cell comprising the ATR of the invention, or the ATR and separate effector protein of the invention. In one embodiment, the descendant cell no longer comprises the ATR and/or separate effector protein of the invention. In another aspect, the present invention provides the cell of the invention for use in therapy.

In another aspect, the present invention provides a method of gene therapy comprising transfecting a cell with the polynucleotides encoding the ATR of the invention, or the ATR and separate effector protein of the invention. The polynucleotides encoding the ATR and separate effector protein of the invention may be in the form of a single vector or comprised within separate vectors.

In one embodiment, the transfection is carried out ex vivo.

In another aspect, the present invention provides a method of gene therapy comprising administering only one ATR and a separate effector protein that is not operably linked to a DNA-binding domain, or polynucleotides encoding therefor, to a subject simultaneously, sequentially or separately. The ATR may comprise a DNA-binding domain operably linked to an effector domain selected from: (a) a KRAB domain or homologue thereof; (b) a DNMT3A, DNMT3B or DNMT1 domain or homologue thereof; or (c) a DNMT3L domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof. Preferably the separate effector protein is different to the effector domain of the ATR. Preferably the separate effector protein is of a different class to the effector domain of the ATR. Preferably the separate effector protein is selected such that it does not comprise a domain belonging to the same group (a), (b) or (c) as the effector domain that constitutes the ATR.

The ATR may also comprise a DNA-binding domain operably linked to a SETDB1 effector domain or homologue thereof. The separate effector protein that is not operably linked to a DNA-binding domain may also comprise a SETDB1 domain or homologue thereof.

In another aspect, the present invention provides a kit comprising only one ATR and a separate effector protein that is not operably linked to a DNA-binding domain, or polynucleotides encoding therefor. The ATR may comprise a DNA-binding domain operably linked to an effector domain selected from: (a) a KRAB domain or homologue thereof; (b) a DNMT3A, DNMT3B or DNMT1 domain or homologue thereof; or (c) a DNMT3L domain or homologue thereof (i.e. the ATR may be as described herein). The separate effector protein that is not operably linked to a DNA-binding domain may comprise a KRAB, DNMT3A, DNMT3B, DNMT1 or DNMT3L domain or homologue thereof. The separate effector protein may be an effector domain/protein as described herein. The separate effector protein may be a full-length protein or functional fragment thereof. Preferably the separate effector protein is different to the effector domain of the ATR. Preferably the separate effector protein is of a different class to the effector domain of the ATR. Preferably the separate effector protein is selected such that it does not comprise a domain belonging to the same group (a), (b) or (c) as the effector domain that constitutes the ATR.

The ATR may also comprise a DNA-binding domain operably linked to a SETDB1 effector domain or homologue thereof. The separate effector protein that is not operably linked to a DNA-binding domain may also comprise a SETDB1 domain or homologue thereof.

In another aspect, the present invention provides a method of silencing a target gene comprising the step of administering the ATR of the invention, or the ATR and separate effector protein of the invention, or polynucleotides encoding therefor, to a cell. The method may be an in vitro method.

In addition, it is envisaged that the ATR or separate effector protein of the invention may comprise a SETDB1 domain or homologue thereof, when another component of the product of the invention (i.e. the ATR or separate effector protein) comprises a DNMT3A, DNMT3B or DNMT1 domain or homologue thereof.

The methods and uses of the present invention, for example methods of gene therapy or silencing a target gene, may also include a step of inactivating an endogenous gene that may counteract the activity of the ATRs or separate effector proteins of the invention. For example, the DNMT3B gene may be inactivated. The inactivation of this method step may, for example, be transient or permanent. The inactivation may, for example, be accomplished by genetic deletion, for example by using CRISPR/Cas9-based approaches, or by post-transcriptional downregulation, for example by using sh/siRNAs, or by transcriptional down-regulation, for example by using an individual KRAB-based ATR targeted to the regulatory sequences of the gene of interest. Inactivating DNMT3B may be particularly preferred when three ATRs individually comprising KRAB, DNMT3A and DNMT3L domains are used.

Schematic detailing the experimental cell model.

An eGFP expression cassette (based on the hPGK promoter) followed by the TetO7 sequence is integrated within the first intron of the PPP1R12C gene (also known as the AAVS1 locus) of K562 cell line. Single cell derived clones containing homozygous insertion of the cassette are then transduced with a vector expressing ATRs (with candidate Repressive-Rep.-domains) and, after deposition of repressive epigenetic marks (red lollipops), the cells are treated or not with doxycycline. Maintenance of silencing or reactivation of eGFP expression is then evaluated by measuring eGFP expression.

FIGS. 2A-2F

Comparison of epigenetic silencing induced by tetR:K and tetR:D3A.

Figure 2A:
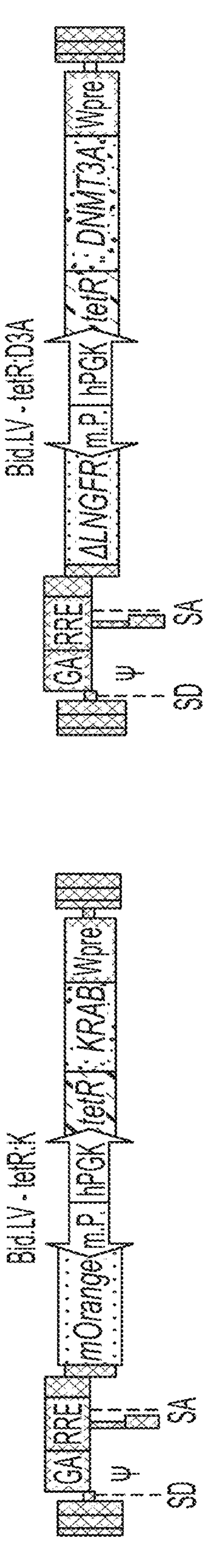
Figure 2B:
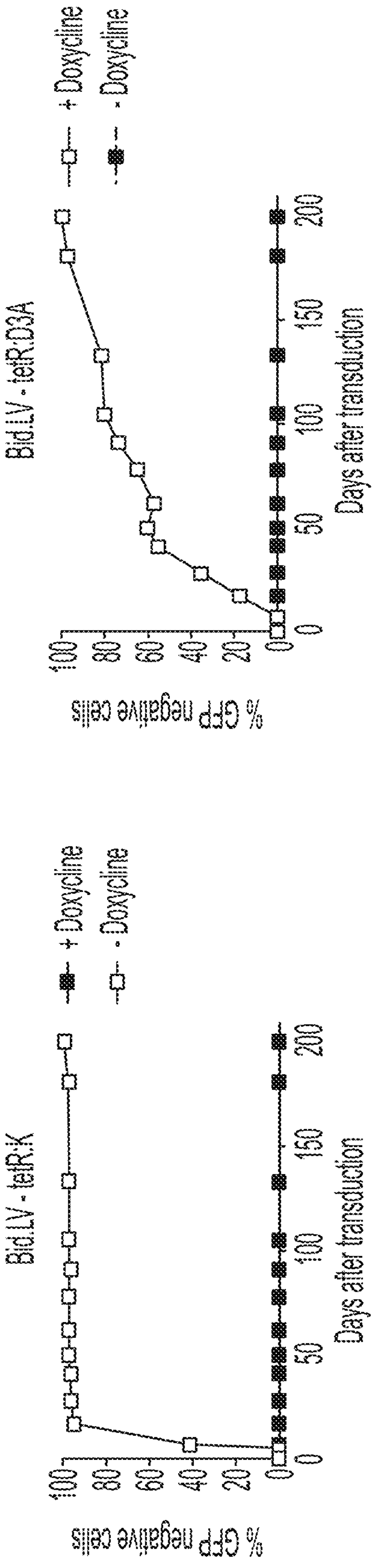
Figure 2C:
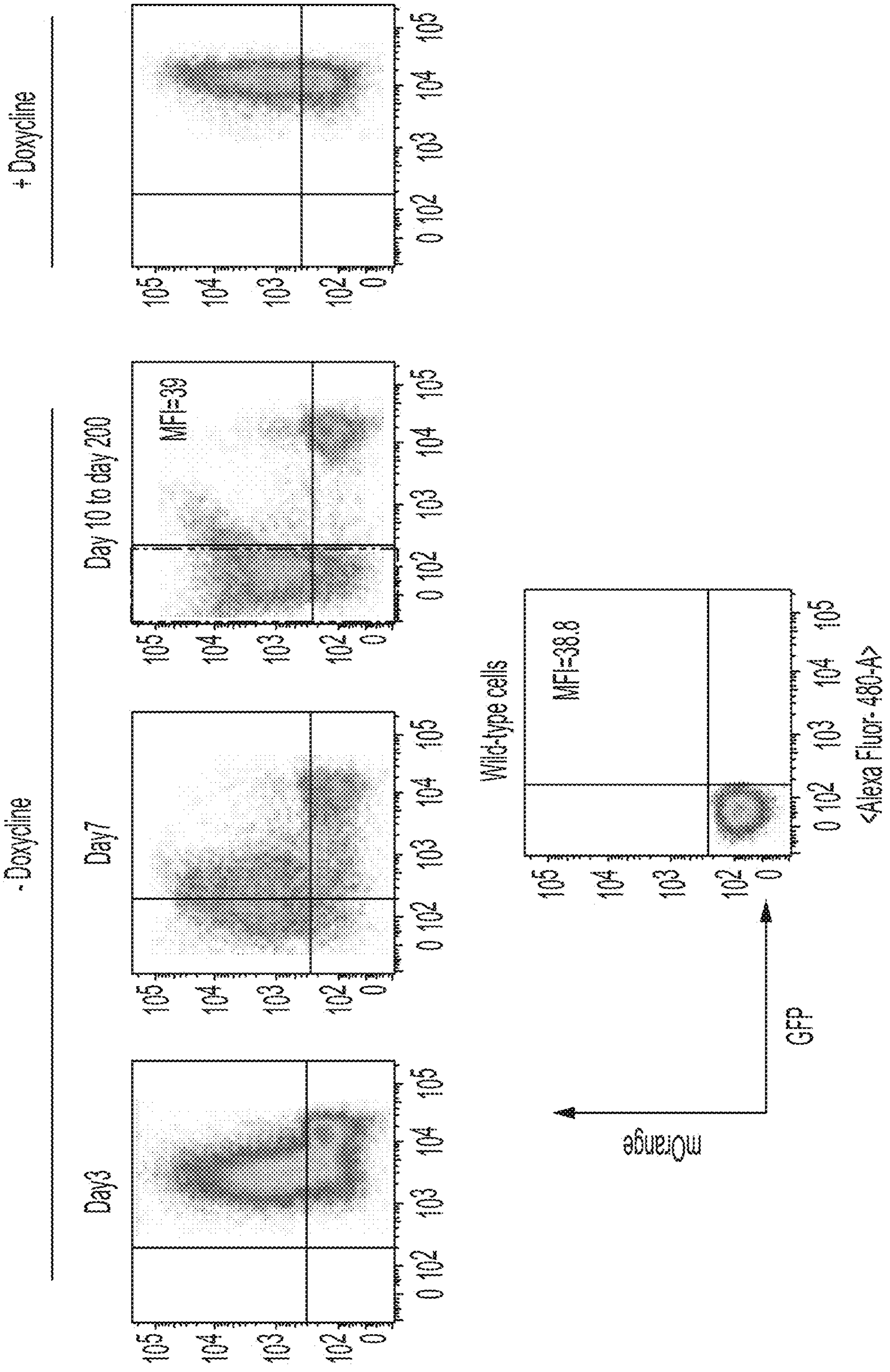
Figure 2D:
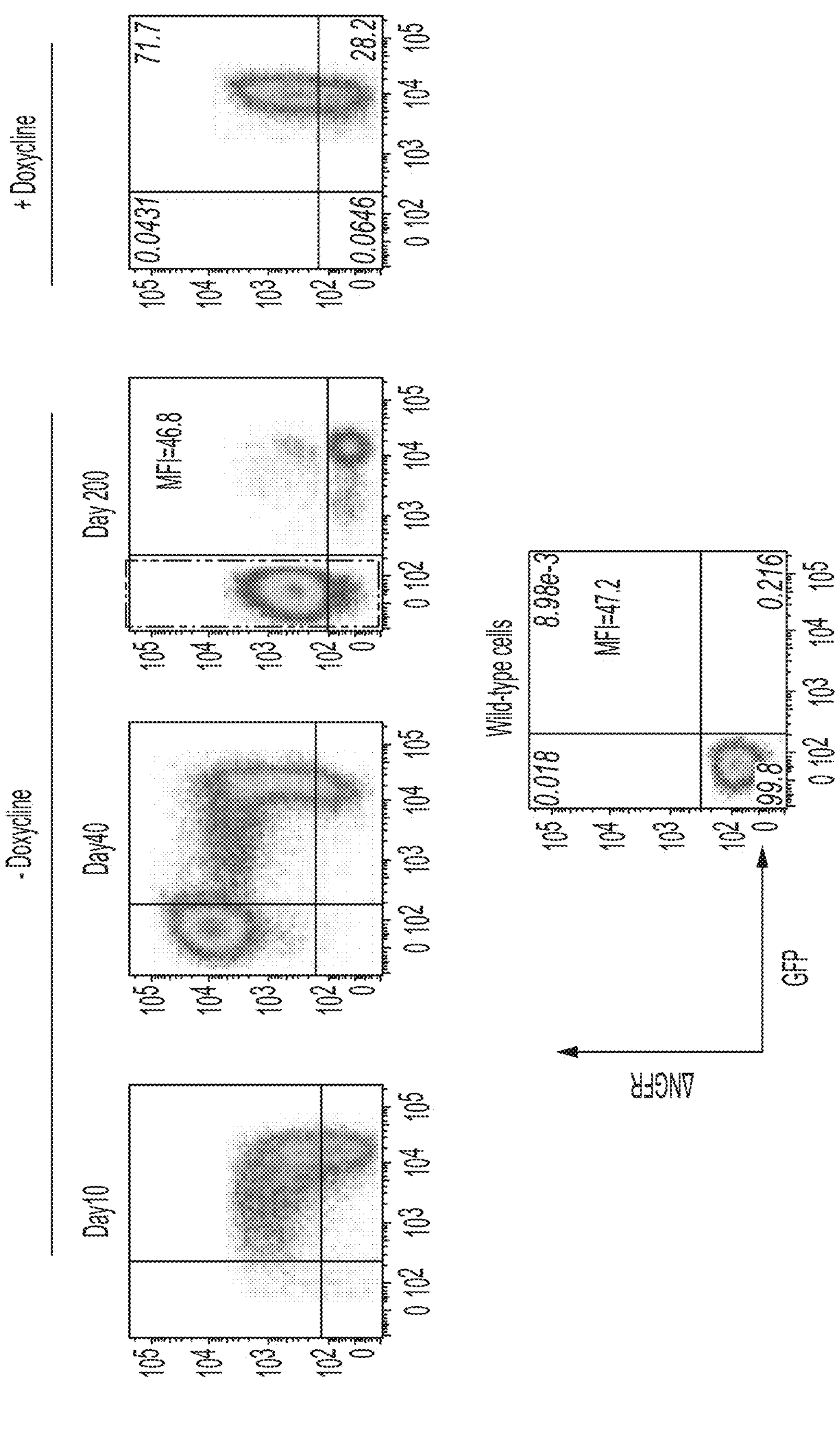
Figure 2E:
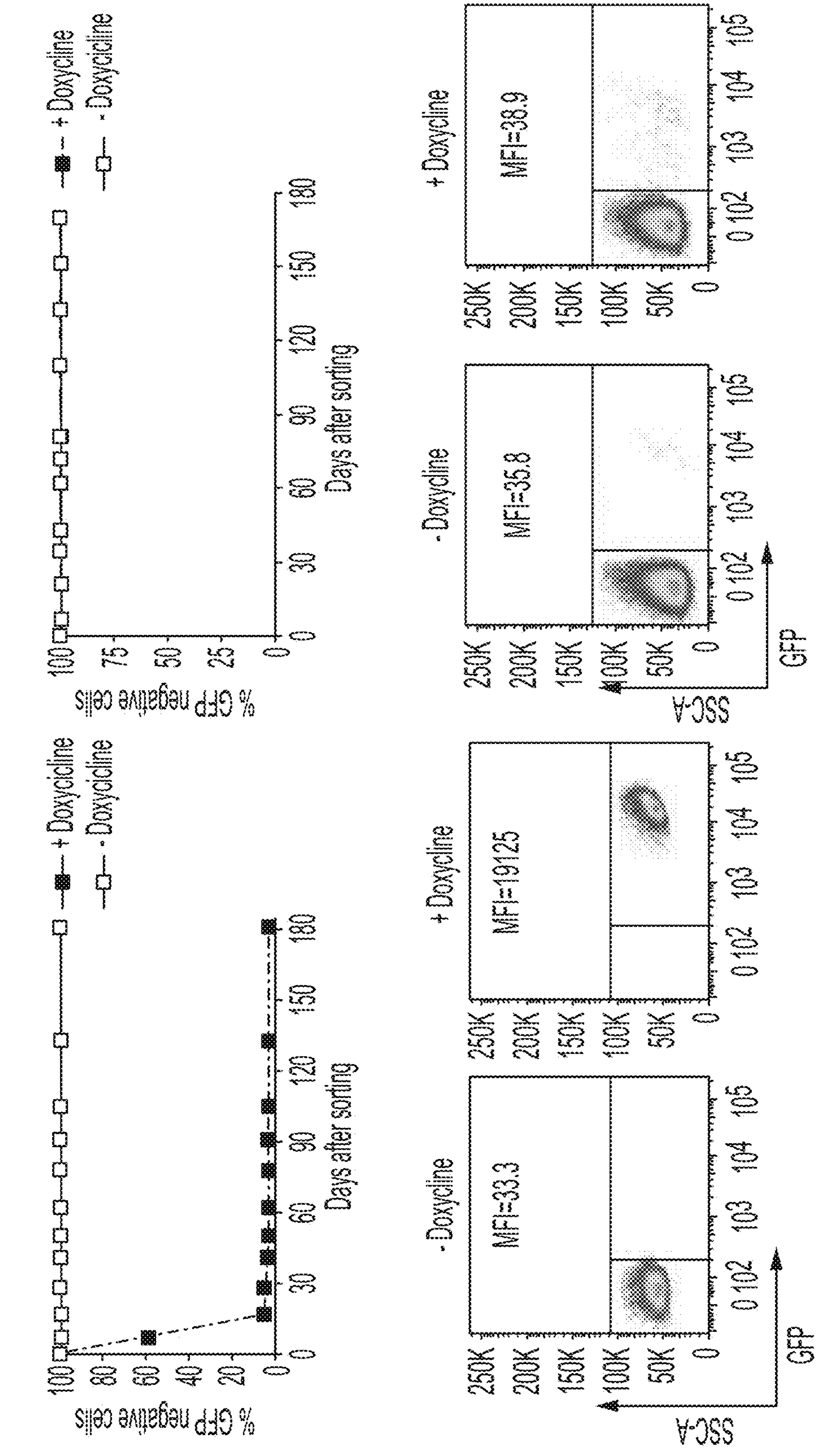
Figure 2F:
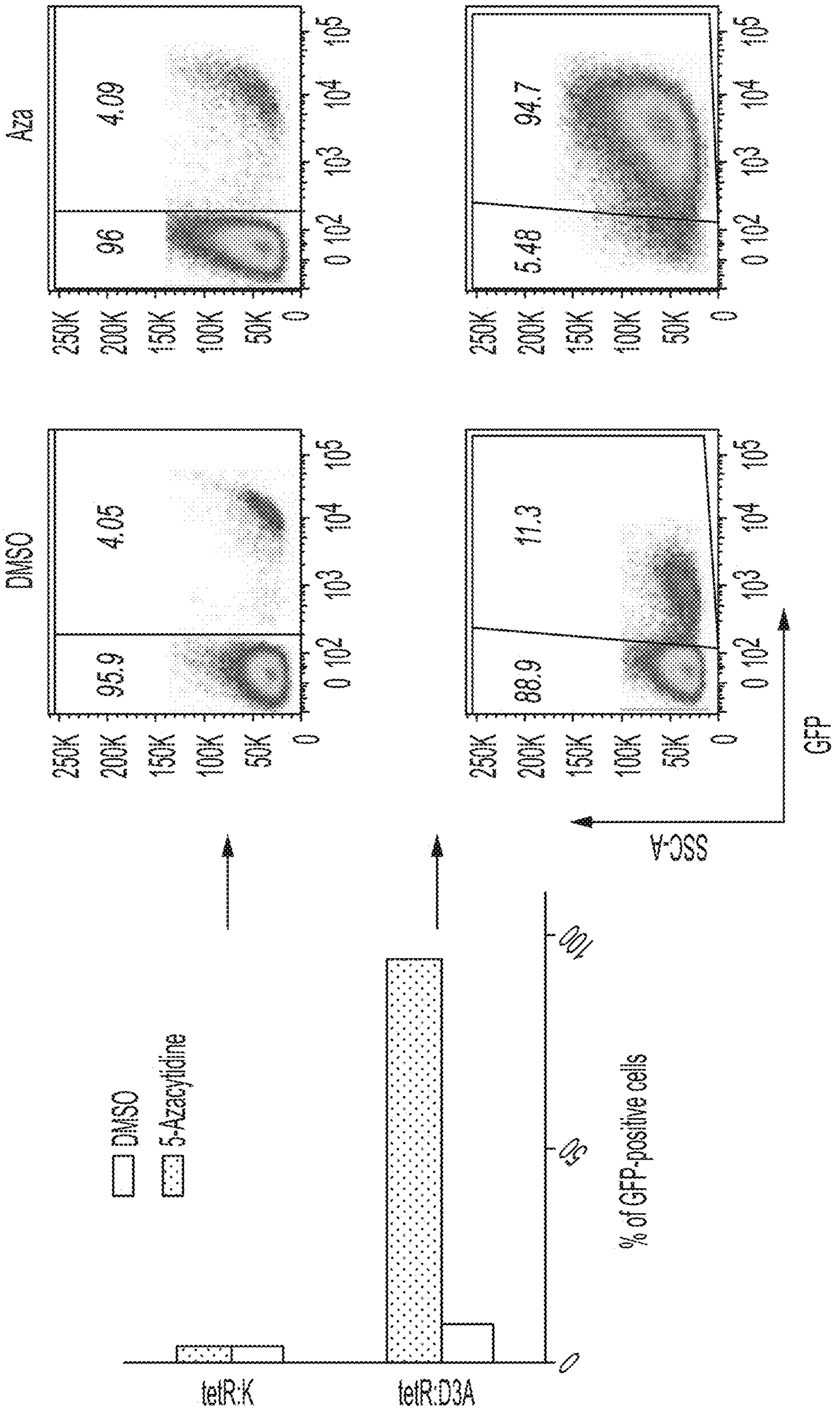

FIG. 2A. Schematics of the Bidirectional Lentiviral Vectors (Bid.LVs) expressing tetR:K and the marker gene mOrange (on the left) or tetR:DNMT3A and the marker gene ΔLNGFR (on the right). FIG. 2B. TetO7.eGFP reporter clones were transduced with the Bid.LV-tetR:K or with the Bid.LV-tetR:D3A in presence or in absence of doxycycline (right and left graphs, respectively), and analysed by flow cytometry over time to measure the percentage of eGFP-negative cells. FIGS. 2C-2D. Representative dot plot analysis at the indicated time-points of TetO7.eGFP reporter cell line transduced with Bid.LV-tetR:K or Bid.LV-tetR:D3A in presence or absence of doxycycline. The Mean Fluorescence Intensity (MFI) of eGFP silenced cells is compared to the MFI of untreated, wild-type cells. FIG. 2E. Silenced cells from the minus doxycycline conditions in (B) were sorted to purity and kept in culture with or without doxycycline to assess of eGFP reactivation. Representative dot plots of the cells in presence or absence of the drug are shown at the bottom. FIG. 2F. The silenced sorted cells from the conditions in (B) were treated for 7 days with AZA (1 μM) or vehicle (DMSO) and analysed for expression of eGFP (histogram on the left). Representative dot plots of vehicle and AZA treated cells are shown.

FIGS. 3A-3B

TetR:D3A-induced transcriptional repression is confined to the target locus.

Figure 3:
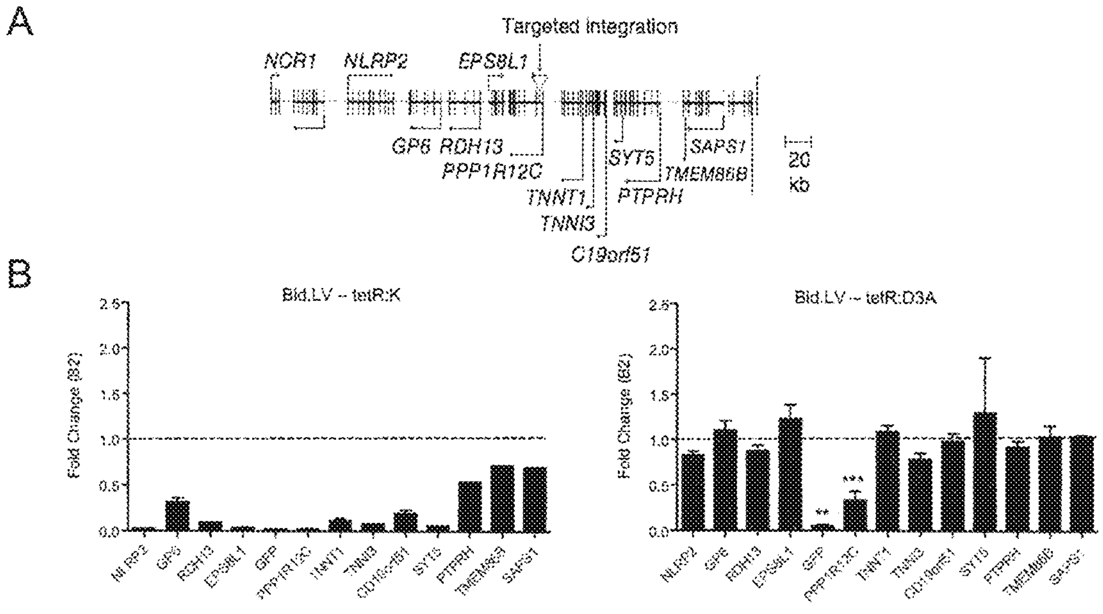

FIG. 3A. Schematic of the AAVS1 locus. The genes surrounding the reporter cassette are indicated. FIG. 3B. Histograms showing the fold changes in the expression levels of the indicated genes between eGFP-negative cells silenced with either the Bid.LV-tetR:K or the Bid.LV-tetR:D3A, and untreated cells. The relative expression level of each gene was normalised to the expression of B2M, and represented as fold change relative to the untreated cells (calibrator) (n=3).

FIGS. 4A-4E

Synergistic activity of tetR:K and tetR:D3A upon their transient co-delivery.

Figure 4A:
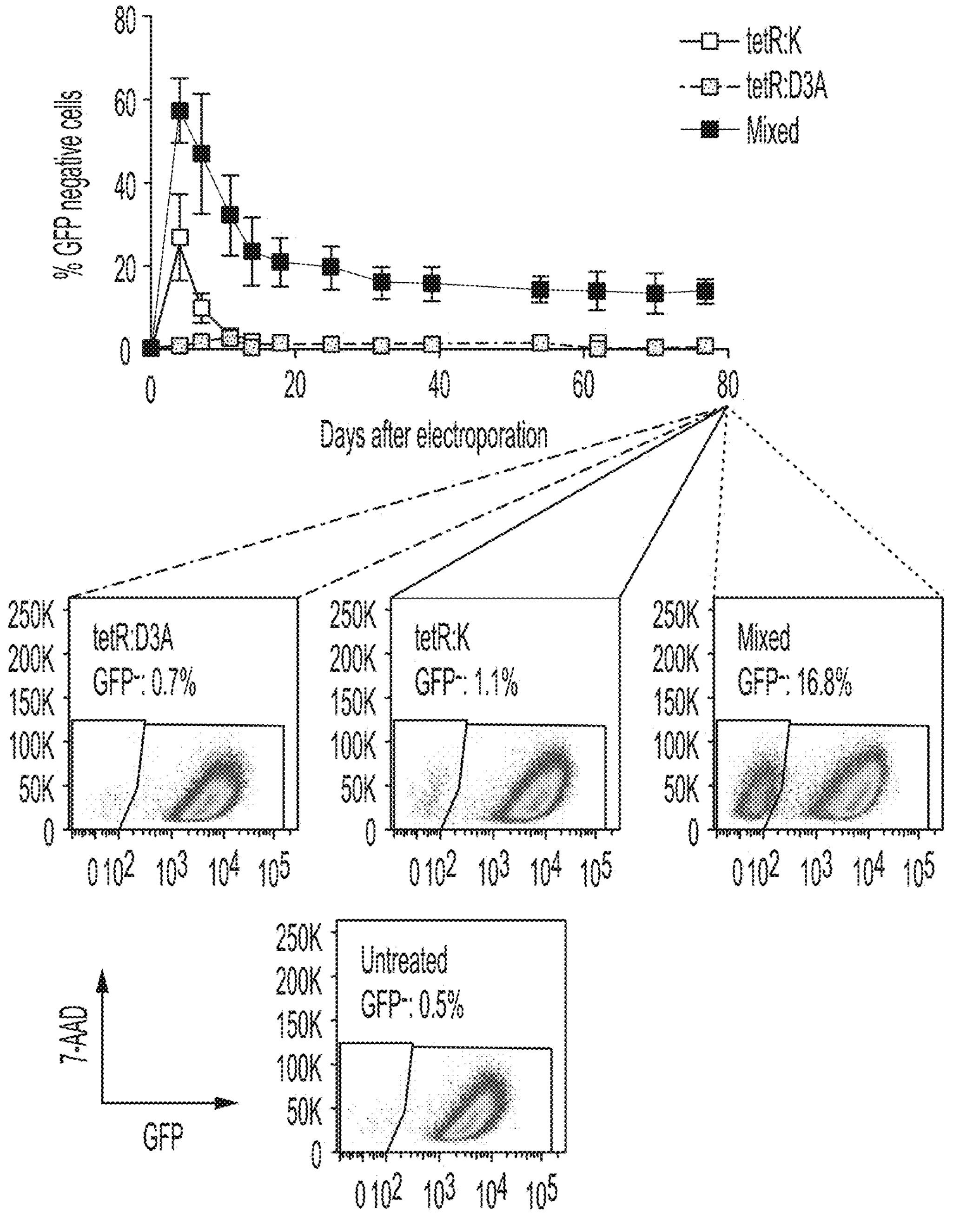
Figure 4B:
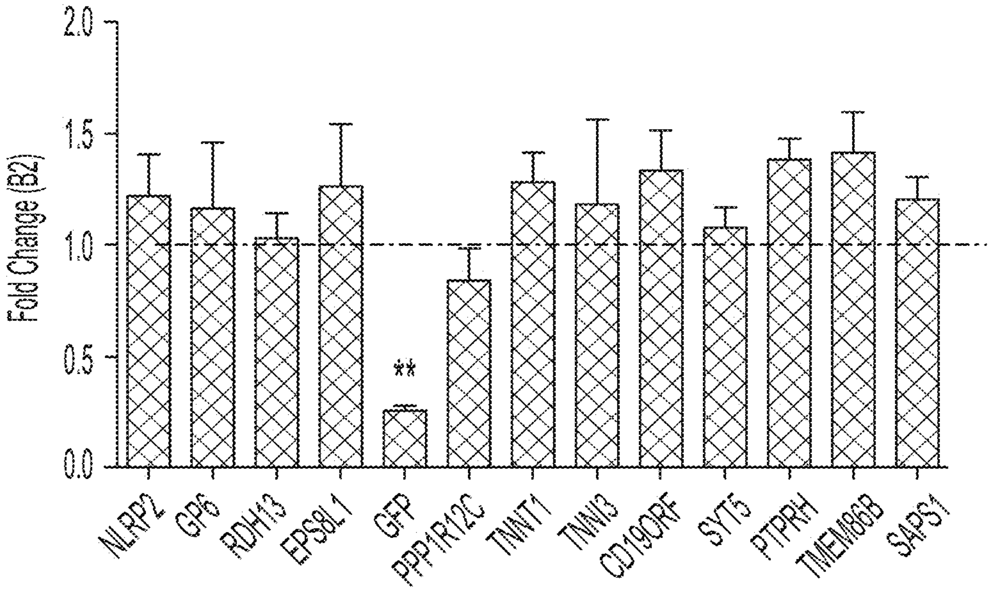
Figure 4C:
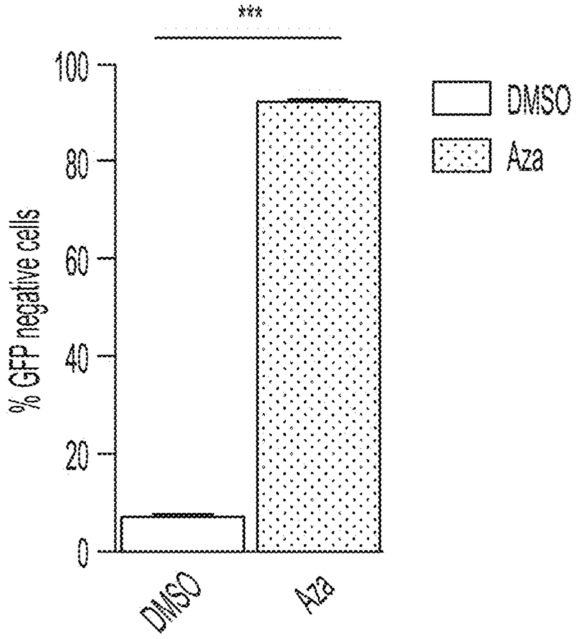
Figure 4D:
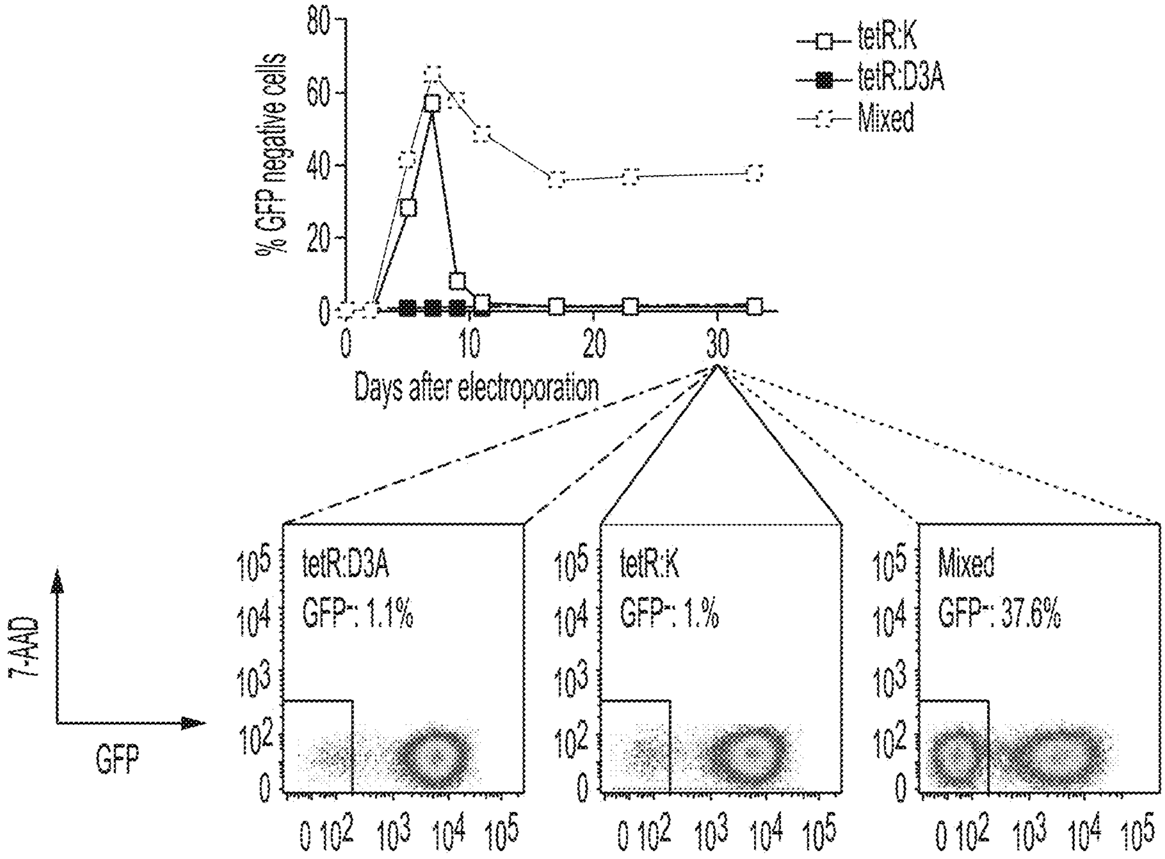
Figure 4E:
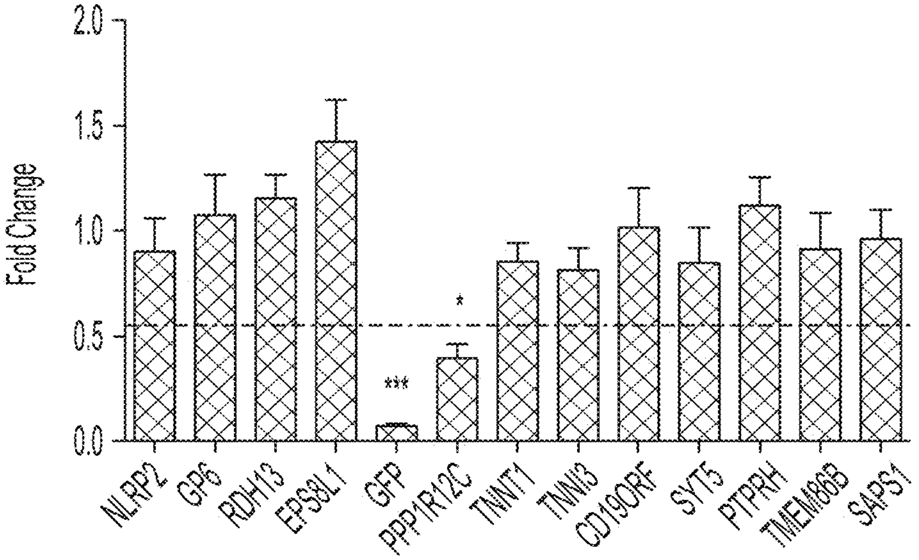

FIG. 4A. The TetO7.eGFP reporter cell line was transiently transfected with plasmids encoding for tetR:K and tetD3A, either alone or in combination. The cells were analysed by flow cytometry over time and efficiency of silencing was measured as percentage of eGFP negative cells after transfection. Representative dot plot for each transfection condition are shown at the bottom of the histogram (n=3). FIG. 4B. Histogram showing the fold changes in the expression levels of the indicated genes between sorted eGFP-silenced cells from the mixed conditions shown in (A) and untreated cells. The relative expression level of each gene was normalised to B2M, and represented as fold change relative to the untreated cells (calibrator) (n=3). FIG. 4C. The eGFP-negative cells from the mixed-treated condition in (A) were sorted and then treated with AZA or DMSO (histogram showing the percentage of eGFP positive cells after 7 day from the indicated treatments; n=3). FIG. 4D. Similar experiment as in (A) but performed with in vitro transcribed mRNA encoding for tetR:K and tetD3A, delivered either alone or in combination. FIG. 4E. Histogram showing the fold changes in expression levels of the indicated genes between sorted eGFP-silenced cells from the mixed conditions shown in (D) and untreated cells (n=3).

FIGS. 5A-5D

Gene silencing with the tetR:K and tetR:D3A combination is locus and cell-type independent.

Figure 5:
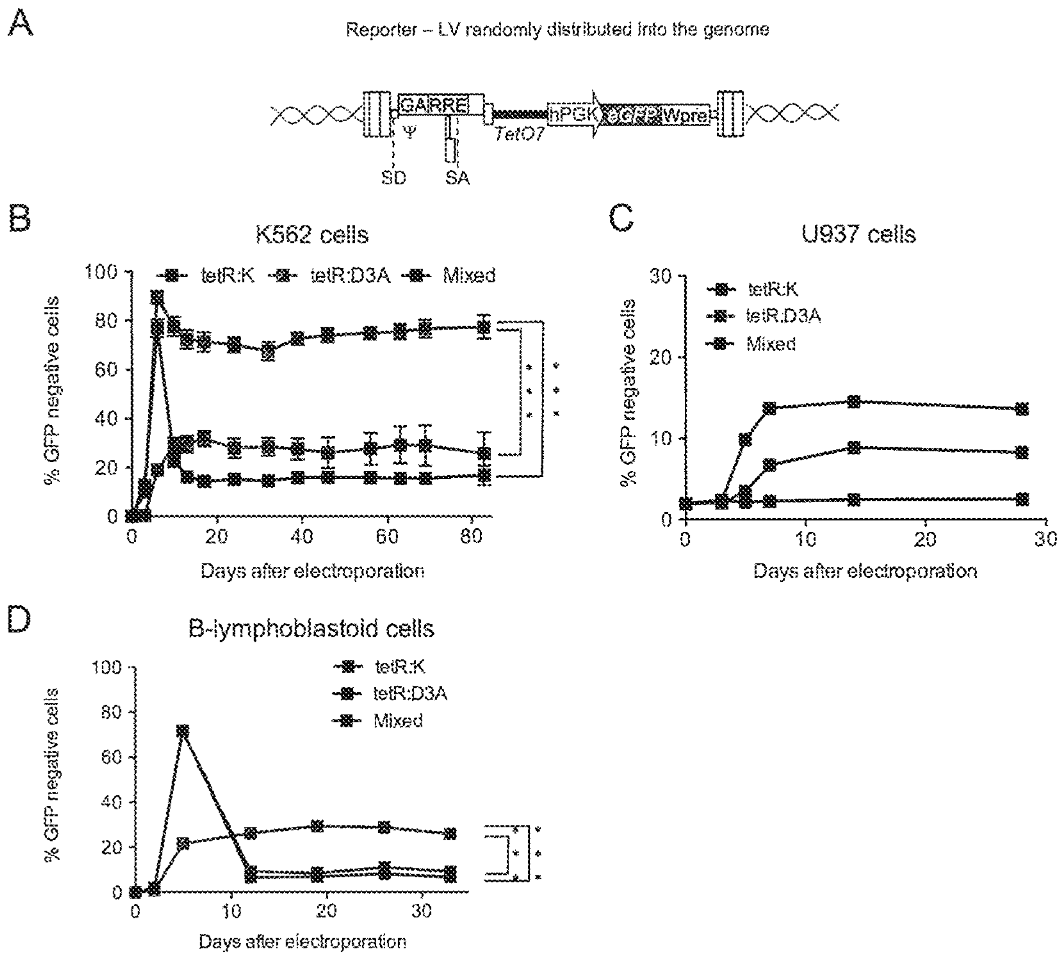

FIG. 5A. Schematic of the TetO7 reporter LV used in the study. TetO7 sequence was cloned upstream the hPGK promoter driving the expression of the eGFP reporter transgene. B. Graph showing the kinetics of eGFP silencing (% of eGFP-negative cells by flow cytometry) in the K562 LV/TETO7 reporter cell line transfected with in vitro transcribed mRNA encoding for tetR:K and tetR:D3A, delivered either alone or in combination (n=3; data are represented as mean±S.E.M.). FIGS. 5C-5D. Graphs showing the kinetics of eGFP silencing (% of eGFP-negative cells by flow cytometry) in the U937LV/TETO7 cell line (C) or in the B-lymphoblastoid LV/TETO7 reporter cell line (D). Cells were transfected as indicated in (B) (n=1 for U937 and n=3 for B-lymphoblastoid cells).

FIGS. 6A-6C

Screening of additional epigenetic effector domains for ATRs.

Figure 6:
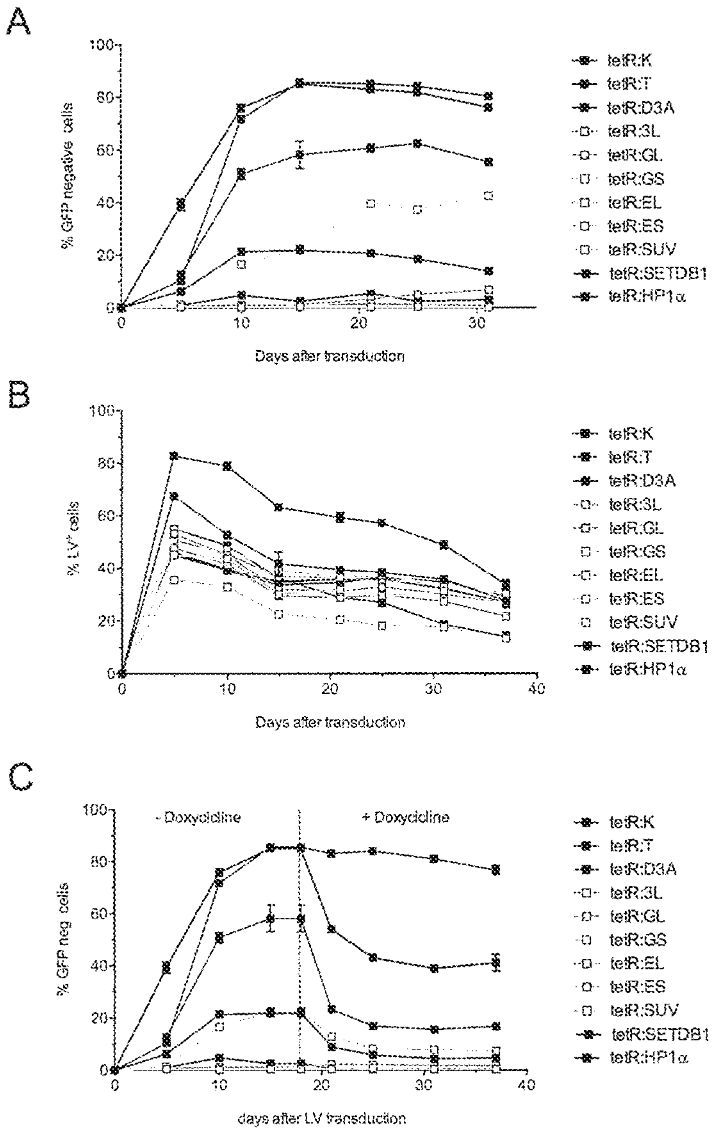

FIG. 6A. Graph showing the kinetics of eGFP silencing (% of eGFP-negative cells by flow cytometry) in the K562 LV/TETO7 reporter cell line upon transduction with lentiviral vectors expressing the indicated tetR-based ATRs (n=3). FIG. 6B. Graph showing the percentage of cells positive for the indicated LVs over time in culture (n=3). FIG. 6C. Graph showing the kinetics of eGFP silencing (% of eGFP-negative cells by flow cytometry) in the K562 LV/TETO7 reporter cell line transduced with lentiviral vectors stably expressing the indicated tetR-based ATRs, before and after doxycycline administration (n=3).

FIGS. 7A-7H

Screening of additional combinations of artificial transcription repressors (ATRs) in different mammalian cells.

FIGS. 7A-7D. Graphs showing the kinetics of eGFP silencing (% of eGFP-negative cells by flow cytometry) in the K562 LV/TETO7 reporter cell line upon electroporation with individual plasmids encoding for the indicated tetR-based ATRs (FIG. 7A; n=3; data are represented as mean±S.E.M.), or upon electroporation with the plasmid encoding for tetR:D3A plus the plasmid encoding for one of the other tetR-based ATRs (FIG. 7B; n=3; data are represented as mean±S.E.M.), or upon electroporation with the plasmid encoding for tetR:K plus the plasmid encoding for one of the other tetR-based ATRs (FIG. 7C; n=3; data are represented as mean±S.E.M.), or upon electroporation with the plasmids encoding for tetR:D3A+tetR:K in conjunction with the plasmid encoding for one of the other tetR-based ATRs (FIG. 7D; n=3; data are represented as mean±S.E.M.). FIG. 7E. Histogram showing the efficacy of eGFP silencing 21 days post electroporation of the K562 LV/TETO7 reporter cell line with plasmids encoding for the indicated tetR-based ATRs (later time-points of A-D; n=3; data are represented as mean±S.E.M.). FIG. 7F. Histogram showing the efficiency eGFP silencing 30 days post electroporation of the K562 LV/TETO7 reporter cell line with plasmids encoding for the indicated tetR-based ATRs, including that based on SETDB1 (n=3; data are represented as mean±S.E.M.). FIG. 7G. Graph showing the kinetics of eGFP silencing of the B-lymphoblastoid LV/TETO7 reporter cell line electroporated with mRNA encoding for the indicated tetR-based ATRs (n=3; data are represented as mean±S.E.M.). FIG. 7H. Graph showing the kinetics of eGFP silencing of the murine NIH/3T3 LV/TETO7 reporter cell line electroporated with mRNA encoding for the indicated tetR-based ATRs (n=2; data are represented as mean±range).

FIGS. 8A-8C

Gene silencing by transient co-delivery of artificial transcription repressors (ATRs) comprising custom-made DNA-binding domains (head-to-tail orientation).

FIG. 8A. Schematic representation of the various Artificial Tale Binding Sites.(head-to-tail).hPGK.eGFP cassettes semi-randomly integrated in the genome of K562 cells via LV transduction, differing in spacer length between the two ATRs binding sites. Two different TALE domains have been separately fused to each epigenetic effector, thus leading to two alternative co-delivery strategies differing for the D3A-K relative order of binding on the target. FIG. 8B. Graphs showing the silencing efficiency (% of eGFP-negative cells at 34 days post-electroporation) with respect to the spacer length, in the K→D3A (Left) and D3A4→K (Right) relative ATRs order of binding on the target. FIG. 8C. Graphs showing the kinetics of eGFP silencing in the cell line with the 25 bp spacer (the best-performing spacer tested in the experiments shown in B) in the K→4D3A (Left) and D3A→K (Right) relative ATRs order of binding on the target (n=3; data are represented as mean±S.E.M.).

FIGS. 9A-9C

Gene silencing by transient co-delivery of artificial transcription repressors (ATRs) comprising custom-made DNA-binding domains (head-to-head orientation).

FIG. 9A. Schematic representation of the various Artificial Tale Binding Sites.(head-to-head).hPGK.eGFP cassettes semi-randomly integrated in the genome via LV transduction, differing in the spacer length between the two ATRs binding sites. Two different TALE domains have been separately fused to each epigenetic effector, thus leading to two alternative co-delivery strategies differing for the D3A-K relative order of binding on the target. FIG. 9B. Graphs showing silencing efficiency (i.e. % of eGFP-negative cells at 34 days post-electroporation) with respect to the spacer length, in the D3A4K (Left) and K4D3A (Right) relative ATRs order of binding on the target. FIG. 9C. Graphs showing the kinetics of eGFP silencing in the cell line with the 15 bp spacer (the best-performing spacer tested in the experiments shown in B) in the D3A4K (Left) and K4D3A (Right) relative ATRs order of binding on the target (n=3; data are represented as mean±S.E.M.).

FIGS. 10A-10B

Gene silencing with artificial transcription repressors (ATRs) comprising more than one effector domain.

Figure 10:
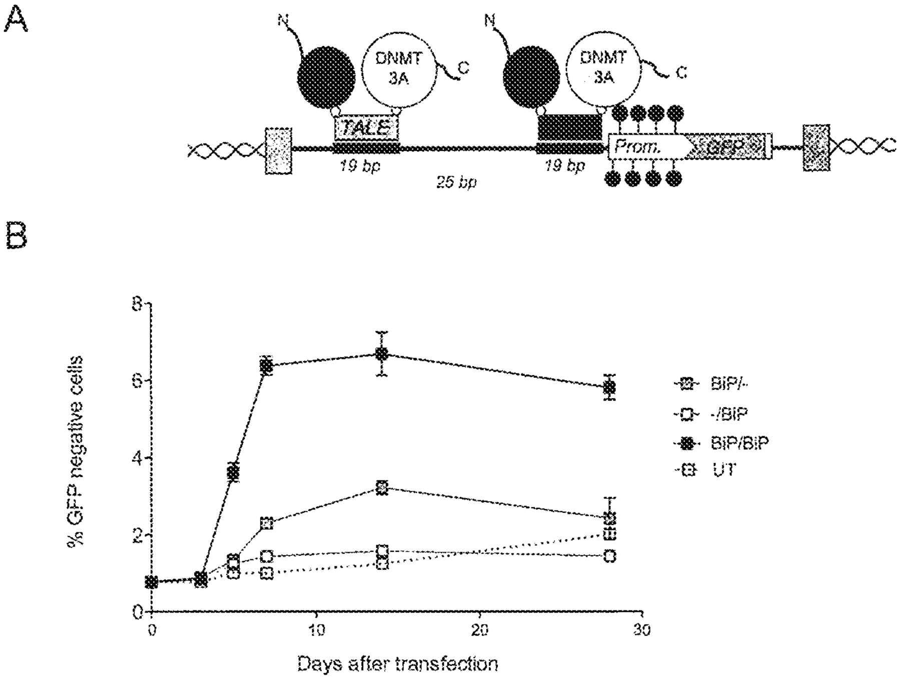

FIG. 10A. Schematic representation of the Artificial Tale Binding Sites (head-to-head).hPGK.eGFP cassette semi-randomly integrated in the genome of K562 cells via LV transduction bound by chimeric K:tetR:D3A ATR (Bi-Partite; BiP), where KRAB and DNMT3A domains were fused to the N- and C-terminus (respectively) of the same DNA binding domain. FIG. 10B. Graphs showing the kinetics of eGFP silencing in the cell line with the 25 bp spacer (the same line used in of FIG. 8B), transfected with plasmids encoding for the Bi-Partite (BiP) fusion protein, when transfected alone or in combination (n=3; data are represented as mean±S.E.M.).

FIGS. 11A-11C

Permanent epigenetic silencing in human haematopoietic stem and progenitor cells (HSPCs) by using different combinations of artificial transcription repressors (ATRs).

Figure 11:
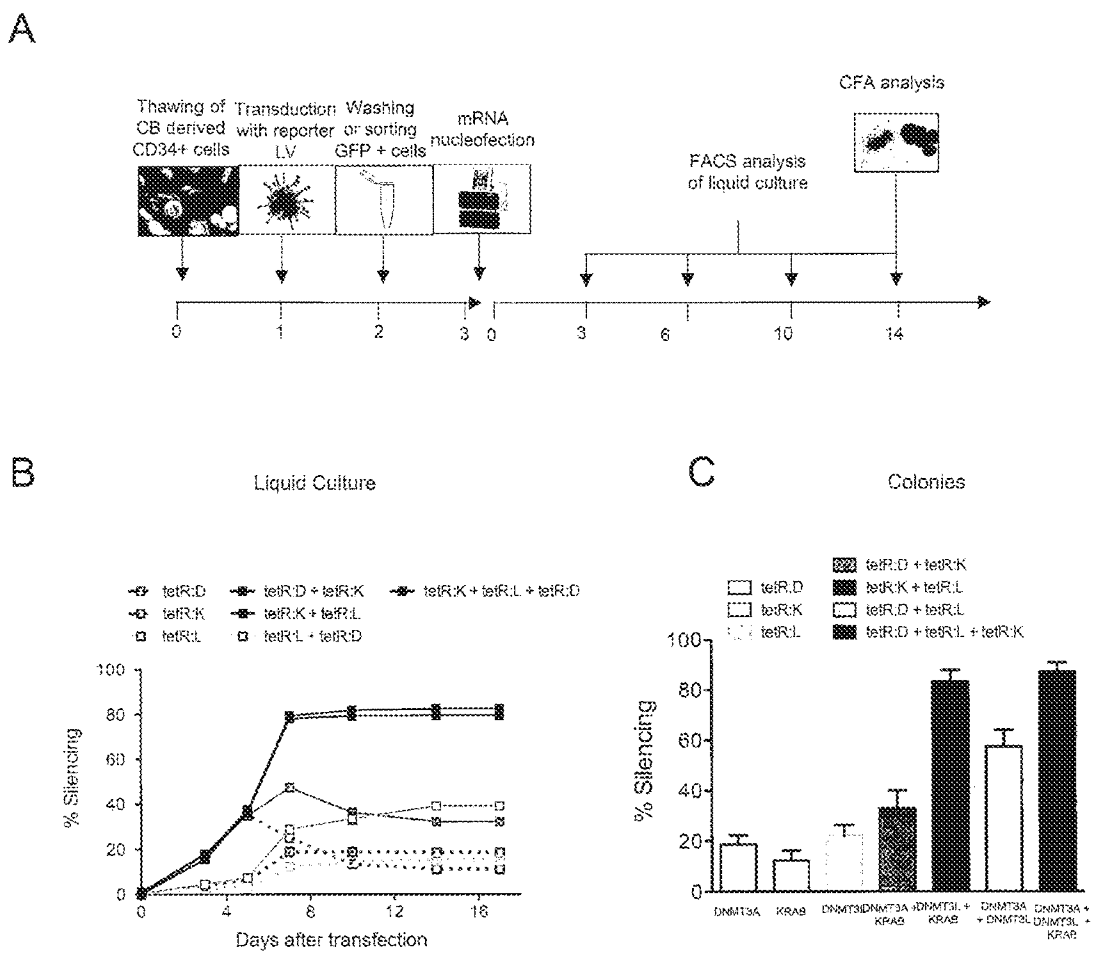

FIG. 11A. Schematic time-line of the protocol used to assess efficiency of silencing in HSPCs. Briefly, on day 0, the human CD34+ cells were thawed in stimulating media with early acting cytokines and transduced at day 1 with the TetO7 reporter LV (schematic of the vector in FIG. 5A). Cells were then washed and electroporated with in vitro transcribed mRNA on day 3 from thawing. The day after, 800 cells were plated for CFC-U assays, while the remaining cells were grown in liquid culture and analysed by flow cytometry at the indicated time points. CFC-U analysis was performed 14 days after thawing. FIG. 11B. Graph showing the kinetic of silencing of eGFP in liquid cultured human $CD34^+$ transfected with in vitro transcribed mRNA encoding for the indicated ATRs, delivered either alone, or in double, or triple combinations (data were normalised to the un-electroporated but LV-transduced control; n=3; data are represented as mean±S.E.M.). FIG. 11C. Histogram showing the percentage of eGFP-silencing in erythroid and myeloid colonies derived from the human CD34+ transfected with in vitro transcribed mRNAs as indicated in (B) (n=3; data are represented as mean±S.E.M.).

FIGS. 12A-12B

Permanent epigenetic silencing in human T lymphocytes by using different combinations of artificial transcription repressors (ATRs).

Figure 12:
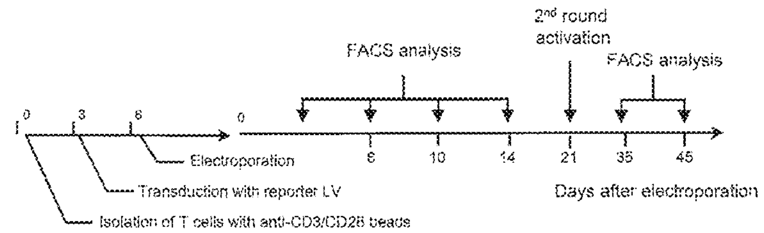
Figure 12:
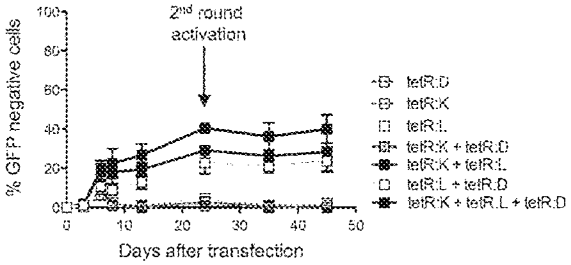

FIG. 12A. Schematic time-line of the protocol used in this study to assess efficiency of silencing in human primary T cells. Briefly, on day 0, T-cells were isolated with anti-CD3/CD28 coated beads and left in culture 3 days before transduction with the reporter TetO.LV. On day 6, the cells were transfected with in vitro transcribed mRNA encoding for the indicated ATRs, and expression of eGFP was measured by flow cytometry at the indicated time points. At 3 weeks post-transfection, cells were re-stimulated and stability of eGFP silencing was measured by flow cytometry. FIG. 12B. Graph showing the kinetic of eGFP-silencing in human primary T cells transfected with in vitro transcribed mRNA encoding for the indicated ATRs, which were delivered either alone, or in double, or triple combinations normalised over untreated cells (data were normalised to the un-electroporated but LV-transduced control; n=2; data are represented as mean±range).

FIGS. 13A-13H

Permanent epigenetic silencing of the human β2-microglobulin (B2M) gene using artificial transcription repressor (ATR) combinations.

Figure 13A:
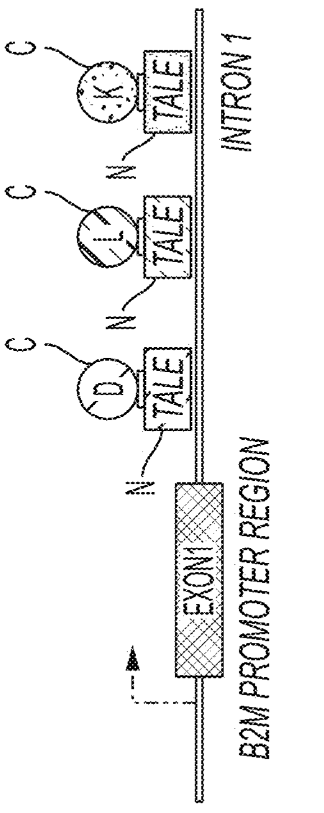
Figure 13B:
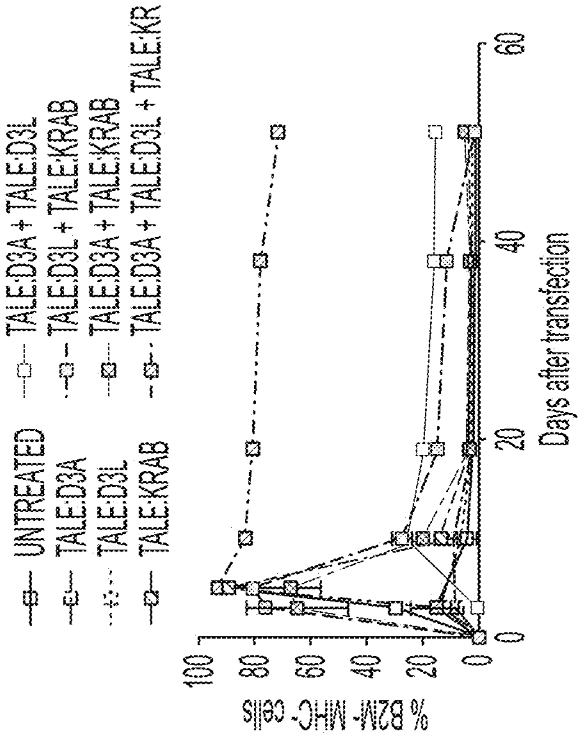
Figure 13C:
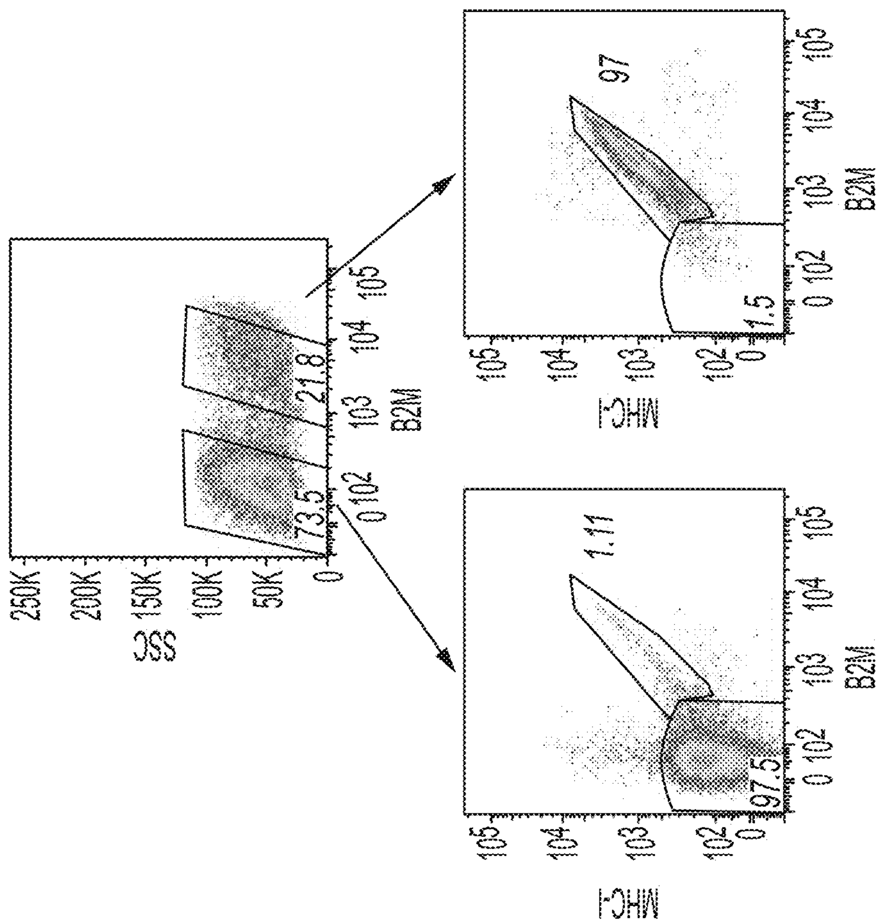
Figure 13D:
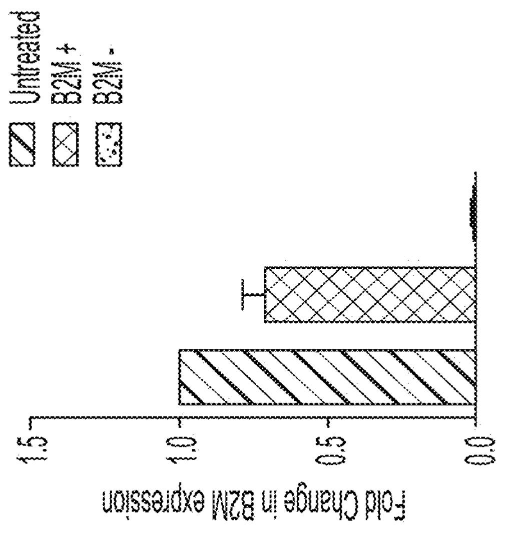
Figure 13E:
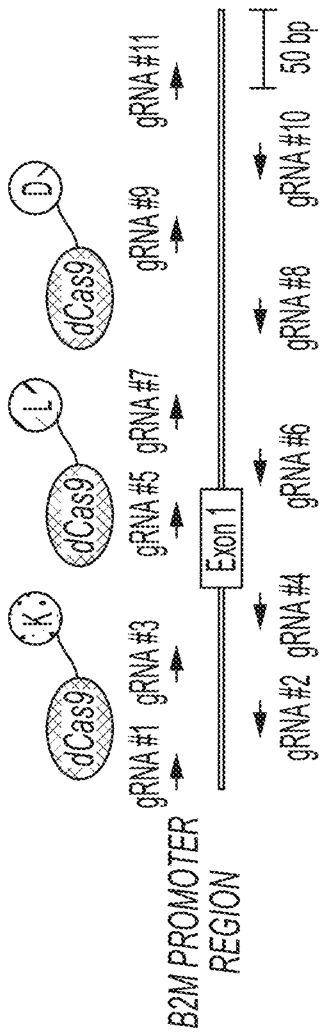
Figure 13F:
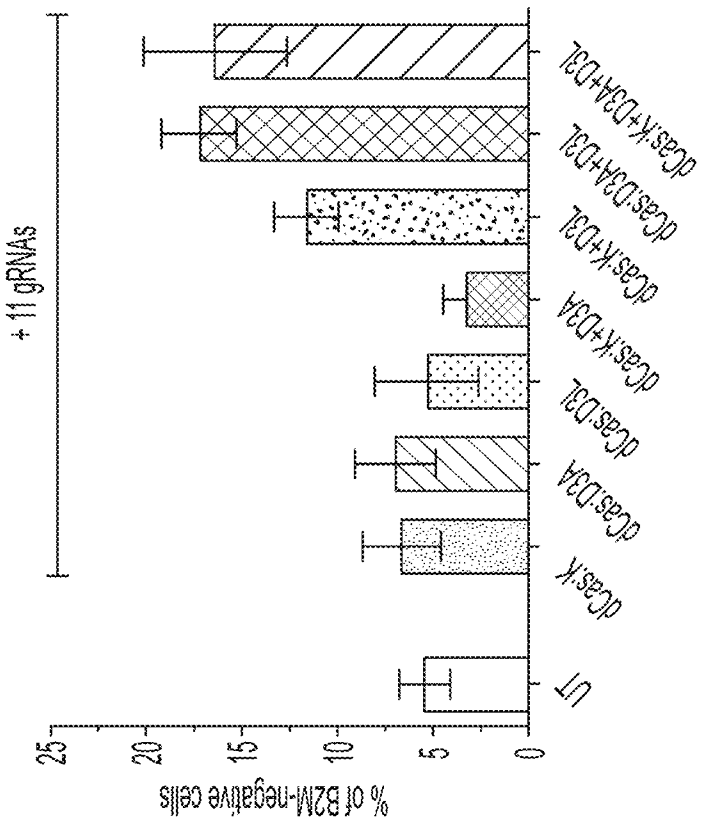
Figure 13G:
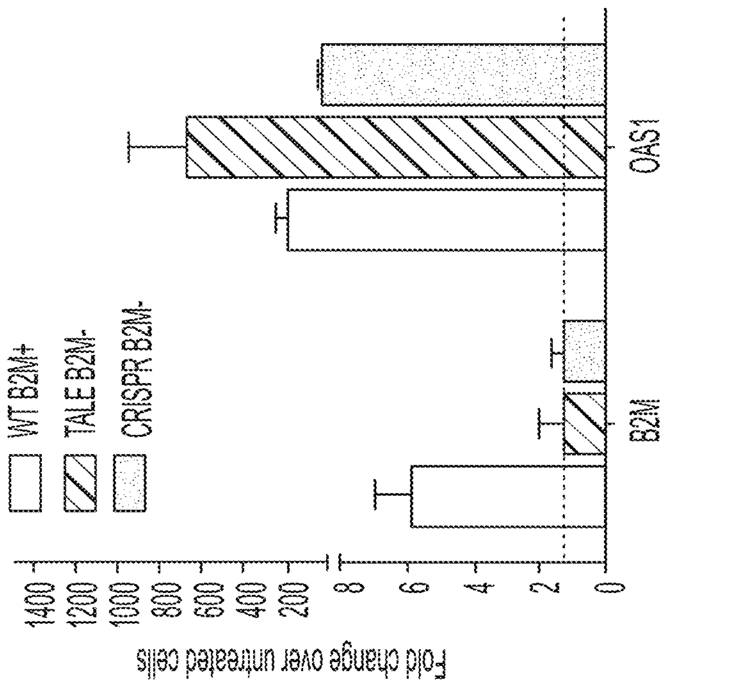
Figure 13H:
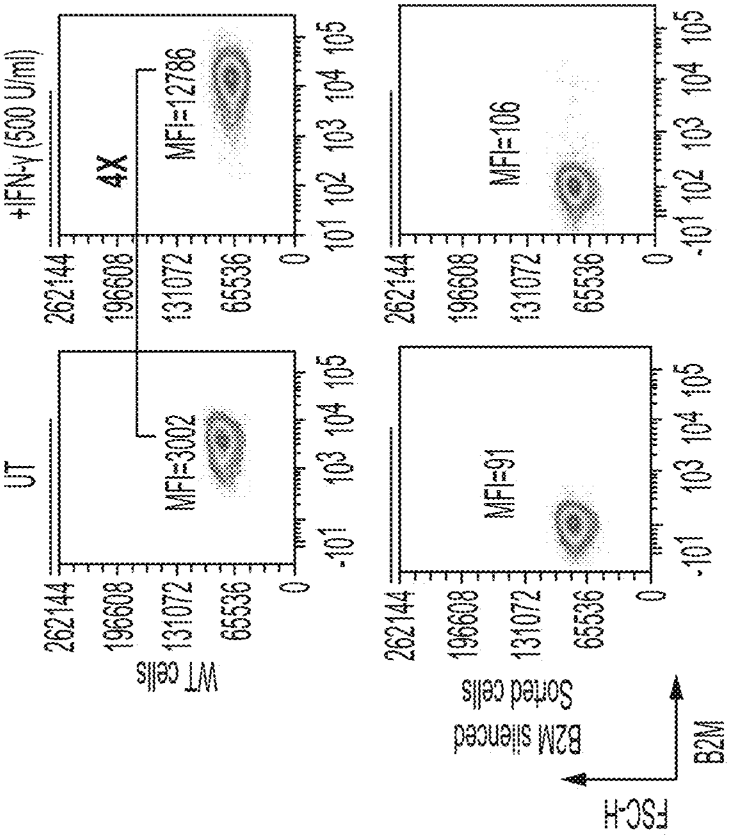

FIG. 13A. Schematic representation of the B2M locus indicating the binding sites of the TALE-based ATRs. FIG. 13B. Graph showing the kinetics of B2M silencing in HEK-293T cells electroporated with plasmids encoding for the indicated TALE-based ATRs, which were delivered either alone or in combination (n=3; data are represented as mean±S.E.M.). FIG. 13C. Representative flow cytometry dot plots of HEK-293T cells transfected with plasmids encoding for the triple TALE:ATR combination (plot on the top), and the cell sorting strategy used to enrich for the double negative (bottom plot on the left) and the double positive (bottom plot on the right) cells. FIG. 13D. Histogram showing the fold change in the expression levels of the B2M gene in the sorted cells from (C) and in untreated HEK293T cells (n=3; data are represented as mean±S.E.M.). FIG. 13E. Schematics of the dCas9-based ATRs and of the gRNAs selected to target the CpG island located in the B2M promoter region. FIG. 13F. Histogram showing the silencing efficiency at day 33 post-CRISPR/dCas9-based ATRs plasmid electroporation (n=3; data are represented as mean±S.E.M.). FIG. 13G. The B2M silenced cells from FIGS. 2C-2D (named TALE B2M− in this panel), the B2M-silenced cells sorted from the triple-CRISPR/dCas9 based ATR combination in FIG. 2F (named TALE B2M− in this panel), and wild-type HeK-293T cells (named WT B2M+ in this panel) were exposed or not to IFN-γ, and then analysed to measure the expression levels of B2M and OAS1. Histogram showing the fold change in the expression levels of the B2M and the OAS1 gene between IFN-γ and untreated cells. The expression of the Hypoxanthine Phosphoribosyltansferase 1 (HPRT1) gene was used as normaliser (n=3; data are represented as mean±S.E.M.). FIG. 13H. Representative flow cytometry dot plots of the indicated HEK-293T populations either untreated (plots on the left) or at 4 days post IFN-γ treatment (plots on the right). Numbers indicate the MFI B2M.

FIGS. 14A-14E

Silencing of β2-microglobulin (B2M) is associated with significant epigenetic editing of the gene.

Figures 14A, 14B:
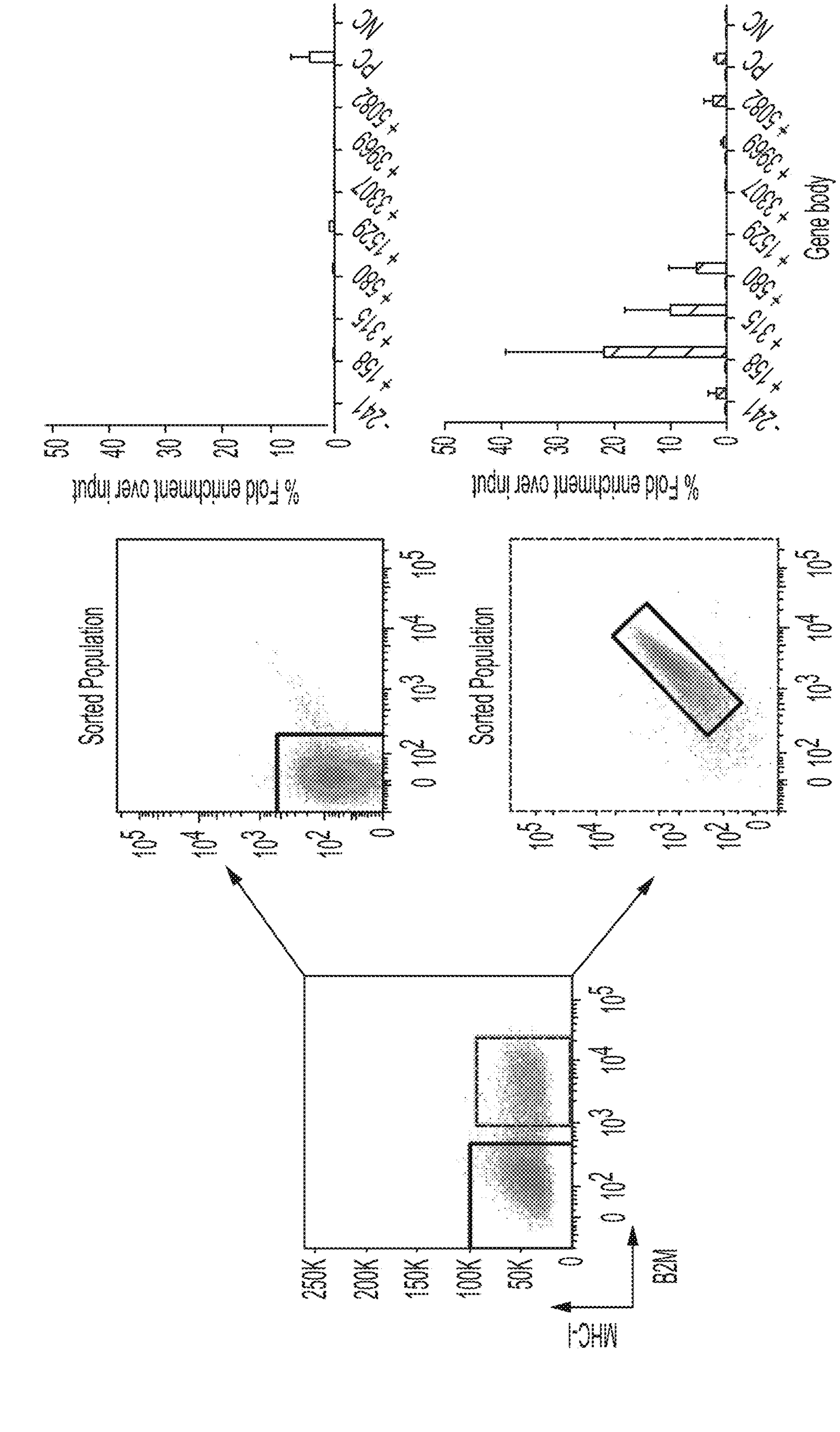
Figure 14D:
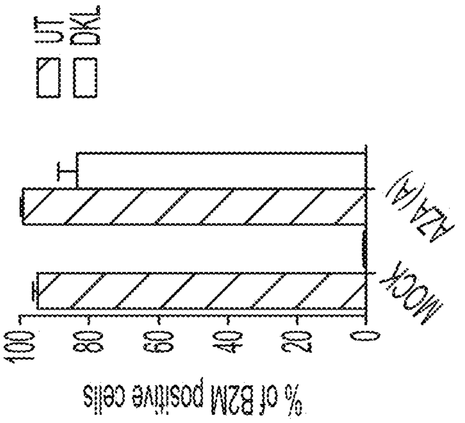
Figure 14C:
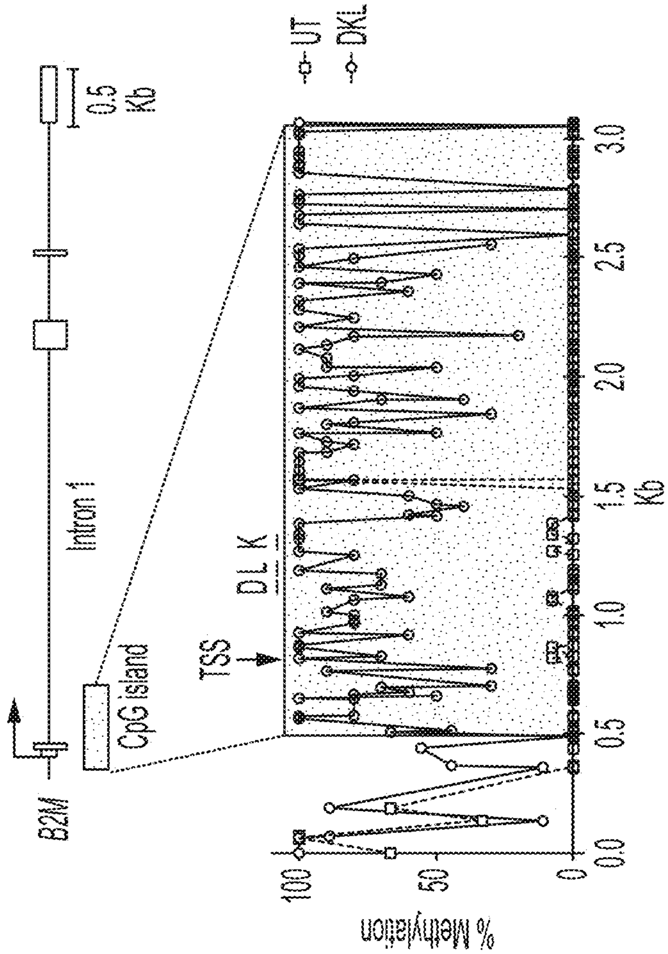
Figure 14E:
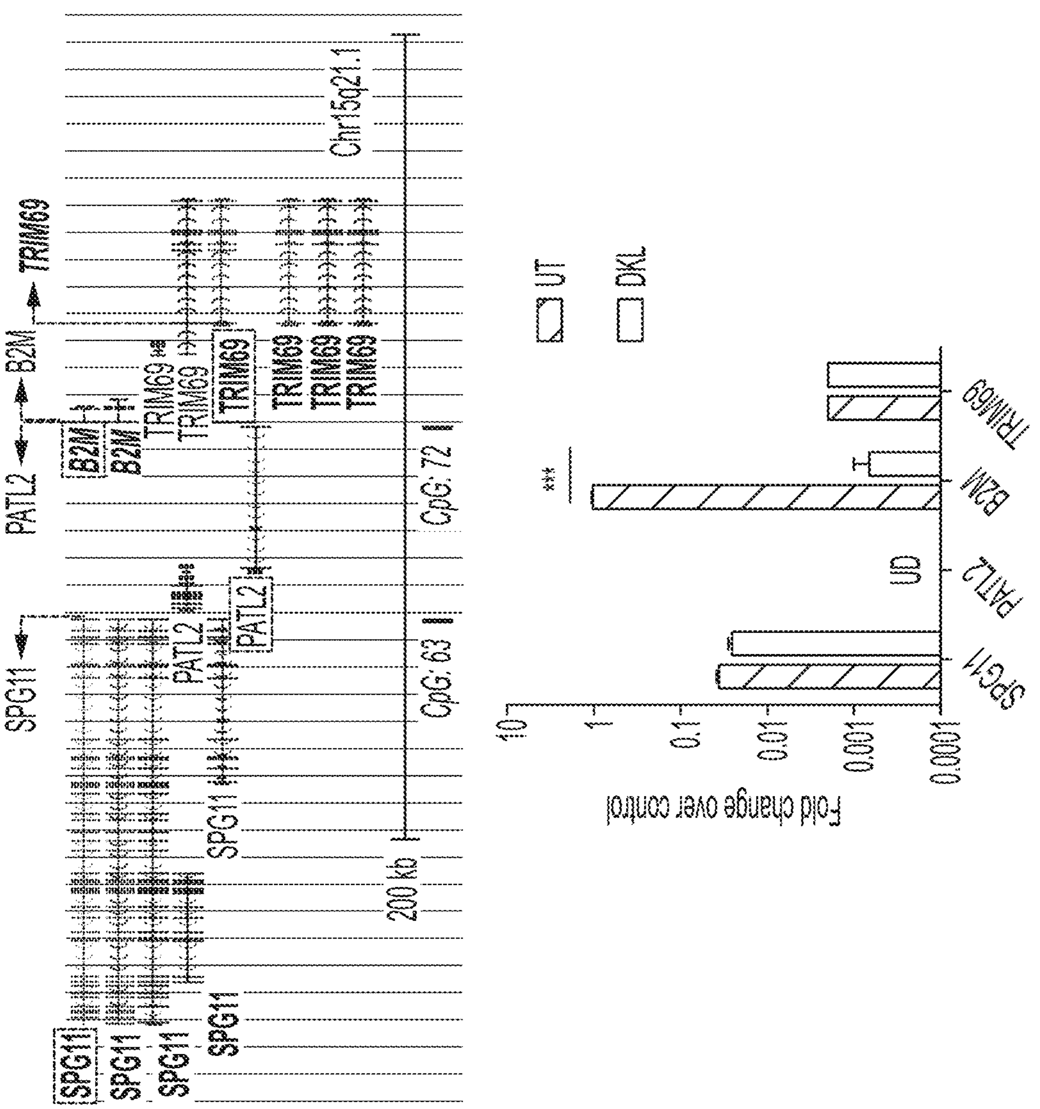

FIG. 14A. Representative flow cytometry dot plots of HEK-293T cells transfected with plasmids encoding for the triple TALE:ATR combination, and the cell sorting strategy used to enrich for the double positive and double negative cells. FIG. 14B. ChIP analysis performed on untreated (top histogram) and silenced cells from (A) (bottom histogram) for the presence of the RNA PolII. Histogram shows the fold enrichment in RNA PolII over the input in relation to the distance of the qPCRs assays from the Transcription Start Site (TSS; set at +1) of the gene (n=3; data are represented as mean±S.E.M.). The ubiquitously transcribed AAVS1 locus was used as Positive Control (PC) for RNA PolII enrichment, while the silent CCR5 gene as a Negative Control (NC). FIG. 14C. Bisulfite analysis of the B2M CpG island in untreated (UT) and silenced cells. The TSS of the gene and relative position of binding site of the three TALE:ATRs (D;L;K) are indicated. FIG. 14D. Histogram showing the percentage of B2M positive cells at day 7 upon AZA treatment (n=3; data are represented as mean±S.E.M.). FIG. 14E. Top: schematic representation of the B2M locus. The CpG islands within this locus are depicted. Bottom: histogram showing the fold change in gene expression levels of the indicated genes between silenced and untreated cells. Genes with a Ct value ≥37 were excluded from the analysis. The relative expression level of each gene was normalized to HPRT, and represented as fold change relative to the untreated cells (calibrator).

FIGS. 15A-15D

Silencing of β2-microglobulin (B2M) is effective in another human cell line.

Figure 15A:
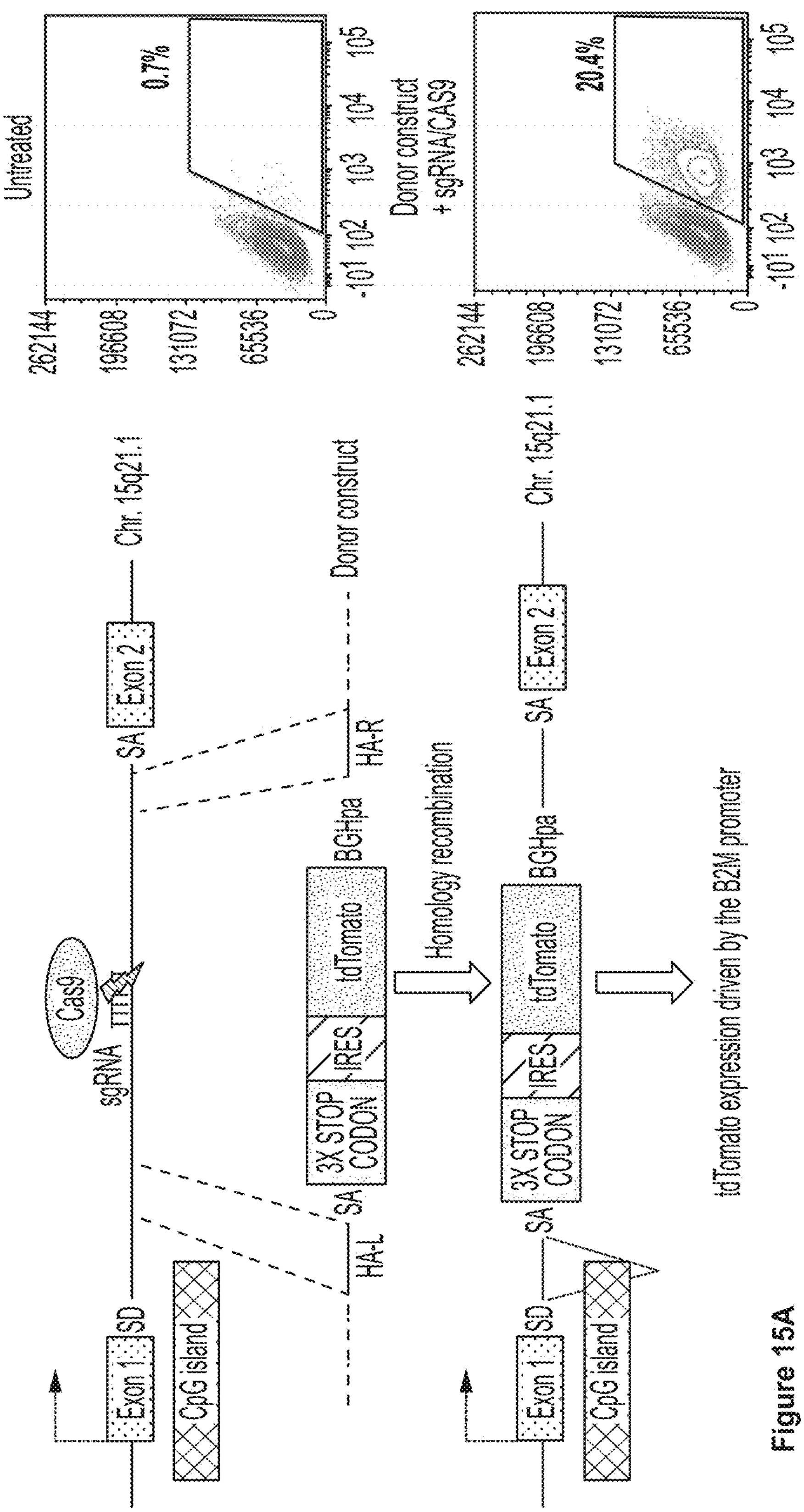
Figure 15B:
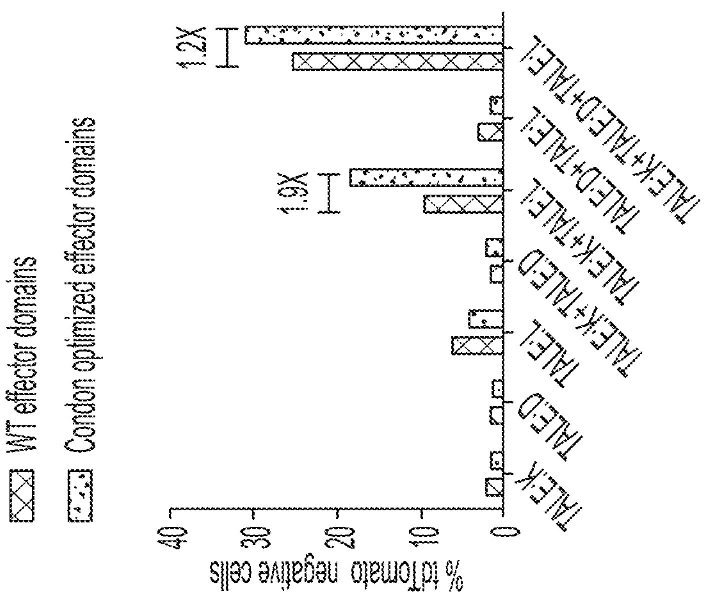
Figure 15C:
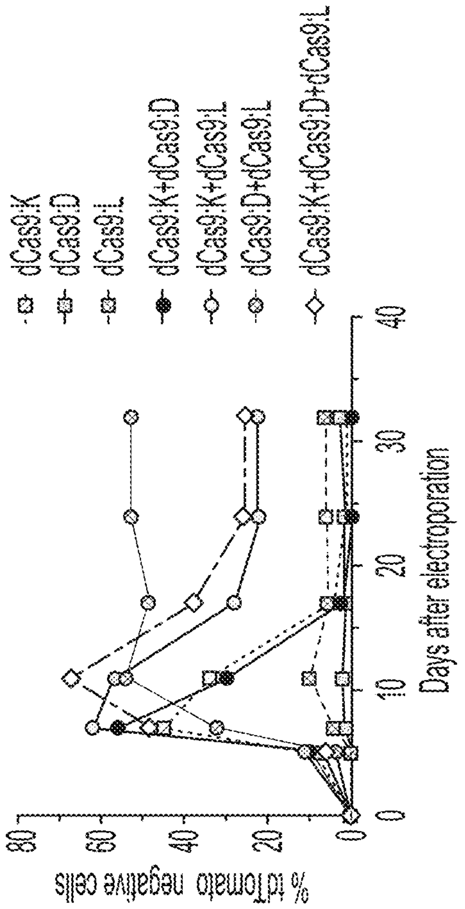
Figure 15D:
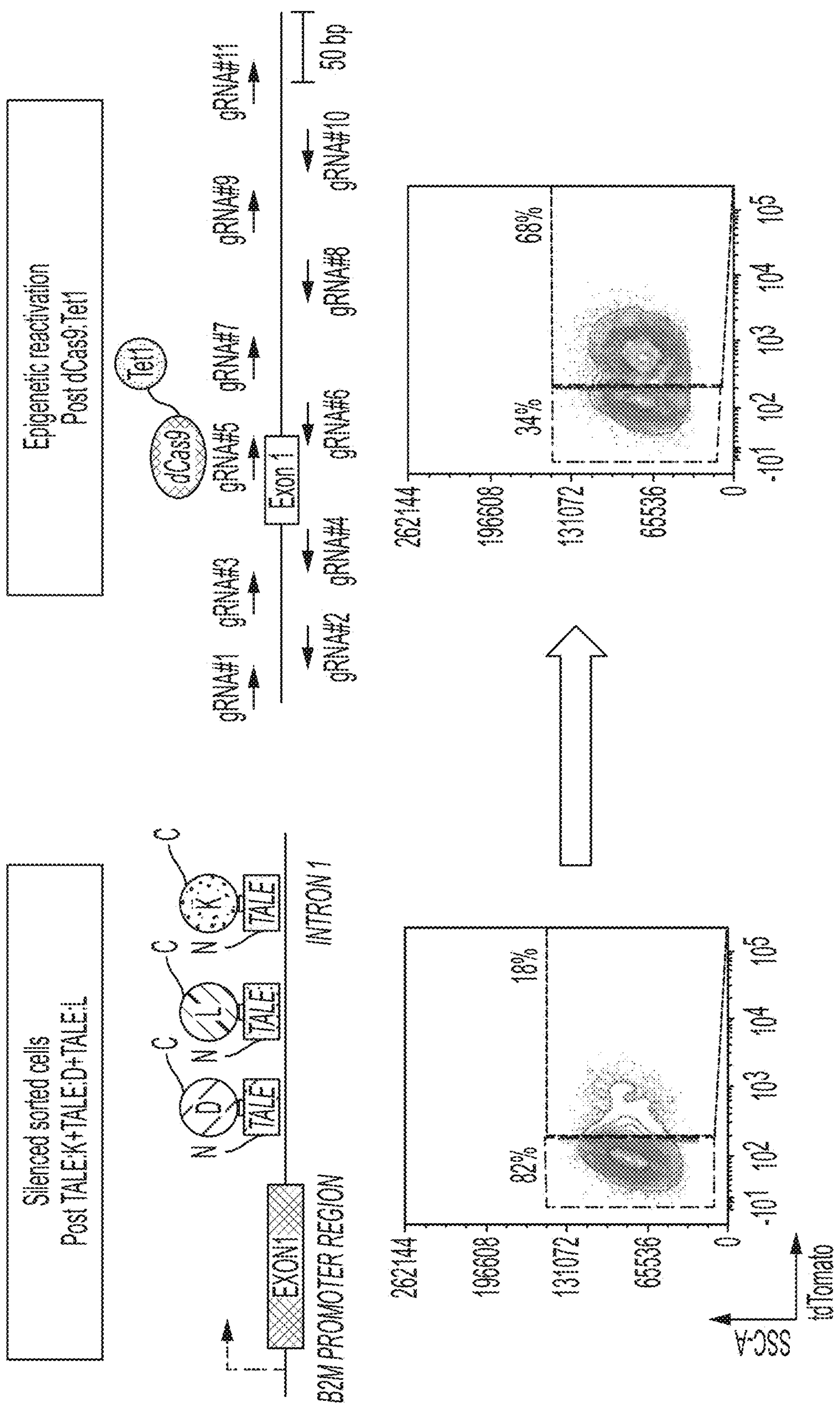

FIG. 15A. Schematics (on the left) of the CRISPR/Cas9-based gene targeting strategy used to insert the tdTomato transgene under the control of the B2M promoter. Representative flow cytometry dot plots of K-562 cells pre- and post-gene targeting (upper and bottom right, respectively). FIG. 15B. Histogram showing the B2M silencing efficiency (i.e. dtTomato-negative cells) at day 30 post electroporation with plasmids encoding for the indicated TALE-based ATRs carrying either the wild-type (WT) or the codon-optimised effector domains (n=1). FIG. 15C. Graph showing the kinetics of B2M silencing (measured as % of dtTomato-negative cells) of K-562 cells electroporated with plasmids encoding for the indicated CRISPR/dCas9-based ATRs (n=1). FIG. 15D. Representative flow cytometry analyses of: (i) sorted tdTomato-negative cells post-transfection with in vitro transcribed mRNAs encoding for the triple TALE:ATR combination (left schematic and dot plot); (ii) the cells from (i) upon transfection with a plasmid encoding for the dCas9:Tet1 in conjunction with plasmids for the B2M gRNAs (left schematic and dot plot) (n=1).

FIGS. 16A-16C

Silencing of β2-microglobulin (B2M) is effective in primary T-lymphocytes.

Figure 16:
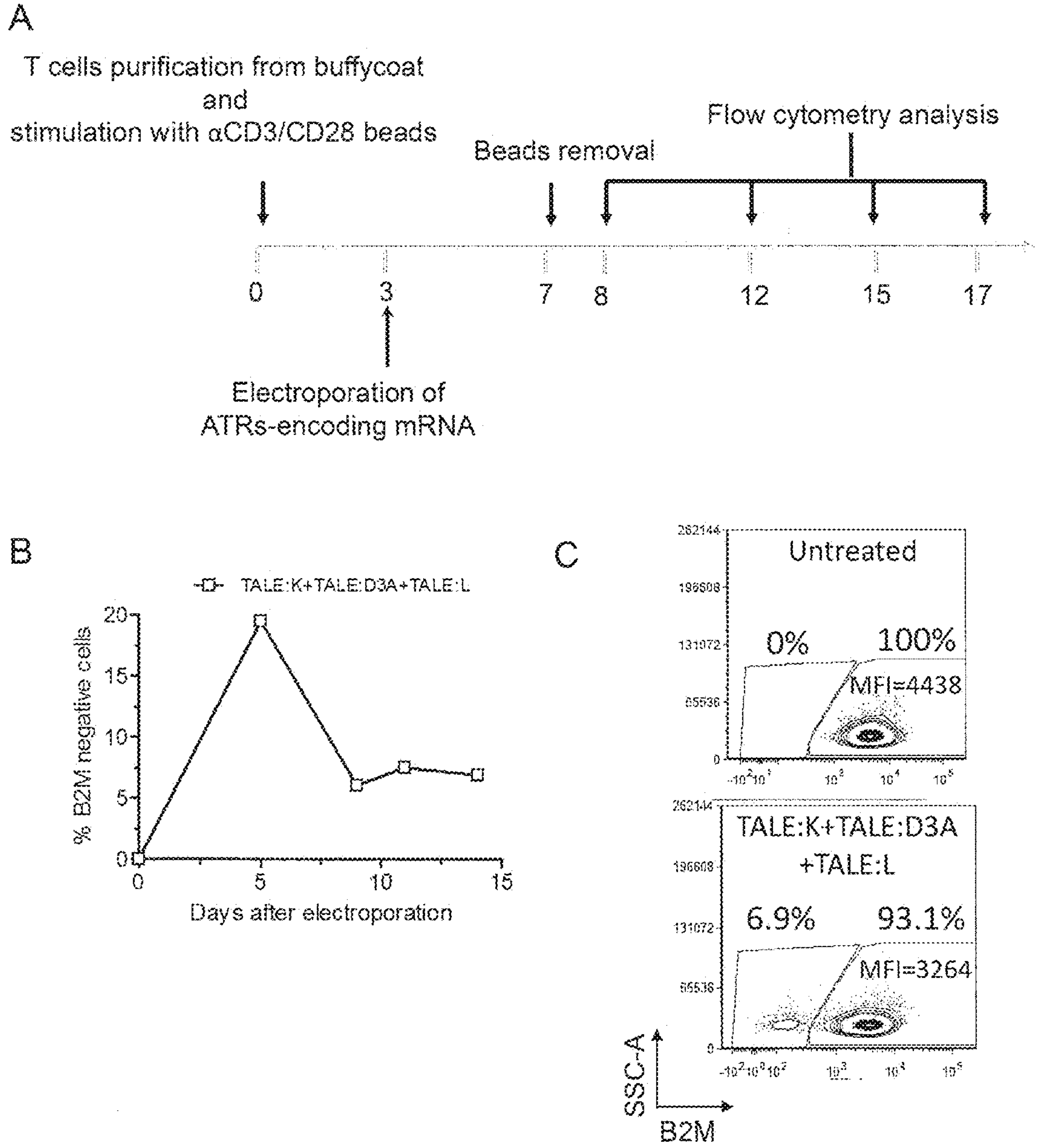

FIG. 16A. Schematics of the experimental workflow. FIG. 16B. Graph showing the kinetics of B2M silencing in human T-lymphocytes electroporated with mRNAs encoding for the triple TALE-based ATRs (n=1). FIG. 16C. Representative flow cytometry dot plots of the indicated T-lymphocytes populations 14 days post-treatment. The percentage of cells within the indicated gates and the B2M MFI are shown.

FIGS. 17A-17B

Single ATR binding site is sufficient for effective silencing of the endogenous gene both with Cas9 and TALE-Based ATRs.

FIG. 17A. Top: schematic of the B2M gene indicating the relative location of the gRNAs (read arrows) selected to target the CpG island of this gene. Bottom: histogram showing the efficiency of B2M silencing (calculated as % of tdTomato-negative cells) 18 days post CRISPR/dCas9-based ATRs plasmid electroporation in the K562 B2M_tdTomato reporter cell line (n=1). FIG. 17B. Left: schematic of binding of TALE based-ATRs on the DNA. In the grey boxes are indicated the conditions in which each of the three different DNA binding domains (form #1 to #3; named in the figure as Repeat Variable Diresidue—RDV) are equipped with both of the three different effector domains. Bottom to this schematic is depicted the condition in which the three different RDVs are equipped each with a different effector domain, as already shown in FIG. 13A. Right: histogram showing the percentage of tdTomato-negative cells upon transfection with plasmids encoding for the indicated TALE-based ATR combinations (n=3; data are represented as mean±S.E.M.).

FIGS. 18A-18D

Transient expression of an un-targeted DNMT3L improves and rescues silencing efficiency of the DNMT3A+KRAB based ATRs in refractory cell types.

Figure 18A:
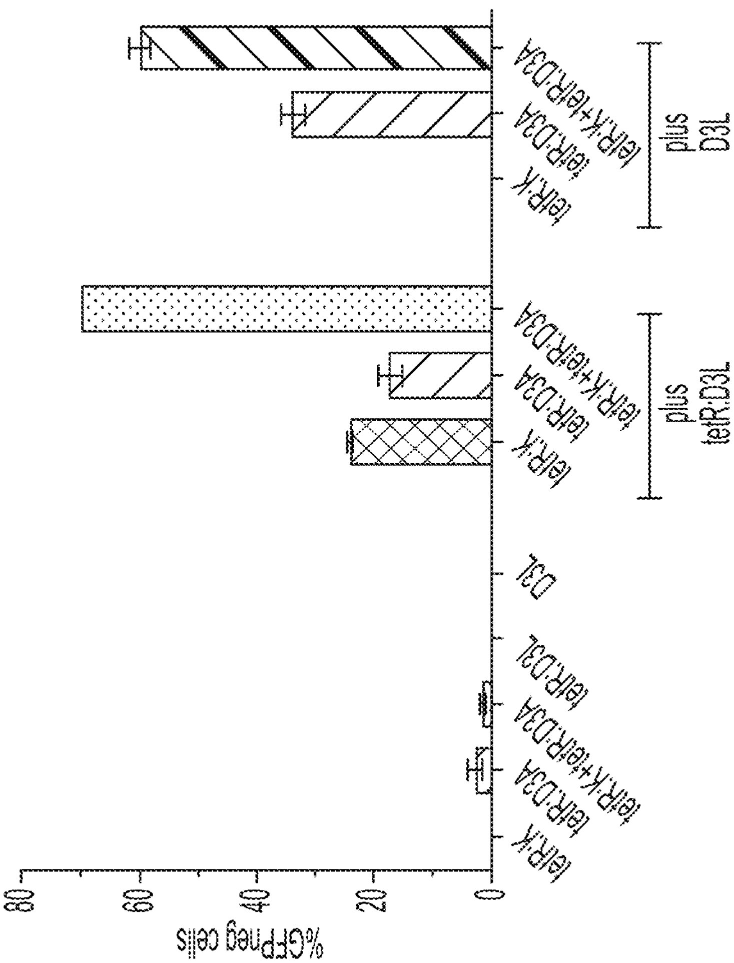
Figure 18B:
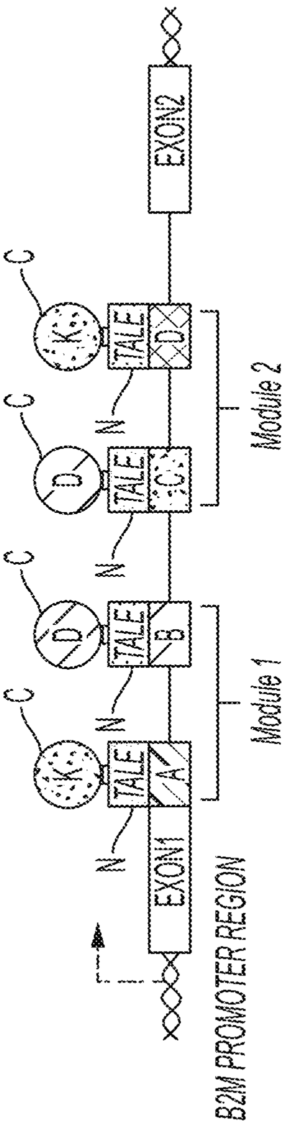
Figure 18C:
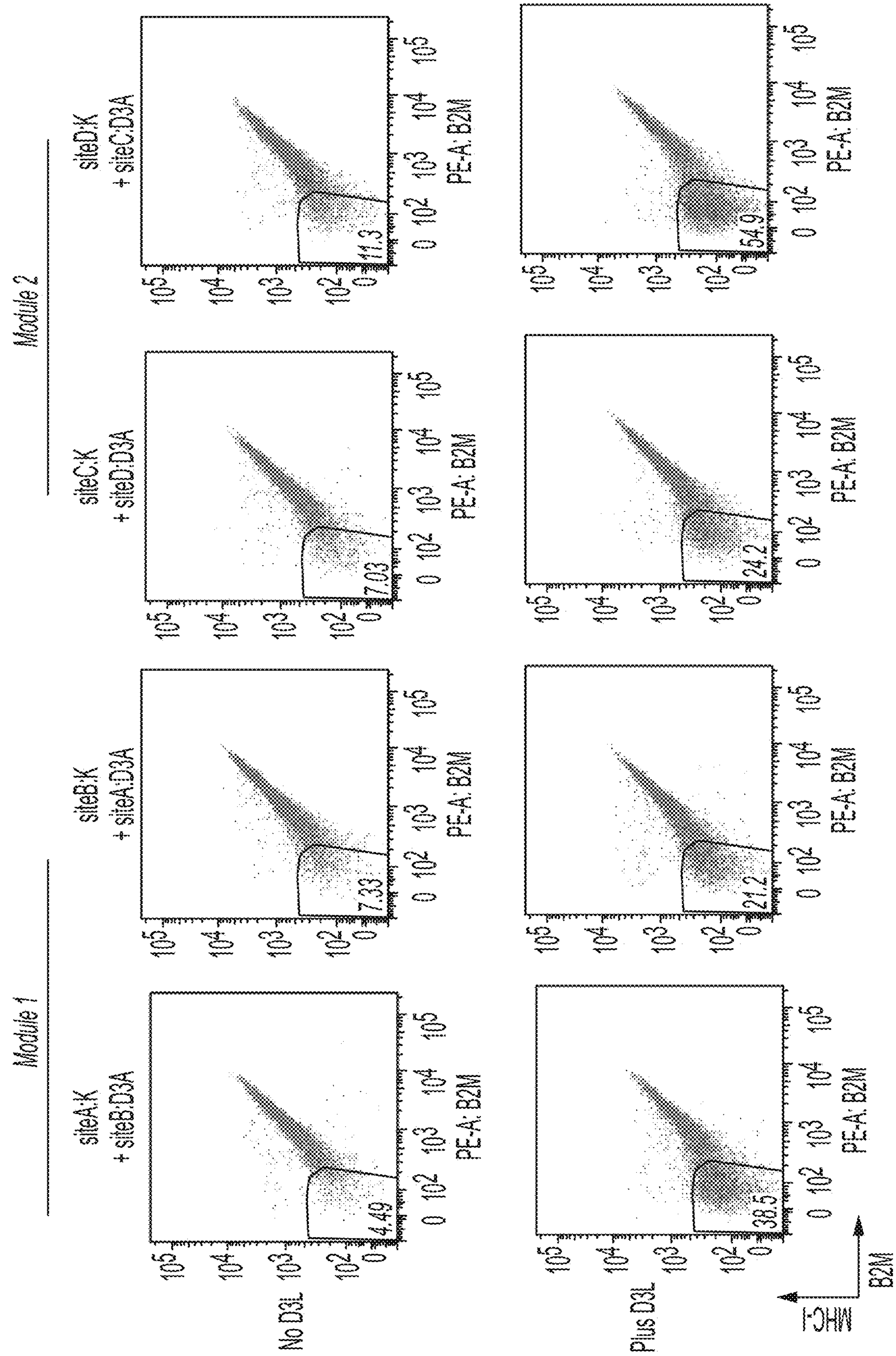
Figure 18D:
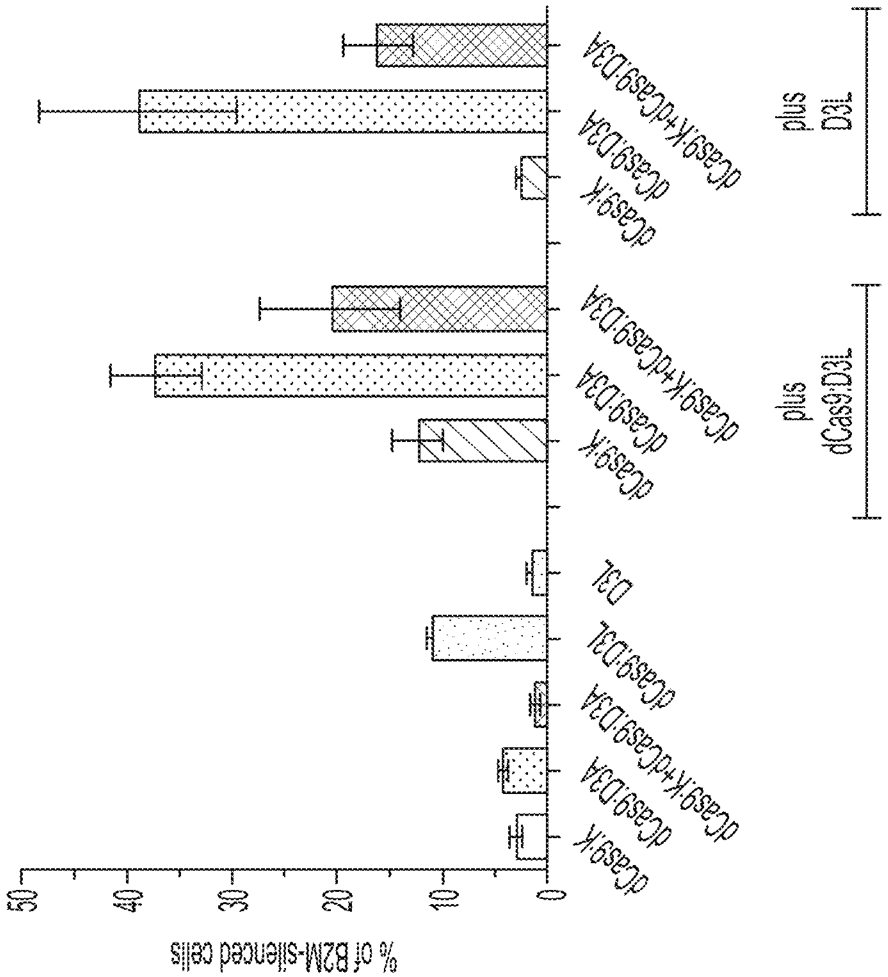

FIG. 18A. Histogram showing the percentage of eGFP silencing of B-lymphoblastoid LV-TetO7 reporter cell line at 27 days post-transfection with in vitro transcribed mRNAs encoding for the indicated tetR-based ATRs, which were delivered in conjunction or not with either the tetR:D3L or with the un-targeted, full-length DNMT3L-encoding mRNA (n=2; data are represented as mean±range). FIG. 18B. Schematics of the B2M locus depicting the binding sites and the relative arrangement of the indicated TALE-based ATRs. Note that each Module can be bound by a pair of TALE-based ATRs. Moreover, for each Module, the relative order of the effector domain can be swapped. For example, for Module 1, site A can be bound by the KRAB-based ATR, while site B by DNMT3A-based ATR, or vice versa. FIG. 18C. Representative flow cytometry dot plots of B2M silencing in HEK-293T cells 21 days post-transfection with plasmids encoding for the indicated pairs of TALE-based ATRs (Module 1 or Module 2, shown for the two possible relative order of binding of the ATRs), which were delivered either alone (top plots row) or in combination with the un-targeted DNMT3L (bottom plots row). FIG. 18D. Histogram showing the percentage of B2M silencing of HEK-293T cells at 45 days post-transfection with plasmids encoding for the indicated dCas9-based ATRs and the cognate gRNAs (as those depicted in FIG. 13E), which were delivered either alone or in conjunction with the dCas9:D3L or with un-targeted, full-length DNMT3L-encoding plasmid (n=3; data are represented as mean±S.E.M.).

FIGS. 19A-19E

Genetic inactivation of the DNMT3B increases the silencing efficiency of the triple ATR combination in permissive cell lines, while transient expression of an un-targeted DNMT3B rescues silencing efficiency of the DNMT3A+KRAB combination in refractory cell types.

Figure 19A:
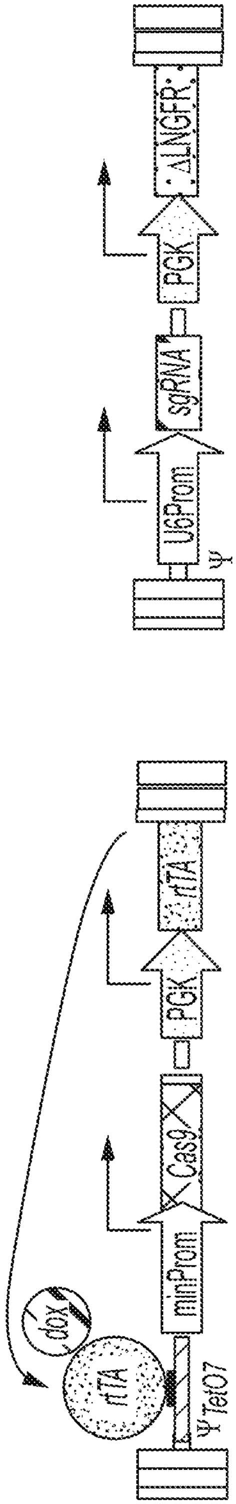
Figure 19B:
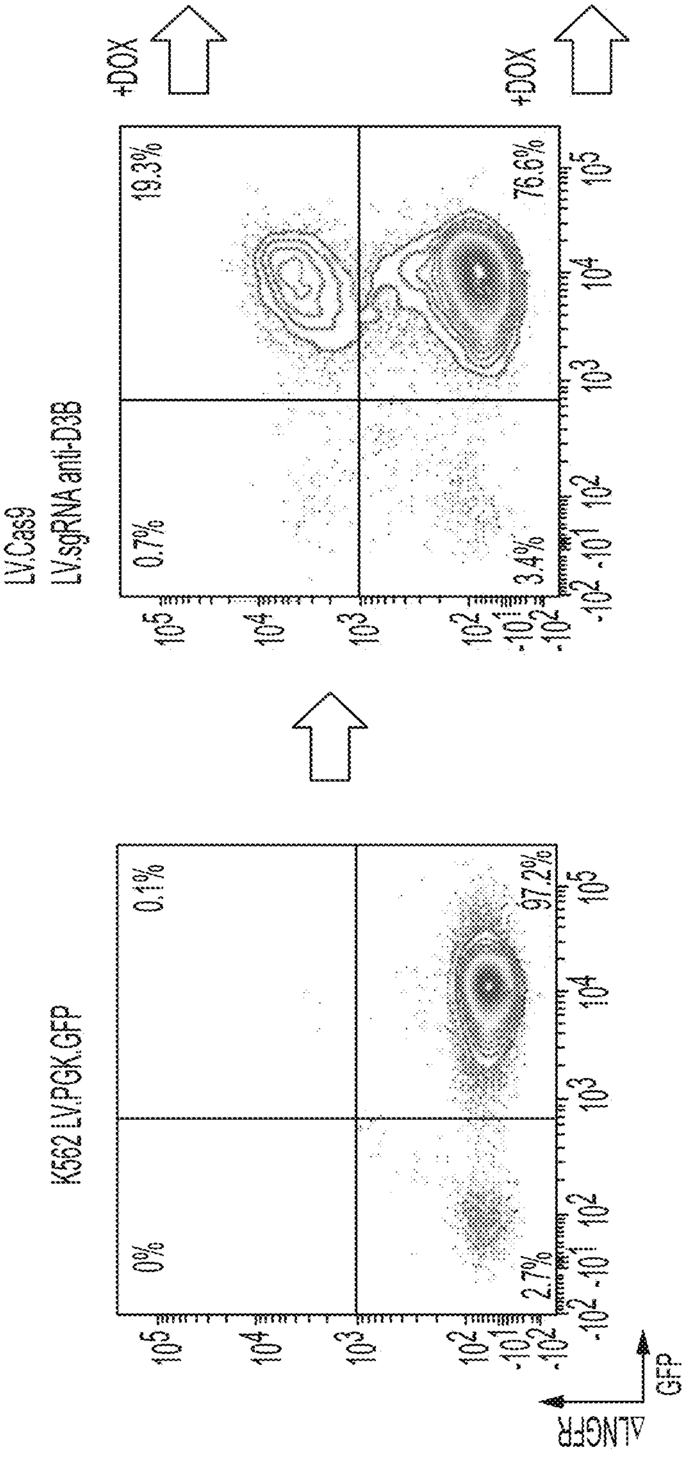
Figure 19C:
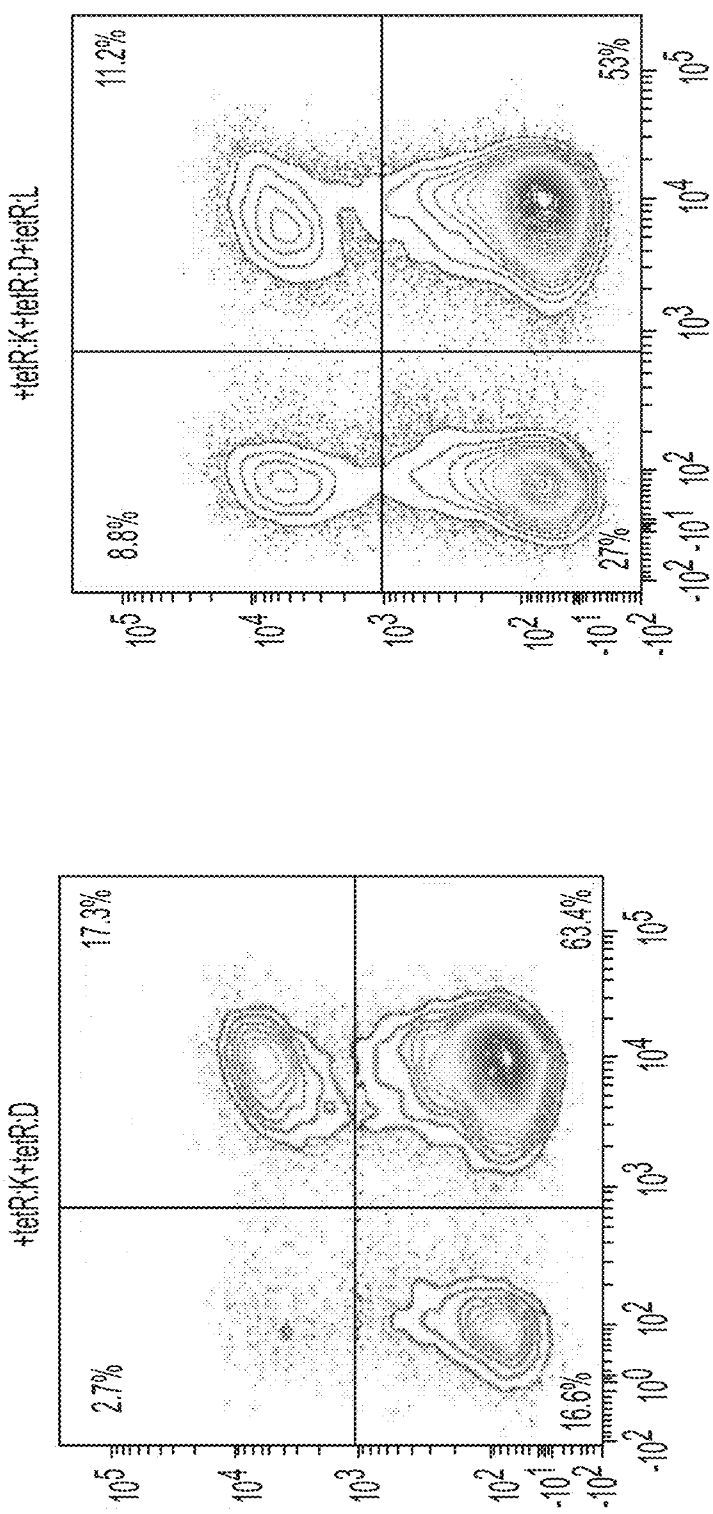
Figure 19D:
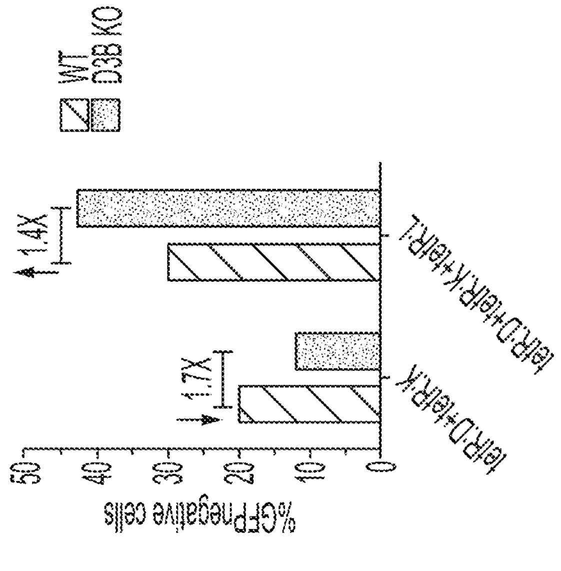
Figure 19E:
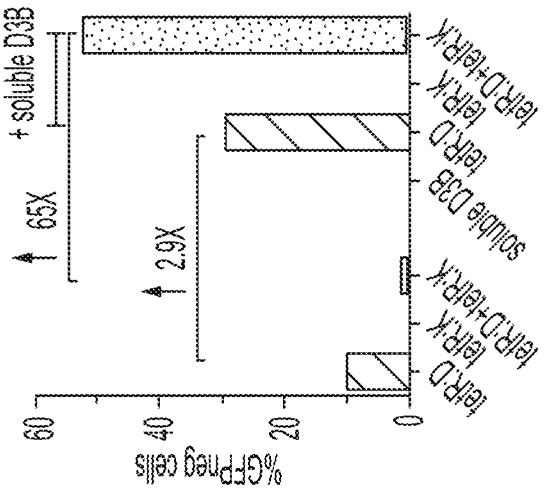

FIG. 19A. Schematics of the lentiviral vectors used to conditionally express Cas9 upon doxycycline administration (left) or to express the gRNA of interest (right). FIGS. 19B-19C. Representative flow cytometry analyses of: i) eGFP-positive K-562 cells upon transduction with the lentiviral vector described in FIG. 5A and then sorted to near purity for eGFP-expression (left plot); ii) the cell line from (i) upon were transduction with the LV encoding for the inducible Cas9 and with the LV encoding for the DNMT3B-gRNA (ΔLNGFR was used as a marker of transduction for the latter LV; middle plot). Note that this second cell line was then exposed to doxycycline for 7 days in order to activate the Cas9 expression and disrupt the coding sequence of the endogenous DNMT3B gene; iii) the cells from (ii) upon electroporation with plasmids encoding for either the double tetR:K+tetR:D3A (top right plot) or the triple tetR:K+tetR:D3A+tetR:D3L (bottom right plot) ATRs combinations. FIG. 19D. Histogram showing the percentage of eGFP silenced cells at day 19 post genetic disruption of the DNMT3B gene by the CRISPR/inducibleCas9 system (n=1). These numbers were obtained by calculating the silencing efficiencies in ΔLNGFR-positive (the cells with disruption of DNMT3B; stippled bars) and -negative cells (wild-type K-562 cells; striped bars). FIG. 19E. Histogram showing the silencing efficiency (% of eGFP-negative cells) in the B-lymphoblastoid TetO7 reporter cell line at day 27 post-transfection with mRNAs encoding for the indicated tetR-based ATRs, which were delivered in conjunction or not with the mRNA encoding for the un-targeted, wild-type DNMT3B sequence (data are shown as mean of the two experiments).

FIGS. 20A-20F

Permanent epigenetic silencing of additional human endogenous genes (using artificial transcription repressor (ATR) combinations.

Figure 20A:
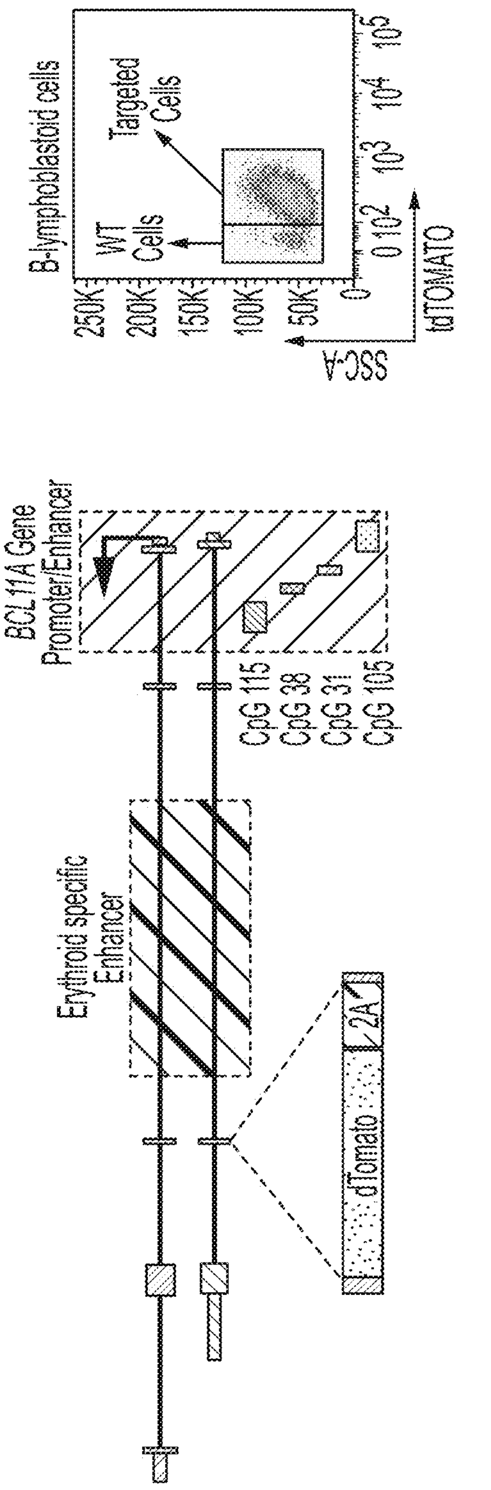
Figure 20C:
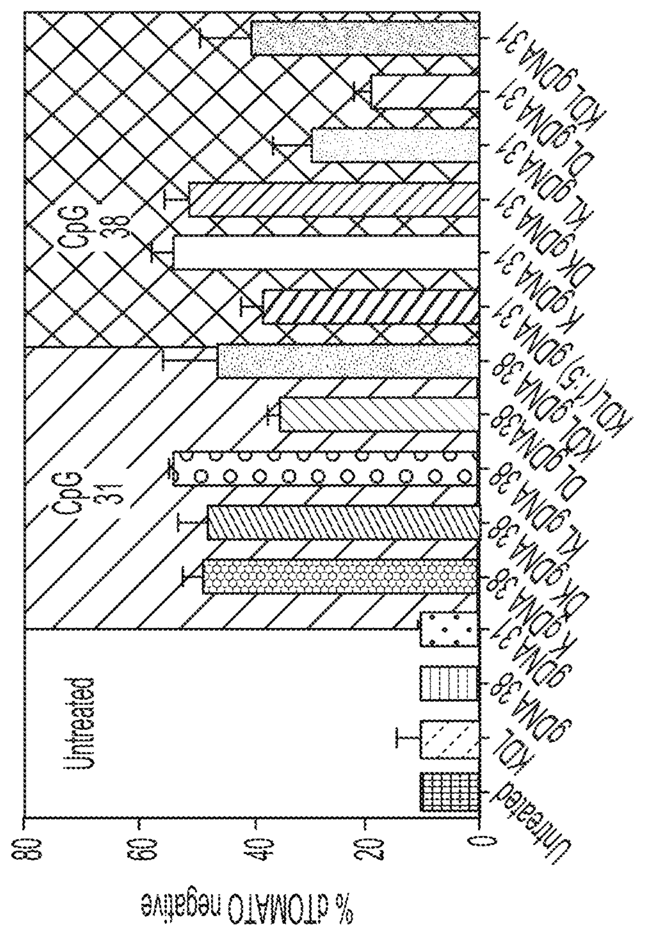
Figure 20B:
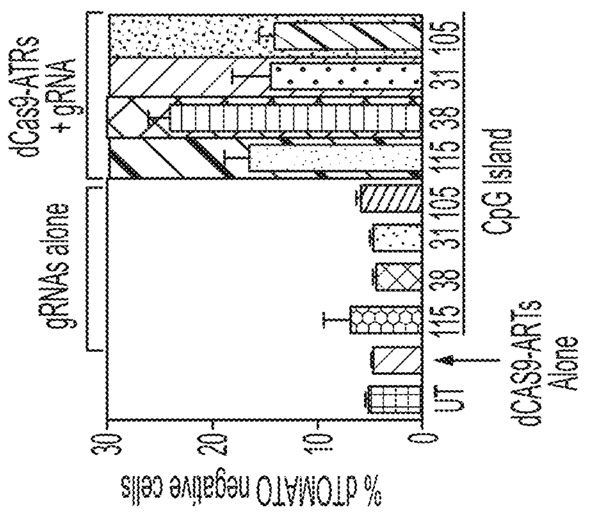
Figure 20D:
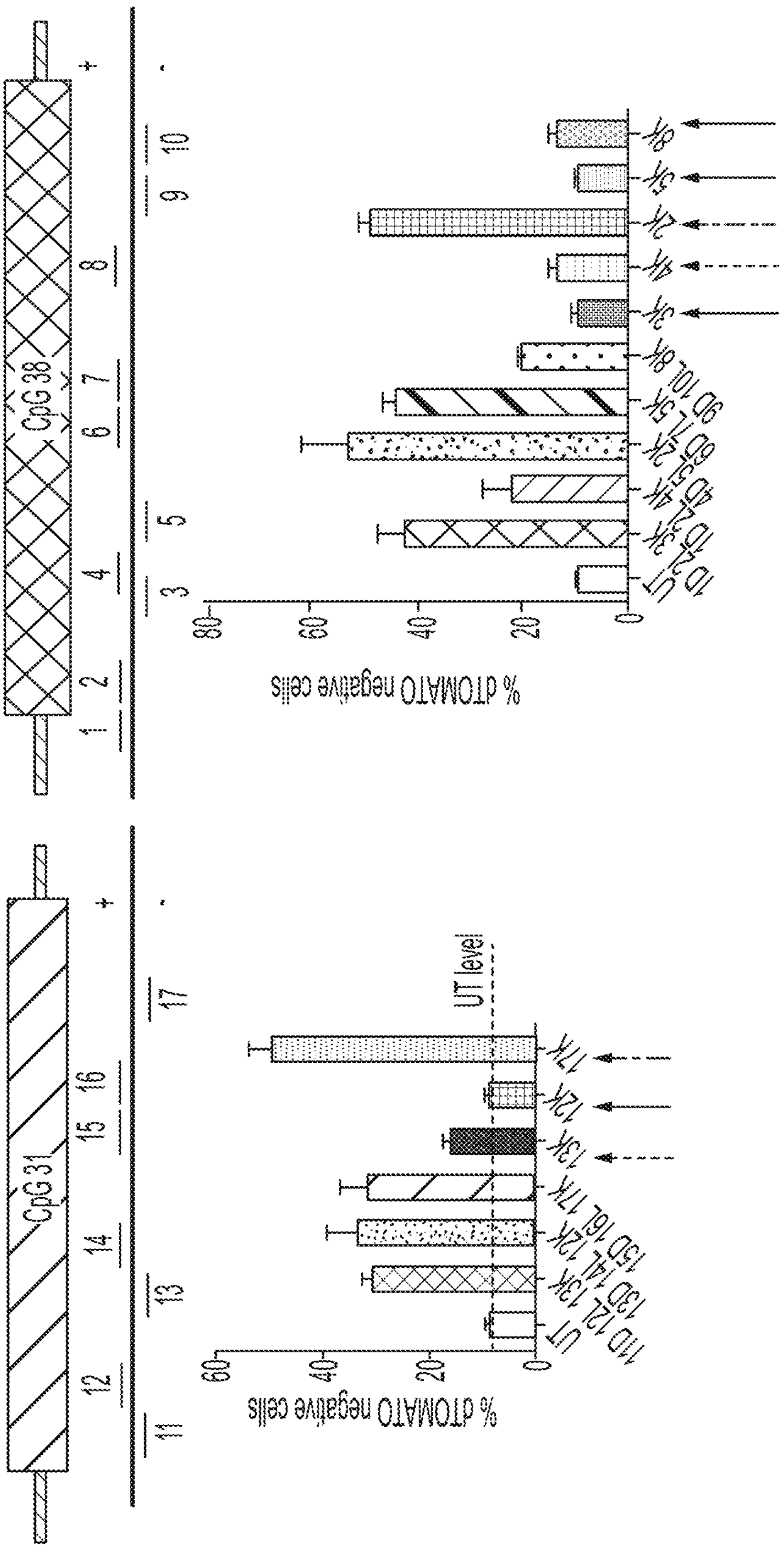
Figure 20E:
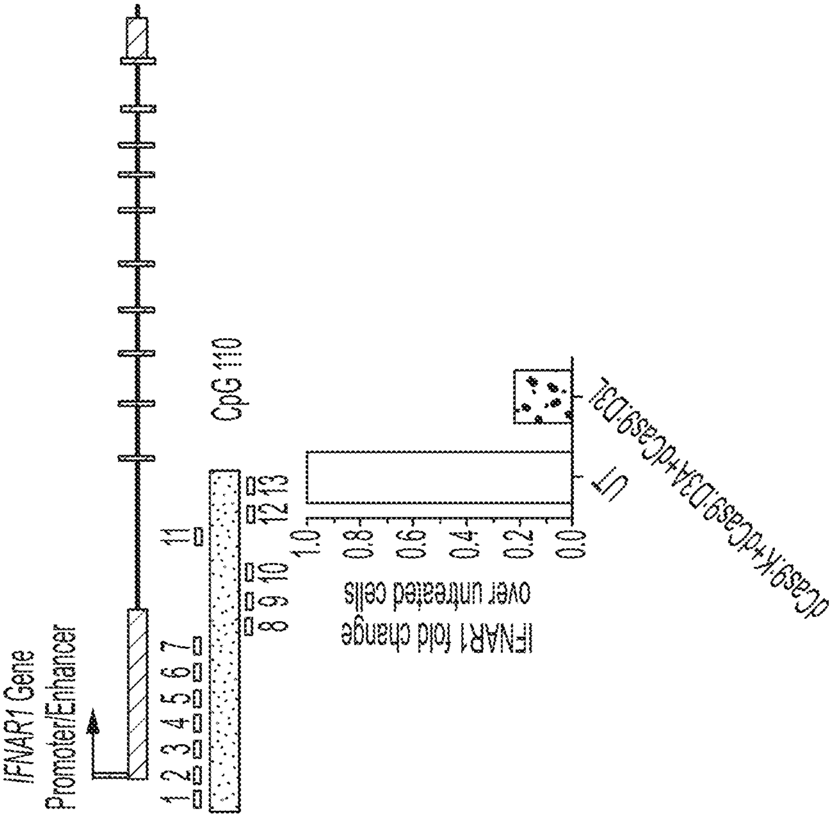
Figure 20F:
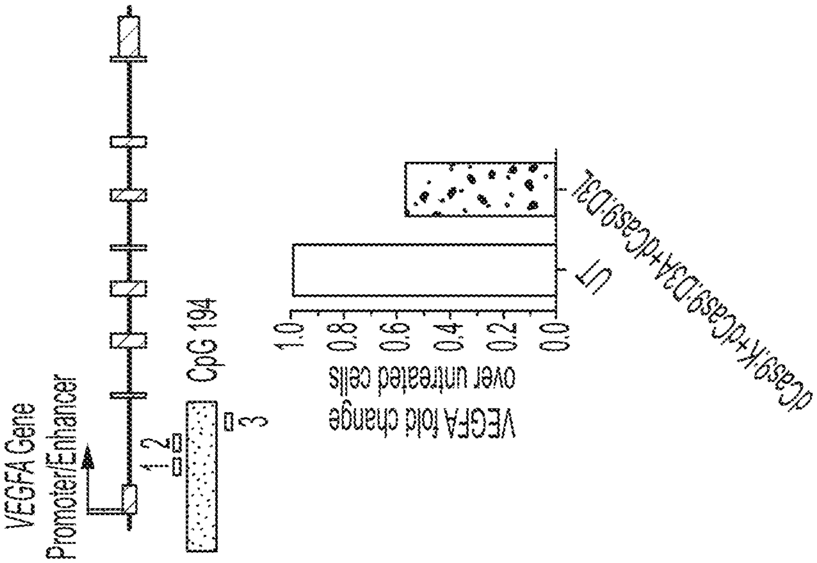

FIG. 20A. Schematic (on the left) of the B-Cell Lymphoma/leukemia 11A (BCL11A) gene showing the two transcript variants of this gene. Dashed boxes highlight gene regulatory elements. In particular, the gene promoter/enhancer region at the level of the transcription start site with cluster of 4 different CpG islands varying in size and number of CpG residues, and the erythroid specific enhancer responsible for the lineage restricted expression of the gene within the second intron of gene. In order to study both gene promoter and erythroid specific enhancer functions, the tdTomato transgene linked to the BCL11A transcript through a 2A self-catalytic peptide was targeted within the third exon of the gene. On the right, is shown a representative dot plot of B-lymphoblastoid cells after sorting of the tdTomato-positive cells. FIG. 20B. Histogram showing the percentage of tdTomato-negative cells at day 32 post-transfection with the indicated dCas9-based ATRs and the corresponding pools of gRNAs (namely, 11 gRNAs for CpG105; 8 gRNAs for CpG31; 9 gRNAs for CpG38; 10 gRNAs for CpG115) targeting the indicated CpG islands of BCL11A (n=3; data are represented as mean±S.E.M.). Untreated cells, or cells transfected with the pools of gRNAs alone or with the dCas9-based ATRs alone were used as controls. FIG. 20C. The tdTomato reporter cell line was co-transfected with plasmids encoding for dCas9-based ATRs, either alone, or in double or triple combination, and with plasmids for a pool of 9 gRNAs targeting the CpG 38, or with plasmids for a pool of 8 gRNAs for CpG 31. Silencing efficiency was measured at 2 weeks post-transfection and is reported in the histogram (n=3; data are represented as mean±S.E.M.). FIG. 20D. Top: Schematics of the binding sites of TALE-based ATRs targeting CpG 31 (top left) or CpG 31 (top right) of the BCL11A promoter region, and their relative orientation of binding on the DNA (+ indicates Watson strand, while—indicates Crick strand). Bottom: the dTomato reporter cell line was transfected with plasmids encoding TALE:KRAB alone, or with the indicated combinations of triple TALE-based ATRs, as labelled on the x axis of the histograms. Silencing efficiency is reported as percentage of dTomato-negative cells. Analysis was performed at day 18 post-plasmid transfection (n=3; data are represented as mean±S.E.M.). FIG. 20E. Top: Schematic of the Interferon (alpha, beta and omega) Receptor 1 (IFNAR1) gene. The stippled box highlights a CpG island (the number of CpG residues are indicated) at the level of the gene promoter/enhancer region. Bottom: Histogram showing the fold change in the expression level of the IFNAR1 gene between cells electroporated with plasmids encoding for a pool of 13 gRNAs against the IFNAR1 CpG island plus the dCas9:K+dCas9:D3A+dCas9:D3L ATRs (18 days post treatment) and untreated cells. The relative expression level of the IFNAR1 gene was normalised to the expression of DNMT1, and represented as fold change relative to the untreated cells (calibrator) (n=1). FIG. 20F. Top: Schematic of the Vascular Endothelial Growth Factor A (VEGFA) gene. The stippled box highlights a CpG island (the number of CpG residues are indicated) at the level of the gene promoter/enhancer region. Bottom: Histogram showing the fold change in the expression level of the VEGFA gene between cells electroporated with plasmids encoding for a pool of 3 gRNAs against the VEGFA CpG island plus the dCas9:K+dCas9:D3A+dCas9:D3L ATRs (14 days post treatment) and untreated cells. The relative expression level of the VEGFA gene was normalised to the expression of DNMT1, and represented as fold change relative to the untreated cells (calibrator) (n=1).

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F., and Maniatis, T. (1989) *Molecular Cloning: A Laboratory Manual,* 2nd Edition, Cold Spring Harbor Laboratory Press; Ausubel, F. M. et al. (1995 and periodic supplements) *Current Protocols in Molecular Biology*, Ch. 9, 13 and 16, John Wiley & Sons; Roe, B., Crabtree, J., and Kahn, A. (1996) *DNA Isolation and Sequencing: Essential Techniques*, John Wiley & Sons; Polak, J. M., and McGee, J. O'D. (1990) *In Situ Hybridization: Principles and Practice*, Oxford University Press; Gait, M. J. (1984) *Oligonucleotide Synthesis: A Practical Approach*, IRL Press; and Lilley, D. M., and Dahlberg, J. E. (1992) *Methods in Enzymology: DNA Structures Part A: Synthesis and Physical Analysis of DNA*, Academic Press. Each of these general texts is herein incorporated by reference.

In one aspect, the present invention provides a product comprising two or more artificial transcription repressors (ATRs), or polynucleotides encoding therefor, selected from groups (a), (b) or (c):

(a) an ATR comprising a DNA-binding domain operably linked to a KRAB domain or homologue thereof;

(b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof wherein at least two of the ATRs are selected from different groups (a), (b) or (c).

The product of the present invention may, for example, be a composition (e.g. a pharmaceutical composition) comprising two or more ATRs, or polynucleotides encoding therefor, selected from groups (a), (b) or (c): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof, in admixture, wherein at least two of the ATRs are selected from different groups (a), (b) or (c). Alternatively, the product may, for example, be a kit comprising a preparation of two or more ATRs, or polynucleotides encoding therefor, selected from groups (a), (b) or (c): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof, wherein at least two of the ATRs are selected from different groups (a), (b) or (c), and, optionally, instructions for the simultaneous, sequential or separate administration of the preparations to a subject in need thereof.

Artificial transcription repressors (ATRs) are agents that act to reduce the transcription of a target gene. ATRs may be chimeric proteins that are comprised of a DNA-binding domain operably linked to an effector domain (e.g. a KRAB domain, a DNMT3A, DNMT3B or DNMT1 domain or a DNMT3L domain, or homologues thereof). The DNA-binding domain enables binding of the ATR to a specific nucleic acid sequence, and may be engineered to bind to a nucleic acid sequence of choice. The effector domain may harbour a catalytic activity which enables repression of transcription of the target gene. Alternatively, or additionally, the effector domain may recruit additional agents within the cell to the target gene, which results in the repression of transcription of the target gene.

By "operably linked", it is to be understood that the individual components are linked together in a manner which enables them to carry out their function (e.g. binding to DNA, catalysing a reaction or recruiting additional agents from within a cell) substantially unhindered. For example, a DNA-binding domain may be conjugated to an effector domain, for example to form a fusion protein. Methods for conjugating polypeptides are known in the art, for example through the provision of a linker amino acid sequence connecting the polypeptides. Alternative methods of conjugating polypeptides known in the art include chemical and light-induced conjugation methods (e.g. using chemical cross-linking agents). Preferably, the DNA-binding domain and effector domain (e.g. KRAB domain, DNMT3A, DNMT3B or DNMT1 domain or DNMT3L domain, or homologue thereof) of the ATR form a fusion protein.

Effector Domains

The term "effector domain", is to be understood as referring to the part of the ATR which provides for the silencing effect on a target gene, for example by catalysing a reaction on the DNA or chromatin (e.g. methylation of DNA), or by recruiting an additional agent from within a cell, resulting in the repression of the transcription of a gene.

"Domain" is to be understood in this context as referring to a part of the ATR that harbours a certain function. The domain may be an individual domain (e.g. a catalytic domain) isolated from a natural protein or it may be an entire, full-length natural protein. Put another way, either the full-length protein or a functional fragment thereof can be used as an effector domain. Therefore, for example, "KRAB domain" refers to the part of the ATR that comprises an amino acid sequence with the function of a KRAB domain.

Chromatin remodelling enzymes that are known to be involved in the permanent epigenetic silencing of endogenous retroviruses (ERVs; Feschotte, C. et al. (2012) *Nat. Rev. Genet.* 13: 283-96; Leung, D. C. et al. (2012) *Trends Biochem. Sci.* 37: 127-33) may provide suitable effector domains for exploitation in the present invention.

The family of the Krüppel-associated box containing zinc finger proteins (KRAB-ZFP; Huntley, S. et al. (2006) *Genome Res.* 16: 669-77) plays an important role in the silencing of endogenous retroviruses. These transcription factors bind to specific ERV sequences through their ZFP DNA binding domain, while they recruit the KRAB Associated Protein 1 (KAP1) with their conserved KRAB domain. KAP1 in turn binds a large number of effectors that promote the local formation of repressive chromatin (Iyengar, S. et al. (2011) *J. Biol. Chem.* 286: 26267-76).

In the early embryonic development, KAP1 is known to recruit SET domain bifurcated 1 (SETDB1), a histone methyltransferase that deposits histone H3 lysine-9 di- and tri-methylation (H3K9me2 and H3K9me3, respectively), two histone marks associated with transcriptional repression. Concurrently, KAP1 binds to Heterochromatin Protein 1 alpha (HP1α), which reads H3K9me2 and H3K9me3 and stabilises the KAP1-containing complex. KAP1 can also interact with other well known epigenetic silencers, such as the lysine-specific histone demethylase 1 (LSD1) that inhibits transcription by removing histone H3 lysine-4 methylation, and the nucleosome remodelling and deacetylase complex (NURD), which removes acetyl groups from histones. Finally, the KAP1-containing complex contributes to the recruitment of the de novo DNA methyltransferase 3A (DNMT3A), which methylates cytosines at CpG sites (Jones, P. A. (2012) *Nat. Rev. Genet.* 13: 484-92). Together, these data suggest a model in which, in the pre-implantation embryo, the KAP1-complex ensures ERV silencing through the concerted action of histone modifying enzymes and DNA methylation. Then, after implantation, the DNA methylation previously targeted by KRAB-ZFPs to the ERVs becomes stable (Reik, W. (2007) *Nature* 447: 425-32), being inherited throughout mitosis and somatic cell differentiation without the need of the continuous expression of ERVs-specific KRAB-ZFPs. Contrary to embryonic stem cells, the KAP1-complex is not able to efficiently induce DNA methylation in somatic cells, being only able to deposit H3K9 methylation. However, this histone mark is not maintained without being continuously deposited at the targeted site by the KRAB-ZFPs (Hathaway, N. A. et al. (2012) *Cell* 149: 1447-60).

Therefore, in view of an epigenetic therapy approach based on the transient expression of ATRs in somatic cells, the KRAB-ZFPs/KAP1 machinery is expected not to be functional if employed alone. On the other hand, we consider a preferable strategy to co-deliver two distinct ATRs: one based on, for example, the KRAB domain, the initiator of the epigenetic cascade occurring at ERVs in embryonic stem cells, and the other based on, for example, DNMT3A, the final lock of this process. This approach may allow recapitulating on a pre-selected target gene those repressive chromatin states established at ERVs in the pre-implantation embryo and then permanently inherited throughout mammalian development and adult life.

An ATR of the present invention may, for example, comprise a KRAB domain. Various KRAB domains are known in the family of KRAB-ZFP proteins. For example, an ATR of the present invention may comprise the KRAB domain of human zinc finger protein 10 (ZNF10; Szulc, J. et al. (2006) *Nat. Methods* 3: 109-16):

```
                                        (SEQ ID NO: 1)
ALSPQHSAVTQGSIIKNKEGMDAKSLTAWSRTLVTFKDVFVDFTREEWK
LLDTAQQIVYRNVMLENYKNLVSLGYQLTKPDVILRLEKGEEPWLVERE
IHQETHPDSETAFEIKSSV
```

Further examples of suitable KRAB domains for use in the present invention include:

```
              (the KRAB domain of the ZNF350 protein; SEQ ID NO: 2)
ITLEDVAVDFTWEEWQLLGAAQKDLYRDVMLENYSNLVAVGYQASKPDALFKLEQGEQ
LWTIEDGIHSGACS

              (the KRAB domain of the ZNF197 protein; SEQ ID NO: 3)
VMFEEVSVCFTSEEWACLGPIQRALYWDVMLENYGNVTSLEWETMTENEEVTSKPSS
SQRADSHKGTSKRLQG

                (the KRAB domain of the RBAK protein; SEQ ID NO: 4)
VSFKDVAVDFTQEEWQQLDPDEKITYRDVMLENYSHLVSVGYDTTKPNVIIKLEQGEEP
WIMGGEFPCQHSP

             (the KRAB domain of the ZKSCAN1 protein; SEQ ID NO: 5)
VKIEDMAVSLILEEWGCONLARRNLSRDNRQENYGSAFPQGGENRNENEESTSKAET
SEDSASRGETTGRSQKE

              (the KRAB domain of the KRBOX4 protein; SEQ ID NO: 6)
LTFKDVFVDFTLEEWQQLDSAQKNLYRDVMLENYSHLVSVGYLVAKPDVIFRLGPGEE
SWMADGGTPVRTCA

              (the KRAB domain of the ZNF274 protein; SEQ ID NO: 7)
VTFEDVTLGFTPEEWGLLDLKQKSLYREVMLENYRNLVSVEHQLSKPDVVSQLEEAED
FWPVERGIPQDTIP
```

An ATR of the present invention may, for example, comprise a domain of human DNA methyltransferase 3A (DNMT3A; Law, J. A. et al. (2010) *Nat. Rev. Genet.* 11: 204-20), preferably the catalytic domain. For example, an ATR of the present invention may comprise the sequence:

```
                                        (SEQ ID NO: 8)
TYGLLRRREDWPSRLQMFFANNHDQEFDPPKVYPPVPAEKRKPIRVLSL

FDGIATGLLVLKDLGIQVDRYIASEVCEDSITVGMVRHQGKIMYVGDVR

SVTQKHIQEWGPFDLVIGGSPCNDLSIVNPARKGLYEGTGRLFFEFYRL

LHDARPKEGDDRPFFWLFENVVAMGVSDKRDISRFLESNPVMIDAKEVS

AAHRARYFWGNLPGMNRPLASTVNDKLELQECLEHGRIAKFSKVRTITT

RSNSIKQGKDQHFPVFMNEKEDILWCTEMERVFGFPVHYTDVSNMSRLA

RQRLLGRSWSVPVIRHLFAPLKEYFACV
```

DNA methyltransferases 3B and 1 (DNMT3B and DNMT1), similarly to DNMT3A, are also responsible for the deposition and maintenance of DNA methylation, and may also be used in an ATR of the present invention. For example, an ATR of the present invention may comprise any of the sequences:

(the catalytic domain of human DNMT3B; SEQ ID NO: 9)

CHGVLRRRKDWNVRLQAFFTSDTGLEYEAPKLYPAIPAARRRPIRVLSLFDGIATGYLVL

KELGIKVGKYVASEVCEESIAVGTVKHEGNIKYVNDVRNITKKNIEEWGPFDLVIGGSPC

NDLSNVNPARKGLYEGTGRLFFEFYHLLNYSRPKEGDDRPFFWMFENVVAMKVGDKR

DISRFLECNPVMIDAIKVSAAHRARYFWGNLPGMNRPVIASKNDKLELQDCLEYNRIAKL

KKVQTITTKSNSIKQGKNQLFPVVMNGKEDVLWCTELERIFGFPVHYTDVSNMGRGAR

QKLLGRSWSVPVIRHLFAPLKDYFACE (DNMT3B: SEQ ID NO: 36)

MVAELISEEDLEFMKGDTRHLNGEEDAGGREDSILVNGACSDQSSDSPPILEAIRTPEIR

GRRSSSRLSKREVSSLLSYTQDLTGDGDGEDGDGSDTPVMPKLFRETRTRSESPAVR

TRNNNSVSSRERHRPSPRSTRGRQGRNHVDESPVEFPATRSLRRRATASAGTPWPS

PPSSYLTIDLTDDTEDTHGTPQSSSTPYARLAQDSQQGGMESPQVEADSGDGDSSEY

QDGKEFGIGDLVWGKIKGFSWWPAMVVSWKATSKRQAMSGMRWVQWFGDGKFSEV

SADKLVALGLFSQHFNLATFNKLVSYRKAMYHALEKARVRAGKTFPSSPGDSLEDQLK

PMLEWAHGGFKPTGIEGLKPNNTQPENKTRRRTADDSATSDYCPAPKRLKTNCYNNG

KDRGDEDQSREQMASDVANNKSSLEDGCLSCGRKNPVSFHPLFEGGLCQTCRDRFL

ELFYMYDDDGYQSYCTVCCEGRELLLCSNTSCCRCFCVECLEVLVGTGTAAEAKLQEP

WSCYMCLPQRCHGVLRRRKDWNVRLQAFFTSDTGLEYEAPKLYPAIPAARRRPIRVLS

LFDGIATGYLVLKELGIKVGKYVASEVCEESIAVGTVKHEGNIKYVNDVRNITKKNIEEWG

PFDLVIGGSPCNDLSNVNPARKGLYEGTGRLFFEFYHLLNYSRPKEGDDRPFFWMFEN

VVAMKVGDKRDISRFLECNPVMIDAIKVSAAHRARYFWGNLPGMNRPVIASKNDKLEL

QDCLEYNRIAKLKKVQTITTKSNSIKQGKNQLFPVVMNGKEDVLWCTELERIFGFPVHY

TDVSNMGRGARQKLLGRSWSVPVIRHLFAPLKDYFACE (the catalytic domain of human DNMT1; SEQ ID NO: 10)

LRTLDVFSGCGGLSEGFHQAGISDTLWAIEMWDPAAQAFRLNNPGSTVFTEDCNILLKL

VMAGETTNSRGQRLPQKGDVEMLCGGPPCQGFSGMNRFNSRTYSKFKNSLVVSFLS

YCDYYRPRFFLLENVRNFVSFKRSMVLKLTLRCLVRMGYQCTFGVLQAGQYGVAQTR

RRAIILAAAPGEKLPLFPEPLHVFAPRACQLSVVVDDKKFVSNITRLSSGPFRTITVRDTM

SDLPEVRNGASALEISYNGEPQSWFQRQLRGAQYQPILRDHICKDMSALVAARMRHIP

LAPGSDWRDLPNIEVRLSDGTMARKLRYTHHDRKNGRSSSGALRGVCSCVEAGKACD

PAARQFNTLIPWCLPHTGNRHNHWAGLYGRLEWDGFFSTTVTNPEPMGKQGRVLHP

EQHRVVSVRECARSQGFPDTYRLFGNILDKHRQVGNAVPPPLAKAIGLEIKLCMLAKAR

ESASAKIKEEEAAKD

An ATR of the present invention may, for example, comprise DNA (cytosine-5)-methyltransferase 3-like (DNMT3L), a catalytically inactive DNA methyltransferase that activates DNMT3A by binding to its catalytic domain. For example, an ATR of the present invention may comprise the sequence:

(SEQ ID NO: 11)

MAAIPALDPEAEPSMDVILVGSSELSSSVSPGTGRDLIAYEVKANQRNI

EDICICCGSLQVHTQHPLFEGGICAPCKDKFLDALFLYDDDGYQSYCSI

CCSGETLLICGNPDCTRCYCFECVDSLVGPGTSGKVHAMSNWVCYLCLP

-continued

SSRSGLLQRRRKWRSQLKAFYDRESENPLEMFETVPVWRRQPVRVLSLF

EDIKKELTSLGFLESGSDPGQLKHVVDVTDTVRKDVEEWGPFDLVYGAT

PPLGHTCDRPPSWYLFQFHRLLQYARPKPGSPRPFFWMFVDNLVLNKED

LDVASRFLEMEPVTIPDVHGGSLQNAVRVWSNIPAIRSRHWALVSEEEL

SLLAQNKQSSKLAAKWPTKLVKNCFLPLREYFKYFSTELTSSL

An ATR of the present invention may, for example, comprise a SETDB1 domain. For example, an ATR of the present invention may comprise any of the sequences:

(SEQ ID NO: 12)
MSSLPGCIGLDAATATVESEEIAELQQAVVEELGISMEELRHFIDEELEKMDCVQQRKK

QLAELETWVIQKESEVAHVDQLFDDASRAVTNCESLVKDFYSKLGLQYRDSSSEDESS

RPTEIIEIPDEDDDVLSIDSGDAGSRTPKDQKLREAMAALRKSAQDVQKFMDAVNKKSS

SQDLHKGTLSQMSGELSKDGDLIVSMRILGKKRTKTWHKGTLIAIQTVGPGKKYKVKFD

NKGKSLLSGNHIAYDYHPPADKLYVGSRVVAKYKDGNQVWLYAGIVAETPNVKNKLRF

LIFFDDGYASYVTQSELYPICRPLKKTWEDIEDISCRDFIEEYVTAYPNRPMVLLKSGQLI

KTEWEGTWWKSRVEEVDGSLVRILFLDDKRCEWIYRGSTRLEPMFSMKTSSASALEK

KQGQLRTRPNMGAVRSKGPVVQYTQDLTGTGTQFKPVEPPQPTAPPAPPFPPAPPLS

PQAGDSDLESQLAQSRKQVAKKSTSFRPGSVGSGHSSPTSPALSENVSGGKPGINQT

YRSPLGSTASAPAPSALPAPPAPPVFHGMLERAPAEPSYRAPMEKLFYLPHVCSYTCL

SRVRPMRNEQYRGKNPLLVPLLYDFRRMTARRRVNRKMGFHVIYKTPCGLCLRTMQEI

ERYLFETGCDFLFLEMFCLDPYVLVDRKFQPYKPFYYILDITYGKEDVPLSCVNEIDTTP

PPQVAYSKERIPGKGVFINTGPEFLVGCDCKDGCRDKSKCACHQLTIQATACTPGGQIN

PNSGYQYKRLEECLPTGVYECNKRCKCDPNMCTNRLVQHGLQVRLQLFKTQNKGWGI

RCLDDIAKGSFVCIYAGKILTDDFADKEGLEMGDEYFANLDHIESVENFKEGYESDAPC

SSDSSGVDLKDQEDGNSGTEDPEESNDDSSDDNFCKDEDFSTSSVWRSYATRRQTR

GQKENGLSETTSKDSHPPDLGPPHIPVPPSIPVGGCNPPSSEETPKNKVASWLSCNSV

SEGGFADSDSHSSFKTNEGGEGRAGGSRMEAEKASTSGLGIKDEGDIKQAKKEDTDD

RNKMSVVTESSRNYGYNPSPVKPEGLRRPPSKTSMHQSRRLMASAQSNPDDVLTLSS

STESEGESGTSRKPTAGQTSATAVDSDDIQTISSGSEGDDFEDKKNMTGPMKRQVAV

KSTRGFALKSTHGIAIKSTNMASVDKGESAPVRKNTRQFYDGEESCYIIDAKLEGNLGR

YLNHSCSPNLFVQNVFVDTHDLRFPWVAFFASKRIRAGTELTWDYNYEVGSVEGKELL

CCCGAIECRGRLL (the catalytic domain of human SETDB1; SEQ ID NO: 13)
VGCDCKDGCRDKSKCACHQLTIQATACTPGGQINPNSGYQYKRLEECLPTGVYECNK

RCKCDPNMCTNRLVQHGLQVRLQLFKTQNKGWGIRCLDDIAKGSFVCIYAGKILTDDFA

DKEGLEMGDEYFANLDHIESVENFKEGYESDAPCSSDSSGVDLKDQEDGNSGTEDPE

ESNDDSSDDNFCKDEDFSTSSVWRSYATRRQTRGQKENGLSETTSKDSHPPDLGPPH

IPVPPSIPVGGCNPPSSEETPKNKVASWLSCNSVSEGGFADSDSHSSFKTNEGGEGRA

GGSRMEAEKASTSGLGIKDEGDIKQAKKEDTDDRNKMSVVTESSRNYGYNPSPVKPE

GLRRPPSKTSMHQSRRLMASAQSNPDDVLTLSSSTESEGESGTSRKPTAGQTSATAV

DSDDIQTISSGSEGDDFEDKKNMTGPMKRQVAVKSTRGFALKSTHGIAIKSTNMASVDK

GESAPVRKNTRQFYDGEESCYIIDAKLEGNLGRYLNHSCSPNLFVQNVFVDTHDLRFP

WVAFFASKRIRAGTELTWDYNYEVGSVEGKELLCCCGAIECRGRLL

The ATR of the present invention may, for example, comprise an amino acid sequence that has 50%, 60%, 70%, 80%, 90%, 95%, 99% or 100% identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

The ATR of the present invention may, for example, be encoded by a polynucleotide comprising a nucleic acid sequence which encodes the protein of SEQ ID NOs: 1, 2, 3, 4, 5, 6, 7, 8, 9, 10, 11, 12 or 13, or a protein that has 50%, 60%, 70%, 80%, 90%, 95%, 99% or 100% amino acid identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or13.

The ATR of the present invention may, for example, comprise an amino acid sequence that has at least 50%, 60%, 70%, 80%, 90%, 95%, 99% or 100% identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

The ATR of the present invention may, for example, be encoded by a polynucleotide comprising a nucleic acid sequence which encodes the protein of SEQ ID NOs: 1, 2, 3, 4, 5, 6, 7, 8, 9, 10, 11, 12 or 13, or a protein that has at least 50%, 60%, 70%, 80%, 90%, 95%, 99% or 100% amino acid identity to SEQ ID NOs: 1, 2, 3, 4, 5, 6, 7, 8, 9, 10, 11, 12 or 13 wherein the amino acid sequence substantially retains the natural function of the protein represented by SEQ ID NOs: 1, 2, 3, 4, 5, 6, 7, 8, 9, 10, 11, 12 or 13.

DNA-Binding Domains

The ATRs of the invention comprise a DNA-binding domain which binds a specific nucleic acid sequence and enables the ATR to be targeted to specific site in a polynucleotide, for example the genome of a cell. The DNA-binding domain may, for example, be protein-, DNA-, RNA- or chemical-based.

A number of suitable DNA-binding domains are known in the art, for example transcription-activator like effector (TALE) domains and zinc finger proteins (ZFPs) (Gaj, T. et al. (2013) *Trends Biotechnol.* 31: 397-405).

The tetracycline-controlled repressor (tetR) DNA-binding domain, for example the *E. coli* tetR DNA-binding domain (Gossen, M. et al. (1992) *Proc. Natl. Acad. Sci. USA* 89: 5547-51), may also be employed as a suitable DNA-binding domain in the ATRs of the present invention. The tetR system is particularly advantageous for use in model systems, because it allows temporal control of binding of tetR to its target nucleotide sequence, the tetracycline operon (TetO), by doxycycline (doxy) administration. This allows investigation of whether the chromatin states induced by the ATRs can be maintained after the release of the ATRs from their target locus.

In addition, methods for the engineering of DNA-binding domains to bind to desired nucleic acid sequences are known in the art.

Example sequences of suitable TALE domains include:

```
                                              (SEQ ID NO: 14)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPEQVVAIA

SNIGGKQALETVQRLLPVLCQAHGLTPEQVVAIASHDGGKQALETVQRLLPVLCQAHGL

TPEQVVAIASHDGGKQALETVQRLLPVLCQAHGLTPEQVVAIASHDGGKQALETVQRLL

PVLCQAHGLTPEQVVAIASNIGGKQALETVQRLLPVLCQAHGLTPEQVVAIASNNGGKQ

ALETVQRLLPVLCQAHGLTPEQVVAIASNIGGKQALETVQRLLPVLCQAHGLTPEQVVAI

ASNGGGKQALETVQRLLPVLCQAHGLTPEQVVAIASNGGGKQALETVQRLLPVLCQAH

GLTPEQVVAIASNNGGKQALETVQRLLPVLCQAHGLTPEQVVAIASNNGGKQALETVQ

RLLPVLCQAHGLTPEQVVAIASHDGGKQALETVQRLLPVLCQAHGLTPEQVVAIASHDG

GKQALETVQRLLPVLCQAHGLTPEQVVAIASHDGGKQALETVQRLLPVLCQAHGLTPE

QVVAIASHDGGKQALETVQRLLPVLCQAHGLTPEQVVAIASNIGGKQALETVQRLLPVL

CQAHGLTPEQVVAIASHDGGKQALETVQRLLPVLCQAHGLTPQQVVAIASNGGGRPAL

ESIVAQLSRPDPALAALTNDHLVALACLGGRPALDAVKKGLPHAPALIKRTNRRIPERTS

HRVA,

which targets the binding site:
                                              (SEQ ID NO: 34)
5'-TACCCAGATTGGCCCCACT-3'
and:

                                              (SEQ ID NO: 15)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPEQVVAIA

SNIGGKQALETVQRLLPVLCQAHGLTPEQVVAIASHDGGKQALETVQRLLPVLCQAHGL

TPEQVVAIASHDGGKQALETVQRLLPVLCQAHGLTPEQVVAIASNGGGKQALETVQRL

LPVLCQAHGLTPEQVVAIASNIGGKQALETVQRLLPVLCQAHGLTPEQVVAIASNNGGK

QALETVQRLLPVLCQAHGLTPEQVVAIASNIGGKQALETVQRLLPVLCQAHGLTPEQVV

AIASNNGGKQALETVQRLLPVLCQAHGLTPEQVVAIASNNGGKQALETVQRLLPVLCQA

HGLTPEQVVAIASNIGGKQALETVQRLLPVLCQAHGLTPEQVVAIASNNGGKQALETVQ

RLLPVLCQAHGLTPEQVVAIASNIGGKQALETVQRLLPVLCQAHGLTPEQVVAIASNIGG
```

-continued

KQALETVQRLLPVLCQAHGLTPEQVVAIASNIGGKQALETVQRLLPVLCQAHGLTPEQV
VAIASNNGGKQALETVQRLLPVLCQAHGLTPEQVVAIASNNGGKQALETVQRLLPVLCQ
AHGLTPEQVVAIASNGGGKQALETVQRLLPVLCQAHGLTPQQVVAIASNGGGRPALESI
VAQLSRPDPALAALTNDHLVALACLGGRPALDAVKKGLPHAPALIKRTNRRIPERTSHR
VA, which targets the binding site:

(SEQ ID NO: 35)
5'-TACCTAGAGGAGAAAGGTT-3'

Example sequences of TALE domains that have been designed to target the promoter region of the β2-microglobulin gene include:

(SEQ ID NO: 16)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASNGGGKQALETVQ
RLLPVLCQDHGLTPDQVVAIASHDGGKQALETVQRLLPVLCQDHGLTPDQVVAIASHD
GGKQALETVQRLLPVLCQDHGLTPDQVVAIASNGGGKQALETVQRLLPVLCQDHGLTP
DQVVAIASNIGGKQALETVQRLLPVLCQDHGLTPDQVVAIASHDGGKQALETVQRLLPV
LCQDHGLTPDQVVAIASHDGGKQALETVQRLLPVLCQDHGLTPDQVVAIASHDGGKQA
LETVQRLLPVLCQDHGLTPDQVVAIASNGGGKQALETVQRLLPVLCQDHGLTPDQVVAI
ASHDGGKQALETVQRLLPVLCQDHGLTPDQVVAIASHDGGKQALETVQRLLPVLCQDH
GLTPDQVVAIASHDGGKQALETVQRLLPVLCQDHGLTPDQVVAIASNHGGKQALETVQ
RLLPVLCQDHGLTPDQVVAIASHDGGKQALETVQRLLPVLCQDHGLTPDQVVAIASNG
GGKQALESIVAQLSRPDPALAALTNDHLVALACLGGRPALDAVKKGLPHAPALIKRTNR
RIPERTSHRVAGSGGG, which targets the binding site:

(SEQ ID NO: 17)
5'-TCTCTCCTACCCTCCCGCT-3'

(SEQ ID NO: 18)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SNNGGKQALETVQRLLPVLCQDHGLTPDQVVAIASNNGGKQALETVQRLLPVLCQDH
GLTPDQVVAIASNGGGKQALETVQRLLPVLCQDHGLTPDQVVAIASHDGGKQALETVQ
RLLPVLCQDHGLTPDQVVAIASHDGGKQALETVQRLLPVLCQDHGLTPDQVVAIASNG
GGKQALETVQRLLPVLCQDHGLTPDQVVAIASNGGGKQALETVQRLLPVLCQDHGLTP
DQVVAIASHDGGKQALETVQRLLPVLCQDHGLTPDQVVAIASHDGGKQALETVQRLLP
VLCQDHGLTPDQVVAIASNGGGKQALETVQRLLPVLCQDHGLTPDQVVAIASHDGGKQ
ALETVQRLLPVLCQDHGLTPDQVVAIASNGGGKQALETVQRLLPVLCQDHGLTPDQVV
AIASHDGGKQALETVQRLLPVLCQDHGLTPDQVVAIASHDGGKQALETVQRLLPVLCQ
DHGLTPDQVVAIASHDGGKQALETVQRLLPVLCQDHGLTPDQVVAIASNGGGKQALET

-continued

VQRLLPVLCQDHGLTPDQVVAIASHDGGKQALETVQRLLPVLCQDHGLTPDQVVAIAS

NGGGKQALESIVAQLSRPDPALAALTNDHLVALACLGGRPALDAVKKGLPHAPALIKRT

NRRIPERTSHRVAGSGGG, which targets the binding site:

(SEQ ID NO: 19)
5'-TGGTCCTTCCTCTCCCGCT-3'

(SEQ ID NO: 20)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASNNGGKQALETVQRLLPVLCQDH

GLTPDQVVAIASHDGGKQALETVQRLLPVLCQDHGLTPDQVVAIASNGGGKQALETVQ

RLLPVLCQDHGLTPDQVVAIASHDGGKQALETVQRLLPVLCQDHGLTPDQVVAIASHD

GGKQALETVQRLLPVLCQDHGLTPDQVVAIASNNGGKQALETVQRLLPVLCQDHGLTP

DQVVAIASNGGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASHDGGKQ

ALETVQRLLPVLCQDHGLTPDQVVAIASNGGGKQALETVQRLLPVLCQDHGLTPDQVV

AIASNGGGKQALETVQRLLPVLCQDHGLTPDQVVAIASHDGGKQALETVQRLLPVLCQ

DHGLTPDQVVAIASHDGGKQALETVQRLLPVLCQDHGLTPDQVVAIASHDGGKQALET

VQRLLPVLCQDHGLTPDQVVAIASNGGGKQALETVQRLLPVLCQDHGLTPDQVVAIAS

NGGGKQALESIVAQLSRPDPALAALTNDHLVALACLGGRPALDAVKKGLPHAPALIKRT

NRRIPERTSHRVAGSGGG, which targets the binding site:

(SEQ ID NO: 21)
5'-TCGCTCCGTGACTTCCCTT-3'

Example sequences of TALE domains that have been designed to target the BCL11A gene include:

TALE BCL11A #1

(SEQ ID NO: 37)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASNNGGKQALETVQ

RLLPVLCQDHGLTPDQVVAIASNNGGKQALETVQRLLPVLCQDHGLTPDQVVAIASNG

GGKQALETVQRLLPVLCQDHGLTPDQVVAIASHDGGKQALETVQRLLPVLCQDHGLTP

DQVVAIASHDGGKQALETVQRLLPVLCQDHGLTPDQVVAIASNNGGKQALETVQRLLP

VLCQDHGLTPDQVVAIASHDGGKQALETVQRLLPVLCQDHGLTPDQVVAIASHDGGKQ

ALETVQRLLPVLCQDHGLTPDQVVAIASHDGGKQALETVQRLLPVLCQDHGLTPDQVV

AIASHDGGKQALETVQRLLPVLCQDHGLTPDQVVAIASHDGGKQALETVQRLLPVLCQ

-continued

DHGLTPDQVVAIASNIGGKQALETVQRLLPVLCQDHGLTPDQVVAIASNNGGKQALETV

QRLLPVLCQDHGLTPDQVVAIASHDGGKQALETVQRLLPVLCQDHGLTPDQVVAIASNI

GGKQALESIVAQLSRPDPALAALTNDHLVALACLGGRPALDAVKKGLPHAPALIKRTNR

RIPERTSHRVAGSGGG, which targets the binding site:

(SEQ ID NO: 38)
5'-TCCAAAAGCCAGTCTCACC-3'

TALE BCL11A #2

(SEQ ID NO: 39)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SNNGGKQALETVQRLLPVLCQDHGLTPDQVVAIASHDGGKQALETVQRLLPVLCQDH

GLTPDQVVAIASHDGGKQALETVQRLLPVLCQDHGLTPDQVVAIASNNGGKQALETVQ

RLLPVLCQDHGLTPDQVVAIASNIGGKQALETVQRLLPVLCQDHGLTPDQVVAIASNNG

GKQALETVQRLLPVLCQDHGLTPDQVVAIASNIGGKQALETVQRLLPVLCQDHGLTPD

QVVAIASHDGGKQALETVQRLLPVLCQDHGLTPDQVVAIASHDGGKQALETVQRLLPV

LCQDHGLTPDQVVAIASNGGGKQALETVQRLLPVLCQDHGLTPDQVVAIASHDGGKQA

LETVQRLLPVLCQDHGLTPDQVVAIASNGGGKQALETVQRLLPVLCQDHGLTPDQVVAI

ASNGGGKQALETVQRLLPVLCQDHGLTPDQVVAIASHDGGKQALETVQRLLPVLCQDH

GLTPDQVVAIASNGGGKQALETVQRLLPVLCQDHGLTPDQVVAIASHDGGKQALETVQ

RLLPVLCQDHGLTPDQVVAIASNNGGKQALETVQRLLPVLCQDHGLTPDQVVAIASNIG

GKQALESIVAQLSRPDPALAALTNDHLVALACLGGRPALDAVKKGLPHAPALIKRTNRRI

PERTSHRVAGSGGG, which targets the binding site:

(SEQ ID NO: 40)
5'-TCTCCCCGGGAATCGTTTT-3'

TALE BCL11A #3

(SEQ ID NO: 41)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASNNGGKQALETVQRLLPVLCQDH

GLTPDQVVAIASNNGGKQALETVQRLLPVLCQDHGLTPDQVVAIASHDGGKQALETVQ

RLLPVLCQDHGLTPDQVVAIASNGGGKQALETVQRLLPVLCQDHGLTPDQVVAIASNG

GGKQALETVQRLLPVLCQDHGLTPDQVVAIASNGGGKQALETVQRLLPVLCQDHGLTP

DQVVAIASNNGGKQALETVQRLLPVLCQDHGLTPDQVVAIASHDGGKQALETVQRLLP

VLCQDHGLTPDQVVAIASNIGGKQALETVQRLLPVLCQDHGLTPDQVVAIASNIGGKQA

LETVQRLLPVLCQDHGLTPDQVVAIASNIGGKQALETVQRLLPVLCQDHGLTPDQVVAI

ASNHGGKQALETVQRLLPVLCQDHGLTPDQVVAIASHDGGKQALETVQRLLPVLCQDH

GLTPDQVVAIASNIGGKQALETVQRLLPVLCQDHGLTPDQVVAIASNGGGKQALETVQR

LLPVLCQDHGLTPDQVVAIASNGGGKQALETVQRLLPVLCQDHGLTPDQVVAIASNGG

GKQALESIVAQLSRPDPALAALTNDHLVALACLGGRPALDAVKKGLPHAPALIKRTNRRI

PERTSHRVAGSGGG,

-continued which targets the binding site:

(SEQ ID NO: 42)
5'-TCCTCCCGCTGCACACTTG-3'

TALE BCL11A #4

(SEQ ID NO: 43)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SNNGGKQALETVQRLLPVLCQDHGLTPDQVVAIASHDGGKQALETVQRLLPVLCQDH
GLTPDQVVAIASNIGGKQALETVQRLLPVLCQDHGLTPDQVVAIASNIGGKQALETVQR
LLPVLCQDHGLTPDQVVAIASNIGGKQALETVQRLLPVLCQDHGLTPDQVVAIASNNGG
KQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASNNGGKQALETVQRLLPVLC
QDHGLTPDQVVAIASNIGGKQALETVQRLLPVLCQDHGLTPDQVVAIASNNGGKQALET
VQRLLPVLCQDHGLTPDQVVAIASNGGGKQALETVQRLLPVLCQDHGLTPDQVVAIAS
NGGGKQALETVQRLLPVLCQDHGLTPDQVVAIASNGGGKQALETVQRLLPVLCQDHG
LTPDQVVAIASHDGGKQALETVQRLLPVLCQDHGLTPDQVVAIASNIGGKQALETVQRL
LPVLCQDHGLTPDQVVAIASHDGGKQALETVQRLLPVLCQDHGLTPDQVVAIASHDGG
KQALESIVAQLSRPDPALAALTNDHLVALACLGGRPALDAVKKGLPHAPALIKRTNRRIP
ERTSHRVAGSGGG, which targets the binding site:

(SEQ ID NO: 44)
5'-TAGTCATCCCCACAATAGT-3'

TALE BCL11A #5

(SEQ ID NO: 45)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGOLLKIAKRGGVTAVEAVHAWRNALTGAPLNLTPDQVVAIA
SNIGGKQALETVQRLLPVLCQDHGLTPDQVVAIASHDGGKQALETVQRLLPVLCQDHG
LTPDQVVAIASNIGGKQALETVQRLLPVLCQDHGLTPDQVVAIASNNGGKQALETVQRL
LPVLCQDHGLTPDQVVAIASNGGGKQALETVQRLLPVLCQDHGLTPDQVVAIASNGGG
KQALETVQRLLPVLCQDHGLTPDQVVAIASNNGGKQALETVQRLLPVLCQDHGLTPDQ
VVAIASHDGGKQALETVQRLLPVLCQDHGLTPDQVVAIASHDGGKQALETVQRLLPVLC
QDHGLTPDQVVAIASHDGGKQALETVQRLLPVLCQDHGLTPDQVVAIASNGGGKQALE
TVQRLLPVLCQDHGLTPDQVVAIASNNGGKQALETVQRLLPVLCQDHGLTPDQVVAIAS
HDGGKQALETVQRLLPVLCQDHGLTPDQVVAIASNIGGKQALETVQRLLPVLCQDHGL
TPDQVVAIASNIGGKQALETVQRLLPVLCQDHGLTPDQVVAIASNIGGKQALETVQRLLP
VLCQDHGLTPDQVVAIASNIGGKQALETVQRLLPVLCQDHGLTPDQVVAIASNGGGKQ
ALESIVAQLSRPDPALAALTNDHLVALACLGGRPALDAVKKGLPHAPALIKRTNRRIPER
TSHRVAGSGGG, which targets the binding site:

(SEQ ID NO: 46)
5'-TCCCGCTGCCTTTTGTGCC-3'

TALE BCL11A #6

(SEQ ID NO: 47)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE

-continued

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASHDGGKQALETVQRLLPVLCQDH

GLTPDQVVAIASNNGGKQALETVQRLLPVLCQDHGLTPDQVVAIASHDGGKQALETVQ

RLLPVLCQDHGLTPDQVVAIASHDGGKQALETVQRLLPVLCQDHGLTPDQVVAIASHD

GGKQALETVQRLLPVLCQDHGLTPDQVVAIASNGGGKQALETVQRLLPVLCQDHGLTP

DQVVAIASNNGGKQALETVQRLLPVLCQDHGLTPDQVVAIASNNGGKQALETVQRLLP

VLCQDHGLTPDQVVAIASNNGGKQALETVQRLLPVLCQDHGLTPDQVVAIASNGGGKQ

ALETVQRLLPVLCQDHGLTPDQVVAIASNIGGKQALETVQRLLPVLCQDHGLTPDQVVA

IASHDGGKQALETVQRLLPVLCQDHGLTPDQVVAIASNGGGKQALETVQRLLPVLCQD

HGLTPDQVVAIASNGGGKQALETVQRLLPVLCQDHGLTPDQVVAIASNGGGKQALETV

QRLLPVLCQDHGLTPDQVVAIASHDGGKQALETVQRLLPVLCQDHGLTPDQVVAIASN

GGGKQALESIVAQLSRPDPALAALTNDHLVALACLGGRPALDAVKKGLPHAPALIKRTN

RRIPERTSHRVAGSGGG, which targets the binding site:
(SEQ ID NO: 48)
5'-TCCTCGCGCTTGCCCTCCC-3'

TALE BCL11A #7
(SEQ ID NO: 49)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASNGGGKQALETVQRLLPVLCQDH

GLTPDQVVAIASHDGGKQALETVQRLLPVLCQDHGLTPDQVVAIASNGGGKQALETVQ

RLLPVLCQDHGLTPDQVVAIASNGGGKQALETVQRLLPVLCQDHGLTPDQVVAIASNN

GGKQALETVQRLLPVLCQDHGLTPDQVVAIASNGGGKQALETVQRLLPVLCQDHGLTP

DQVVAIASHDGGKQALETVQRLLPVLCQDHGLTPDQVVAIASHDGGKQALETVQRLLP

VLCQDHGLTPDQVVAIASNIGGKQALETVQRLLPVLCQDHGLTPDQVVAIASHDGGKQ

ALETVQRLLPVLCQDHGLTPDQVVAIASNIGGKQALETVQRLLPVLCQDHGLTPDQVVA

IASNHGGKQALETVQRLLPVLCQDHGLTPDQVVAIASHDGGKQALETVQRLLPVLCQD

HGLTPDQVVAIASNGGGKQALETVQRLLPVLCQDHGLTPDQVVAIASHDGGKQALETV

QRLLPVLCQDHGLTPDQVVAIASNNGGKQALETVQRLLPVLCQDHGLTPDQVVAIASN

NGGKQALESIVAQLSRPDPALAALTNDHLVALACLGGRPALDAVKKGLPHAPALIKRTN

RRIPERTSHRVAGSGGG, which targets the binding site:
(SEQ ID NO: 50)
5'-TCCCCCGGCCCTAGCTCCT-3'

TALE BCL11A #8
(SEQ ID NO: 51)
MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASNGGGKQALETVQRLLPVLCQDH

GLTPDQVVAIASHDGGKQALETVQRLLPVLCQDHGLTPDQVVAIASHDGGKQALETVQ

RLLPVLCQDHGLTPDQVVAIASHDGGKQALETVQRLLPVLCQDHGLTPDQVVAIASNN

-continued

GGKQALETVQRLLPVLCQDHGLTPDQVVAIASHDGGKQALETVQRLLPVLCQDHGLTP

DQVVAIASNGGGKQALETVQRLLPVLCQDHGLTPDQVVAIASNNGGKQALETVQRLLP

VLCQDHGLTPDQVVAIASNIGGKQALETVQRLLPVLCQDHGLTPDQVVAIASHDGGKQ

ALETVQRLLPVLCQDHGLTPDQVVAIASNGGGKQALETVQRLLPVLCQDHGLTPDQVV

AIASNHGGKQALETVQRLLPVLCQDHGLTPDQVVAIASHDGGKQALETVQRLLPVLCQ

DHGLTPDQVVAIASNHGGKQALETVQRLLPVLCQDHGLTPDQVVAIASHDGGKQALET

VQRLLPVLCQDHGLTPDQVVAIASHDGGKQALETVQRLLPVLCQDHGLTPDQVVAIAS

NGGGKQALESIVAQLSRPDPALAALTNDHLVALACLGGRPALDAVKKGLPHAPALIKRT

NRRIPERTSHRVAGSGGG, which targets the binding site:

(SEQ ID NO: 52)

5'-TCCTGGTCCGCCCCCAGCA-3'

TALE BCL11A #9

(SEQ ID NO: 53)

MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SHDGGKQALETVQRLLPVLCQDHGLTPDQVVAIASHDGGKQALETVQRLLPVLCQDH

GLTPDQVVAIASHDGGKQALETVQRLLPVLCQDHGLTPDQVVAIASNGGGKQALETVQ

RLLPVLCQDHGLTPDQVVAIASNGGGKQALETVQRLLPVLCQDHGLTPDQVVAIASNN

GGKQALETVQRLLPVLCQDHGLTPDQVVAIASHDGGKQALETVQRLLPVLCQDHGLTP

DQVVAIASNGGGKQALETVQRLLPVLCQDHGLTPDQVVAIASNNGGKQALETVQRLLP

VLCQDHGLTPDQVVAIASHDGGKQALETVQRLLPVLCQDHGLTPDQVVAIASHDGGKQ

ALETVQRLLPVLCQDHGLTPDQVVAIASNIGGKQALETVQRLLPVLCQDHGLTPDQVVA

IASNIGGKQALETVQRLLPVLCQDHGLTPDQVVAIASNIGGKQALETVQRLLPVLCQDH

GLTPDQVVAIASHDGGKQALETVQRLLPVLCQDHGLTPDQVVAIASNGGGKQALETVQ

RLLPVLCQDHGLTPDQVVAIASNGGGKQALETVQRLLPVLCQDHGLTPDQVVAIASNG

GGKQALESIVAQLSRPDPALAALTNDHLVALACLGGRPALDAVKKGLPHAPALIKRTNR

RIPERTSHRVAGSGGG, which targets the binding site:

(SEQ ID NO: 54)

5'-TGCCGAGACCTCTTCTCGA-3'

TALE BCL11A #10

(SEQ ID NO: 55)

MGKPIPNPLLGLDSTGGMAPKKKRKVDGGVDLRTLGYSQQQQEKIKPKVRSTVAQHH

EALVGHGFTHAHIVALSQHPAALGTVAVKYQDMIAALPEATHEAIVGVGKQWSGARALE

ALLTVAGELRGPPLQLDTGQLLKIAKRGGVTAVEAVHAWRNALTGAPLNLTPDQVVAIA

SNNGGKQALETVKRLLPVLCQDHGLTPDQVVAIASNNGGKQALETVQRLLPVLCQDHG

LTPDQVVAIASNNGGKQALETVQRLLPVLCQDHGLTPDQVVAIASHDGGKQALETVQR

LLPVLCQDHGLTPDQVVAIASHDGGKQALETVQRLLPVLCQDHGLTPDQVVAIASHDG

GKQALETVQRLLPVLCQDHGLTPDQVVAIASNGGGKQALETVQRLLPVLCQDHGLTPD

QVVAIASHDGGKQALETVQRLLPVLCQDHGLTPDQVVAIASNIGGKQALETVQRLLPVL

CQDHGLTPDQVVAIASHDGGKQALETVQRLLPVLCQDHGLTPDQVVAIASNNGGKQAL

ETVQRLLPVLCQDHGLTPDQVVAIASHDGGKQALETVQRLLPVLCQDHGLTPDQVVAIA

SHDGGKQALETVQRLLPVLCQDHGLTPDQVVAIASNGGGKQALETVQRLLPVLCQDH

-continued

GLTPDQVVAIASNGGGKQALETVQRLLPVLCQDHGLTPDQVVAIASNGGGKQALETVQ
RLLPVLCQDHGLTPDQVVAIASHDGGKQALETVQRLLPVLCQDHGLTPDQVVAIASNG
GGKQALESIVAQLSRPDPALAALTNDHLVALACLGGRPALDAVKKGLPHAPALIKRTNR
RIPERTSHRVAGSGGG, which targets the binding site:

(SEQ ID NO: 56)
5'-TCGGCTTTGCAAAGCATTT-3'

TALE BCL11A #11

(SEQ ID NO: 57)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASNGGGKQALETVQRLLPVLCQDH
GLTPDQVVAIASHDGGKQALETVQRLLPVLCQDHGLTPDQVVAIASHDGGKQALETVQ
RLLPVLCQDHGLTPDQVVAIASHDGGKQALETVQRLLPVLCQDHGLTPDQVVAIASHD
GGKQALETVQRLLPVLCQDHGLTPDQVVAIASNNGGKQALETVQRLLPVLCQDHGLTP
DQVVAIASNNGGKQALETVQRLLPVLCQDHGLTPDQVVAIASNNGGKQALETVQRLLP
VLCQDHGLTPDQVVAIASNIGGKQALETVQRLLPVLCQDHGLTPDQVVAIASNIGGKQA
LETVQRLLPVLCQDHGLTPDQVVAIASNGGGKQALETVQRLLPVLCQDHGLTPDQVVAI
ASHDGGKQALETVQRLLPVLCQDHGLTPDQVVAIASNNGGKQALETVQRLLPVLCQDH
GLTPDQVVAIASNGGGKQALETVQRLLPVLCQDHGLTPDQVVAIASNGGGKQALETVQ
RLLPVLCQDHGLTPDQVVAIASNGGGKQALETVQRLLPVLCQDHGLTPDQVVAIASNG
GGKQALESIVAQLSRPDPALAALTNDHLVALACLGGRPALDAVKKGLPHAPALIKRTNR
RIPERTSHRVAGSGGG, which targets the binding site:

(SEQ ID NO: 58)
5'-TGCAAAGCCGAGTTTCACC-3'

TALE BCL11A #12

(SEQ ID NO: 59)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASHDGGKQALETVQRLLPVLCQDH
GLTPDQVVAIASNIGGKQALETVQRLLPVLCQDHGLTPDQVVAIASNIGGKQALETVQR
LLPVLCQDHGLTPDQVVAIASNIGGKQALETVQRLLPVLCQDHGLTPDQVVAIASNIGGK
QALETVQRLLPVLCQDHGLTPDQVVAIASNHGGKQALETVQRLLPVLCQDHGLTPDQV
VAIASHDGGKQALETVQRLLPVLCQDHGLTPDQVVAIASHDGGKQALETVQRLLPVLC
QDHGLTPDQVVAIASNIGGKQALETVQRLLPVLCQDHGLTPDQVVAIASNNGGKQALET
VQRLLPVLCQDHGLTPDQVVAIASNGGGKQALETVQRLLPVLCQDHGLTPDQVVAIAS
HDGGKQALETVQRLLPVLCQDHGLTPDQVVAIASNGGGKQALETVQRLLPVLCQDHGL
TPDQVVAIASHDGGKQALETVQRLLPVLCQDHGLTPDQVVAIASNIGGKQALETVQRLL
PVLCQDHGLTPDQVVAIASHDGGKQALETVQRLLPVLCQDHGLTPDQVVAIASHDGGK
QALESIVAQLSRPDPALAALTNDHLVALACLGGRPALDAVKKGLPHAPALIKRTNRRIPE
RTSHRVAGSGGG,

-continued which targets the binding site:

(SEQ ID NO: 60)
5'-TACAGTTGCCCTGCAAAAT-3'

TALE BCL11A #13

(SEQ ID NO: 61)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASHDGGKQALETVQRLLPVLCQDH
GLTPDQVVAIASNGGGKQALETVQRLLPVLCQDHGLTPDQVVAIASHDGGKQALETVQ
RLLPVLCQDHGLTPDQVVAIASHDGGKQALETVQRLLPVLCQDHGLTPDQVVAIASHD
GGKQALETVQRLLPVLCQDHGLTPDQVVAIASNNGGKQALETVQRLLPVLCQDHGLTP
DQVVAIASHDGGKQALETVQRLLPVLCQDHGLTPDQVVAIASNGGGKQALETVQRLLP
VLCQDHGLTPDQVVAIASNNGGKQALETVQRLLPVLCQDHGLTPDQVVAIASHDGGKQ
ALETVQRLLPVLCQDHGLTPDQVVAIASNIGGKQALETVQRLLPVLCQDHGLTPDQVVA
IASHDGGKQALETVQRLLPVLCQDHGLTPDQVVAIASNIGGKQALETVQRLLPVLCQDH
GLTPDQVVAIASHDGGKQALETVQRLLPVLCQDHGLTPDQVVAIASNGGGKQALETVQ
RLLPVLCQDHGLTPDQVVAIASNGGGKQALETVQRLLPVLCQDHGLTPDQVVAIASNN
GGKQALESIVAQLSRPDPALAALTNDHLVALACLGGRPALDAVKKGLPHAPALIKRTNR
RIPERTSHRVAGSGGG, which targets the binding site:

(SEQ ID NO: 62)
5'-TCCGCCCTGGGTACTTTCT-3'

TALE BCL11A #14

(SEQ ID NO: 63)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SNIGGKQALETVQRLLPVLCQDHGLTPDQVVAIASNNGGKQALETVQRLLPVLCQDHG
LTPDQVVAIASNGGGKQALETVQRLLPVLCQDHGLTPDQVVAIASHDGGKQALETVQR
LLPVLCQDHGLTPDQVVAIASNIGGKQALETVQRLLPVLCQDHGLTPDQVVAIASNGGG
KQALETVQRLLPVLCQDHGLTPDQVVAIASHDGGKQALETVQRLLPVLCQDHGLTPDQ
VVAIASHDGGKQALETVQRLLPVLCQDHGLTPDQVVAIASHDGGKQALETVQRLLPVLC
QDHGLTPDQVVAIASHDGGKQALETVQRLLPVLCQDHGLTPDQVVAIASNIGGKQALET
VQRLLPVLCQDHGLTPDQVVAIASHDGGKQALETVQRLLPVLCQDHGLTPDQVVAIAS
NIGGKQALETVQRLLPVLCQDHGLTPDQVVAIASNIGGKQALETVQRLLPVLCQDHGLT
PDQVVAIASNGGGKQALETVQRLLPVLCQDHGLTPDQVVAIASNIGGKQALETVQRLLP
VLCQDHGLTPDQVVAIASNNGGKQALETVQRLLPVLCQDHGLTPDQVVAIASNGGGKQ
ALESIVAQLSRPDPALAALTNDHLVALACLGGRPALDAVKKGLPHAPALIKRTNRRIPER
TSHRVAGSGGG, which targets the binding site:

(SEQ ID NO: 64)
5'-TCTCTTGTCCACAGCTCGG-3'

TALE BCL11A #15

(SEQ ID NO: 65),
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE

-continued

ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASHDGGKQALETVQRLLPVLCQDH
GLTPDQVVAIASHDGGKQALETVQRLLPVLCQDHGLTPDQVVAIASNNGGKQALETVQ
RLLPVLCQDHGLTPDQVVAIASHDGGKQALETVQRLLPVLCQDHGLTPDQVVAIASNG
GGKQALETVQRLLPVLCQDHGLTPDQVVAIASNNGGKQALETVQRLLPVLCQDHGLTP
DQVVAIASHDGGKQALETVQRLLPVLCQDHGLTPDQVVAIASHDGGKQALETVQRLLP
VLCQDHGLTPDQVVAIASNGGGKQALETVQRLLPVLCQDHGLTPDQVVAIASNGGGKQ
ALETVQRLLPVLCQDHGLTPDQVVAIASNGGGKQALETVQRLLPVLCQDHGLTPDQVV
AIASNGGGKQALETVQRLLPVLCQDHGLTPDQVVAIASNNGGKQALETVQRLLPVLCQ
DHGLTPDQVVAIASNGGGKQALETVQRLLPVLCQDHGLTPDQVVAIASNNGGKQALET
VQRLLPVLCQDHGLTPDQVVAIASHDGGKQALETVQRLLPVLCQDHGLTPDQVVAIAS
HDGGKQALESIVAQLSRPDPALAALTNDHLVALACLGGRPALDAVKKGLPHAPALIKRT
NRRIPERTSHRVAGSGGG which targets the binding site:

(SEQ ID NO: 66)
5'-TCTCCCGCTGACTGCGCCT-3'

TALE BCL11A #16

(SEQ ID NO: 67)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASHDGGKQALETVQRLLPVLCQDH
GLTPDQVVAIASNGGGKQALETVQRLLPVLCQDHGLTPDQVVAIASHDGGKQALETVQ
RLLPVLCQDHGLTPDQVVAIASNNGGKQALETVQRLLPVLCQDHGLTPDQVVAIASHD
GGKQALETVQRLLPVLCQDHGLTPDQVVAIASNNGGKQALETVQRLLPVLCQDHGLTP
DQVVAIASHDGGKQALETVQRLLPVLCQDHGLTPDQVVAIASNGGGKQALETVQRLLP
VLCQDHGLTPDQVVAIASNGGGKQALETVQRLLPVLCQDHGLTPDQVVAIASNNGGKQ
ALETVQRLLPVLCQDHGLTPDQVVAIASHDGGKQALETVQRLLPVLCQDHGLTPDQVV
AIASHDGGKQALETVQRLLPVLCQDHGLTPDQVVAIASHDGGKQALETVQRLLPVLCQ
DHGLTPDQVVAIASNGGGKQALETVQRLLPVLCQDHGLTPDQVVAIASHDGGKQALET
VQRLLPVLCQDHGLTPDQVVAIASHDGGKQALETVQRLLPVLCQDHGLTPDQVVAIAS
HDGGKQALESIVAQLSRPDPALAALTNDHLVALACLGGRPALDAVKKGLPHAPALIKRT
NRRIPERTSHRVAGSGGG, which targets the binding site:

(SEQ ID NO: 68)
5'-TCCCTTGCTGCCAAACTTT-3'

TALE BCL11A #17

(SEQ ID NO: 69)
MGKPIPNPLLGLDSTGGMAPKKKRKVDGGVDLRTLGYSQQQQEKIKPKVRSTVAQHH
EALVGHGFTHAHIVALSQHPAALGTVAVKYQDMIAALPEATHEAIVGVGKQWSGARALE
ALLTVAGELRGPPLQLDTGQLLKIAKRGGVTAVEAVHAWRNALTGAPLNLTPDQVVAIA
SHDGGKQALETVQRLLPVLCQDHGLTPDQVVAIASHDGGKQALETVQRLLPVLCQDH
GLTPDQVVAIASHDGGKQALETVQRLLPVLCQDHGLTPDQVVAIASHDGGKQALETVQ
RLLPVLCQDHGLTPDQVVAIASHDGGKQALETVQRLLPVLCQDHGLTPDQVVAIASNN

-continued

```
GGKQALETVQRLLPVLCQDHGLTPDQVVAIASNNGGKQALETVQRLLPVLCQDHGLTP
DQVVAIASHDGGKQALETVQRLLPVLCQDHGLTPDQVVAIASHDGGKQALETVQRLLP
VLCQDHGLTPDQVVAIASHDGGKQALETVQRLLPVLCQDHGLTPDQVVAIASNGGGKQ
ALETVQRLLPVLCQDHGLTPDQVVAIASNIGGKQALETVQRLLPVLCQDHGLTPDQVVA
IASNNGGKQALETVQRLLPVLCQDHGLTPDQVVAIASHDGGKQALETVQRLLPVLCQD
HGLTPDQVVAIASNGGGKQALETVQRLLPVLCQDHGLTPDQVVAIASHDGGKQALETV
QRLLPVLCQDHGLTPDQVVAIASHDGGKQALETVQRLLPVLCQDHGLTPDQVVAIASN
GGGKQALESIVAQLSRPDPALAALTNDHLVALACLGGRPALDAVKKGLPHAPALIKRTN
RRIPERTSHRVAGSGGG,
which targets the binding site:
                                                  (SEQ ID NO: 70)
5'-TGGGCCCTCACGCCTTTCT-3'
```

Meganucleases (Silve, G. et al. (2011) *Cur. Gene Ther.* 11: 11-27) and CRISPR/Cas systems (Sander, J. D. et al. (2014) *Nat. Biotechnol.* 32: 347-55) may also be employed as suitable DNA-binding domains in the ATRs of the present invention.

The CRISPR/Cas system is an RNA-guided DNA binding system (van der Oost et al. (2014) *Nat. Rev. Microbiol.* 12: 479-92), wherein the guide RNA (gRNA) may be selected to enable an ATR comprising a Cas9 domain to be targeted to a specific sequence. Thus, to employ the CRISPR/Cas system as a DNA-binding domain in the present invention it is to be understood that an ATR effector domain may be operably linked to a Cas9 endonuclease. Preferably, the ATR effector domain is operably linked to a Cas9 endonuclease which has been inactivated such that it substantially does not possess nuclease activity. The ATR comprising the Cas9 endonuclease may be delivered to a target cell in combination with one or more guide RNAs (gRNAs). The guide RNAs are designed to target the ATR to a target gene of interest or a regulatory element (e.g. promoter, enhancer or splicing sites) of the target gene. Methods for the design of gRNAs are known in the art. Furthermore, fully orthogonal Cas9 proteins, as well as Cas9/gRNA ribonucleoprotein complexes and modifications of the gRNA structure/composition to bind different proteins, have been recently developed to simultaneously and directionally target different effector domains to desired genomic sites of the cells (Esvelt et al. (2013) *Nat. Methods* 10: 1116-21; Zetsche, B. et al. (2015) Cell pii: S0092-8674(15)01200-3; Dahlman, J. E. et al. (2015) Nat. Biotechnol. 2015 Oct. 5. doi: 10.1038/nbt.3390. [Epub ahead of print]; Zalatan, J. G. et al. (2015) Cell 160: 339-50; Paix, A. et al. (2015) Genetics 201: 47-54), and are suitable for use in the present invention.

For example, an ATR of the present invention may comprise the sequence:

```
                        (catalytically inactive Cas9; SEQ ID NO: 22)
MGGRRVRWEVYISRALWLTREPTAYWLIEINTTHYRETQATGATMYPYDVPDYASPKK
KRKVEASDKKYSIGLAIGTNSVGWAVITDEYKVPSKKFKVLGNTDRHSIKKNLIGALLFD
SGETAEATRLKRTARRRYTRRKNRICYLQEIFSNEMAKVDDSFFHRLEESFLVEEDKKH
ERHPIFGNIVDEVAYHEKYPTIYHLRKKLVDSTDKADLRLIYLALAHMIKFRGHFLIEGDLN
PDNSDVDKLFIQLVQTYNQLFEENPINASGVDAKAILSARLSKSRRLENLIAQLPGEKKN
GLFGNLIALSLGLTPNFKSNFDLAEDAKLQLSKDTYDDDLDNLLAQIGDQYADLFLAAKN
LSDAILLSDILRVNTEITKAPLSASMIKRYDEHHQDLTLLKALVRQQLPEKYKEIFFDQSK
NGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPW
NFEEVVDKGASAQSFIERMTNFDKNLPNEKVLPKHSLLYEYFTVYNELTKVKYVTEGMR
KPAFLSGEQKKAIVDLLFKTNRKVTVKQLKEDYFKKIECFDSVEISGVEDRFNASLGTYH
DLLKIIKDKDFLDNEENEDILEDIVLTLTLFEDREMIEERLKTYAHLFDDKVMKQLKRRRY
TGWGRLSRKLINGIRDKQSGKTILDFLKSDGFANRNFMQLIHDDSLTFKEDIQKAQVSG
QGDSLHEHIANLAGSPAIKKGILQTVKVVDELVKVMGRHKPENIVIEMARENQTTQKGQ
KNSRERMKRIEEGIKELGSQILKEHPVENTQLQNEKLYLYYLQNGRDMYVDQELDINRL
SDYDVDAIVPQSFLKDDSIDNKVLTRSDKNRGKSDNVPSEEVVKKMKNYWRQLLNAKLI
```

-continued

TORKFDNLTKAERGGLSELDKAGFIKRQLVETRQITKHVAQILDSRMNTKYDENDKLIRE

VKVITLKSKLVSDFRKDFQFYKVREINNYHHAHDAYLNAVVGTALIKKYPKLESEFVYGD

YKVYDVRKMIAKSEQEIGKATAKYFFYSNIMNFFKTEITLANGEIRKRPLIETNGETGEIV

WDKGRDFATVRKVLSMPQVNIVKKTEVQTGGFSKESILPKRNSDKLIARKKDWDPKKY

GGFDSPTVAYSVLVVAKVEKGKSKKLKSVKELLGITIMERSSFEKNPIDFLEAKGYKEVK

KDLIIKLPKYSLFELENGRKRMLASAGELQKGNELALPSKYVNFLYLASHYEKLKGSPED

NEQKQLFVEQHKHYLDEIIEQISEFSKRVILADANLDKVLSAYNKHRDKPIREQAENIIHLF

TLTNLGAPAAFKYFDTTIDRKRYTSTKEVLDATLIHQSITGLYETRIDLSQLGGDSPKKKR

KVG

The ATR of the present invention may, for example, comprise an amino acid sequence that has 50%, 60%, 70%, 80%, 90%, 95%, 99% or 100% identity to SEQ ID NO: 22 wherein the amino acid sequence substantially retains the natural function of the protein represented by SEQ ID NO: 22.

The ATR of the present invention may, for example, be encoded by a polynucleotide comprising a nucleic acid sequence which encodes the protein of SEQ ID NO: 22, or a protein that has 50%, 60%, 70%, 80%, 90%, 95%, 99% or 100% amino acid identity to SEQ ID NO: 22 wherein the amino acid sequence substantially retains the natural function of the protein represented by SEQ ID NO: 22.

The ATR of the present invention may, for example, comprise an amino acid sequence that has at least 50%, 60%, 70%, 80%, 90%, 95%, 99% or 100% identity to SEQ ID NO: 22 wherein the amino acid sequence substantially retains the natural function of the protein represented by SEQ ID NO: 22.

The ATR of the present invention may, for example, be encoded by a polynucleotide comprising a nucleic acid sequence which encodes the protein of SEQ ID NO: 22, or a protein that has at least 50%, 60%, 70%, 80%, 90%, 95%, 99% or 100% amino acid identity to SEQ ID NO: 22 wherein the amino acid sequence substantially retains the natural function of the protein represented by SEQ ID NO: 22.

Example sequences of genomic target sites recognised by guide RNAs (gRNAs) for use in targeting the β2-microglobulin gene include:

gRNA #1: (SEQ ID NO: 23)
TATAAGTGGAGGCGTCGCGC gRNA #2: (SEQ ID NO: 24)
GCCCGAATGCTGTCAGCTTC gRNA #3: (SEQ ID NO: 25)
TGCGTCGCTGGCTTGGAGAC gRNA #4: (SEQ ID NO: 26)
CCAATCAGGACAAGGCCCGC gRNA #5: (SEQ ID NO: 27)
AGGGTAGGAGAGACTCACGC

-continued gRNA #6: (SEQ ID NO: 28)
GCGGGCCACCAAGGAGAACT gRNA #7: (SEQ ID NO: 29)
GCTACTCTCTCTTTCTGGCC gRNA #8: (SEQ ID NO: 30)
CTCCCGCTCTGCACCCTCTG gRNA #9: (SEQ ID NO: 31)
TTTGGCCTACGGCGACGGGA gRNA #10: (SEQ ID NO: 32)
GGGGCAAGTAGCGCGCGTCC gRNA #11: (SEQ ID NO: 33)
TAGTCCAGGGCTGGATCTCG Example of guide RNAs (gRNAs) for use in targeting the β2-microglobulin gene include:

gRNA #1: (SEQ ID NO: 149)
UAUAAGUGGAGGCGUCGCGC gRNA #2: (SEQ ID NO: 150)
GCCCGAAUGCUGUCAGCUUC gRNA #3: (SEQ ID NO: 151)
UGCGUCGCUGGCUUGGAGAC gRNA #4: (SEQ ID NO: 152)
CCAAUCAGGACAAGGCCCGC gRNA #5: (SEQ ID NO: 153)
AGGGUAGGAGAGACUCACGC gRNA #6: (SEQ ID NO: 154)
GCGGGCCACCAAGGAGAACU gRNA #7: (SEQ ID NO: 155)
GCUACUCUCUCUUUCUGGCC gRNA #8: (SEQ ID NO: 156)
CUCCCGCUCUGCACCCUCUG

-continued gRNA #9:
(SEQ ID NO: 157)
UUUGGCCUACGGCGACGGGA gRNA #10:
(SEQ ID NO: 158)
GGGGCAAGUAGCGCGCGUCC gRNA #11:
(SEQ ID NO: 159)
UAGUCCAGGGCUGGAUCUCG All the above gRNAs may be fused to the gRNA scaffold with the following sequence:

(SEQ ID NO: 160)
GUUUAAGAGCUAUGCUGGAAACAGCAUAGCAAGUUUAAAUAAGG
CUAGUCCGUUAUUCAACUUGAAAAAGUGGCACCGAGUCGGUGCU.

Example sequences of gRNAs targeting the BCL11A gene include:

gRNA #1 against CpG 105:
(SEQ ID NO: 71)
GCCUUUCUGCAGACGUUCCC gRNA #2 against CpG 105:
(SEQ ID NO: 72)
UGGGUGUGCGCCUUGGCCGG gRNA #3 against CpG 105:
(SEQ ID NO: 73)
CGGUGGUGAGAUGACCGCCU gRNA #4 against CpG 105:
(SEQ ID NO: 74)
GGAAUGUGCUCACGGCGCCG gRNA #5 against CpG 105:
(SEQ ID NO: 75)
GACUGCCCGCGCUUUGUCCU gRNA #6 against CpG 105:
(SEQ ID NO: 76)
CCAGAGUCUGGCCCCCGGAG gRNA #7 against CpG 105:
(SEQ ID NO: 77)
UCUGCGACCCUUAGGAGCCG gRNA #8 against CpG 105:
(SEQ ID NO: 78)
GAGCGCCCCGCCAAGCGACU gRNA #9 against CpG 105:
(SEQ ID NO: 79)
CAAGUCUCCAGGAGCCCGCG gRNA #10 against CpG 105:
(SEQ ID NO: 80)
CGCGGAAUCCAGCCUAAGUU gRNA #11 against CpG 105:
(SEQ ID NO: 81)
CCCGCUGCGGAGCUGUAACU gRNA #1 against CpG 31:
(SEQ ID NO: 82)
CGCUCCUGAGUCCGCGGAGU gRNA #2 against CpG 31:
(SEQ ID NO: 83)
CACGGCUCUCCCCGUCGCCG -continued gRNA #3 against CpG 31:
(SEQ ID NO: 84)
CCGCCUUUUGUUCCGGCCAG gRNA #4 against CpG 31:
(SEQ ID NO: 85)
GCGCGAGGAGCCGGCACAAA gRNA #5 against CpG 31:
(SEQ ID NO: 86)
GCCACUUUCUCACUAUUGUG gRNA #6 against CpG 31:
(SEQ ID NO: 87)
GCUGCCUCUGAGGUUCGGUC gRNA #7 against CpG 31:
(SEQ ID NO: 88)
AAGGGCAGGAGCUAGGGCCG gRNA #8 against CpG 31:
(SEQ ID NO: 89)
GAGCCCGGACUGCUGCCUCC gRNA #1 against CpG 38:
(SEQ ID NO: 90)
GUUUACAAGCACCGCGUGUG gRNA #2 against CpG 38:
(SEQ ID NO: 91)
AACAGACAGAGGACCGAGCG gRNA #3 against CpG 38:
(SEQ ID NO: 92)
GGCGCCGGGUGGGCGAUCCG gRNA #4 against CpG 38:
(SEQ ID NO: 93)
GGUCGGGCAAGGCCCGGGCG gRNA #5 against CpG 38:
(SEQ ID NO: 94)
AAGAGGUCUCGGCAUUGUGC gRNA #6 against CpG 38:
(SEQ ID NO: 95)
GUUCCACAGCUUCGGGACCGCG gRNA #7 against CpG 38:
(SEQ ID NO: 96)
GAAAUCGGCUGGGUGAAACU gRNA #8 against CpG 38:
(SEQ ID NO: 97)
GCAGUGUCUCCGCGCCAGCC gRNA #9 against CpG 38:
(SEQ ID NO: 98)
CCUCCCCUCCCCUCCGCCCUGGG gRNA #1 against CpG 115:
(SEQ ID NO: 99)
UCCUCCUGUCCCGGGGUUAAAGG gRNA #2 against CpG 115:
(SEQ ID NO: 100)
CAUCUUUUGGGACACUCUAGGCUGG gRNA #3 against CpG 115:
(SEQ ID NO: 101)
AAGUCAGGCCCUUCUUCGGAAGG gRNA #4 against CpG 115:
(SEQ ID NO: 102)
GCAGCCUGGACUGCGCGCCCCGG gRNA #5 against CpG 115:
(SEQ ID NO: 103)
UGCCCGGCGAUUCUCGUCCG -continued gRNA #6 against CpG 115:
(SEQ ID NO: 104)
UGAGCCAUUCGGUCGCUAGG gRNA #7 against CpG 115:
(SEQ ID NO: 105)
GGUGGUACUGAGGACCGGGA gRNA #8 against CpG 115:
(SEQ ID NO: 107)
AUUUUCUGGGUGCUCAGAGG gRNA #9 against CpG 115:
(SEQ ID NO: 108)
UGGUCUCAGCUCGCGCACGG gRNA #10 against CpG 115:
(SEQ ID NO: 109)
ACAAAGACAUACGGGGUGAU Example sequences of gRNAs targeting the IFNAR1 gene include:

gRNA #1:
(SEQ ID NO: 106)
AGGAACGGCGCGUGCGCGGA gRNA #2:
(SEQ ID NO: 161)
AAGAGGCGGCGCGUGCGUAG gRNA #3:
GGGCGGUGUGACUUAGGACG
(SEQ ID NO: 162)

gRNA #4:
(SEQ ID NO: 163)
CCAGAUGAUGGUCGUCCUCC gRNA #5:
(SEQ ID NO: 164)
GACCCUAGUGCUCGUCGCCG gRNA #6:
(SEQ ID NO: 165)
UGGGUGUUGUCCGCAGCCGC gRNA #7:
(SEQ ID NO: 166)
ACGGGGGCGGCGAUGCUGUU gRNA #8:
(SEQ ID NO: 167)
GACCGAAGGUUUCCCAGACU gRNA #9:
(SEQ ID NO: 168)
GUCGGGUUUAAUCUUUGGCG gRNA #10:
(SEQ ID NO: 169)
CGCUCCCGAGGACCCGUACA gRNA #11:
(SEQ ID NO: 170)
CGGGUCCCACCCCCGUGAAA gRNA #12:
(SEQ ID NO: 171)
UCAAACUCGACACAAAGCUC gRNA #13:
(SEQ ID NO: 172)
GCGGAGCCGCGGUACUUUCC

Example sequences of gRNAs targeting the VEGFA gene include:

gRNA #1:
(SEQ ID NO: 173)
GGCGCGCGCGCUAGGUGGGA gRNA #2:
(SEQ ID NO: 174)
AGAGAGGCUCACCGCCCACG gRNA #3:
(SEQ ID NO: 175)
GUACGUGCGGUGACUCCGGU

All the above gRNAs may be fused to the gRNA scaffold with the following sequence:

(SEQ ID NO: 160)
GUUUAAGAGCUAUGCUGGAAACAGCAUAGCAAGUUUAAAUAAGG
CUAGUCCGUUAUUCAACUUGAAAAAGUGGCACCGAGUCGGUGCU.

Target Gene Repression

By "silencing a target gene", it is to be understood that the expression of the target gene is reduced to an extent sufficient to achieve a desired effect. The reduced expression may be sufficient to achieve a therapeutically relevant effect, such as the prevention or treatment of a disease. For example, a dysfunctional target gene which gives rise to a disease is preferably repressed to an extent that there is either no expression of the target gene, or the residual level of expression of the target gene is sufficiently low to ameliorate or prevent the disease state.

The reduced expression may be sufficient to enable investigations to be performed into the gene's function by studying cells reduced in or lacking that function.

Following administration of the two or more ATRs of the invention, the level of transcription or expression of the target gene may be reduced by, for example, at least 50%, 60%, 70%, 80%, 90%, 95%, 99% or 100% compared to the level of transcription or expression in the absence of the two or more ATRs.

Preferably, the two or more ATRs of the present invention have a synergistic effect in silencing a target gene. The two or more ATRs of the present invention may therefore demonstrate synergy, for example therapeutic synergy, when used as described herein.

For example, the two or more ATRs of the present invention may result in a synergistic increase in the fraction of a population of cells comprising the two or more ATRs that exhibits a silenced target gene, in comparison to a population of cells that lacks the two or more ATRs (e.g. comprises only one ATR or comprises a different combination of ATRs). Alternatively, or additionally, the two or more ATRs of the present invention may result in a synergistic increase in the duration that the target gene is silenced in a population of cells comprising the two or more ATRs, in comparison to a population of cells that lacks the two or more ATRs.

Preferably, the silencing of the target gene occurs following transient delivery or expression of the ATRs of the present invention to or in a cell.

By "transient expression", it is to be understood that the expression of the ATR is not stable over a prolonged period of time. Preferably, the polynucleotide encoding the ATR does not integrate into the host genome. More specifically, transient expression may be expression which is substantially lost within 20 weeks following introduction of the polynucleotide encoding the ATR into the cell. Preferably, expression is substantially lost within 12, 6, 4 or 2 weeks following introduction of the polynucleotide encoding the ATR into the cell.

Similarly, by "transient delivery", it is to be understood that the ATR substantially does not remain in the cell (i.e. is substantially lost by the cell) over a prolonged period of time. More specifically, transient delivery may result in the ATR being substantially lost by the cell within 20 weeks following introduction of the ATR into the cell. Preferably, the ATR is substantially lost within 12, 6, 4 or 2 weeks following introduction of the ATR into the cell.

Methods for determining the transcription of a gene, for example the target of an ATR, are known in the art. Suitable methods include reverse transcription PCR and Northern blot-based approaches. In addition to the methods for determining the transcription of a gene, methods for determining the expression of a gene are known in the art. Suitable additional methods include Western blot-based or flow cytometry approaches.

The effect of an ATR or combination of ATRs may be studied by comparing the transcription or expression of the target gene, for example a gene endogenous to a cell, in the presence and absence of the ATRs or combination of ATRs.

The effect of an ATR or combination of ATRs may also be studied using a model system wherein the expression of a reporter gene, for example a gene encoding a fluorescent protein, is monitored. Suitable methods for monitoring expression of such reporter genes include flow cytometry, fluorescence-activated cell sorting (FACS) and fluorescence microscopy.

For example, a population of cells may be transfected with a vector which harbours a reporter gene. The vector may be constructed such that the reporter gene is expressed when the vector transfects a cell. Suitable reporter genes include genes encoding fluorescent proteins, for example green, yellow, cherry, cyan or orange fluorescent proteins. In addition, the population of cells may be transfected with vectors encoding the ATRs of interest. Subsequently, the number of cells expressing and not-expressing the reporter gene, as well as the level of expression of the reporter gene may be quantified using a suitable technique, such as FACS. The level of reporter gene expression may then be compared in the presence and absence of the ATRs.

Preferably, the target gene is silenced permanently. By "permanent silencing" of a target gene, it is to be understood that transcription or expression of the target gene is reduced (e.g. reduced by 100%) compared to the level of transcription or expression in the absence of the two or more ATRs for at least 2 months, 6 months, 1 year, 2 year or the entire lifetime of the cell/organism. Preferably, a permanently silenced target gene remains silenced for the remainder of the cell's life.

Preferably the target gene remains silenced in the progeny of the cell to which the two or more ATRs of the invention has been administered (i.e. the silencing of the target gene is inherited by the cell's progeny). For example, the two or more ATRs of the invention may be administered to a stem cell (e.g. a haematopoietic stem cell) to silence a target gene in a stem cell and also in the stem cell's progeny, which may include cells that have differentiated from the stem cell.

A target gene may be silenced by using ATRs which bind to the target gene itself or to regulatory sequences for the target gene (e.g. promoter or enhancer sequences). Furthermore, alternative splicing of a target gene may be altered by using ATRs which bind to the splicing sites of the target gene itself. The ability to silence a target gene or to modulate its splicing variants by using ATRs which bind to regulatory sequences is not possible with certain other gene silencing technologies and is a particular advantage of the present invention.

Use in Therapy

In another aspect, the present invention provides the products, artificial transcription repressors (ATRs), polynucleotides and cells of the present invention for use in therapy.

The use in therapy may, for example, be a use for the treatment of β-thalassemia or sickle cell anaemia.

The use in therapy may, for example, be a use for the preparation of "universally" allogeneic transplantable cells (e.g. by the silencing of β2-microglobulin, B2M). This use may, for example, be applied to the preparation of haematopoietic stem and/or progenitor cells (HSPCs), whole organ transplantation and cancer immunotherapy.

The two or more ATRs, or polynucleotides encoding therefor, may be administered simultaneously, in combination, sequentially or separately (as part of a dosing regime).

By "simultaneously", it is to be understood that the two agents are administered concurrently, whereas the term "in combination" is used to mean they are administered, if not simultaneously, then "sequentially" within a time frame that they both are available to act therapeutically within the same time frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction there-between, and their respective half-lives.

In contrast to "in combination" or "sequentially", "separately" is to be understood as meaning that the gap between administering one agent and the other agent is significant, i.e. the first administered agent may no longer be present in the bloodstream in a therapeutically effective amount when the second agent is administered.

Target Gene

Preferably, the target gene gives rise to a therapeutic effect when silenced.

By way of example, the products, artificial transcription repressors (ATRs) and polynucleotides of the present invention may be used to silence β2-microglobulin (B2M), BCL11A, KLF1, globin genes, CCR5, CXCR4, TCR genes, miR126, PDL1, CTLA4, COL1A1, viral sequences and oncogenes.

Silencing of the TCR genes, PDL1 and CTLA4 may be used to improve efficacy of cancer immunotherapy approaches.

Silencing of B2M may be used to generate allogeneic HSPCs, T-cells or mesenchymal cells to be used for transplantation.

Silencing of miR126 may be used to expand the more primitive haematopoietic stem cell pool prior to or after their infusion.

By way of example, the products, artificial transcription repressors (ATRs), polynucleotides and cells of the present invention may be used in the treatment of, for example, Huntington's disease, Spinocerebellar ataxias, collagenopathies, haemaglobinopathies and diseases caused by trinucleotide expansions. Furthermore, the product of the present invention may be used in the treatment or prevention of certain infectious diseases (e.g. CCR5-tropic HIV infections) by inactivating either pathogen-associated gene products or host genes that are necessary for the pathogen life cycle.

In addition, or in the alternative, the products, artificial transcription repressors (ATRs), polynucleotides and cells of the present invention may be useful in the treatment of the disorders listed in WO 1998/005635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the products, artificial transcription repressors (ATRs), polynucleotides and cells of the present invention may be useful in the treatment of the disorders listed in WO 1998/007859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); anti-inflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the products, artificial transcription repressors (ATRs), polynucleotides and cells of the present invention may be useful in the treatment of the disorders listed in WO 1998/009985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Polynucleotides

Polynucleotides of the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that the skilled person may, using routine techniques, make nucleotide substitutions that do not affect the polypeptide sequence encoded by the polynucleotides of the invention to reflect the codon usage of any particular host organism in which the polypeptides of the invention are to be expressed.

The polynucleotides may be modified by any method available in the art. Such modifications may be carried out in order to enhance the in vivo activity or lifespan of the polynucleotides of the invention.

Polynucleotides such as DNA polynucleotides may be produced recombinantly, synthetically or by any means available to those of skill in the art. They may also be cloned by standard techniques.

Longer polynucleotides will generally be produced using recombinant means, for example using polymerase chain reaction (PCR) cloning techniques. This will involve making a pair of primers (e.g. of about 15 to 30 nucleotides) flanking the target sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture with an agarose gel) and recovering the amplified DNA. The primers may be designed to contain suitable restriction enzyme recognition sites so that the amplified DNA can be cloned into a suitable vector.

Proteins

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question substantially retains at least one of its endogenous functions. A variant sequence can be obtained by addition, deletion, substitution, modification, replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide substantially retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence substantially retains the required activity or ability. Amino acid substitutions may include the use of non-naturally occurring analogues.

Proteins used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity and/or the amphipathic nature of the residues as long as the endogenous function is retained. For example, negatively charged amino acids include aspartic acid and glutamic acid; positively charged amino acids include lysine and arginine; and amino acids with uncharged polar head groups having similar hydrophilicity values include asparagine, glutamine, serine, threonine and tyrosine.

Conservative substitutions may be made, for example according to the table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R H |
| AROMATIC | | F W Y |

The term "homologue" as used herein means an entity having a certain homology with the wild type amino acid sequence and the wild type nucleotide sequence. The term "homology" can be equated with "identity".

A homologous sequence may include an amino acid sequence which may be at least 50%, 55%, 65%, 75%, 85% or 90% identical, preferably at least 95% or 97% or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

A homologous sequence may include a nucleotide sequence which may be at least 50%, 55%, 65%, 75%, 85% or 90% identical, preferably at least 95% or 97% or 99% identical to the subject sequence. Although homology can also be considered in terms of similarity, in the context of the present invention it is preferred to express homology in terms of sequence identity.

Preferably, reference to a sequence which has a percent identity to any one of the SEQ ID NOs detailed herein refers to a sequence which has the stated percent identity over the entire length of the SEQ ID NO referred to.

Homology comparisons can be conducted by eye or, more usually, with the aid of readily available sequence comparison programs. These commercially available computer programs can calculate percentage homology or identity between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion in the nucleotide sequence may cause the following codons to be put out of alignment, thus potentially resulting in a large reduction in percent homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible, reflecting higher relatedness between the two compared sequences, will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al. (1984) *Nucleic Acids Res.* 12: 387). Examples of other software that can perform sequence comparisons include, but are not limited to, the BLAST package (see Ausubel et al. (1999) *ibid*—Ch. 18), FASTA (Atschul et al. (1990) *J. Mol. Biol.* 403-410) and the GENEWORKS suite of comparison tools. Both BLAST and FASTA are available for offline and online searching (see Ausubel et al. (1999) *ibid*, pages 7-58 to 7-60). However, for some applications, it is preferred to use the GCG Bestfit program. Another tool, called BLAST 2 Sequences is also available for comparing protein and nucleotide sequences (see *FEMS Microbiol. Lett.* (1999) 174: 247-50; *FEMS Microbiol. Lett.* (1999) 177: 187-8).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see the user manual for further details). For some applications, it is preferred to use the public default values for the GCG package, or in the case of other software, the default matrix, such as BLOSUM62.

Once the software has produced an optimal alignment, it is possible to calculate percentage homology, preferably percentage sequence identity. The software typically does this as part of the sequence comparison and generates a numerical result.

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site may be made. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Codon Optimisation

The polynucleotides used in the present invention may be codon-optimised. Codon optimisation has previously been described in WO 1999/41397 and WO 2001/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Vectors

A vector is a tool that allows or facilitates the transfer of an entity from one environment to another. In accordance with the present invention, and by way of example, some vectors used in recombinant nucleic acid techniques allow entities, such as a segment of nucleic acid (e.g. a heterologous DNA segment, such as a heterologous cDNA segment), to be transferred into a target cell. The vector may serve the purpose of maintaining the heterologous nucleic acid (DNA or RNA) within the cell, facilitating the replication of the vector comprising a segment of nucleic acid, or facilitating the expression of the protein encoded by a segment of nucleic acid. Vectors may be non-viral or viral. Examples of vectors used in recombinant nucleic acid techniques include, but are not limited to, plasmids, mRNA molecules (e.g. in vitro transcribed mRNAs), chromosomes, artificial chromosomes and viruses. The vector may also be, for example, a naked nucleic acid (e.g. DNA). In its simplest form, the vector may itself be a nucleotide of interest.

The vectors used in the invention may be, for example, plasmid, mRNA or virus vectors and may include a promoter for the expression of a polynucleotide and optionally a regulator of the promoter.

Vectors comprising polynucleotides used in the invention may be introduced into cells using a variety of techniques known in the art, such as transfection, transformation and transduction. Several such techniques are known in the art, for example infection with recombinant viral vectors, such as retroviral, lentiviral (e.g. integration-defective lentiviral), adenoviral, adeno-associated viral, baculoviral and herpes simplex viral vectors; direct injection of nucleic acids and biolistic transformation.

Non-viral delivery systems include but are not limited to DNA transfection methods. Here, transfection includes a process using a non-viral vector to deliver a gene to a target cell. Typical transfection methods include electroporation, DNA biolistics, lipid-mediated transfection, compacted DNA-mediated transfection, liposomes, immunoliposomes, lipofectin, cationic agent-mediated transfection, cationic facial amphiphiles (CFAs) (*Nat. Biotechnol.* (1996) 14: 556) and combinations thereof.

The term "transfection" is to be understood as encompassing the delivery of polynucleotides to cells by both viral and non-viral delivery.

Protein Transduction

As an alternative to the delivery of polynucleotides to cells, the products and artificial transcription repressors (ATRs) of the present invention may be delivered to cells by protein transduction.

Protein transduction may be via vector delivery (Cai, Y. et al. (2014) *Elife* 3: e01911; Maetzig, T. et al. (2012) *Curr. Gene Ther.* 12: 389-409). Vector delivery involves the engineering of viral particles (e.g. lentiviral particles) to comprise the proteins to be delivered to a cell. Accordingly, when the engineered viral particles enter a cell as part of their natural life cycle, the proteins comprised in the particles are carried into the cell.

Protein transduction may be via protein delivery (Gaj, T. et al. (2012) *Nat. Methods* 9: 805-7). Protein delivery may be achieved, for example, by utilising a vehicle (e.g. liposomes) or even by administering the protein itself directly to a cell.

Pharmaceutical Composition

The products, artificial transcription repressors (ATRs), polynucleotides and cells of the present invention may be formulated for administration to subjects with a pharmaceutically acceptable carrier, diluent or excipient. Suitable carriers and diluents include isotonic saline solutions, for example phosphate-buffered saline, and potentially contain human serum albumin.

Handling of the cell therapy products is preferably performed in compliance with FACT-JACIE International Standards for cellular therapy.

Kit

In one aspect, the present invention provides a kit comprising two or more artificial transcription repressors (ATRs), or polynucleotides encoding therefor, selected from groups (a), (b) or (c): (a) an ATR comprising a DNA-binding domain operably linked to a KRAB domain or homologue thereof; (b) an ATR comprising a DNA-binding domain operably linked to a DNMT3A, DNMT3B or DNMT1 domain or homologue thereof; and (c) an ATR comprising a DNA-binding domain operably linked to a DNMT3L domain or homologue thereof, wherein at least two of the ATRs are selected from different groups (a), (b) or (c).

The two or more ATRs, or polynucleotides encoding therefor, may be provided in suitable containers.

The kit may also include instructions for use, for example instructions for the simultaneous, sequential or separate administration of the two or more ATRs, or polynucleotides encoding therefor, to a subject in need thereof.

Method of Treatment

It is to be appreciated that all references herein to treatment include curative, palliative and prophylactic treatment; although in the context of the present invention references to preventing are more commonly associated with prophylactic treatment. The treatment of mammals, particularly humans, is preferred. Both human and veterinary treatments are within the scope of the present invention.

EXAMPLES

Example 1

With the aim of recapitulating the endogenous epigenetic mechanisms that permanently silence endogenous retroviruses (ERVs) during development, we employed the Krüppel-associated box (KRAB) domain of human zinc finger protein 10 (ZNF10; Szulc, J. et al. (2006) *Nat. Methods* 3: 109-16) and the catalytic domain of human DNA methyltransferase 3A (DNMT3A; Law, J. A. et al. (2010) *Nat. Rev. Genet.* 11: 204-20). The amino acid sequences of these domains are shown in Table 1.

To test the activity and stability of gene silencing induced by these two effector domains we used the tetracycline (tet) responsive system. We separately fused the two effector domains to the *E. coli* tetracycline-controlled Repressor (tetR) DNA-binding domain (Gossen, M. et al. (1992) *Proc. Natl. Acad. Sci. USA* 89: 5547-51), generating the tetR:KRAB and the tetR:DNMT3A artificial transcription repressors (ATRs, hereafter referred as tetR:K and tetR:D3A, respectively). The advantage of the tetR system is that it allows temporal control of binding of tetR to its target nucleotide sequence, the tetracycline operon (TetO), by doxycycline (doxy) administration. This allows us to investigate if the chromatin states induced by the ATRs can be maintained after the release of the ATRs from their target locus.

Figure 1:
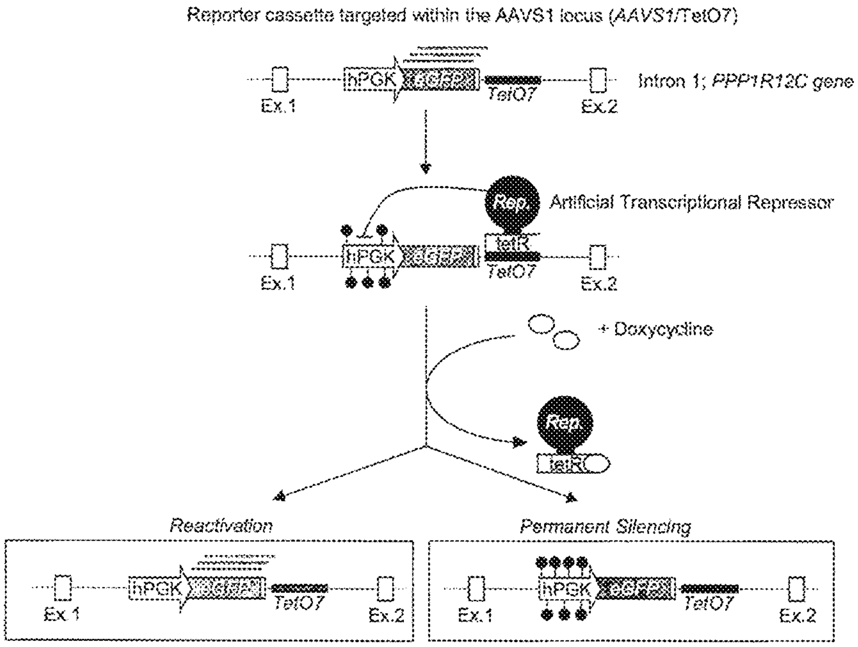
FIG. 1

To rapidly assess activity of the ATRs we devised an experimental cell model in which activity of the ATRs can be easily followed over time by flow cytometry analyses (FIG. 1). Specifically, we generated single cell-derived clones of K562 cells engineered to contain within the first intron of the PPP1R12C gene (Lombardo, A. et al. (2011) *Nat. Methods* 8: 861-9; also known as the AAVS1 locus) homozygous insertion of an eGFP-expression cassette followed by seven tandem repeats of TetO (TetO7; FIG. 1, top schematic). Expression of the eGFP marker in this reporter construct is driven by the ubiquitously expressed human phosphoglycerate kinase (hPGK) gene promoter. This reporter cell line will hereafter be referred to as the AAVS1/TetO7 cell line.

Upon expression of the ATRs, these chimeric proteins bind to the TetO7 element through their tetR DNA binding domain, thus eventually leading to the deposition of repressive epigenetic marks over the nearby chromatin (shown as red lollipops on the hPGK promoter; FIG. 1, middle schematic). This induces transcriptional silencing of the cassette. Upon conditional release of the ATR from the TetO7 element by doxy administration, the repressive marks can be either erased or propagated to the cell progeny by the endogenous cell machinery, thereby leading to transcriptional reactivation or permanent silencing of eGFP expression, respectively (FIG. 1, bottom schematics). Major advantages in the use of such an experimental model are: i) activity of the ATRs can be rapidly and easily monitored by observing eGFP expression by flow cytometry analysis; and ii) because these clones were engineered to contain homozygous insertion of the cassette, we can study the epigenetic and transcriptional impact of silencing on the genes at and nearby the integration site without the confounding effect of the unmodified wild-type locus.

In order to assess if the new ATRs were biologically active, we delivered the tetR:K and tetR:D3A into the AAVS1/TetO7 cell line using standard integrating bidirectional lentiviral vectors (Amendola, M. et al. (2005) *Nat. Biotechnol.* 23: 108-16; Bid.LV; FIG. 2A). The advantage of these vectors is that they constitutively co-express the ATRs and a marker gene (either the truncated low-affinity nerve growth factor receptor -ΔLNGFR- or monomeric orange-mOrange-) from the same promoter, thus allowing us to restrict our analysis of silencing exclusively to the cells expressing the ATRs.

In summary, by virtue of the experimental setting described, we can test if constitutive binding of candidate ATRs to the TetO7 cassette is able to deposit repressive epigenetic marks over the nearby chromatin and to induce transcriptional silencing of the reporter cassette. In this case, the subsequent conditional release of ATR binding by doxy administration allows us to discern if the artificially induced repressive marks are then erased (thereby leading to transcriptional reactivation), or propagated to the cell progeny by the endogenous machinery (thus indicating that a permanently inherited epigenetic silencing state has been established).

Upon molecular characterisation, the AAVS1/TetO7 cell line was transduced with either Bid.LV-tetR:K or Bid.LV-tetR:D3A in the presence or absence of doxy and then maintained in these culture conditions for up to 200 days. During this time, the cells were periodically analysed by flow cytometry to measure the percentage of eGFP-negative (eGFP-) cells within the Bid.LV-transduced cell populations. As shown in FIG. 2B, constitutive binding of the ATRs to the TetO7 sequence (doxy− conditions) eventually led to eGFP silencing in 100% of the transduced cells, although with different kinetics between the two ATRs. Specifically, the tetR:K transduced cells rapidly became eGFP− (FIG. 2B, left histogram) and this effect was independent of the level of transduction (FIGS. 2C-2D, left flow cytometry dot blots). On the other hand, silencing induced by tetR:D3A was significantly slower (FIG. 2B, right histogram). In this case, the cells with the higher expression level of the marker gene (likely those with higher vector copy number, VCN) were the first to be silenced (FIGS. 2C-2D, right flow cytometry dot blots), indicating the requirement of a certain level of expression of the tetR:D3A to ensure faster repression. Importantly, at later time points (~200 days), flow cytometry analyses showed that the mean fluorescence intensity (MFI) of eGFP was superimposable between silenced and wild-type (WT) K562 cells (compare MFIs in FIGS. 2C-2D), indicating complete silencing of eGFP expression. When doxy was present in the cultures (doxy+ conditions), none of the transduced cells silenced eGFP, indicating that ATR binding to the target sequence is necessary to induce silencing. Overall, these data show that both ATRs are functional although they induce silencing with different kinetics.

We then assessed if release of the ATRs from the locus would result in eGFP reactivation. To this aim, we sorted the eGFP− cells at day 21 post Bid.LVs transduction and then cultured these cells in the presence or absence of doxy for an additional 170 days. Interestingly, doxy administration resulted in two opposite outcomes according to the ATR used: silencing induced by tetR:K was rapidly (within 15 days post doxy administration) and fully erased in the whole cell population (FIG. 2E, left histogram and representative flow cytometry analyses at the bottom); while silencing induced by tetR:D3A was maintained unaltered throughout the duration of the experiment (FIG. 2E, right histogram and representative flow cytometry analyses at the bottom). This clearly indicates that, opposite to tetR:K which has to be continuously active on the locus to repress it, tetR:D3A is able to establish repressive epigenetic modifications that can be permanently propagated by the endogenous cellular machinery even in the absence of the initial stimulus. This difference can be explained by the fact that in somatic cells, the KRAB-based machinery is not able to efficiently induce DNA methylation (which can be stably propagated), and deposits only reversible epigenetic marks, such as H3K9 methylation (Hathaway, N. A. et al. (2012) *Cell*149: 1447-60).

Overall, these experiments clearly show that even in the absence of binding of tetR:D3A to the TetO7 element, silencing of the reporter cassette can be maintained unaltered throughout several cell generations. On the other hand, conditional release of tetR:K from the TetO7 element leads to rapid and full reactivation of eGFP expression in tetR:K transduced cells.

DNA Methylation is Involved in the Maintenance of Permanent Silencing Induced by tetR:D3A In order to understand if DNA methylation was necessary to maintain the repressive state induced by tetR:D3A, the eGFP− cells from the doxy− conditions in FIG. 2E were treated with either 5-Aza-2'-deoxycytidine (5-Aza) or vehicle (i.e. Dimethyl Sulfoxide, DMSO) and then analysed by flow cytometry to measure eGFP expression. 5-Aza is a cytosine analogue that after becoming incorporated into DNA is recognised by DNA methyltransferase as a substrate, establishing a covalent bond that, contrary to cytosine, is not resolved, thus blocking DNMT activity (Issa, J. P. et al. (2005) *Nat. Rev. Drug Discov.* Suppl. S6-7). As shown in FIG. 2F, treatment with 5-Aza resulted in full reactivation of eGFP expression. As expected, DMSO treatment did not alter silencing of eGFP, with eGFP+ cells in the culture representing contaminant cells from the cell sorting procedure.

Contrary to tetR:K, tetR:D3A-Induced Repression is Confined to the Target Locus

One of the requisites necessary for a safe epigenetic therapy approach is that silencing should not spread into the genes surrounding the desired target gene. Note that the site-specific integration of the reporter cassette into the AAVS1 locus allows us to easily analyse the impact of our silencing platform on the expression of genes embedded near the reporter cassette integration site. Thus, we compared the expression levels of the genes at and nearby the AAVS1 integration site (FIG. 3A) between the eGFP− cells from FIG. 2 and the untreated AAVS1/Tet07 cell line.

eGFP− cells transduced with tetR:K significantly down-regulated all the analysed genes (FIG. 3B, left histogram; data are represented as mean±SEM, n=3), indicating that this ATR deposits repressive marks able to spread for at least 340 kb (~170 kb on both sides of the ATR binding site). This finding is consistent with previous studies performed in other somatic cell lines and showing that tetR:K can silence promoters located several tens of kilobases away from the ATR binding sites through the long-range spreading of H3K9me3 (Groner, A. C. et al. (2010) *PLoS Genet.* 6: e1000869). Importantly, when analysing the eGFP− cells transduced with tetR:D3A and grown with doxy, only eGFP and, to a lesser extent, the PPP1R12C gene (hosting the reporter cassette in its first intron) showed a significant down-regulation (FIG. 3B, right histogram; data are represented as mean±SEM, n=3; *$p<0.0001$ and $p<0.001$, one-way anova and Bonferroni post-test), indicating a very localised epigenetic repression.

Overall, these experiments show that tetR:K induces a rapid and robust transcriptional repression, capable of long-range spreading, which however is reversible upon ATR release from the locus. On the other hand, tetR:D3A induces silencing with slower kinetics, but this transcriptional repression is sharply confined to the target locus and permanently maintained even in the absence of the initial stimulus Synergistic Activity of the ATRs Upon their Transient Co-Delivery We then asked if the transient co-delivery of these two ATRs was sufficient to induce rapid (as tetR:K) and permanent (as tetR:D3A) epigenetic silencing. To answer to this question we transfected the AAVS1/TetO7 cell line with plasmids encoding for the ATRs, either alone or in combination, and then followed eGFP expression in these cells by time course flow cytometry analysis. Representative examples of these experiments are shown in FIG. 4A, in which we report the kinetics of silencing of the eGFP-expression cassette (% of eGFP− cells; data are represented as mean±SEM, n=3) in cells transfected with the plasmids encoding for the indicated ATRs, and the corresponding flow cytometry dot plot analyses performed at termination of the experiments. From these analyses we found that: i) none of the cells transfected with the plasmid encoding for either the tetR:K or tetR:D3A became eGFP negative, although transient delivery of the tetR:K was associated with a short wave of repression that rapidly returned to control levels by day 10 post-transfection (this latter data indicates transient deposition of H3K9me3 followed by its disappearance concomitantly with the mitotic dilution of the tetR:K encoding plasmid); and ii) remarkably, up to 20% of the cells co-transfected with the plasmids encoding for the tetR:K and tetR:D3A became stably silenced. These data revealed a significant degree of synergy between the DNMT3A- and the KRAB-based repressors, and represent the first demonstration of permanent epigenetic silencing upon transient co-delivery of ATRs.

We then asked whether the silencing induced by the tetR:K/tetR:D3A combination was limited to the reporter cassette or instead spread along the AAVS1 locus, thus also affecting the genes nearby the insertion site of the reporter cassette. To answer to this question, we compared the expression profile of the genes at and nearby the AAVS1 integration site (a schematic of the locus is shown in FIG. 3A) between the eGFP-negative and the eGFP-positive populations sorted from the tetR:K/tetR:D3A treated conditions. In these analyses we found that the treatment resulted in significant silencing only of the reporter transgene (FIG. 4B; data are represented as mean±SEM, n=3; p<0.001, one-way anova and Bonferroni post-test). These important data indicate that the tetR:K/tetR:D3A combination deposited punctuated epigenetic silencing only at the intended target gene, highlighting the safety our approach. Finally, treatment of the eGFP-negative sorted cells from tetR:K/tetR:D3A conditions with 5-Aza completely reactivated eGFP expression in these cells (FIG. 4C; data are represented as mean±SEM, n=3; *p<0.0001, two-tailed unpaired t test), thus indicating that DNA methylation plays an important role in the maintenance of these epigenetic states of repression. Similar results were also found by transfecting the AAVS1/TetO7 reporter cell lines with in vitro transcribed mRNAs encoding for the ATRs (FIG. 4D). Remarkably, the extent of silencing measured in these experiments was ~2-fold higher than that measured upon plasmid transfection, likely reflecting the better tolerability and the higher expression levels achieved by mRNA transfection. Gene expression analyses showed that only eGFP and the gene lodging the eGFP-reporter cassette (i.e. PPP1R12C) were down-regulated by the treatment (FIG. 4E; data are represented as mean±SEM, n=3; ***p<0.0001 and *p<0.01, one-way anova and Bonferroni post-test).

Silencing with ATR Combinations is Locus and Cell-Type Independent

Having shown that the two ATRs are capable of inducing permanent silencing even when transiently delivered to the cells, we then asked if this effect was locus independent. Indeed, the efficacy of an epigenetic therapy approach might depend on the chromatin environment in which the target locus is embedded, with theoretically some loci being more refractory to a specific repressive mechanism than others. For example, some published evidence suggests that loci enriched in H3K4 methylation may be protected from DNA methylation (Ooi, S. K. et al. (2007) *Nature* 448: 714-7). In line with this, endogenous epigenetic factors naturally present at the target locus or in its neighbouring regions may counteract the activity of the ATRs or restore the original physiological epigenetic profile of the target gene.

To address this question, we inserted the TetO7 sequence upstream of the hPGK promoter of an eGFP expression cassette, and then delivered this construct semi-randomly in the genome of the K562 cells by standard lentiviral vector transduction (a schematic of the provirus used is shown in FIG. 5A). We then sorted to purity the eGFP-expressing cells (hereafter referred as the TetO7.LV-reporter cell line) and transfected them with in vitro transcribed mRNAs encoding for the tetR:K or the tetR:D3A, either alone or in combination. Time-course flow cytometry analyses of these cells (FIG. 5B; data are represented as mean±SEM, n=3; *p<0.0001, two-way anova and Bonferroni post-test) showed that: i) up to 32% of the cells transfected with the mRNA encoding for tetR:D3A progressively became eGFP-negative, reaching a plateau of repression in two weeks after transfection; ii) up to 80% of the cells transfected with the plasmid encoding for tetR:K rapidly became eGFP-negative but soon after most of these cells reactivated eGFP expression (contrary to the experiment performed with the AAVS1/TetO7 cell line, up to 19% of the cells remained eGFP negative); and iii) remarkably, up to 80% of the cells co-transfected with mRNAs encoding for the tetR:K/tetR:D3A became permanently silenced. Interestingly, even if we measured comparable efficiencies of silencing between the tetR:K and the tetR:K/tetR:D3A conditions at short term post-transfection, only the combination of the two factors resulted in high levels of permanent epigenetic silencing. Similar results were also found in U937 cells with random insertion of the TetO7/eGFP cassette (FIG. 5C). Here, however, the efficiencies of silencing for all treatment conditions were lower than those obtained in K562 cells, although the overall efficiencies of transfection between these two cell types were comparable. Unexpectedly, when we performed a similar experiment in B-lymphoblastoid cells containing random insertion of the TetO7/eGFP cassette, long-term stable silencing was observed only in the conditions treated with the tetR:D3A (FIG. 5D; data are represented as mean±SEM, n=3; *p<0.0001, two-way anova and Bonferroni post-test). Contrary to the results of all the above experiments, silencing induced by the combination of the ATRs was transient, displaying kinetics that were superimposable to those measured under the tetR:K-treated conditions.

Overall, these results clearly demonstrate that the two ATRs cooperate in the establishment of stable states of epigenetic repression also when their target sites are randomly distributed throughout the lentiviral vector accessible genome of different cell types, thus indicating that the silencing mechanism might be locus-independent. Yet, these studies suggest that that several cell-intrinsic factors can modulate the in vivo activity of these proteins.

Identification of Novel ATRs Able to Increase the Silencing Efficiency of Our Platform While the above data provide the first demonstration to our knowledge of permanent epigenetic silencing upon transient expression of ATRs, they also indicate that several cell-intrinsic factors can modulate the in vivo activity of these proteins. For instance, the lower level of silencing observed in the U937 cell line and the unexpected lack of silencing activity of the ATR combination found in B-lymphoblastoid cells might be explained by the absence of a cofactor(s) involved in the silencing process or by the presence of a cell-type specific repressor(s). Because of this reason, the inclusion of another ATR in our cocktail might be useful to increase the efficiency of silencing of the KRAB/DNMT3A combination, either by obviating to the absence of a cofactor, or by allowing proper function of the repressive complex even when the ATRs are present at low concentrations. Thus, we investigated whether any alternative effector domains (or combination thereof) from chromatin remodelling enzymes involved in the establishment of permanent states of epigenetic repression could be used to increase the silencing efficiency of our ATRs. To this end, by mining the literature for known interactors of the DNMT3A or KRAB-ZFPs proteins (Chen, T. et al. (2014) *Nat. Rev. Genet.* 15: 93-106) and, more broadly, for molecules involved in the transcriptional control of cell fate specification and development (Schwartz, Y. B. et al. (2013) *Nat. Rev. Genet.* 14: 853-64), we identified the following candidates:

- Euchromatic histone-lysine N-methyltransferase 2 (EHMT2 also known as G9a): a histone methyltransferase that catalyses dimethylation of histone H3 lysine-9 and recruits several histone deacetylases;
- SET domain bifurcated 1 (SETDB1): a histone methyltransferase that deposits histone H3 lysine-9 di- and tri-methylation (two histone marks associated with transcriptional repression);
- Chromobox protein homolog 5 (CBX5, also known as HP1a): a component of heterochromatin that recognises and binds histone H3K9me, leading to epigenetic repression;
- DNA (cytosine-5)-methyltransferase 3-like (DNMT3L): a catalytically inactive DNA methyltransferase that activates DNMT3A by binding to its catalytic domain;
- Enhancer of Zeste homolog 2 (EZH2): the catalytic subunit of the polycomb repressive complex 2, which methylates lysine-9 and lysine-27 of histone H3, thus creating binding sites for the canonical polycomb repressive complex 1;
- Suppressor of variegation 4-20 homolog 2 (SUV420H2): a histone methyltransferase that specifically trimethylates lysine-20 of histone H4 (a specific histone mark associated with transcriptional repression at pericentric heterochromatin); and
- Transducin-like enhancer protein 1 (TLE1): a chromatin-associated transcriptional co-repressor that binds to and inhibits the activity of a number of transcription factors.

We generated new ATRs containing the effector domains of these proteins and the DNA binding domain of tetR. Hereafter, the new ATRs will be referred as: tetR:SET (SETDB1); tetR:H (HP1-a); tetR:T (TLE1); tetR:GS or tetR:GL (according to the length of the effector domain cloned from G9a); tetR:ES or tetR:EL (according to length of the effector domain cloned from EZH2); tetR:D3L (DNMT3L); and tetR:SUV (SUV420H2). The amino acid sequences of the effector domains are listed in Table 1.

We initially tested the activity of these novel ATRs in the LV/TetO7 K562 reporter cell line by using standard integrating Bid.LV and found that, among the new ATRs, tetR:SET, tetR:GS and tetR:H efficiently induced silencing when individually and stably expressed (FIG. 6A; data are represented as mean±SEM, n=3). However, none of these ATRs reached the silencing efficiency of tetR:K and tetR:D3A. Unlike tetR:GS, tetR:GL was not efficient in this experimental setting, suggesting that inclusion of the ankyrin repeats in this longer version of G9A was negatively impacting the silencing efficiency. The inefficiency of tetR:T, tetR:SUV, tetR:ES and tetR:EL in this experimental setting may be due to the intrinsic biological inactivity of the chosen domains or to the absence in this cell line of endogenous interactors necessary for the activity of these proteins. Furthermore, we noticed a decrease in the percentage of transduced cells over time for some of the ATRs used (FIG. 6B; data are represented as mean±SEM, n=3). This data indicates a growth disadvantage of cells stably expressing the ATRs, thus strengthening the rationale of using transient delivery approaches to safely express the ATRs.

We then assessed if silencing induced by the new ATRs could be maintained even in the absence of the ATRs on the target locus. To this aim, 18 days after Bid.LV-ATR transduction, we treated the samples with doxy, and monitored eGFP expression by flow cytometry analysis (FIG. 6C; data are represented as mean±SEM, n=3). As expected, tetR:D3A-induced silencing was maintained after doxy administration. Considering the other samples, silencing was maintained only in a fraction of the originally repressed cells, which varied among the different ATRs. Particularly, tetR:K-induced silencing resulted to be more stable than the others, being maintained in up to 45.8% of the originally repressed cells. This is in contrast with that observed using the AAVS1/TetO7 K562 reporter cell line, in which 7 days post doxy administration eGFP was fully reactivated in all the transduced cells. This data indicate a role in that positioning of the TetO7 relative to the hPGK promoter and/or the epigenetic environments in which the cassette is integrated might play an important role in the maintenance of the tetR:K-induced repressive state.

We then tested the efficiency of the ATRs upon their transient delivery in the same LV/TetO7 K562 reporter cell line. Particularly, we tested the ATRs either individually (FIG. 7A) or in combination with tetR:D3A (FIG. 7B), tetR:K (FIG. 7C) or with the tetR:K+tetR:D3A combination (FIG. 7D). To better appreciate any eventual increase in the silencing efficiency above the levels measured in positive controls, these experiments were performed using non-saturating doses of the ATR-expressing plasmids. tetR:T was not tested in this experiment, since it was not available in the same plasmid backbone as the other ATRs at the time of the experiment.

Figure 7B:
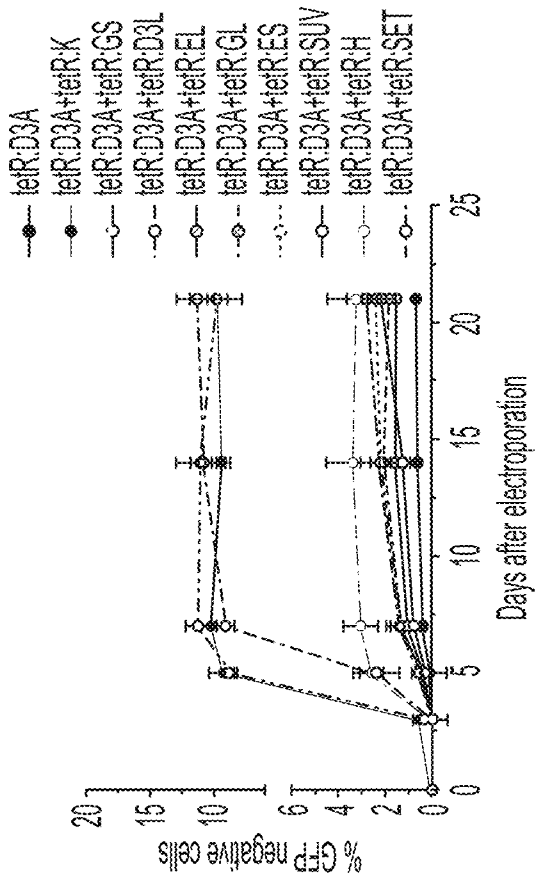
Figure 7A:
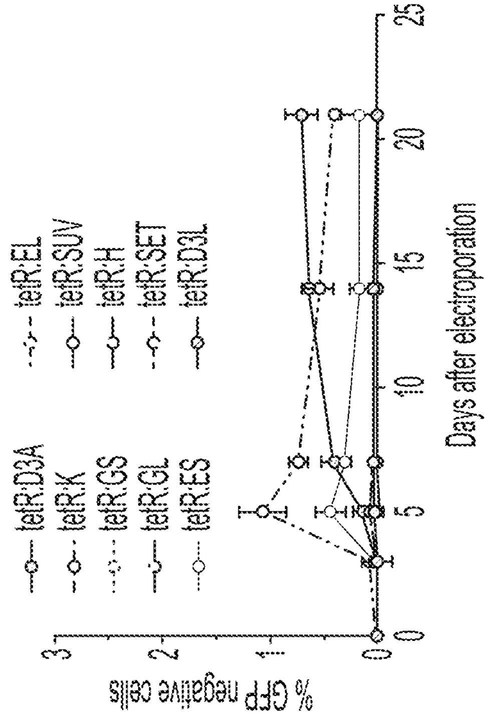
Figure 7D:
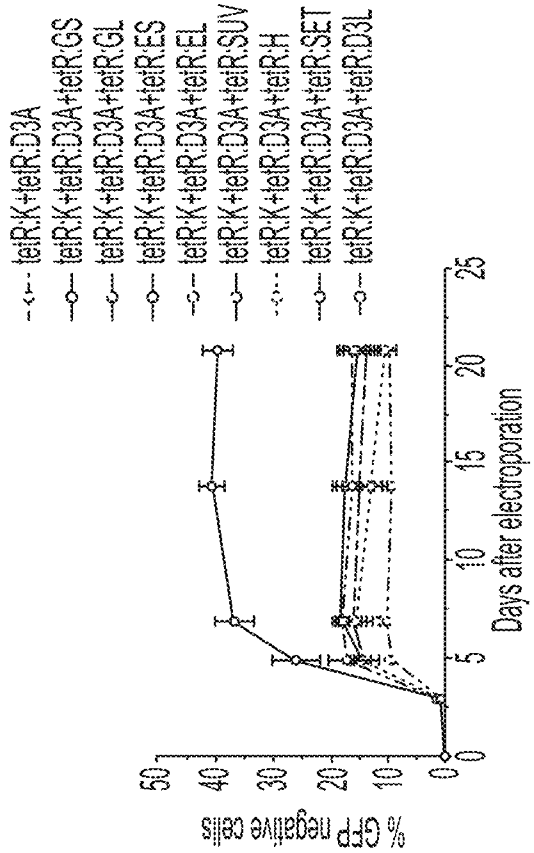
Figure 7C:
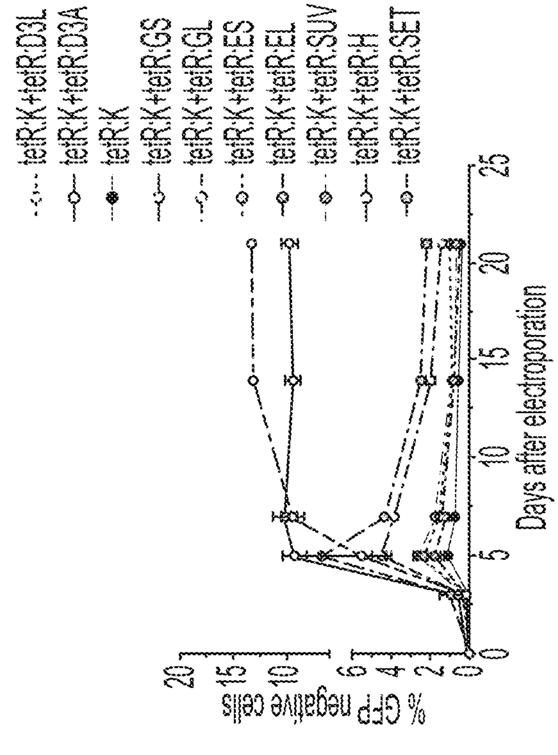
Figure 7E:
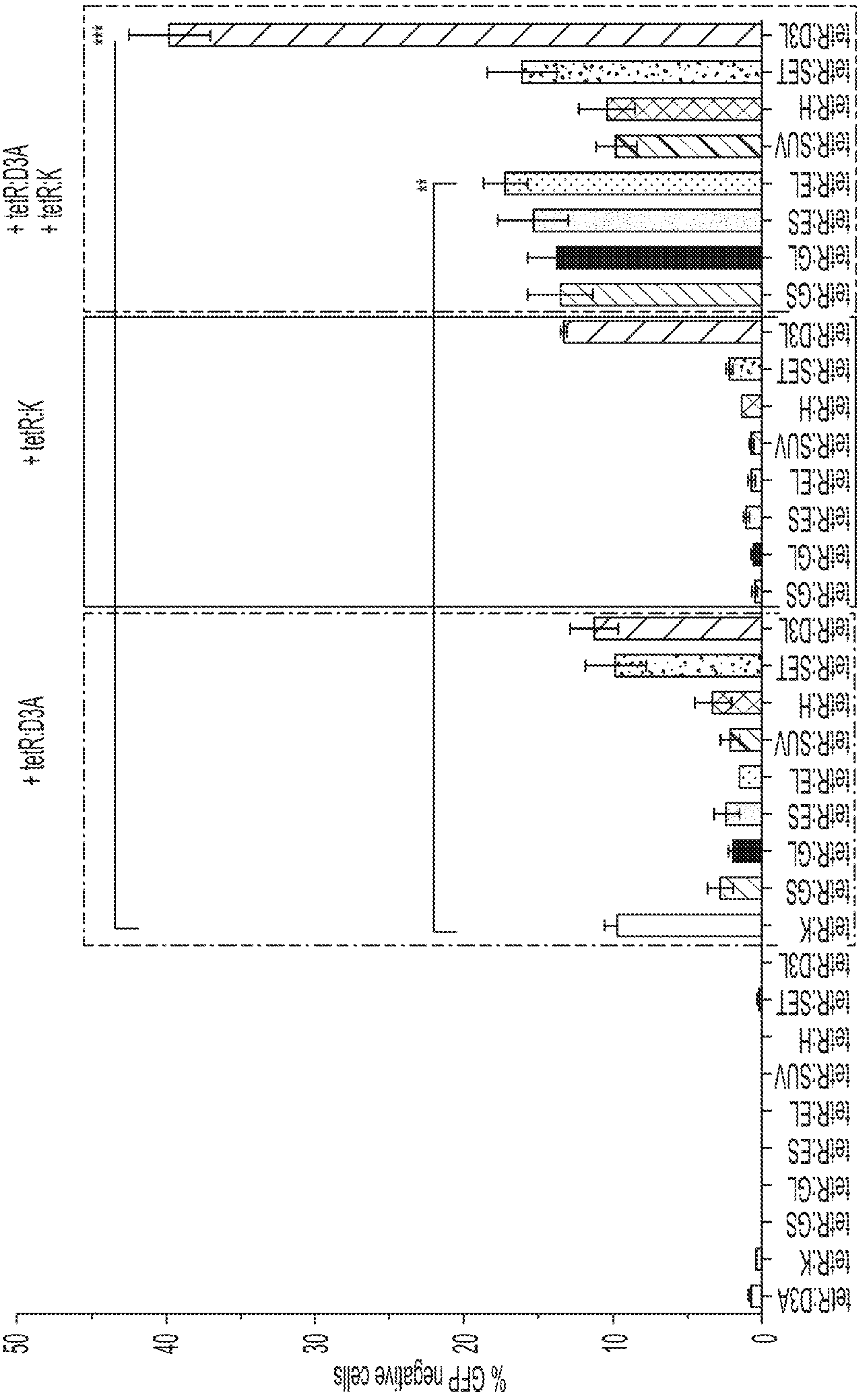
Figure 7F:
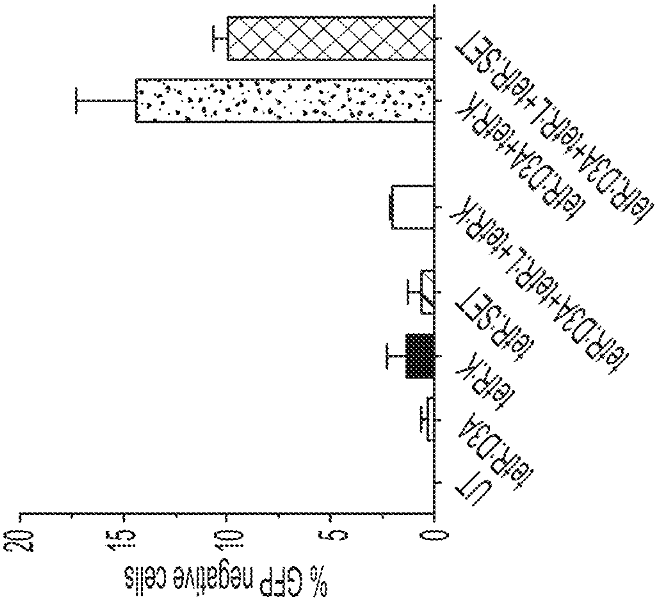
Figure 7G:
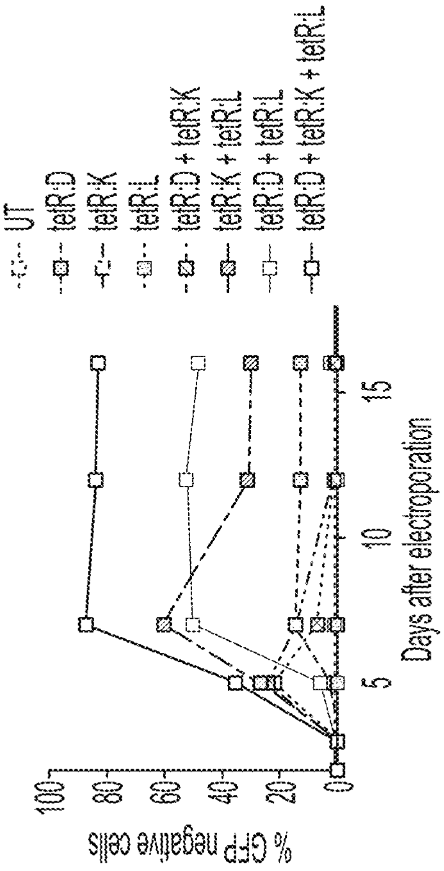
Figure 7H:
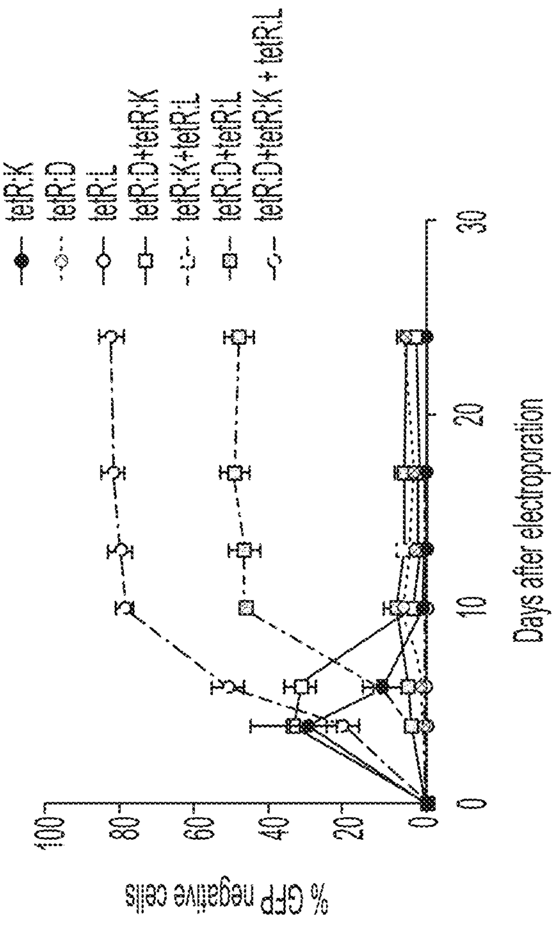

By following eGFP expression in the treated cells over time by flow cytometry, we found that when individually expressed, none of the ATRs efficiently induced silencing, with tetR:K, tetR:D3A and tetR:SET repressing only up to 1% of the cell (FIG. 7A; data are represented as mean±SEM, n=3). When combined to tetR:D3A (FIG. 7B; data are represented as mean±SEM, n=3), all the new ATRs conferred a gain in silencing efficiency. However, an efficiency similar to that measured with the tetR:K+tetR:D3A condition was achieved only when tetR:D3A was combined with either tetR:SET or tetR:D3L. Furthermore, when co-delivered with tetR:K (FIG. 7C; data are represented as mean±SEM, n=3), only tetR:D3L among the new ATRs synergised better than tetR:D3A. Finally, when adding one of the new ATRs to the tetR:K+tetR:D3A combination (FIG. 7D; data are represented as mean±SEM, n=3), most of the ATRs increased silencing efficiency, thus indicating a biological activity also for those ATRs that were not working when stably, but individually, delivered (FIG. 6A). Importantly, this experiment identified the tetR:K+tetR:D3A+tetR:D3L combination as the best-performing combination, showing a striking efficiency considering the low plasmid doses employed in these experiments. Specifically, the tetR:K+tetR:D3A+tetR:D3L combination resulted in a 4.1-fold increase in silencing efficiency compared to the tetR:K+tetR:D3A combination (FIG. 7E; data are represented as mean±SEM, n=3; *p<0.0001, one-way anova and Bonferroni post-test). Given the increment in silencing efficiency compared to both the tetR:D3A+tetR:D3L, tetR:K+tetR:D3A and tetR:D3L+tetR:K combinations, all the three ATRs play a relevant role in the tetR:K+tetR:D3A+tetR:D3L cocktail. Interestingly, starting from the evidence that tetR:SET was able to synergise with both tetR:D3A and tetR:D3A+tetR:K (see FIG. 7E), we reloaded a similar experiment at even lower ATR doses, and found that tetR:SET was also able to significantly synergise with the tetR:D3A+tetR:D3L combination (FIG. 7**F; tetR:D3L shown as tetR:L). This data indicates that the tetR:D3A+tetR:D3L+tetR:SET combination can be a valid alternative to the tetR:D3A+tetR:D3L+tetR:K combination, even if with lower silencing efficiency.

Inclusion of tetR:D3L to the tetR:K+tetR:D3A Combination Allows Rescue of Silencing Efficiency In Refractory Cell Types We then asked if the use of the tetR:K+tetR:D3A+tetR:D3L combination was able to overcome the block observed in B-lymphoblastoid cells (see FIG. 5D). To address this question, the TetO7.LV-reporter B-lymphoblastoid cell line was transfected with in vitro transcribed mRNAs encoding for the three ATRs, either alone or in different combinations (FIG. 7G; tetR:D3A shown as tetR:D; tetR:D3L shown as tetR:L; data are represented as mean±SEM, n=3). As expected from previous experiments, tetR:K+tetR:D3A co-delivery resulted in a transient wave of silencing that was completely erased after dilution of the transfected mRNAs, resulting in the absence of eGFP negative cells. However, both tetR:D3A+tetR:D3L and tetR:D3L+tetR:K were capable of inducing high levels of silencing (50% and 60%, respectively). These levels are substantially higher than those observed in conditions in which the ATRs were delivered alone (14% for tetR:D3A, and levels comparable to untreated samples for tetR:K and tetR:D3L transfected cells). Strikingly, when the three ATRs were delivered together, most of the cells became eGFP negative (up to 80%), clearly demonstrating that the addition of one single factor to the tetR:D3A/tetR:K mix was sufficient to restore silencing induction and maintenance in previously refractory cell lines. Based on these promising results, we also asked if our silencing platform could be effective in experimentally relevant cell types derived from other organisms, such as mice. To answer this question, we first transduced the murine NIH/3T3 cell line with the TetO7.LV, sorted the cells to obtain a pure eGFP-positive population (hosting on average 1 copy of vector per cell), and finally transfected them with mRNAs encoding for the tetR-based ATRs, which were delivered individually or in combination. Remarkably, flow cytometry analysis of the treated cells showed effective and long-term silencing also in this cell model: a single administration of the tetR:D3A+tetR:D3L or of the triple ATR combination led to 45% or 80% gene silencing efficiency, respectively (FIG. 7H). On the other hand, the tetR:D3A+tetR:K combination did not work, as previously observed in B-lymphoblastoid cells.

Effective Silencing by Transient Co-Delivery of ATRs Equipped with Custom-Made DNA Binding Domains The main objective of this project was to develop an epigenetic therapy platform that can be used to silence expression of any gene of interest. Although we have already identified effector domains that when fused to the tetR synergistically cooperate to silence the promoter nearby the TetO7 element, the artificial nature of the prokaryotic TetO7/tetR system hinders therapeutic application of this technology. Moreover, the TetO7 element can accommodate with high avidity 7 tetR dimers, thus leading to stochastic homo- or hetero-dimerisation of the ATRs on this element. This occurrence may favour mutual positive interactions between repressors. For these reasons, several questions remain to be addressed in order to translate the findings obtained with the TetO7/tetR system to a situation in which each of the ATRs has single and yet independent binding site on the target gene. In particular, it is unknown whether one element (defined as a given genomic sequence containing the binding site for each of the repressors, hereafter referred as the "Silencing Element") would be sufficient to silence a gene of interest. Furthermore, the relative order and the orientation in which the two repressors are arranged on the Silencing Element, and the distance between their binding sites might represent important determinants for the activity of the repressive complex. Of note, it is impossible to define these determinants based on the literature or by empirically testing them on an endogenous gene, as it would require designing several different ATRs each with its own binding site and affinity.

To address these questions, we developed an ad hoc engineered cell model that easily reports the silencing activity of ATRs containing transcription-activator like effector (TALE; Gaj, T. et al. (2013) *Trends Biotechnol.* 31: 397-405) DNA-binding domains. In this set of experiments we initially tested ATRs corresponding to the tetR:K+tetR:D3A combination.

Figure 8:
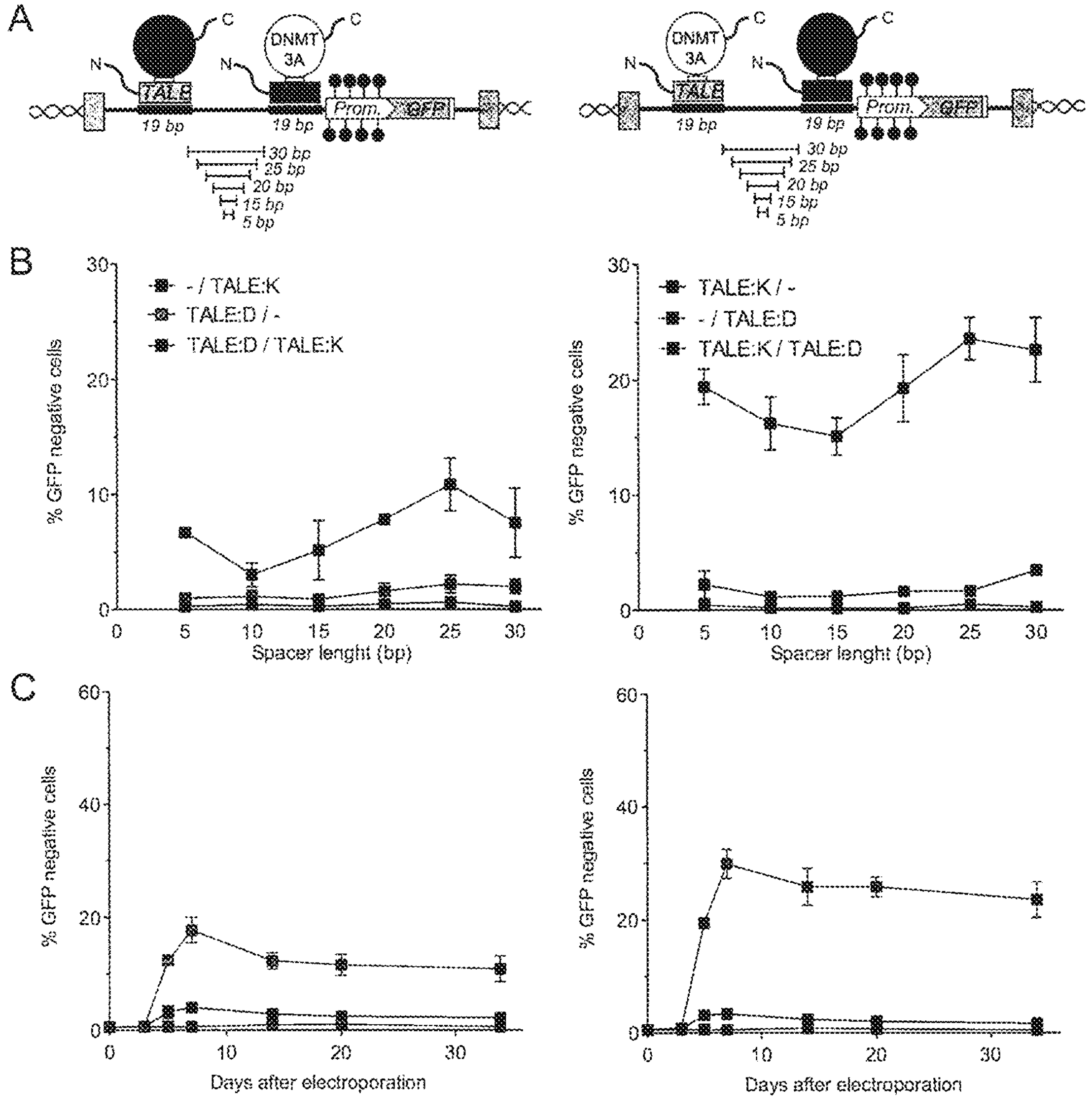

Briefly, we fused the KRAB and DNMT3A domains to the DNA binding domains of two TALEs that recognise two different genomic target sites with high efficiency (the amino acid sequences of the two TALEs are listed in Table 2). Using this approach we obtained two TALE:KRAB fusion proteins (hereafter referred as TALE:K) and two TALE:DNMT3A fusion proteins (hereafter referred as TALE:D3A) corresponding to each of the two genomic target sites. In parallel, we inserted the two TALE target sites, spaced by progressively longer nucleotide sequences (5, 10, 15, 20, 25 and 30 bp), upstream of the hPGK promoter of an eGFP expression cassette, and then delivered these constructs semi-randomly in the genome of the K562 cell line by standard lentiviral vector transduction. Of note, the target sites for the two TALEs were placed in such a way that binding of the TALE-repressors occurs in head-to-tail (H-T) configuration. A schematic representation of these vectors is shown in FIG. 8A (on the left is depicted the vector containing the binding sites for the TALE:K→TALE:D3A configuration; on the right is depicted the vector containing the binding sites for the TALE:D3A→TALE:K configuration. We then sorted to purity the eGFP expressing cells and transfected these lines with in vitro transcribed mRNAs encoding for the TALE:K or the TALE:D3A, either alone or in combination. The cells were then analysed by time-course flow cytometry to measure the extent and duration of silencing. Representative examples of these analyses can be seen in FIG. 8, in which we report the silencing efficiencies (% of eGFP-negative cells) of the indicated ATRs with respect to the length of the spacers (FIG. 8B; data are represented as mean±SEM, n=3), and the kinetics of silencing of the eGFP-expression cassette measured in the cell line with the 25 bp spacer (FIG. 8C; data are represented as mean±SEM, n=3; *$p<0.0001$ and $p<0.001$, two-way anova and Bonferroni post-test).

From these experiments we found that: i) co-delivery of TALE:D3A and TALE:K resulted in full silencing of eGFP-expression cassette in up to 25% of the treated cells; ii) the relative order of binding of the two ATRs on the target locus impacted on the overall silencing efficiency, with the TALE:D3A$\rightarrow$TALE:K configuration performing from 2.2 to 5.4-fold better than the opposite one; iii) among the spacer lengths tested, the 25 and the 30 bp performed better than the others; and iv) individual delivery of TALE:K or TALE:D3A resulted in low (3%) or absent silencing of the eGFP-expression cassette, respectively.

Figure 9:
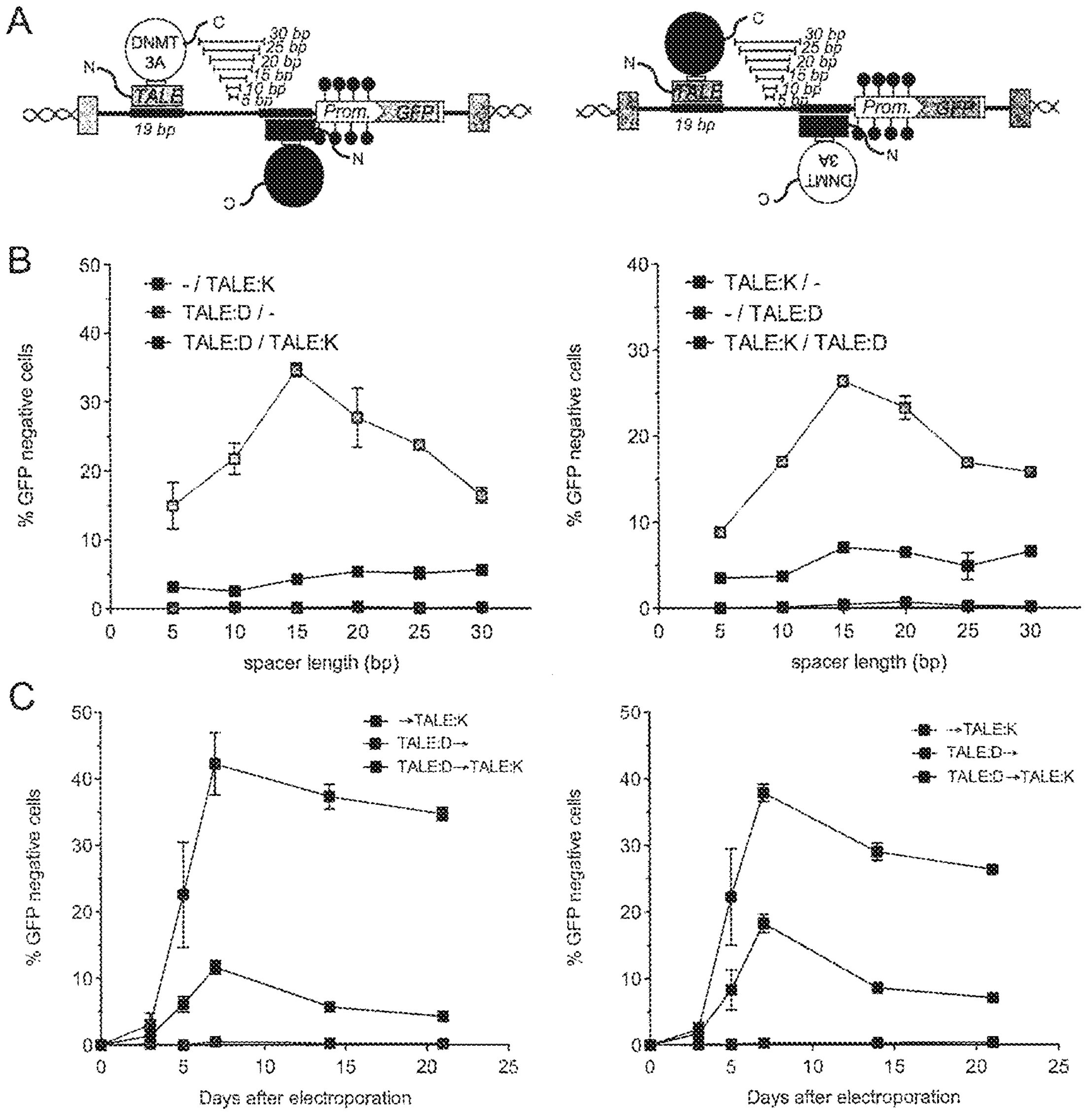

Considering the significant impact of structural variables (such as spacer length and the relative order of binding of the two ATRs on the target sequence) on the silencing efficiency, we then asked if moving to a head-to-head (H-H) configuration in which the C-termini of the two ATRs face each other could be beneficial for our strategy. To move from the head-to-tail to the head-to-head configuration, starting from the reporter cassette described in FIG. 8 we maintained the 5' TALE binding site unaltered, while we changed the orientation of the 3' TALE binding site. This simple change allowed us to use the same four ATRs employed in the previous experiments. We also generated six eGFP reporter cassettes differing in spacer length between the two TALE target sites (5, 10, 15, 20, 25 and 30 bp) and we delivered these constructs to K562 cells via lentiviral vector transduction (a schematic of these vectors is shown in FIG. 9A). Transduced cells were then sorted to obtain pure eGFP+ populations and electroporated with plasmids encoding for TALE:K or TALE:D3A, either alone or in combination. Treated cells were then analysed by time-course flow cytometry to measure the extent and duration of silencing. To stringently compare the head-to-head to the head-to-tail configuration, we included the cell line containing the 25 bp spacer and the H-T, TALE:D3A$\rightarrow$TALE:K configuration described in FIG. 8C in this experiment. The results of these experiments indicated that: i) co-delivery of TALE:K and TALE:D3A resulted in evident synergy even in the H-H configuration, allowing long-term silencing of the reporter cassette in up to 34.7% of the treated cells (FIG. 9B; data are represented as mean±SEM, n=3); ii) individual delivery of TALE:K or TALE:D3A resulted in low (up to 7.1%) or absent permanent silencing, respectively; and iii) the relative order of binding of the two ATRs on the target locus impacted on the overall silencing efficiency, with the TALE:D3A$\rightarrow$TALE:K configuration performing from 1.3 to 1.7 fold better than the opposite one (FIG. 9C; data are represented as mean±SEM, n=3). However, the relative order of binding seems to have a greater impact on silencing efficiency in the head-to-tail configuration than in the head-to-head configuration (compare FIG. 8 with FIG. 9). A bell-shaped trend seems to describe the impact of the tested spacer lengths on silencing efficiency of the H-H configuration, with the 15 bp spacer performing best both in the TALE:D3A$\rightarrow$TALE:K and in the TALE:K$\rightarrow$TALE:D3A configurations (even outperforming the 25 bp spacer in the head-to-tail experiment). However, the difference between the 15 bp head-to-head configuration and the 25 bp head-to-tail configuration was minimal (34.7% versus 26.8% long-term eGFP-cells, respectively, i.e. a 1.3-fold increase).

Overall, these data show for the first time to our knowledge the feasibility of achieving permanent epigenetic silencing of a desired target gene upon transient delivery of a combination of ATRs equipped with custom-made DNA binding domains. Moreover, from these studies we were able to define rules for the selection of TALE binding sites that can be used for the identification of Silencing Elements on a desired target gene. By targeting multiple Silencing Elements on the regulatory sequence of this gene we should be able to increase the efficiency of silencing.

In parallel to these studies we developed bipartite ATRs by coupling two effector domains on the same TALE, i.e. the KRAB domain at the N terminus and the DNMT3A domain at the C terminus of the TALEs (FIG. 10A). Even if transient transfection of the individual proteins was not sufficient to induce appreciable levels of gene silencing, their combination was sufficient to silence eGFP in up to 7% of the treated cells (FIG. 10B; data are represented as mean±SEM, n=3). The advantages provided by such an approach are that multiple effector domains can be delivered to the same target site while reducing the number of different mRNAs required to be produced and transfected.

Permanent Epigenetic Silencing in Human HSPCs by Using Different Combinations of ATRs Primary haematopoietic stem cells (HSPCs) are a clinically relevant human cell type for most of the ex vivo gene therapy applications (Biffi, A. et al. (2013) *Science* 341: 1233158; Aiuti, A. et al. (2013) *Science* 341: 1233151; Aiuti, A. et al. (2009) *N. Engl. J. Med.* 360, 447-458; Cartier, N. et al. (2009) *Science* 326: 818-23; Hacein-Bey-Abina, S. et al. (2010) *N. Engl. J. Med.* 363: 355-64; Cavazzana-Calvo, M. et al. (2010) *Nature* 467: 318-22) due to their life-long self-renewal capacity and multilineage differentiation potential. HSPC differentiation is accompanied by global chromatin remodelling, which results in a progressive transition from an open chromatin configuration to a more compacted and repressive one. As such, this cell type represents the most appropriate and stringent model to test efficacy and prove stability of our epigenetic platform. To assess if the delivery of various ATR combinations was sufficient to induce significant levels of silencing in human HSPCs, we transduced human cord blood-derived CD34+ cells from healthy individuals with the TetO7/eGFP-reporter LV described in FIG. 5A. We then transfected the cells with in vitro transcribed mRNAs encoding for tetR:D3A, tetR:K or tetR:D3L, either alone or in combinations. Transfected and un-transfected cells were then grown in liquid culture for 2 weeks in myeloid-differentiation conditions or plated in semi-solid media for a Colony Forming Unit-Cells (CFU-C) assay (for the layout of these experiments refer to FIG. 11A).

Flow cytometry analyses of the cells grown in liquid culture showed that treatment with the tetR:K resulted in a transient wave of eGFP repression that was then maintained in up to 20% of the treated cells until the end of the experiment (FIG. 11B; data are represented as mean±SEM, n=3). A similar phenotype was observed in CD34+ cells transfected with mRNA encoding for tetR:D3A and tetR:D3L. Treatment with tetR:K/tetR:D3A combination or with tetR:D3A/tetR:D3L combination resulted in a cooperative effect, showing that up to 40% of the treated cells fully silenced eGFP expression. Strikingly, by combining tetR:D3L/tetR:K or tetR:D3L/tetR:K/tetR:D3A we reached up to 90% of silencing of the reporter gene. Importantly, similar levels of silencing were observed in erythroid and myeloid cells originating in the CFU-C assay (FIG. 11C; data are represented as mean±SEM, n=3), thus indicating that silencing was maintained even upon HSPC differentiation.

Permanent Epigenetic Silencing in Human T Lymphocytes Using Different Combinations of ATRs To assess if the delivery of various ATR combinations was sufficient to induce significant levels of silencing in human T lymphocytes, a clinically relevant cell type for many cell-based gene therapy applications including cancer immunotherapy, we transduced human T cells from healthy individuals with the TetO7/eGFP-reporter LV described in FIG. 5A. We then transfected the cells with in vitro transcribed mRNAs encoding for tetR:D3A, tetR:K or tetR:D3L, either alone or in various combinations. Transfected and un-transfected cells were then kept in liquid culture for 3 weeks in media enriched with IL-15 and IL-7 before reactivation (for the layout of these experiments, refer to FIG. 12A).

Flow cytometry analyses of the cells showed that treatment with individual ATRs and tetR:D3A/tetR:K resulted in no or transient eGFP repression. On the other hand treatment with all the other possible ATR combinations resulted in permanent silencing of the reporter gene. Importantly, the levels of silencing measured during the initial phase of cell proliferation and in the resting phase were super-imposable, indicating that silencing is maintained even after the transcriptional and metabolic states of the cells have changed (FIG. 12B; data are represented as mean±SEM, n=3).

Permanent Epigenetic Silencing of a Human Endogenous Gene Using Custom-Made ATRs In order to assess if the results obtained with the eGFP reporter system could also be translated to an endogenous gene embedded in its natural epigenetic context, we generated custom-made TALEs targeting the promoter region of the 32-Microglobulin (B2M) gene (the amino acid sequences of these TALEs and the nucleotide sequences of their corresponding binding sites are listed in Table 3), and fused these TALEs to the KRAB, DNMT3A and DNMT3L effector domains (for a schematic of the system refer to FIG. 13A). The spacer length between the first and the second, or between the second and the third TALE is 1 or 20 bp, respectively. We then co-transfected HEK-293T cells with the plasmids encoding for these novel ATRs and analysed the cells by flow cytometry for B2M expression.

At 50 days post-transfection, when the percentage of B2M-negative cells was stable, we measured a significant fraction of B2M-negative cells only in the conditions treated with the TALE:D3A+TALE:D3L and the TALE:D3A+TALE:D3L+TALE:K combinations (FIG. 13B; data are represented as mean±SEM, n=3; *p<0.0001, one-way anova and Bonferroni post-test). Remarkably, up to 80% of the cells treated with all the ATRs permanently lost B2M surface expression. In parallel experiments, we sorted the B2M-negative and the B2M-positive cells, and analysed them for surface expression of MHC-I molecules, which require B2M to be presented on the plasma membrane. We found that, contrary to the B2M-positive cells, nearly all the B2M-negative cells were also negative for MHC-I expression (FIG. 13C). We also performed on the B2M-negative and B2M-positive sorted cells gene expression analysis and found that the negative cells expressed ~100-fold less B2M that the positive cells (FIG. 13D; data are represented as mean±SEM, n=3). Then we assessed if the three effector domains were capable of inducing permanent epigenetic silencing also when targeted to the B2M gene via the RNA-guided CRISPR/Cas9 system. To this aim, we fused in frame to a catalytically dead Cas9 (D10A+H840A; dCas9; amino acid sequence listed in Table 4) the KRAB, the DNMT3A or the DNMT3L effector domains (FIG. 13E; top drawings), and designed 11 guide RNAs (gRNAs; nucleotide sequences listed in Table 4) targeting the promoter region of the B2M gene (FIG. 13E; bottom schematic, arrows indicate the location of the CRISPR/dCas9 target sites). We then co-transfected HEK-293T cells with plasmids expressing the 11 B2M gRNAs together with all the possible combinations of the plasmids encoding for the dCas9 fusion proteins. Flow cytometry analysis of the treated HEK-293T cells 33 days after transfection showed that only the dCas9:K+dCas9:D3L, dCas9:D3A+dCas9:D3L and dCas9:K+dCas9:D3a+dCas9:D3L combinations were able to induce silencing of the B2M gene (FIG. 13F; data are represented as mean±SEM, n=3). We then assessed if B2M silencing was resistant to IFN-γ treatment, a potent inducer of B2M expression (Vraetz, T. et al. (1999) Nephrol. Dial. Transplant. 14: 2137-43; Gobin, S. J. et al. (2003) Blood 101: 3058-64). For this experiment, we used wild-type and B2M-negative cells, the latter being sorted from the triple ATR treated conditions described in FIGS. 13B and 13F. As expected, IFN-γ treatment caused a significant upregulation in the expression of the 2'-5'-oligoadenylate synthetase 1 (OAS1) gene (>100-fold) in all cell types tested (FIG. 13G). On the other hand, while wild-type cells significantly upregulated B2M expression upon IFN-γ treatment both at the transcriptional and at the protein level, no increase in the expression of this gene was measured in the B2M-negative cells (FIG. 13G and FIG. 13**H, respectively).

In order to assess if silencing induced by our ATRs was associated with the deposition of repressive epigenetic marks on the targeted gene, we analysed the epigenetic state of the B2M gene in wild-type and silenced cells. To this aim, we sorted to purity the cells treated with plasmid encoding for the triple TALE:ATR combination in order to obtain a pure population of silenced cells (FIG. 14A, showing representative FACS dot plot). Chromatin Immunoprecipitation (ChIP) followed by quantitative PCR analysis for the RNA polymerase II (RNA PolII) on the promoter region and the gene body of B2M showed complete absence of this protein in silenced cells, while it was highly enriched at the promoter region of untreated cells (the PPP1R12C and the CCR5 gene were used as positive or negative controls for these experiments, respectively; FIG. 14B). We also performed bisulfite analysis of B2M CpG island and found that in untreated cells the promoter region was almost deprived of 5mC at the level of the CpGs (less than 1%), while the same region in silenced cells was highly decorated with de novo DNA methylation (more than 80% on average) (FIG. 14C). DNA methylation was also responsible for silencing maintenance as AZA treatment was associated to re-expression of the B2M gene in previously silenced cells (FIG. 14D). Finally, in order to address if silencing was confined to the B2M gene, we performed transcriptional analysis of the B2M locus by RT-qPCR (FIG. 14E top schematic), and found that the only gene that was down-regulated upon transient delivery of the triple ATR combination was B2M, while expression of its neighbouring gene was unaffected (FIG. 14E).

In parallel to these experiments, we also tested silencing of the B2M gene in K-562 cells. Because this cell line does not express the MHC-I, which is strictly required for B2M surface expression, we targeted the coding sequence of the fluorescent marker tdTomato into the first intron of the B2M gene in order to faithfully report for the B2M transcriptional state (FIG. 15A). After gene targeting by CRISPR/Cas9, the tdTomato positive cells were sorted and then electroporated with plasmids encoding for either TALE- or CRISPR/ dCas9-based ATRs against the B2M promoter/enhancer (the target sequences of these ATRs are the same as those of FIG. 13). Concerning the TALE-based ATRs, we found that both the TALE:D3L+TALE:K and the TALE:D3A+TALE:D3L+TALE:K combinations were able to stably silence B2M expression, with the triple ATR combination being the best performing (FIG. 15B). Condon-optimisation of the effector domains of the TALE-based ATRs improved silencing efficiency of the above-mentioned combinations (FIG. 151B; compare the red versus the green bars). Concerning the silencing activity of the CRISPR/dCas9-based ATRs, we found that all but the dCas9:D3A+dCas9:K combination was able to induce high silencing efficiency of the B2M gene (up to 55% of stably silenced cells; FIG. 15C). Finally, targeting of dCas9 fused to the catalytic domain of the TET1 enzyme (which is known to demethylate DNA; Maeder, M. L. et al. (2013) Nat. Biotechnol. 31: 1137-42) to the B2M promoter/enhancer of sorted silenced cells resulted in reactivation of the expression of this gene (FIG. 15D), further corroborating the notion that silencing induced by the triple ATR combination is dependent on DNA methylation.

To assess if B2M silencing could also be effective in primary human T lymphocytes, we electroporated human T cells from a healthy donor with in vitro transcribed mRNAs encoding for the TALE:K+TALE:D3A+TALE:D3L ATRs described above. Transfected and un-transfected cells were then kept in liquid culture for 2 weeks in media enriched with IL-15 and IL-7 (experimental scheme in FIG. 16A). Flow cytometry analyses of the cells showed that treatment with the TALE:K+TALE:D3A+TALE:D3L ATRs resulted in silencing of the B2M gene (kinetic of silencing in FIG. 16B, FACS plots in FIG. 16C).

Figure 17:
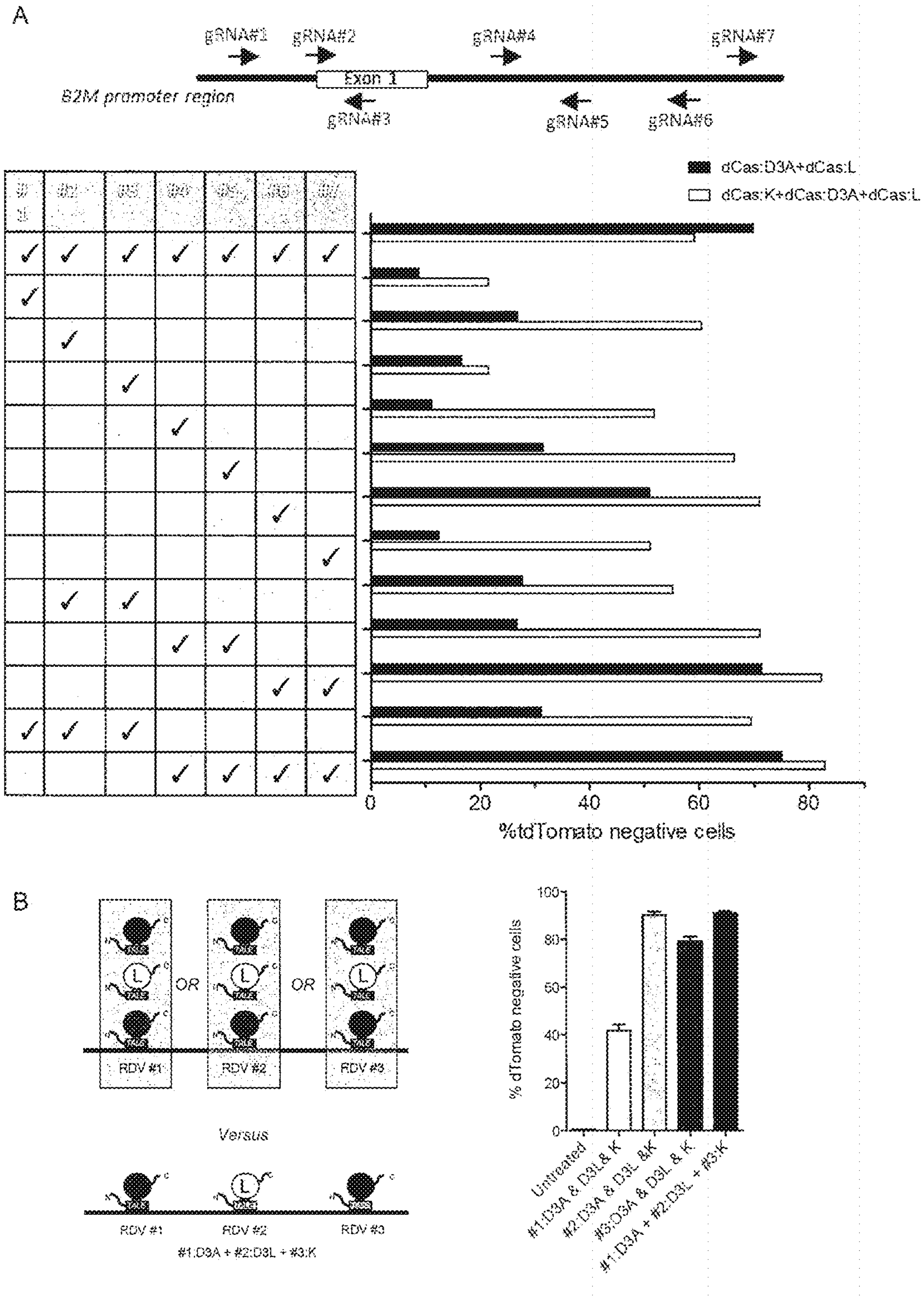

Intriguingly, functional deconvolution of 7 gRNAs into quartets until individual singlets showed that even one gRNA was sufficient to drive efficient silencing of B2M with both the triple and the dCas9:D3A+dCas9:D3L combination (FIG. 17). Unexpectedly, some of the single gRNA were able to induce silencing efficiencies that were comparable to those measured in the 7 gRNA pool. Furthermore, in several instances, we observed that the triple ATR combination was performing better than the dCas9:D3A+dCas9:D3L combination. Altogether, these data indicates that even one well properly positioned gRNA tethering the three ATRs on the target gene can induce its efficient silencing.

Similarly, we also investigated if a single TALE protein was sufficient to induce efficient and permanent epigenetic silencing. To this aim we generated four TALE proteins, to each of which we fused the three different effector domains, namely KRAB, DNMT3A and DNMT3L (FIG. 17B; schematic on the left). As a model we used the TALE proteins targeting B2M gene and the K562 B2M tdTomato reporter cell line previously described (FIGS. 13A and 15A, respectively). Unexpectedly, also in the conditions in which the repressive domains were competing for the same binding site on the B2M gene, we obtained efficient and permanent gene silencing of the B2M gene (FIG. 17B, grey bars in the histogram). The different degree of efficiency was most likely reflecting the different binding affinity of the TALEs, with some of these working as efficiently as the control condition in which each effector domain was fused to a different DNA-binding domain (FIG. 17B; black bar in the histogram).

Overall, these data show for the first time to our knowledge permanent silencing of an endogenous gene in human cells using custom made ATRs. Importantly, silencing was fully resistant to external stimuli impinging on the B2M promoter/enhancer, thus providing another line of evidence of the stability of the epigenetic modifications deposed by the triple ATRs combination. Moreover, we provide evidence of the broad applicability of our strategy by tethering the repressor domains to the endogenous gene by means of two different DNA binding technologies, namely TALE and CRISPR/Cas9.

Transient Expression of an Un-Targeted DNMT3L Improves and Rescues Silencing Efficiency of the DNMT3A+KRAB Based ATRs in Refractory Cell Types In order to reduce the number of different ATRs to design and construct, we investigated if at least one of the effector domains can be delivered to the cells without a DNA binding domain, and still be able to effectively cooperate with the other two ATRs targeted on the desired gene of interest. To assess if delivery of an un-targeted DNMT3L (hereafter referred to as D3L) might be as effective as its targeted counterpart in cooperating with the other two effector domains (specifically DNMT3A and KRAB), we initially took advantage of the TetO7/tetR system. We thus transfected the TetO7.LV-reporter B-lymphoblastoid cells with in vitro transcribed mRNAs encoding for the tetR-based ATRs and for the un-targeted D3L, and measured by time-course flow cytometry analysis the percentage of eGFP-negative cells in the different transfection conditions (FIG. 18A; data are represented as mean±range, n=2). At 27 days post-transfection we found little if any silencing in cells treated with either the individual ATRs or the tetR:K+tetR:D3A combination. Instead, up to 70% of the cells treated with the combination of the 3 ATRs become eGFP-negative. The targeted tetR:D3L synergised also with tetR:K or tetR:D3A, although the levels of silencing measured in these two experimental conditions were 3.5-fold lower (~20% eGFP-negative cells) than those measured with the triple ATR combination (FIG. 18A; compare the plus tetR:D3L conditions). These data are in line with those previously found with the TetO7.LV-reporter B-lymphoblastoid cell line, in which the unexpected drop in the silencing efficiency of the tetR:D3A+tetR:K combination was completely rescued by inclusion of the tetR:D3L to the cocktail (see FIG. 7G for comparison). When the un-targeted D3L was delivered either alone or in combination with the tetR:K, no eGFP-negative cells were found. On the other hand, D3L was able to effectively synergise with both the tetR:D3A and the tetR:D3A+tetR:K combination (FIG. 18A; see the plus D3L conditions). Importantly, the levels of silencing measured in these two experimental conditions were comparable to those found by co-tethering DNMT3L and DNMT3A; or DNMT3L, DNMT3A and KRAB to the TetO7 sequence. These data indicate that the un-targeted D3L can effectively synergise with the KRAB+DNMT3A combination.

We then assessed if these findings also held true with ATRs based on custom-made DNA binding domains. To this end, we selected 4 different TALE binding sites in the B2M promoter region and constructed the corresponding TALE DNA binding domains (a schematic of the B2M locus showing the different TALEs binding sites is depicted in FIG. 18B; the amino acid sequences of the TALE A and the nucleotide sequences of its corresponding binding sites is listed in Table 5; TALEs B, C and D were described previously and correspond to TALE #1, #2 and #3 of Table 3). Each of these TALEs were equipped with KRAB or DNMT3A. The 4 different TALE binding sites constitute two independent silencing modules (Module 1: site A plus site B; Module 2: site C plus site D), at which the TALE:D3A and TALE:K can bind in two different orders (siteA:K-siteB:D3A or siteA:D3A-siteB:K). We then transfected HEK-293T cells with plasmids encoding for the TALE-based ATRs and for the untargeted D3L, and measured by time-course flow cytometry analysis the percentage of double B2M/MHCl-negative cells in the different transfection conditions (FIG. 18C). At 12 days post-transfection we measured a low fraction of B2M/MHCl-negative cells in all the conditions treated with the TALE:D3A+TALE:K combination (upper plots in FIG. 18C). On the other hand, co-treatment of the cells with the combination of the two ATRs plus the untargeted D3L resulted on average in a 5-fold increase in the efficiency of silencing (lower plots FIG. 18C) over the levels measured in the absence of D3L. This increase was independent of the relative order of binding of the TALE proteins on the B2M promoter and was confirmed for both of the silencing modules.

Finally, we performed similar experiments using ATRs based on the CRISPR/Cas9 system (FIG. 18D; data are represented as mean±SEM, n=3). Here, we found that transient expression of D3L in HEK-293T cells transfected with the dCas9:K+dCas9:D3A ATRs plus the B2M gRNAs (those used in FIG. 13E) resulted in levels of gene silencing comparable to those obtained with the triple combination of the dCas9-based ATRs plus the B2M gRNAs (FIG. 18D). Similar results were obtained by delivering D3L with the DNMT3A ATR.

Overall, these data clearly show that the un-targeted DNMT3L can effectively replace its targeted counterpart in our cocktail of ATRs.

Transient Expression of an Untargeted DNMT3B Rescues Silencing Efficiency of the DNMT3A+KRAB Based ATRs in Refractory Cell Types Considering the role of the DNMT3B in the establishment of de novo DNA methylation, we asked if the endogenous DNMT3B could cooperate with our ATRs. To answer this question, we performed a genetic knock-out of DNMT3B by CRISPR/Cas9 in the TetO7.LV K562 reporter cell line. To do this, we transduced the cells with two lentiviral vectors, one encoding for a doxycycline-inducible Cas9 nuclease (Wang, T. et al. (2014) *Science* 343: 80-4) and another encoding for both a gRNA against the exon 2 of the DNMT3B gene and the ΔLNGFR marker (schematic of the vectors in FIG. 19A; middle FACS plot for the double transduced cells). Upon Cas9 activation by doxycycline administration, we electroporated the cells with plasmids encoding for the different combinations of the ATRs, and then measured by flow cytometry the efficiency of silencing in the ΔLNGFR-positive and -negative cells. By comparing these numbers, we can appreciate if inactivation of the DNMT3B gene improves or not the efficiency of silencing of the different ATR combination. Here, we observed that the subpopulation expressing the gRNAs anti-DNMT3B (i.e. ΔLNGFR-positive cells) was less permissive than wild-type cells (i.e. those negative for ΔLNGFR) to silencing by tetRK+tetR:D3A combination (FIGS. 19B-19D; left FACS plot of FIG. 19C), thus indicating that the endogenous DNMT3B is a relevant partner of these two ATRs. Remarkably, genetic knock-out of DNMT3B increased silencing efficiency of the tetR:K+tetR:D3A+tetR:D3L combination, thus suggesting that in this case DNMT3B is acting as a decoy for these ATRs (FIGS. 19B-19D; right FACS plot of FIG. 19C). For all the other ATR combinations and the individual ATR, inactivation of DNMT3B did not cause any significant difference in the silencing efficiency as compared to wild-type cells. Furthermore, considering that, in contrast to K562 cells, the B-lymphoblastoid cell line described above lacks DNMT3B expression (as measured by RT-qPCR analysis), we asked if DNMT3B overexpression could increase ATRs silencing efficiency in this cell line refractory to the DNMT3A+KRAB combination. In particular, we transiently transfected the TetO7.LV B-lymphoblastoid reporter cell line with an mRNA encoding for the full-length DNMT3B (without fusing it to the tetR DNA binding domain; the amino acid sequence of the DNMT3B is in Table 1) with or without the two ATRs. Remarkably, DNMT3B overexpression significantly rescued activity of the tetR:K+tetR:D3A combination, enabling stable eGFP silencing in 52% of the treated cells, with a 65-fold increase compared to tetR:K+tetR:D3A alone (FIG. 19D). Of note, DNMT3B overexpression generated also a 2.9-fold increase in the silencing efficiency of the tetR:D3A condition (FIG. 19E).

Overall, these data clearly show that the un-targeted DNMT3B can effectively rescue activity of the DNMT3A+KRAB combination in refractory cell types.

Silencing of the BCL11A Gene Using Both CRISPR/dCas9- and TALE-Based ATRs.

We then exploited the ATR combination to silence BCL11A, a gene whose repression has been proposed as a potential therapeutic intervention for β-Thalassemia and Sickle Cell Anaemia. To easily assess activity of the ATRs on the BCL11A gene, we targeted the tdTomato transgene within the third exon of the gene in human B-lymphoblastoid cells by means of gene targeting with CRISPR/Cas-based technology (FIG. 20A). Such targeting strategy allows expressing the tdTomato transgene from the regulatory sequences of the BCL11A gene, thus faithfully reporting the expression level of this gene. We then enriched to near purity the tdTomato-positive cells by cell sorting, and targeted 4 CpG islands in the promoter/enhancer region of this gene with CRISPR/dCas9-based ATRs containing DNMT3A or DNMT3L. Each of the 4 CpG island was individually interrogated using a separate pool of gRNAs (also known as CRISPR; the nucleotide sequences of the gRNAs are reported in Table 6). By comparing tdTomato expression between treated and untreated controls, we were able to measure the relative contribution of each island to the expression of BCL11A (FIG. 20B). When compared to control-treated cells, silencing of each CpG island was associated with long-term stable repression of BCL11A expression (shown here as % of tdTomato-negative cells), although the extent of silencing of this gene varied according to the CpG island targeted by the ATRs. We then selected the CpG island 31 and 38 for further studies aiming at assessing the activity of the triple ATR combination. In these studies we also included all possible double-ATR combinations and the single KRAB-based ATRs. Remarkably, all conditions tested were able to induce significant levels of gene silencing, with epigenetic editing of CpG 38 (the best responsive island in the previous experiments) with the triple ATR combination resulting in up to 55% gene silencing (FIG. 20C). Finally, we designed 17 different TALE-based ATRs targeting the CpG island 31 and 38 (7 and 10 TALE protein, respectively; the amino acid sequences of these TALEs and their cognate target sequences are listed in Table 7; FIG. 20D top schematics), and tested their silencing activity either as a triple-ATR combination or as KRAB-based ATR. Silencing of both CpG island with all triple ATR combination resulted in effective and long-term silencing of BCL11A (reaching up to 55% of tdTomato-negative cells), while silencing with TALE:KRAB was associated with different degrees of gene silencing, some being as efficient as the triple ATR combination, while others being completely inactive. Overall, these data show the feasibility of permanently silencing the human BCL11A gene.

Silencing of Additional Human Endogenous Genes Using CRISPR/dCas9-Based ATRs.

We finally challenged our epigenetic silencing technology against two additional human endogenous genes, that are the Interferon (alpha, beta and omega) Receptor 1 (IFNAR1) gene and the Vascular Endothelial Growth Factor A (VEGFA) gene. Both genes show a CpG island at the gene promoter/enhancer region. Therefore, we designed 13 gRNAs against the IFNAR1 CpG island (FIG. 20E, Top) 3 gRNAs against the VEGFA CpG island (FIG. 20F, Top) (the nucleotide sequences of the gRNAs are reported in Table 6). Interestingly, by electroporating K562 cells with plasmids encoding for the pool of 13 gRNAs against the IFNAR1 gene plus the triple dCas9-based ATRs combination, we achieved long-term downregulation of the IFNAR1 transcript level (0.22 fold change) in treated cells compared to the untreated sample (FIG. 20E, Bottom). Furthermore, by electroporating K562 cells with plasmids encoding for the pool of 3 gRNAs against the VEGFA gene plus the triple dCas9-based ATRs combination, we achieved long-term downregulation of the VEGFA transcript level (0.57 fold change) in treated cells compared to the untreated sample (FIG. 20F, Bottom). Overall, these data show the feasibility of silencing various human endogenous genes by CRISPR/dCas9-based ATRs.

Material and Methods

Lentiviral Vectors and ATR Constructions

The ATR-reporter Lentiviral Vectors (LV) containing the TetO7 sequence or the TALE binding sites, and the DNMT3B gRNA-expressing LV were generated from the self-inactivating transfer construct pCCLsin-.cPPT.hPGK.eGFP.Wpre (Follenzi, A. et al. (2000) Nat. Genet. 25: 217-22), while ATR-expressing Bid.LVs were generated from the transfer construct pCCLsin.cPPT.dLNG-FR.mhCMV.hPGK.GFP.Wpre (Gentner, B. et al. (2010) Sci. Transl. Med. 2: 58ra84). The doxycycline-inducible Cas9 expressing vector was obtained from Addgene (pCW-Cas9; #50661; Wang, T. et al. (2014) Science 343: 80-4). LV stocks were prepared as previously described (Follenzi, A. et al. (2002) Methods Mol. Med. 69:259-74). Briefly, HEK293T cells were cotransfected by calcium phosphate precipitation with the transfer construct plasmid, the pMD.Lg/pRRE packaging plasmid, the pMD2.VSV-G envelope-encoding plasmid and pRSV-Rev in the following amounts: 35/12.5/9/6.25 μg DNA per 15 cm dish, respectively. Vector particles were concentrated 300-fold by ultracentrifugation and titred by serial dilution on HEK293T cells as previously described (Cantore, A. et al. (2015) *Sci. Transl. Med.* 7: 277ra28). All other tetR-based ATRs were generated by replacing the KRAB domain in tetR:KRAB (which is itself discussed in Szulc, J. et al. (2006) Nat. Methods 3: 109-16) with the relevant other effector domains. TALE-based ATRs were generated using a modified version of the Golden Gate TALEN Kit 2.0a (Addgene, Kit #1000000024; Cermak, T. et al. (2011) *Nucleic Acids Res.* 39: e82) containing the following architectural changes: the Golden Gate TALE C- and N-terminal subregions were replaced with the +163 and a +63 terminal deletions, respectively. These constructs were adapted to accommodate in frame the effector domains. The Cas9-based ATRs were generated by replacing the VP160 transactivator from the plasmid pAC154-dual-dCas9VP160-sgExpression (Addgene #48240; Cheng, A. W. et al. (2013) *Cell Res.* 23: 1163-71) with the effector domains or with the catalytic domain of TET1.

Cell Culture Conditions and Engineering

Human Epstein-Barr Virus-immortalised B lymphocytes (B-lymphoblastoid cells) and U-937 cells were maintained in RPMI-1640 (Sigma); HEK293T and K-562 in IMDM (Sigma); NIH/3T3 in DMEM (Sigma). All media were supplemented with 10% FBS (Foetal Bovine Serum; EuroClone), L-glutamine (EuroClone) and 1% Penicillin/Streptomycin (100 U/mL final concentration; EuroClone). Cells were cultured at 37° C. in a 5% $CO_2$ humidified incubator. The reporter cell lines were generated by transducing the cells with the indicated ATR-reporter LVs at a Multiplicity of Infection (MOI) of 0.1, and then enriched for eGFP expression using a MoFlo XDP Cell Sorter (Beckman Coulter). The reporter cell lines with targeted integration were generated as follows: i) for the insertion of the eGFP-cassette into the AAVS1 locus, we co-transfected a donor construct (containing the TetO7 sequence downstream or upstream of the cassette; 1.5 μg of donor plasmid) and the previously described AAVS1-ZFNs in forms or mRNAs (0.5 μg each ZFN; Lombardo, A. et al. (2011) Nat. Methods 8: 861-9). Single-cell derived clones were then obtained by limiting dilution plating, and analysed by Southern blot to confirm targeted integration of the cassette as previously described (Lombardo, A. et al. (2011) Nat. Methods 8: 861-9); ii) for the insertion of the tdTomato cassette within the third exon of BCL11A, we co-transfected a donor construct containing the tdTomato transgene fused to 2A self-catalytic peptide (2 μg), together with a plasmid encoding for Cas9 (1 μg) and another expressing a gRNA targeting exon 3 (125 ng; sequence of the gRNA: 5'-GGAGCTCTAATCCCCACGCCTGG-3', SEQ ID NO: 110); iii) a similar targeting strategy to that used for BCL11A was used to insert a splice acceptor-IRES-tdTomato cassette into intron 1 of B2M (sequence of the gRNA: 5'-AGGCTACTAGCCCCATCAAGAGG-3'. SEQ ID NO: 111). Both the tdTomato cell lines were generated by FACS-sorting of the positive cells.

To test activity of the ATRs, the reporter cell lines were transduced with the ATR-expressing Bid.LV at a MOI of 10, or transfected with plasmids or in vitro transcribed mRNAs expressing the ATRs (4D-Nucleofector™ System; Lonza) according to the manufacturer's instruction for K-562, U937 and NIH/3T3, or using the pulse program EW-113 and the SF solution for B-lymphoblastoid cells. We routinely transfected 2 μg of nucleic acid (both plasmid and in vitro transcribed mRNA) for each tetR- or TALE-based ATR, except for experiments conducted in non-saturating conditions in which we used 500 ng of plasmid encoding for each of the ATRs. On the other hand, we electroporated 1-2 μg of plasmid encoding for the dCas9-based ATRs and 125-250 ng of plasmids expressing for the gRNAs. In vitro transcribed mRNAs were produced as previously described (Genovese, P. et al. (2014) Nature 510: 235-40). When indicated, cells were treated with 1 μM of 5-Aza-2-deoxycytidine (AZA, Sigma) or with 12 μg/mL of doxycycline (Sigma). The AZA-containing media was replaced every day, and the cells were analysed by flow cytometry at day 4 and 7 after treatment. When indicated, cells were treated with 500 U/mL of Recombinant Human IFN-γ (R&D Systems). The IFN-γ-containing media was replaced every day, and the cells were analysed by flow cytometry at day 2 and 4 after treatment. Cord-blood derived CD34+ cells from healthy donors were purchased from Lonza. $10^6$ CD34+ cells/mL were stimulated overnight in serum-free StemSpan medium (StemCell Technologies) supplemented with penicillin, streptomycin and the following human early-acting cytokines: Stem Cell Factor (SCF) 50 ng/mL, Flt3 ligand (Flt3-L)

50 ng/mL, thrombopoietin (TPO) 50 ng/mL, and interleukin 6 (IL-6) 50 ng/mL (all purchased from Peprotech). The cells were then transduced with the TetO7-reporter LV at MOI of 30-50. After 48 hours, the cells were electroporated with 2 μg of the ATR-encoding mRNAs (P3 Primary Cell 4D-Nucleofector X Kit, program EO-100; Lonza). 1 μM of SR1 (BioVision Inc.) was added at every medium change. After one week in stimulating media, cells were grown in liquid culture in IMDM 10% FBS. For CFC assays, 800 cells/plate were seeded one day after electroporation in methylcellulose-based medium (MethoCult H4434, StemCell Technologies). Two weeks after plating, colonies were counted and identified according to morphological criteria and analysed by flow cytometry.

Resting T-lymphocytes were isolated from Peripheral Blood Mononuclear Cells (PBMCs) of healthy donors by leukapheresis and Ficoll-Hypaque gradient separation. The cells were activated and sorted using magnetic beads conjugated to antibodies to CD3 and CD28 (ClinExVivo CD3/CD28; Invitrogen), following the manufacturer instructions, and grown at a concentration of $1\times10^6$ cells per mL in RPMI (Sigma) supplemented with penicillin, streptomycin, 10% FBS and 5 ng/mL of IL-7 and IL-15 (PeproTech) as previously described (Kaneko, S. et al. (2009) Blood 113: 1006-15). After three days in culture, the cells were transduced with the TetO7-reporter the LV at the MOI of 10. Three days after transduction, the cells were washed and electroplated with 2 μg of mRNA encoding for the ATRs. To test silencing resistance to polyclonal TCR stimulation, we co-cultured the bulk-treated T-lymphocytes with a pool of 6000 rad irradiated PMBCs from unrelated donors and 10000 rad irradiated JY cells in presence of anti-CD3 antibody (OKT3) 30 ng/mL (Orthoclone, Milan, Italy) and human recombinant IL-2 50 U/mL (PrepoTech). Regarding silencing of B2M in primary T-lymphocytes, these cells were isolated from PBMCs of a healthy donor by leukapheresis, Ficoll-Hypaque gradient separation and final selection with the Pan T Cell Isolation Kit (Miltenyi Biotec). The T-cells were then activated with magnetic beads conjugated to antibodies to CD3 and CD28 (ClinExVivo CD3/CD28; Invitrogen), following the manufacturer's instructions, and grown at a concentration of $1\times10^6$ cells per mL in RPMI (Sigma) supplemented with penicillin, streptomycin, 10% FBS and 5 ng/mL of IL-7 and IL-15 (PeproTech) as previously described (Kaneko, S. et al. (2009) Blood 113: 1006-15). After three days in culture, the cells were electroporated with in vitro transcribed mRNA encoding for TALE-based ATRs and kept in culture for further 2 weeks, with beads removal 4 days post electroporation. The use of human CB-derived CD34+ cells and of primary T-lymphocytes was approved by the San Raffaele Hospital Bioethical Committee.

Flow Cytometry and Gene Expression Analyses

For immunophenotypic analysis of Bid.LV transduced cells, CD34+ cells and their progeny, and T lymphocytes (performed by FACSCanto II; BD Pharmingen) we used the following antibodies.

| Antibody | Conjugated | Company |
|---|---|---|
| anti-human CD133/2 | PE | Miltenyi Biotec |
| anti-human CD34 | PECy7 | BD Pharmingen |
| anti-human CD90 | APC | BD Pharmingen |
| anti-human CD45 | PB | BioLegend |
| anti-human CD3 | PE | BD Pharmingen |
| anti-human CD13 | APC | BD Pharmingen |
| anti-human CD33 | PeCy7 | BD Pharmingen |
| anti-human CD235a | PE, APC | BD Pharmingen |

-continued

| Antibody | Conjugated | Company |
|---|---|---|
| anti-human B2M | PE | Biolegend |
| anti-human MHC-I | APC | Santa Cruz Biotechnology, Inc |
| anti-human CD271 | Alexa Fluor 647 | BD Pharmingen |

Aminoactinomicin D (7-AAD) positive, nonviable cells were excluded from the analysis, and $1\text{-}5\times10^5$ viable cells were scored per analysis. Single stained and FMO stained cells were used as controls.

For the gene expression analyses, total RNA extracted from $2\text{-}6\times10^6$ cells (RNeasy Mini kit; Qiagen) was reverse-transcribed using random examers according to the SuperScript Ill First-Strand Synthesis Systemn (Invitrogen) manufacturer's protocol. We analysed 15-100 rig of cDNA from K-562 an d HEK293T cells in triplicate with TaqMan Gene Expression assays (Applied Biosystems).

| Catalog number | Gene Name [ID] |
|---|---|
| Hs00215284_m1 | NLR family, pyrin domain containing 2 [NLRP2] |
| Hs00212574_m1 | Glycoprotein VI (platelet) [GP6] |
| Hs00293416_m1 | Retinol dehydrogenase 13 (all-trans/9-cis) [RDH13] |
| Hs00373719_m1 | EPS8-like 1 [EPS8L1] |
| Hs01085949_m1 | Protein phosphatase 1, regulatory (inhibitor) subunit 12C [PPP1R12C] |
| Hs00165957_m1 | Troponin T type 1 (skeletal, slow) [TNNT1] |
| Hs00162848_m1 | Troponin I type 3 (cardiac) [TNNI3] |
| Hs00332766_m1 | Chromosome 19 open reading frame 51 [C19orf51] |
| Hs00162516_m1 | Synaptotagmin V [SYT5] |
| Hs00936202_m1 | Protein tyrosine phosphatase, receptor type, H [PTPRH] |
| Hs00382401_m1 | Transmembrane protein 86B [TMEM86B] |
| Hs00208777_m1 | SAPS domain family, member 1 [SAPS1] |
| Hs99999907_m1 | Beta-2-microglobulin [B2M] |
| Hs02758991_g1 | Glyceraldehyde-3-phosphate dehydrogenase [GAPDH] |
| Hs01060665_g1 | Actin beta [ACTB] |
| Hs99999909_m1 | Hypoxanthine phosphoribosyltransferase 1 [HPRT1] |
| Hs00973637_m1 | 2'-5'-oligoadenylate synthetase 1 [OAS1] |
| Hs00276752_m1 | Spastic paraplegia 11 [SPG11] |
| Hs01388797_m1 | Protein associated with topoisomerase II homolog 2 [PATL2] |
| Hs04399718_m1 | Tripartite motif containing 69 [TRIM69] |
| Hs00900055_m1 | Vascular Endothelial Growth Factor A [VEGFA] |
| Hs01066116_m1 | Interferon (alpha, beta and omega) Receptor 1 [IFNAR1] |

The gene expression assay used to detect the eGFP transcript was previously described (Lombardo, A. et al. (2011) *Nat. Methods* 8: 861-9). Real-time PCRs were performed with a ViiA 7 Real-Time POR Systemn (Applied Biosystems) and dedicated software was used to extract raw data (Ct and raw fluorescence). Genes with a Ct value 37 were excluded from the analyses. The relative expression level of each gene was calculated by the ΔΔCt method, normalised to HPPT or B2M expression (housekeeping gene controls), and represented as fold change relative to the mock-treated samples (calibrator).

Molecular Analyses

For bisulfite sequencing, genomic DNA was extracted with DNeasy Blood & Tissue Kit or QIAamp DNA Mini Kit (QIAGEN) and then treated with EpiTect Bisulfite kit (Qiagen) according to manufacturer's instructions. The converted products were then used to PCR amplify the B2M-promoter region using the primers listed below. PCR fragments were purified and cloned into pCRII-TOPO TA (Inivitrogen), and five to ten clones for each sample were verified by sequencing using the M13 universal primer.

| | |
|---|---|
| BIS B2M #1 F | GTTGTGTTTTTTGGGGAAGTTAG (SEQ ID NO: 112) |
| BIS B2M #1 R | AAAATTCCTCCCTATATCCTTA (SEQ ID NO: 113) |
| BIS B2M #2 F | AAGAATGGAGAAATTTTGTAGGGAATT (SEQ ID NO: 114) |
| BIS B2M #2 R | ACCACCAAAAAAAACTTAAAAAAAA (SEQ ID NO: 115) |
| BIS B2M #3 F | TTTTTTTGGTTTGGAGGTTATTTAG (SEQ ID NO: 116) |
| BIS B2M #3 R | CAAAACACATAAAATCCTTAACACA (SEQ ID NO: 117) |
| BIS B2M #4 F | TTTTAGATTGGAGAGTTGTGGATTT (SEQ ID NO: 118) |
| BIS B2M #4 R | AATTTTACAACTCCCCTAACTAACA (SEQ ID NO: 119) |

Chromatin immunoprecipitation (ChIP) analysis was performed as previously described (Lombardo, A. et al. (2011) Nat. Methods 8: 861-9) using 5-10 μg of ChIP-grade antibodies (Abcam) raised against the human H3 or the RNA Polymerase II CTD repeat YSPTSPS. IgG isotypes were also used as controls. The primers used for these studies are listed below. The percentage of enrichment of RNA PolII for each investigated site was calculated by the ΔCt method using the Input as normaliser.

| | |
|---|---|
| B2M -241 F | GCAAGTCACTTAGCATCTCTGGG (SEQ ID NO: 120) |
| B2M -241 R | TTGCTGTCTGTACATCGGCG (SEQ ID NO: 121) |
| B2M +158 F | TCTCTCGCTCCGTGACTTCC (SEQ ID NO: 122) |
| B2M +158 R | CGCTTCCCCGAGATCCAGCCC (SEQ ID NO: 123) |
| B2M +315 F | AGGGGAGACCTTTGGCCTAC (SEQ ID NO: 124) |
| B2M +315 R | CTCTGACGCTTATCGACGCC (SEQ ID NO: 125) |
| B2M +580 F | AGACTGGAGAGCTGTGGACTTCG (SEQ ID NO: 126) |
| B2M +580 R | GCCAAGCATTCTACAAACGTCG (SEQ ID NO: 127) |
| B2M +1529 F | CAGTCAGGGGAGCTGTAAAACC (SEQ ID NO: 128) |
| B2M +1529 R | TTGCCAGGTACTTAGAAAGTGC (SEQ ID NO: 129) |
| B2M +3307 F | CCTTGGGTTGATCCACTTAGG (SEQ ID NO: 130) |
| B2M +3307 R | TAGTAGAGTGCCTGGGACATAGC (SEQ ID NO: 131) |
| B2M +3969 F | GTGTCTGGGTTTCATCCATCCG (SEQ ID NO: 132) |

-continued

| | |
|---|---|
| B2M +3969 R | GCTGAAAGACAAGTCTGAATGC (SEQ ID NO: 133) |
| B2M +5082 F | AGGATAAAGGCAGGTGGTTACC (SEQ ID NO: 134) |
| B2M +5082 R | AGATGTCCAATGTGGAAATGGC (SEQ ID NO: 135) |
| CCR5 -305 F | AGTCTGACTACAGAGGCCACTGG (SEQ ID NO: 136) |
| CCR5 R -255 | AGGCAAATGAGACCCCAAACAGC (SEQ ID NO: 137) |
| PPP1R12C -861 F | TAAGAACCGAGGACAAGTAGTGC (SEQ ID NO: 138) |
| PPP1R12C -768R | TGCTGGGATGACGAGCGTAAGC (SEQ ID NO: 139) |

Statistical Analysis

One-way ANOVA test with Bonferroni's multiple comparison post-test was used to assess statistical significance of differences in gene expression among all samples ($P<0.05$).

TABLE 1

ZNF10
ALSPQHSAVTQGSIIKNKEGMDAKSLTAWSRTLVTFKDVF
VDFTREEWKLLDTAQQIVYRNVMLENYKNLVSLGYQLTKP
DVILRLEKGEEPWLVEREIHQETHPDSETAFEIKSSV
(SEQ ID NO: 1)

DNMT3A
TYGLLRRREDWPSRLQMFFANNHDQEFDPPKVYPPVPAEK
RKPIRVLSLFDGIATGLLVLKDLGIQVDRYIASEVCEDSI
TVGMVRHQGKIMYVGDVRSVTQKHIQEWGPFDLVIGGSPC
NDLSIVNPARKGLYEGTGRLFFEFYRLLHDARPKEGDDRP
FFWLFENVVAMGVSDKRDISRFLESNPVMIDAKEVSAAHR
ARYFWGNLPGMNRPLASTVNDKLELQECLEHGRIAKFSKV
RTITTRSNSIKQGKDQHFPVFMNEKEDILWCTEMERVFGF
PVHYTDVSNMSRLARQRLLGRSWSVPVIRHLFAPLKEYFA
CV
(SEQ ID NO: 8)

EZH2 (short variant)
NVSCKNCSIQRGSKKHLLLAPSDVAGWGIFIKDPVQKNEF
ISEYCGEIISQDEADRRGKVYDKYMCSFLFNLNNDFVVDA
TRKGNKIRFANHSVNPNCYAKVMMVNGDHRIGIFAKRAIQ
TGEELFFDYRYSQADALKYVGIEREMEIP
(SEQ ID NO: 140)

EZH2 (long variant)
RLWAAHCRKIQLKKDGSSNHVYNYQPCDHPRQPCDSSCPC
VIAQNFCEKFCQCSSECQNRFPGCRCKAQCNTKQCPCYLA
VRECDPDLCLTCGAADHWDSKNVSCKNCSIQRGSKKHLLL
APSDVAGWGIFIKDPVQKNEFISEYCGEIISQDEADRRGK
VYDKYMCSFLFNLNNDFVVDATRKGNKIRFANHSVNPNCY
AKVMMVNGDHRIGIFAKRAIQTGEELFFDYRYSQADALKY
VGIEREMEIP
(SEQ ID NO: 141)

TLE1
MFPQSRHPTPHQAAGQPFKFTIPESLDRIKEEFQFLQAQY
HSLKLECEKLASEKTEMQRHYVMYYEMSYGLNIEMHKQTE
IAKRLNTICAQVIPFLSQEHQQQVAQAVERAKQVTMAELN
AIIGQQQLQAQHLSHG
(SEQ ID NO: 142)

G9A (short variant)
LNRKLRLGVGNRAIRTEKIICRDVARGYENVPIPCVNGVD
GEPCPEDYKYISENCETSTMNIDRNITHLQHCTCVDDCSS
SNCLCGQLSIRCWYDKDGRLLQEFNKIEPPLIFECNQACS
CWRNCKNRVVQSGIKVRLQLYRTAKMGWGVRALQTIPQGT
FICEYVGELISDAEADVREDDSYLFDLDNKDGEVYCIDAR
YYGNISRFINHLCDPNIIPVRVFMLHQDLRFPRIAFFSSR TABLE 1-continued DIRTGEELGFDYGDRFWDIKSKYFTCQCGSEKCKHSAEAI
ALEQSRLARLDPHPELLPELGSLPPVNT
(SEQ ID NO: 143)

G9A (long variant)
LEKALVIQESERRKKLRFHPRQLYLSVKQGELQKVILMLL
DNLDPNFQSDQQSKRTPLHAAAQKGSVEICHVLLQAGANI
NAVDKQQRTPLMEAVVNNHLEVARYMVQRGGCVYSKEEDG
STCLHHAAKIGNLEMVSLLLSTGQVDVNAQDSGGWTPIIW
AAEHKHIEVIRMLLTRGADVTLTDNEENICLHWASFTGSA
AIAEVLLNARGNRAIRTEKIICRDVARGYENVPIPCVNGV
DGEPCPEDYKYISENCETSTMNIDRNITHLQHCTCVDDCS
SSNCLCGQLSIRCWYDKDGRLLQEFNKIEPPLIFECNQAC
SCWRNCKNRVVQSGIKVRLQLYRTAKMGWGVRALQTIPQG
TFICEYVGELISDAEADVREDDSYLFDLDNKDGEVYCIDA
RYYGNISRFINHLCDPNIIPVRVFMLHQDLRFPRIAFFSS
RDIRTGEELGFDYGDRFWDIKSKYFTCQCGSEKCKHSAEA
IALEQSRLARLDPHPELLPELGSLPPVNT
(SEQ ID NO: 144)

SETDB1
MSSLPGCIGLDAATATVESEEIAELQQAVVEELGISMEEL
RHFIDEELEKMDCVQQRKKQLAELETWVIQGSRTPKDQKL
REAMAALRKSAQDVQKFMDAVNKKSSSQDLHKGTLSQMSG
ELSKDGDLIVSMRILGKKRTKTWHKGTLIAIQTVGPGKKY
KVKFDNKGKSLLSGNHIAYDYHPPADKLYVGSRVVAKYKD
GNQVWLYAGIVAETPNVKNKLRFLIFFDDGYASYVTQSEL
YPICRPLKKTWEDIEDISCRDFIEEYVTAYPNRPMVLLKS
GQLIKTEWEGTWWKSRVEEVDGSLVRILFLDDKRCEWIYR
GSTRLEPMFSMKTSSASALEKKQGQLRTRPNMGAVRSKGP
VVQYTQDLIGTGTQFKPVEPPQPTAPPAPPFPPAPPLSPQ
AGDSDLESQLAQSRKQVAKKSTSFRPGSVGSGHSSPTSPA
LSENVSGGKPGINQTYRSPLGSTASAPAPSALPAPPAPPV
FHGMLERAPAEPSYRAPMEKLFYLPHVCSYTCLSRVRPMR
NEQYRGKNPLLVPLLYDFRRMTARRRVNRKMGFHVIYKTP
CGLCLRTMQEIERYLFETGCDFLFLEMFCLDPYVLVDRKF
QPYKPFYYILDITYGKEDVPLSCVNEIDTTPPPQVAYSKE
RIPGKGVFINTGPEFLVGCDCKDGCRDKSKCACHQLTIQA
TACTPGGQINPNSGYQYKRLEECLPTGVYECNKRCKCDPN
MCTNRLVQHGLQVRLQLFKTQNKGWGIRCLDDIAKGSFVC
IYAGKILTDDFADKEGLEMGDEYFANLDHIESVENFKEGY
ESDAPCSSDSSGVDLKDQEDGNSGTEDPEESNDDSSDDNF
CKDEDFSTSSVWRSYATRRQTRGQKENGLSETTSKDSHPP
DLGPPHIPVPPSIPVGGCNPPSSEETPKNKVASWLSCNSV
SEGGFADSDSHSSFKTNEGGEGRAGGSRMEAEKASTSGLG
IKDEGDIKQAKKEDTDDRNKMSVVTESSRNYGYNPSPVKP
EGLRRPPSKTSMHQSRRLMASAQSNPDDVLTLSSSTESEG
ESGTSRKPTAGQTSATAVDSDDIQTISSGSEGDDFEDKKN
MTGPMKRQVAVKSTRGFALKSTHGIAIKSTNMASVDKGES
APVRKNTRQFYDGEESCYIIDAKLEGNLGRYLNHSCSPNL
FVQNVFVDTHDLRFPWVAFFASKRIRAGTELTWDYNYEVG
SVEGKELLCCCGAIECRGRLL
(SEQ ID NO: 12)

SUV420H2
MGPDRVTARELCENDDLATSLVLDPYLGFRTHKMNVSPVP
PLRRQQHLRSALETFLRQRDLEAAYRALTLGGWTARYFQS
RGPRQEAALKTHVYRYLRAFLPESGFTILPCTRYSMETNG
AKIVSTRAWKKNEKLELLVGCIAELREADEGLLRAGENDF
SIMYSTRKRSAQLWLGPAAFINHDCKPNCKFVPADGNAAC
VKVLRDIEPGDEVTCFYGEGFFGEKNEHCECHTCERKGEG
AFRTRPREPALPPRPLDKYQLRETKRRLQQGLDSGSRQG
(SEQ ID NO: 145)

HP1-a
MGKKTKRTADSSSSEDEEEYVVEKVLDRRVVKGQVEYLLK
WKGFSEEHNTWEPEKNLDCPELISEFMKKYKKMKEGENNK
PREKSESNKRKSNFSNSADDIKSKKKREQSNDIARGFERG
LEPEKIIGATDSCGDLMFLMKWKDTDEADLVLAKEANVKC
PQIVIAFYEERLTWHAYPEDAENKEKETAKS
(SEQ ID NO: 146)

DNMT3L
MAAIPALDPEAEPSMDVILVGSSELSSSVSPGTGRDLIAY
EVKANQRNIEDICICCGSLQVHTQHPLFEGGICAPCKDKF
LDALFLYDDDGYQSYCSICCSGETLLICGNPDCTRCYCFE
CVDSLVGPGTSGKVHAMSNWVCYLCLPSSRSGLLQRRRKW
RSQLKAFYDRESENPLEMFETVPVWRRQPVRVLSLFEDIK
KELTSLGFLESGSDPGQLKHVVDVTDTVRKDVEEWGPFDL
VYGATPPLGHTCDRPPSWYLFQFHRLLQYARPKPGSPRPF

TABLE 1-continued

FWMFVDNLVLNKEDLDVASRFLEMEPVTIPDVHGGSLQNA
VRVWSNIPAIRSRHWALVSEEELSLLAQNKQSSKLAAKWP
TKLVKNCFLPLREYFKYFSTELTSSL
(SEQ ID NO: 11)

DNMT3B
MVAELISEEDLEFMKGDTRHLNGEEDAGGREDSILVNGAC
SDQSSDSPPILEAIRTPEIRGRRSSSRLSKREVSSLLSYT
QDLTGDGDGEDGDGSDTPVMPKLFRETRTRSESPAVRTRN
NNSVSSRERHRPSPRSTRGRQGRNHVDESPVEFPATRSLR
RRATASAGTPWPSPPSSYLTIDLTDDTEDTHGTPQSSSTP
YARLAQDSQQGGMESPQVEADSGDGDSSEYQDGKEFGIGD
LVWGKIKGFSWWPAMVVSWKATSKRQAMSGMRWVQWFGDG
KFSEVSADKLVALGLFSQHFNLATFNKLVSYRKAMYHALE
KARVRAGKTFPSSPGDSLEDQLKPMLEWAHGGFKPTGIEG
LKPNNTQPENKTRRRTADDSATSDYCPAPKRLKTNCYNNG
KDRGDEDQSREQMASDVANNKSSLEDGCLSCGRKNPVSFH
PLFEGGLCQTCRDRFLELFYMYDDDGYQSYCTVCCEGREL
LLCSNTSCCRCFCVECLEVLVGTGTAAEAKLQEPWSCYMC
LPQRCHGVLRRRKDWNVRLQAFFTSDTGLEYEAPKLYPAI
PAARRRPIRVLSLFDGIATGYLVLKELGIKVGKYVASEVC
EESIAVGTVKHEGNIKYVNDVRNITKKNIEEWGPFDLVIG
GSPCNDLSNVNPARKGLYEGTGRLFFEFYHLLNYSRPKEG
DDRPFFWMFENVVAMKVGDKRDISRFLECNPVMIDAIKVS
AAHRARYFWGNLPGMNRPVIASKNDKLELQDCLEYNRIAK
LKKVQTITTKSNSIKQGKNQLFPVVMNGKEDVLWCTELER
IFGFPVHYTDVSNMGRGARQKLLGRSWSVPVIRHLFAPLK
DYFACE (SEQ ID NO: 36)

TABLE 2

TALE forward
MGKPIPNPLLGLDSTGGMAPKKKRKVDGGVDLRTLGYSQQ
QQEKIKPKVRSTVAQHHEALVGHGFTHAHIVALSQHPAAL
GTVAVKYQDMIAALPEATHEAIVGVGKQWSGARALEALLT
VAGELRGPPLQLDTGQLLKIAKRGGVTAVEAVHAWRNALT
GAPLNLTPEQVVAIASNIGGKQALETVQRLLPVLCQAHGL
TPEQVVAIASHDGGKQALETVQRLLPVLCQAHGLTPEQVV
AIASHDGGKQALETVQRLLPVLCQAHGLTPEQVVAIASHD
GGKQALETVQRLLPVLCQAHGLTPEQVVAIASNIGGKQAL
ETVQRLLPVLCQAHGLTPEQVVAIASNNGGKQALETVQRL
LPVLCQAHGLTPEQVVAIASNIGGKQALETVQRLLPVLCQ
AHGLTPEQVVAIASNGGGKQALETVQRLLPVLCQAHGLTP
EQVVAIASNGGGKQALETVQRLLPVLCQAHGLTPEQVVAI
ASNNGGKQALETVQRLLPVLCQAHGLTPEQVVAIASNNGG
KQALETVQRLLPVLCQAHGLTPEQVVAIASHDGGKQALET
VQRLLPVLCQAHGLTPEQVVAIASHDGGKQALETVQRLLP
VLCQAHGLTPEQVVAIASHDGGKQALETVQRLLPVLCQAH
GLTPEQVVAIASHDGGKQALETVQRLLPVLCQAHGLTPEQ
VVAIASNIGGKQALETVQRLLPVLCQAHGLTPEQVVAIAS
HDGGKQALETVQRLLPVLCQAHGLTPQQVVAIASNGGGRP
ALESIVAQLSRPDPALAALINDHLVALACLGGRPALDAVK
KGLPHAPALIKRTNRRIPERTSHRVA
(SEQ ID NO: 14)

TALE reverse
MGKPIPNPLLGLDSTGGMAPKKKRKVDGGVDLRTLGYSQQ
QQEKIKPKVRSTVAQHHEALVGHGFTHAHIVALSQHPAAL
GTVAVKYQDMIAALPEATHEAIVGVGKQWSGARALEALLT
VAGELRGPPLQLDTGQLLKIAKRGGVTAVEAVHAWRNALT
GAPLNLTPEQVVAIASNIGGKQALETVQRLLPVLCQAHGL
TPEQVVAIASHDGGKQALETVQRLLPVLCQAHGLTPEQVV
AIASHDGGKQALETVQRLLPVLCQAHGLTPEQVVAIASNG
GGKQALETVQRLLPVLCQAHGLTPEQVVAIASNIGGKQAL
ETVQRLLPVLCQAHGLTPEQVVAIASNNGGKQALETVQRL
LPVLCQAHGLTPEQVVAIASNIGGKQALETVQRLLPVLCQ
AHGLTPEQVVAIASNNGGKQALETVQRLLPVLCQAHGLTP
EQVVAIASNNGGKQALETVQRLLPVLCQAHGLTPEQVVAI
ASNIGGKQALETVQRLLPVLCQAHGLTPEQVVAIASNNGG
KQALETVQRLLPVLCQAHGLTPEQVVAIASNIGGKQALET
VQRLLPVLCQAHGLTPEQVVAIASNIGGKQALETVQRLLP
VLCQAHGLTPEQVVAIASNIGGKQALETVQRLLPVLCQAH
GLTPEQVVAIASNNGGKQALETVQRLLPVLCQAHGLTPEQ
VVAIASNNGGKQALETVQRLLPVLCQAHGLTPEQVVAIAS TABLE 2-continued NGGGKQALETVQRLLPVLCQAHGLTPQQVVAIASNGGGRP
ALESIVAQLSRPDPALAALTNDHLVALACLGGRPALDAVK
KGLPHAPALIKRTNRRIPERTSHRVA
(SEQ ID NO: 15)

Nucleotide sequences of the corresponding TALE binding sites

TALE forward
5'-TACCCAGATTGGCCCCACT-3' (SEQ ID NO: 34)

TALE reverse
5'-TACCTAGAGGAGAAAGGTT-3' (SEQ ID NO: 35)

TABLE 3

Amino acid sequences of the TALEs targeting the B2M promoter region

TALE #1
MGKPIPNPLLGLDSTGGMAPKKKRKVDGGVDLRTLGYSQQ
QQEKIKPKVRSTVAQHHEALVGHGFTHAHIVALSQHPAAL
GTVAVKYQDMIAALPEATHEAIVGVGKQWSGARALEALLT
VAGELRGPPLQLDTGQLLKIAKRGGVTAVEAVHAWRNALT
GAPLNLTPDQVVAIASHDGGKQALETVQRLLPVLCQDHGL
TPDQVVAIASNGGGKQALETVQRLLPVLCQDHGLTPDQVV
AIASHDGGKQALETVQRLLPVLCQDHGLTPDQVVAIASNG
GGKQALETVQRLLPVLCQDHGLTPDQVVAIASHDGGKQAL
ETVQRLLPVLCQDHGLTPDQVVAIASHDGGKQALETVQRL
LPVLCQDHGLTPDQVVAIASNGGGKQALETVQRLLPVLCQ
DHGLTPDQVVAIASNIGGKQALETVQRLLPVLCQDHGLTP
DQVVAIASHDGGKQALETVQRLLPVLCQDHGLTPDQVVAI
ASHDGGKQALETVQRLLPVLCQDHGLTPDQVVAIASHDGG
KQALETVQRLLPVLCQDHGLTPDQVVAIASNGGGKQALET
VQRLLPVLCQDHGLTPDQVVAIASHDGGKQALETVQRLLP
VLCQDHGLTPDQVVAIASHDGGKQALETVQRLLPVLCQDH
GLTPDQVVAIASHDGGKQALETVQRLLPVLCQDHGLTPDQ
VVAIASNHGGKQALETVQRLLPVLCQDHGLTPDQVVAIAS
HDGGKQALETVQRLLPVLCQDHGLTPDQVVAIASNGGGKQ
ALESIVAQLSRPDPALAALINDHLVALACLGGRPALDAVK
KGLPHAPALIKRTNRRIPERTSHRVAGSGGG
(SEQ ID NO: 16)

TALE #2
MGKPIPNPLLGLDSTGGMAPKKKRKVDGGVDLRTLGYSQQ
QQEKIKPKVRSTVAQHHEALVGHGFTHAHIVALSQHPAAL
GTVAVKYQDMIAALPEATHEAIVGVGKQWSGARALEALLT
VAGELRGPPLQLDTGQLLKIAKRGGVTAVEAVHAWRNALT
GAPLNLTPDQVVAIASNNGGKQALETVQRLLPVLCQDHGL
TPDQVVAIASNNGGKQALETVQRLLPVLCQDHGLTPDQVV
AIASNGGGKQALETVQRLLPVLCQDHGLTPDQVVAIASHD
GGKQALETVQRLLPVLCQDHGLTPDQVVAIASHDGGKQAL
ETVQRLLPVLCQDHGLTPDQVVAIASNGGGKQALETVQRL
LPVLCQDHGLTPDQVVAIASNGGGKQALETVQRLLPVLCQ
DHGLTPDQVVAIASHDGGKQALETVQRLLPVLCQDHGLTP
DQVVAIASHDGGKQALETVQRLLPVLCQDHGLTPDQVVAI
ASNGGGKQALETVQRLLPVLCQDHGLTPDQVVAIASHDGG
KQALETVQRLLPVLCQDHGLTPDQVVAIASNGGGKQALET
VQRLLPVLCQDHGLTPDQVVAIASHDGGKQALETVQRLLP
VLCQDHGLTPDQVVAIASHDGGKQALETVQRLLPVLCQDH
GLTPDQVVAIASHDGGKQALETVQRLLPVLCQDHGLTPDQ
VVAIASNGGGKQALETVQRLLPVLCQDHGLTPDQVVAIAS
HDGGKQALETVQRLLPVLCQDHGLTPDQVVAIASNGGGKQ
ALESIVAQLSRPDPALAALTNDHLVALACLGGRPALDAVK
KGLPHAPALIKRINRRIPERTSHRVAGSGGG
(SEQ ID NO: 18)

TALE #3
MGKPIPNPLLGLDSTGGMAPKKKRKVDGGVDLRTLGYSQQ
QQEKIKPKVRSTVAQHHEALVGHGFTHAHIVALSQHPAAL
GTVAVKYQDMIAALPEATHEAIVGVGKQWSGARALEALLT
VAGELRGPPLQLDTGQLLKIAKRGGVTAVEAVHAWRNALT
GAPLNLTPDQVVAIASHDGGKQALETVQRLLPVLCQDHGL
TPDQVVAIASNNGGKQALETVQRLLPVLCQDHGLTPDQVV

TABLE 3-continued

AIASHDGGKQALETVQRLLPVLCQDHGLTPDQVVAIASNG
GGKQALETVQRLLPVLCQDHGLTPDQVVAIASHDGGKQAL
ETVQRLLPVLCQDHGLTPDQVVAIASHDGGKQALETVQRL
LPVLCQDHGLTPDQVVAIASNNGGKQALETVQRLLPVLCQ
DHGLTPDQVVAIASNGGGKQALETVQRLLPVLCQDHGLTP
DQVVAIASNNGGKQALETVQRLLPVLCQDHGLTPDQVVAI
ASNIGGKQALETVQRLLPVLCQDHGLTPDQVVAIASHDGG
KQALETVQRLLPVLCQDHGLTPDQVVAIASNGGGKQALET
VQRLLPVLCQDHGLTPDQVVAIASNGGGKQALETVQRLLP
VLCQDHGLTPDQVVAIASHDGGKQALETVQRLLPVLCQDH
GLTPDQVVAIASHDGGKQALETVQRLLPVLCQDHGLTPDQ
VVAIASHDGGKQALETVQRLLPVLCQDHGLTPDQVVAIAS
NGGGKQALETVQRLLPVLCQDHGLTPDQVVAIASNGGGKQ
ALESIVAQLSRPDPALAALINDHLVALACLGGRPALDAVK
KGLPHAPALIKRTNRRIPERTSHRVAGSGGG
(SEQ ID NO: 20)

Nucleotide sequences of the corresponding TALE binding sites

TALE #1
5'-TCTCTCCTACCCTCCCGCT-3' (SEQ ID NO: 17)

TALE #2
5'-TGGTCCTTCCTCTCCCGCT-3' (SEQ ID NO: 19)

TALE #3
5'-TCGCTCCGTGACTTCCCTT-3' (SEQ ID NO: 21)

TABLE 4

Catalytically inactive Cas9 (dCas9)

MGGRRVRWEVYISRALWLTREPTAYWLIEINTTHYHERERETQA
TGATMYPYDVPDYASPKKKRKVEASDKKYSIGLAIHEREGTNSV
GWAVITDEYKVPSKKFKVLGNTDRHSIKKNLIGALHERELFDSG
ETAEATRLKRTARRRYTRRKNRICYLQEIFSNEMAHEREKVDDS
FFHRLEESFLVEEDKKHERHPIFGNIVDEVAYHEKHEREYPTIY
HLRKKLVDSTDKADLRLIYLALAHMIKFRGHFLIEHEREGDLNP
DNSDVDKLFIQLVQTYNQLFEENPINASGVDAKAIHERELSARL
SKSRRLENLIAQLPGEKKNGLFGNLIALSLGLTPNHEREFKSNF
DLAEDAKLQLSKDTYDDDLDNLLAQIGDQYADLFLHEREAAKNL
SDAILLSDILRVNTEITKAPLSASMIKRYDEHHQDHERELTLLK
ALVRQQLPEKYKEIFFDQSKNGYAGYIDGGASQEEHEREFYKFI
KPILEKMDGTEELLVKLNREDLLRKQRTFDNGSIPHEREHQIHL
GELHAILRRQEDFYPFLKDNREKIEKILTFRIPYYHEREVGPLA
RGNSRFAWMTRKSEETITPWNFEEVVDKGASAQSFHEREIERMT
NFDKNLPNEKVLPKHSLLYEYFTVYNELTKVKYVTHEREEGMRK
PAFLSGEQKKAIVDLLFKTNRKVTVKQLKEDYFKKHEREIECFD
SVEISGVEDRFNASLGTYHDLLKIIKDKDFLDNEEHERENEDIL
EDIVLTLTLFEDREMIEERLKTYAHLFDDKVMKQLHEREKRRRY
TGWGRLSRKLINGIRDKQSGKTILDFLKSDGFANRHERENFMQL
IHDDSLTFKEDIQKAQVSGQGDSLHEHIANLAGSPHEREAIKKG
ILQTVKVVDELVKVMGRHKPENIVIEMARENQTTQHEREKGQKN
SRERMKRIEEGIKELGSQILKEHPVENTQLQNEKLHEREYLYYL
QNGRDMYVDQELDINRLSDYDVDAIVPQSFLKDDSHEREIDNKV
LTRSDKNRGKSDNVPSEEVVKKMKNYWRQLLNAKLHEREITQRK
FDNLTKAERGGLSELDKAGFIKRQLVETRQITKHVHEREAQILD
SRMNTKYDENDKLIREVKVITLKSKLVSDFRKDFQHEREFYKVR
EINNYHHAHDAYLNAVVGTALIKKYPKLESEFVYGHEREDYKVY
DVRKMIAKSEQEIGKATAKYFFYSNIMNFFKTEITHERELANGE
IRKRPLIETNGETGEIVWDKGRDFATVRKVLSMPQHEREVNIVK
KTEVQTGGFSKESILPKRNSDKLIARKKDWDPKKYHEREGGFDS
PTVAYSVLVVAKVEKGKSKKLKSVKELLGITIMERHERESSFEK
NPIDFLEAKGYKEVKKDLIIKLPKYSLFELENGRKHERERMLAS
AGELQKGNELALPSKYVNFLYLASHYEKLKGSPEDHERENEQKQ
LFVEQHKHYLDEIIEQISEFSKRVILADANLDKVLHERESAYNK

TABLE 4-continued

HRDKPIREQAENIIHLFTLTNLGAPAAFKYFDTTIHEREDRKRY
TSTKEVLDATLIHQSITGLYETRIDLSQLGGDSPKHEREKKRKV
G
(SEQ ID NO: 22)

Nucleotide sequences of the target sites of the B2M gRNAs gRNA #1
TATAAGTGGAGGCGTCGCGC (SEQ ID NO: 23)

gRNA #2

GCCCGAATGCTGTCAGCTTC (SEQ ID NO: 24)

gRNA #3
TGCGTCGCTGGCTTGGAGAC (SEQ ID NO: 25)

gRNA #4
CCAATCAGGACAAGGCCCGC (SEQ ID NO: 26)

gRNA #5
AGGGTAGGAGAGACTCACGC (SEQ ID NO: 27)

gRNA #6

GCGGGCCACCAAGGAGAACT (SEQ ID NO: 28)

gRNA #7

GCTACTCTCTCTTTCTGGCC (SEQ ID NO: 29)

gRNA #8
CTCCCGCTCTGCACCCTCTG (SEQ ID NO: 30)

gRNA #9
TTTGGCCTACGGCGACGGGA (SEQ ID NO: 31)

gRNA #10

GGGGCAAGTAGCGCGCGTCC (SEQ ID NO: 32)

gRNA #11
TAGTCCAGGGCTGGATCTCG (SEQ ID NO: 33)

Nucleotide sequences of the B2M gRNAs gRNA #1:
UAUAAGUGGAGGCGUCGCGC (SEQ ID NO: 149)

gRNA #2:

GCCCGAAUGCUGUCAGCUUC (SEQ ID NO: 150)

gRNA #3:
UGCGUCGCUGGCUUGGAGAC (SEQ ID NO: 151)

gRNA #4:
CCAAUCAGGACAAGGCCCGC (SEQ ID NO: 152)

gRNA #5:
AGGGUAGGAGAGACUCACGC (SEQ ID NO: 153)

gRNA #6:

GCGGGCCACCAAGGAGAACU (SEQ ID NO: 154)

gRNA #7:

GCUACUCUCUCUUUCUGGCC (SEQ ID NO: 155)

gRNA #8:
CUCCCGCUCUGCACCCUCUG (SEQ ID NO: 156)

gRNA #9:
UUUGGCCUACGGCGACGGGA (SEQ ID NO: 157)

TABLE 4-continued gRNA #10:

GGGGCAAGUAGCGCGCGUCC (SEQ ID NO: 158)

gRNA #11:
UAGUCCAGGGCUGGAUCUCG (SEQ ID NO: 159)

TABLE 5

Amino acid sequence of the TALE A targeting the B2M promoter region
TALE A
MGKPIPNPLLGLDSTGGMAPKKKRKVDGGVDLRTLGYSQQQ
QEKIKPKVRSTVAQHHEALVGHGFTHAHIVALSQHPAALG
TVAVKYQDMIAALPEATHEAIVGVGKQWSGARALEALLTV
AGELRGPPLQLDTGQLLKIAKRGGVTAVEAVHAWRNALTG
APLNLTPDQVVAIASNNGGKQALETVQRLLPVLCQDHGLT
PDQVVAIASHDGGKQALETVQRLLPVLCQDHGLTPDQVVA
IASNGGGKQALETVQRLLPVLCQDHGLTPDQVVAIASHDG
GKQALETVQRLLPVLCQDHGLTPDQVVAIASNNGGKQALE
TVQRLLPVLCQDHGLTPDQVVAIASHDGGKQALETVQRLL
PVLCQDHGLTPDQVVAIASNNGGKQALETVQRLLPVLCQD
HGLTPDQVVAIASHDGGKQALETVQRLLPVLCQDHGLTPD
QVVAIASNGGGKQALETVQRLLPVLCQDHGLTPDQVVAIA
SNIGGKQALETVQRLLPVLCQDHGLTPDQVVAIASHDGGK
QALETVQRLLPVLCQDHGLTPDQVVAIASNGGGKQALETV
QRLLPVLCQDHGLTPDQVVAIASHDGGKQALETVQRLLPV
LCQDHGLTPDQVVAIASNGGGKQALETVQRLLPVLCQDHG
LTPDQVVAIASHDGGKQALETVQRLLPVLCQDHGLTPDQV
VAIASNGGGKQALETVQRLLPVLCQDHGLTPDQVVAIASH
DGGKQALETVQRLLPVLCQDHGLTPDQVVAIASNGGGKQA
LESIVAQLSRPDPALAALINDHLVALACLGGRPALDAVKK
GLPHAPALIKRINRRIPERTSHRVAGSGGG
(SEQ ID NO: 147)

Nucleotide sequence of the corresponding TALE binding site
TALE A
5'-TGCTCGCGCTACTCTCTCT-3' (SEQ ID NO: 148)

TABLE 6

Nucleotide sequences of the gRNAs targeting BCL11A gRNA #1 against CpG 105:
GCCUUUCUGCAGACGUUCCC (SEQ ID NO: 71)

gRNA #2 against CpG 105:
UGGGUGUGCGCCUUGGCCGG (SEQ ID NO: 72)

gRNA #3 against CpG 105:
CGGUGGUGAGAUGACCGCCU (SEQ ID NO: 73)

gRNA #4 against CpG 105:
GGAAUGUGCUCACGGCGCCG (SEQ ID NO: 74)

gRNA #5 against CpG 105:
GACUGCCCGCGCUUUGUCCU (SEQ ID NO: 75)

gRNA #6 against CpG 105:
CCAGAGUCUGGCCCCCGGAG (SEQ ID NO: 76)

gRNA #7 against CpG 105:
UCUGCGACCCUUAGGAGCCG (SEQ ID NO: 77)

gRNA #8 against CpG 105:
GAGCGCCCCGCCAAGCGACU (SEQ ID NO: 78)

gRNA #9 against CpG 105:
CAAGUCUCCAGGAGCCCGCG (SEQ ID NO: 79)

gRNA #10 against CpG 105:
CGCGGAAUCCAGCCUAAGUU (SEQ ID NO: 80)

TABLE 6-continued gRNA #11 against CpG 105:
CCCGCUGCGGAGCUGUAACU (SEQ ID NO: 81)

gRNA #1 against CpG 31:
CGCUCCUGAGUCCGCGGAGU (SEQ ID NO: 82)

gRNA #2 against CpG 31:
CACGGCUCUCCCCGUCGCCG (SEQ ID NO: 83)

gRNA #3 against CpG 31:
CCGCCUUUUGUUCCGGCCAG (SEQ ID NO: 84)

gRNA #4 against CpG 31:
GCGCGAGGAGCCGGCACAAA (SEQ ID NO: 85)

gRNA #5 against CpG 31:
GCCACUUUCUCACUAUUGUG (SEQ ID NO: 86)

gRNA #6 against CpG 31:
GCUGCCUCUGAGGUUCGGUC (SEQ ID NO: 87)

gRNA #7 against CpG 31:
AAGGGCAGGAGCUAGGGCCG (SEQ ID NO: 88)

gRNA #8 against CpG 31:
GAGCCCGGACUGCUGCCUCC (SEQ ID NO: 89)

gRNA #1 against CpG 38:
GUUUACAAGCACCGCGUGUG (SEQ ID NO: 90)

gRNA #2 against CpG 38:
AACAGACAGAGGACCGAGCG (SEQ ID NO: 91)

gRNA #3 against CpG 38:
GGCGCCGGGUGGGCGAUCCG (SEQ ID NO: 92)

gRNA #4 against CpG 38:
GGUCGGGCAAGGCCCGGGCG (SEQ ID NO: 93)

gRNA #5 against CpG 38:
AAGAGGUCUCGGCAUUGUGC (SEQ ID NO: 94)

gRNA #6 against CpG 38:
GUUCCACAGCUUCGGGACCG (SEQ ID NO: 95)

gRNA #7 against CpG 38:
GAAAUCGGCUGGGUGAAACU (SEQ ID NO: 96)

gRNA #8 against CpG 38:
GCAGUGUCUCCGCGCCAGCC (SEQ ID NO: 97)

gRNA #9 against CpG 38:
CCUCCCCUCCCCUCCGCCCU (SEQ ID NO: 98)

gRNA #1 against CpG 115:
UCCUCCUGUCCCGGGGUUAA (SEQ ID NO: 99)

gRNA #2 against CpG 115:
CAUCUUUUGGGACACUCUAGG (SEQ ID NO: 100)

gRNA #3 against CpG 115:
AAGUCAGGCCCUUCUUCGGAA (SEQ ID NO: 101)

gRNA #4 against CpG 115:
GCAGCCUGGACUGCGCGCCC (SEQ ID NO: 102)

gRNA #5 against CpG 115:
UGCCCGGCGAUUCUCGUCCG (SEQ ID NO: 103)

gRNA #6 against CpG 115:
UGAGCCAUUCGGUCGCUAGG (SEQ ID NO: 104)

gRNA #7 against CpG 115:
GGUGGUACUGAGGACCGGGA (SEQ ID NO: 105)

gRNA #8 against CpG 115:
AUUUUCUGGGUGCUCAGAGG (SEQ ID NO: 107)

TABLE 6-continued gRNA #9 against CpG 115:
UGGUCUCAGCUCGCGCACGG (SEQ ID NO: 108)

gRNA #10 against CpG 115:
ACAAAGACAUACGGGGUGAU (SEQ ID NO: 109)

Nucleotide sequences of the gRNAs targeting IFNAR1 gRNA #1:
AGGAACGGCGCGUGCGCGGA (SEQ ID NO: 106)

gRNA #2:
AAGAGGCGGCGCGUGCGUAG (SEQ ID NO: 161)

gRNA #3:
GGGCGGUGUGACUUAGGACG (SEQ ID NO: 162)

gRNA #4:
CCAGAUGAUGGUCGUCCUCC (SEQ ID NO: 163)

gRNA #5:
GACCCUAGUGCUCGUCGCCG (SEQ ID NO: 164)

gRNA #6:
UGGGUGUUGUCCGCAGCCGC (SEQ ID NO: 165)

gRNA #7:
ACGGGGGCGGCGAUGCUGUU (SEQ ID NO: 166)

gRNA #8:
GACCGAAGGUUUCCCAGACU (SEQ ID NO: 167)

gRNA #9:
GUCGGGUUUAAUCUUUGGCG (SEQ ID NO: 168)

gRNA #10:
CGCUCCCGAGGACCCGUACA (SEQ ID NO: 169)

gRNA #11:
CGGGUCCCACCCCCGUGAAA (SEQ ID NO: 170)

gRNA #12:
UCAAACUCGACACAAAGCUC (SEQ ID NO: 171)

gRNA #13:
GCGGAGCCGCGGUACUUUCC (SEQ ID NO: 172)

Nucleotide sequences of the gRNAs targeting VEGFA gRNA #1:
GGCGCGCGCGCUAGGUGGGA (SEQ ID NO: 173)

gRNA #2:
AGAGAGGCUCACCGCCCACG (SEQ ID NO: 174)

gRNA #3:
GUACGUGCGGUGACUCCGGU (SEQ ID NO: 175)

TABLE 7

Amino acid sequence of the TALEs targeting the BCL11A gene

TALE BCL11A #1
MGKPIPNPLLGLDSTGGMAPKKKRKVDGGVDLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPDQVVAIASHDGGKQALETVQRLLPVLCQDHGLTPDQVVAIASHDGGKQALETVQRLLPVLCQDHGLTPDQVVAIASNNGGGKQALETVQRLLPVLCQDHGLTPDQVVAIASNNGGGKQALETVQRLLPVLCQDHGLTPDQVVAIASNGGGKQALETVQRLLPVLCQDHGLTPDQVVAIASHDGGKQALETVQRLLPVLCQDHGLTPDQVVAIASHDGGKQALETVQRLLPVLCQDHGLTPDQVVAIASNNGGKQA

TABLE 7-continued

LETVQRLLPVLCQDHGLTPDQVVAIASHDGGKQAL
ETVQRLLPVLCQDHGLTPDQVVAIASHDGGKQALE
TVQRLLPVLCQDHGLTPDQVVAIASHDGGKQALET
VQRLLPVLCQDHGLTPDQVVAIASHDGGKQALETV
QRLLPVLCQDHGLTPDQVVAIASHDGGKQALETVQ
RLLPVLCQDHGLTPDQVVAIASNIGGKQALETVQR
LLPVLCQDHGLTPDQVVAIASNNGGKQALETVQRL
LPVLCQDHGLTPDQVVAIASHDGGKQALETVQRLL
PVLCQDHGLTPDQVVAIASNIGGKQALESIVAQLS
RPDPALAALTNDHLVALACLGGRPALDAVKKGLPH
APALIKRTNRRIPERTSHRVAGSGGG
(SEQ ID NO: 37)

Nucleotide sequence of the corresponding TALE binding site
5'-TCCAAAAGCCAGTCTCACC-3'
(SEQ ID NO: 38)

TALE BCL11A #2
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SNNGGKQALETVQRLLPVLCQDHGLTPDQVVAIAS
HDGGKQALETVQRLLPVLCQDHGLTPDQVVAIASH
DGGKQALETVQRLLPVLCQDHGLTPDQVVAIASNN
GGKQALETVQRLLPVLCQDHGLTPDQVVAIASNIG
GKQALETVQRLLPVLCQDHGLTPDQVVAIASNNGG
KQALETVQRLLPVLCQDHGLTPDQVVAIASNIGGK
QALETVQRLLPVLCQDHGLTPDQVVAIASHDGGKQ
ALETVQRLLPVLCQDHGLTPDQVVAIASHDGGKQA
LETVQRLLPVLCQDHGLTPDQVVAIASNGGGKQAL
ETVQRLLPVLCQDHGLTPDQVVAIASHDGGKQALE
TVQRLLPVLCQDHGLTPDQVVAIASNGGGKQALET
VQRLLPVLCQDHGLTPDQVVAIASNGGGKQALETV
QRLLPVLCQDHGLTPDQVVAIASHDGGKQALETVQ
RLLPVLCQDHGLTPDQVVAIASNGGGKQALETVQR
LLPVLCQDHGLTPDQVVAIASHDGGKQALETVQRL
LPVLCQDHGLTPDQVVAIASNNGGKQALETVQRLL
PVLCQDHGLTPDQVVAIASNIGGKQALESIVAQLS
RPDPALAALTNDHLVALACLGGRPALDAVKKGLPH
APALIKRINRRIPERTSHRVAGSGGG
(SEQ ID NO: 39)

Nucleotide sequence of the corresponding TALE binding site
5'-TCTCCCCGGGAATCGTTTT-3'
(SEQ ID NO: 40)

TALE BCL11A #3
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKOWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
NNGGKQALETVQRLLPVLCQDHGLTPDQVVAIASN
NGGKQALETVQRLLPVLCQDHGLTPDQVVAIASHD
GGKQALETVQRLLPVLCQDHGLTPDQVVAIASNGG
GKQALETVQRLLPVLCQDHGLTPDQVVAIASNGGG
KQALETVQRLLPVLCQDHGLTPDQVVAIASNGGGK
QALETVQRLLPVLCQDHGLTPDQVVAIASNNGGKQ
ALETVQRLLPVLCQDHGLTPDQVVAIASHDGGKQA
LETVQRLLPVLCQDHGLTPDQVVAIASNIGGKQAL
ETVQRLLPVLCQDHGLTPDQVVAIASNIGGKQALE
TVQRLLPVLCQDHGLTPDQVVAIASNIGGKQALET
VQRLLPVLCQDHGLTPDQVVAIASNHGGKQALETV
QRLLPVLCQDHGLTPDQVVAIASHDGGKQALETVQ
RLLPVLCQDHGLTPDQVVAIASNIGGKQALETVQR
LLPVLCQDHGLTPDQVVAIASNGGGKQALETVQRL
LPVLCQDHGLTPDQVVAIASNGGGKQALETVQRLL
PVLCQDHGLTPDQVVAIASNGGGKQALESIVAQLS
RPDPALAALTNDHLVALACLGGRPALDAVKKGLPH
APALIKRTNRRIPERTSHRVAGSGGG
(SEQ ID NO: 41)

Nucleotide sequence of the corresponding TALE binding site
5'-TCCTCCCGCTGCACACTTG-3'
(SEQ ID NO: 42)

TALE BCL11A #4
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SNNGGKQALETVQRLLPVLCQDHGLTPDQVVAIAS
HDGGKQALETVQRLLPVLCQDHGLTPDQVVAIASN
IGGKQALETVQRLLPVLCQDHGLTPDQVVAIASNI
GGKQALETVQRLLPVLCQDHGLTPDQVVAIASNIG
GKQALETVQRLLPVLCQDHGLTPDQVVAIASNNGG
KQALETVQRLLPVLCQDHGLTPDQVVAIASHDGGK
QALETVQRLLPVLCQDHGLTPDQVVAIASHDGGKQ
ALETVQRLLPVLCQDHGLTPDQVVAIASNNGGKQA
LETVQRLLPVLCQDHGLTPDQVVAIASNIGGKQAL
ETVQRLLPVLCQDHGLTPDQVVAIASNNGGKQALE
TVQRLLPVLCQDHGLTPDQVVAIASNGGGKQALET
VQRLLPVLCQDHGLTPDQVVAIASNGGGKQALETV
QRLLPVLCQDHGLTPDQVVAIASNGGGKQALETVQ
RLLPVLCQDHGLTPDQVVAIASHDGGKQALETVQR
LLPVLCQDHGLTPDQVVAIASNIGGKQALETVQRL
LPVLCQDHGLTPDQVVAIASHDGGKQALETVQRLL
PVLCQDHGLTPDQVVAIASHDGGKQALESIVAQLS
RPDPALAALTNDHLVALACLGGRPALDAVKKGLPH
APALIKRTNRRIPERTSHRVAGSGGG (SEQ ID NO: 43)

Nucleotide sequence of the corresponding TALE binding site
5'-TAGTCATCCCCACAATAGT-3'
(SEQ ID NO: 44)

TALE BCL11A #5
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SNIGGKQALETVQRLLPVLCQDHGLTPDQVVAIAS
HDGGKQALETVQRLLPVLCQDHGLTPDQVVAIASN
IGGKQALETVQRLLPVLCQDHGLTPDQVVAIASNN
GGKQALETVQRLLPVLCQDHGLTPDQVVAIASNGG
GKQALETVQRLLPVLCQDHGLTPDQVVAIASNGGG
KQALETVQRLLPVLCQDHGLTPDQVVAIASNNGGK
QALETVQRLLPVLCQDHGLTPDQVVAIASHDGGKQ
ALETVQRLLPVLCQDHGLTPDQVVAIASHDGGKQA
LETVQRLLPVLCQDHGLTPDQVVAIASHDGGKQAL
ETVQRLLPVLCQDHGLTPDQVVAIASNGGGKQALE
TVQRLLPVLCQDHGLTPDQVVAIASNNGGKQALET
VQRLLPVLCQDHGLTPDQVVAIASHDGGKQALETV
QRLLPVLCQDHGLTPDQVVAIASNIGGKQALETVQ
RLLPVLCQDHGLTPDQVVAIASNIGGKQALETVQR
LLPVLCQDHGLTPDQVVAIASNIGGKQALETVQRL
LPVLCQDHGLTPDQVVAIASNIGGKQALETVQRLL
PVLCQDHGLTPDQVVAIASNGGGKQALESIVAQLS
RPDPALAALINDHLVALACLGGRPALDAVKKGLPH
APALIKRTNRRIPERTSHRVAGSGGG (SEQ ID NO: 45)

Nucleotide sequence of the corresponding TALE binding site
5'-TCCCGCTGCCTTTTGTGCC-3'
(SEQ ID NO: 46)

TALE BCL11A #6
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA

TABLE 7-continued

SHDGGKQALETVQRLLPVLCQDHGLTPDQVVAIAS
HDGGKQALETVQRLLPVLCQDHGLTPDQVVAIASN
NGGKQALETVQRLLPVLCQDHGLTPDQVVAIASHD
GGKQALETVQRLLPVLCQDHGLTPDQVVAIASHDG
GKQALETVQRLLPVLCQDHGLTPDQVVAIASHDGG
KQALETVQRLLPVLCQDHGLTPDQVVAIASNGGGK
QALETVQRLLPVLCQDHGLTPDQVVAIASNNGGKQ
ALETVQRLLPVLCQDHGLTPDQVVAIASNNGGKQA
LETVQRLLPVLCQDHGLTPDQVVAIASNNGGKQAL
ETVQRLLPVLCQDHGLTPDQVVAIASNGGGKQALE
TVQRLLPVLCQDHGLTPDQVVAIASNIGGKQALET
VQRLLPVLCQDHGLTPDQVVAIASHDGGKQALETV
QRLLPVLCQDHGLTPDQVVAIASNGGGKQALETVQ
RLLPVLCQDHGLTPDQVVAIASNGGGKQALETVQR
LLPVLCQDHGLTPDQVVAIASNGGGKQALETVQRL
LPVLCQDHGLTPDQVVAIASHDGGKQALETVQRLL
PVLCQDHGLTPDQVVAIASNGGGKQALESIVAQLS
RPDPALAALTNDHLVALACLGGRPALDAVKKGLPH
APALIKRTNRRIPERTSHRVAGSGGG (SEQ ID NO: 47)

Nucleotide sequence of the corresponding TALE binding site
5'-TCCTCGCGCTTGCCCTCCC-3'
(SEQ ID NO: 48)

TALE BCL11A #7
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
NGGGKQALETVQRLLPVLCQDHGLTPDQVVAIASH
DGGKQALETVQRLLPVLCQDHGLTPDQVVAIASNG
GGKQALETVQRLLPVLCQDHGLTPDQVVAIASNGG
GKQALETVQRLLPVLCQDHGLTPDQVVAIASNNGG
KQALETVQRLLPVLCQDHGLTPDQVVAIASNGGGK
QALETVQRLLPVLCQDHGLTPDQVVAIASHDGGKQ
ALETVQRLLPVLCQDHGLTPDQVVAIASHDGGKQA
LETVQRLLPVLCQDHGLTPDQVVAIASNIGGKQAL
ETVQRLLPVLCQDHGLTPDQVVAIASHDGGKQALE
TVQRLLPVLCQDHGLTPDQVVAIASNIGGKQALET
VQRLLPVLCQDHGLTPDQVVAIASNHGGKQALETV
QRLLPVLCQDHGLTPDQVVAIASHDGGKQALETVQ
RLLPVLCQDHGLTPDQVVAIASNGGGKQALETVQR
LLPVLCQDHGLTPDQVVAIASHDGGKQALETVQRL
LPVLCQDHGLTPDQVVAIASNNGGKQALETVQRLL
PVLCQDHGLTPDQVVAIASNNGGKQALESIVAQLS
RPDPALAALTNDHLVALACLGGRPALDAVKKGLPH
APALIKRTNRRIPERTSHRVAGSGGG (SEQ ID NO: 49)

Nucleotide sequence of the corresponding TALE binding site
5'-TCCCCCGGCCCTAGCTCCT-3'
(SEQ ID NO: 50)

TALE BCL11A #8
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
NGGGKQALETVQRLLPVLCQDHGLTPDQVVAIASH
DGGKQALETVQRLLPVLCQDHGLTPDQVVAIASHD
GGKQALETVQRLLPVLCQDHGLTPDQVVAIASHDG
GKQALETVQRLLPVLCQDHGLTPDQVVAIASNNGG
KQALETVQRLLPVLCQDHGLTPDQVVAIASHDGGK
QALETVQRLLPVLCQDHGLTPDQVVAIASNGGGKQ
ALETVQRLLPVLCQDHGLTPDQVVAIASNNGGKQA
LETVQRLLPVLCQDHGLTPDQVVAIASNIGGKQAL
ETVQRLLPVLCQDHGLTPDQVVAIASHDGGKQALE
TVQRLLPVLCQDHGLTPDQVVAIASNGGGKQALET
VQRLLPVLCQDHGLTPDQVVAIASNHGGKQALETV
QRLLPVLCQDHGLTPDQVVAIASHDGGKQALETVQ
RLLPVLCQDHGLTPDQVVAIASNHGGKQALETVQR
LLPVLCQDHGLTPDQVVAIASHDGGKQALETVQRL
LPVLCQDHGLTPDQVVAIASHDGGKQALETVQRLL
PVLCQDHGLTPDQVVAIASNGGGKQALESIVAQLS
RPDPALAALTNDHLVALACLGGRPALDAVKKGLPH
APALIKRTNRRIPERTSHRVAGSGGG (SEQ ID NO: 51)

Nucleotide sequence of the corresponding TALE binding site
5'-TCCTGGTCCGCCCCCAGCA-3'
(SEQ ID NO: 52)

TALE BCL11A #9
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKOWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
HDGGKQALETVQRLLPVLCQDHGLTPDQVVAIASH
DGGKQALETVQRLLPVLCQDHGLTPDQVVAIASNG
GGKQALETVQRLLPVLCQDHGLTPDQVVAIASNGG
GKQALETVQRLLPVLCQDHGLTPDQVVAIASNNGG
KQALETVQRLLPVLCQDHGLTPDQVVAIASHDGGK
QALETVQRLLPVLCQDHGLTPDQVVAIASNGGGKQ
ALETVQRLLPVLCQDHGLTPDQVVAIASNNGGKQA
LETVQRLLPVLCQDHGLTPDQVVAIASHDGGKQAL
ETVQRLLPVLCQDHGLTPDQVVAIASHDGGKQALE
TVQRLLPVLCQDHGLTPDQVVAIASNIGGKQALET
VQRLLPVLCQDHGLTPDQVVAIASNIGGKQALETV
QRLLPVLCQDHGLTPDQVVAIASNIGGKQALETVQ
RLLPVLCQDHGLTPDQVVAIASHDGGKQALETVQR
LLPVLCQDHGLTPDQVVAIASNGGGKQALETVQRL
LPVLCQDHGLTPDQVVAIASNGGGKQALETVQRLL
PVLCQDHGLTPDQVVAIASNGGGKQALESIVAQLS
RPDPALAALTNDHLVALACLGGRPALDAVKKGLPH
APALIKRTNRRIPERTSHRVAGSGGG (SEQ ID NO: 53)

Nucleotide sequence of the corresponding TALE binding site
5'-TGCCGAGACCTCTTCTCGA-3'
(SEQ ID NO: 54)

TALE BCL11A #10
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SNNGGKQALETVKRLLPVLCQDHGLTPDQVVAIAS
NNGGKQALETVQRLLPVLCQDHGLTPDQVVAIASN
NGGKQALETVQRLLPVLCQDHGLTPDQVVAIASHD
GGKQALETVQRLLPVLCQDHGLTPDQVVAIASHDG
GKQALETVQRLLPVLCQDHGLTPDQVVAIASHDGG
KQALETVQRLLPVLCQDHGLTPDQVVAIASNGGGK
QALETVQRLLPVLCQDHGLTPDQVVAIASHDGGKQ
ALETVQRLLPVLCQDHGLTPDQVVAIASNIGGKQA
LETVQRLLPVLCQDHGLTPDQVVAIASHDGGKQAL
ETVQRLLPVLCQDHGLTPDQVVAIASNNGGKQALE
TVQRLLPVLCQDHGLTPDQVVAIASHDGGKQALET
VQRLLPVLCQDHGLTPDQVVAIASHDGGKQALETV
QRLLPVLCQDHGLTPDQVVAIASNGGGKQALETVQ
RLLPVLCQDHGLTPDQVVAIASNGGGKQALETVQR
LLPVLCQDHGLTPDQVVAIASNGGGKQALETVQRL
LPVLCQDHGLTPDQVVAIASHDGGKQALETVQRLL
PVLCQDHGLTPDQVVAIASNGGGKQALESIVAQLS
RPDPALAALTNDHLVALACLGGRPALDAVKKGLPH
APALIKRINRRIPERTSHRVAGSGGG (SEQ ID NO: 55)

Nucleotide sequence of the corresponding TALE binding site
5'-TCGGCTTTGCAAAGCATTT-3'
(SEQ ID NO: 56)

TALE BCL11A #11
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA

TABLE 7-continued

SHDGGKQALETVQRLLPVLCQDHGLTPDQVVAIAS
NGGGKQALETVQRLLPVLCQDHGLTPDQVVAIASH
DGGKQALETVQRLLPVLCQDHGLTPDQVVAIASHD
GGKQALETVQRLLPVLCQDHGLTPDQVVAIASHDG
GKQALETVQRLLPVLCQDHGLTPDQVVAIASHDGG
KQALETVQRLLPVLCQDHGLTPDQVVAIASNNGGK
QALETVQRLLPVLCQDHGLTPDQVVAIASNNGGKQ
ALETVQRLLPVLCQDHGLTPDQVVAIASNNGGKQA
LETVQRLLPVLCQDHGLTPDQVVAIASNIGGKQAL
ETVQRLLPVLCQDHGLTPDQVVAIASNIGGKQALE
TVQRLLPVLCQDHGLTPDQVVAIASNGGGKQALET
VQRLLPVLCQDHGLTPDQVVAIASHDGGKQALETV
QRLLPVLCQDHGLTPDQVVAIASNNGGKQALETVQ
RLLPVLCQDHGLTPDQVVAIASNGGGKQALETVQR
LLPVLCQDHGLTPDQVVAIASNGGGKQALETVQRL
LPVLCQDHGLTPDQVVAIASNGGGKQALETVQRLL
PVLCQDHGLTPDQVVAIASNGGGKQALESIVAQLS
RPDPALAALTNDHLVALACLGGRPALDAVKKGLPH
APALIKRTNRRIPERTSHRVAGSGGG (SEQ ID
NO: 57)

Nucleotide sequence of the corresponding
TALE binding site
5'-TGCAAAGCCGAGTTTCACC-3'
(SEQ ID NO: 58)

TALE BCL11A #12
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIGV
GKOWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
HDGGKQALETVQRLLPVLCQDHGLTPDQVVAIASN
IGGKQALETVQRLLPVLCQDHGLTPDQVVAIASNI
GGKQALETVQRLLPVLCQDHGLTPDQVVAIASNIG
GKQALETVQRLLPVLCQDHGLTPDQVVAIASNIGG
KQALETVQRLLPVLCQDHGLTPDQVVAIASNHGGK
QALETVQRLLPVLCQDHGLTPDQVVAIASHDGGKQ
ALETVQRLLPVLCQDHGLTPDQVVAIASHDGGKQA
LETVQRLLPVLCQDHGLTPDQVVAIASNIGGKQAL
ETVQRLLPVLCQDHGLTPDQVVAIASNNGGKQALE
TVQRLLPVLCQDHGLTPDQVVAIASNGGGKQALET
VQRLLPVLCQDHGLTPDQVVAIASHDGGKQALETV
QRLLPVLCQDHGLTPDQVVAIASNGGGKQALETVQ
RLLPVLCQDHGLTPDQVVAIASHDGGKQALETVQR
LLPVLCQDHGLTPDQVVAIASNIGGKQALETVQRL
LPVLCQDHGLTPDQVVAIASHDGGKQALETVQRLL
PVLCQDHGLTPDQVVAIASHDGGKQALESIVAQLS
RPDPALAALTNDHLVALACLGGRPALDAVKKGLPH
APALIKRTNRRIPERTSHRVAGSGGG (SEQ ID
NO: 59)

Nucleotide sequence of the corresponding
TALE binding site
5'-TACAGTTGCCCTGCAAAAT-3'
(SEQ ID NO: 60)

TALE BCL11A #13
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
HDGGKQALETVQRLLPVLCQDHGLTPDQVVAIASN
GGGKQALETVQRLLPVLCQDHGLTPDQVVAIASHD
GGKQALETVQRLLPVLCQDHGLTPDQVVAIASHDG
GKQALETVQRLLPVLCQDHGLTPDQVVAIASHDGG
KQALETVQRLLPVLCQDHGLTPDQVVAIASNNGGK
QALETVQRLLPVLCQDHGLTPDQVVAIASHDGGKQ
ALETVQRLLPVLCQDHGLTPDQVVAIASNNGGKQA
LETVQRLLPVLCQDHGLTPDQVVAIASNNGGKQAL
ETVQRLLPVLCQDHGLTPDQVVAIASHDGGKQALE
TVQRLLPVLCQDHGLTPDQVVAIASNIGGKQALET
VQRLLPVLCQDHGLTPDQVVAIASHDGGKQALETV
QRLLPVLCQDHGLTPDQVVAIASNIGGKQALETVQ
RLLPVLCQDHGLTPDQVVAIASHDGGKQALETVQR
LLPVLCQDHGLTPDQVVAIASNGGGKQALETVQRL
LPVLCQDHGLTPDQVVAIASNGGGKQALETVQRLL
PVLCQDHGLTPDQVVAIASNNGGKQALESIVAQLS
RPDPALAALTNDHLVALACLGGRPALDAVKKGLPH
APALIKRTNRRIPERTSHRVAGSGGG (SEQ ID
NO: 61)

Nucleotide sequence of the corresponding
TALE binding site
5'-TCCGCCCTGGGTACTTTCT-3'
(SEQ ID NO: 62)

TALE BCL11A #14
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SNIGGKQALETVQRLLPVLCQDHGLTPDQVVAIAS
NNGGKQALETVQRLLPVLCQDHGLTPDQVVAIASN
GGGKQALETVQRLLPVLCQDHGLTPDQVVAIASHD
GGKQALETVQRLLPVLCQDHGLTPDQVVAIASNIG
GKQALETVQRLLPVLCQDHGLTPDQVVAIASNGGG
KQALETVQRLLPVLCQDHGLTPDQVVAIASHDGGK
QALETVQRLLPVLCQDHGLTPDQVVAIASHDGGKQ
ALETVQRLLPVLCQDHGLTPDQVVAIASHDGGKQA
LETVQRLLPVLCQDHGLTPDQVVAIASHDGGKQAL
ETVQRLLPVLCQDHGLTPDQVVAIASNIGGKQALE
TVQRLLPVLCQDHGLTPDQVVAIASHDGGKQALET
VQRLLPVLCQDHGLTPDQVVAIASNIGGKQALETV
QRLLPVLCQDHGLTPDQVVAIASNIGGKQALETVQ
RLLPVLCQDHGLTPDQVVAIASNGGGKQALETVQR
LLPVLCQDHGLTPDQVVAIASNIGGKQALETVQRL
LPVLCQDHGLTPDQVVAIASNNGGKQALETVQRLL
PVLCQDHGLTPDQVVAIASNGGGKQALESIVAQLS
RPDPALAALTNDHLVALACLGGRPALDAVKKGLPH
APALIKRTNRRIPERTSHRVAGSGGG (SEQ ID
NO: 63)

Nucleotide sequence of the corresponding
TALE binding site
5'-TCTCTTGTCCACAGCTCGG-3'
(SEQ ID NO: 64)

TALE BCL11A #15
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
HDGGKQALETVQRLLPVLCQDHGLTPDQVVAIASH
DGGKQALETVQRLLPVLCQDHGLTPDQVVAIASNN
GGKQALETVQRLLPVLCQDHGLTPDQVVAIASHDG
GKQALETVQRLLPVLCQDHGLTPDQVVAIASNGGG
KQALETVQRLLPVLCQDHGLTPDQVVAIASNNGGK
QALETVQRLLPVLCQDHGLTPDQVVAIASHDGGKQ
ALETVORLLPVLCQDHGLTPDQVVAIASHDGGKQA
LETVQRLLPVLCQDHGLTPDQVVAIASNGGGKQAL
ETVQRLLPVLCQDHGLTPDQVVAIASNGGGKQALE
TVQRLLPVLCQDHGLTPDQVVAIASNGGGKQALET
VQRLLPVLCQDHGLTPDQVVAIASNGGGKQALETV
QRLLPVLCQDHGLTPDQVVAIASNNGGKQALETVQ
RLLPVLCQDHGLTPDQVVAIASNGGGKQALETVQR
LLPVLCQDHGLTPDQVVAIASNNGGKQALETVQRL
LPVLCQDHGLTPDQVVAIASHDGGKQALETVQRLL
PVLCQDHGLTPDQVVAIASHDGGKQALESIVAQLS
RPDPALAALTNDHLVALACLGGRPALDAVKKGLPH
APALIKRTNRRIPERTSHRVAGSGGG (SEQ ID
NO: 65)

Nucleotide sequence of the corresponding
TALE binding site
5'-TCTCCCGCTGACTGCGCCT-3'
(SEQ ID NO: 66)

TALE BCL11A #16
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKQWSGARALEALLTVAGELRGPPLQLDTGQLLKI
AKRGGVTAVEAVHAWRNALTGAPLNLTPDQVVAIA

TABLE 7-continued

SHDGGKQALETVQRLLPVLCQDHGLTPDQVVAIAS
HDGGKQALETVQRLLPVLCQDHGLTPDQVVAIASN
GGGKQALETVQRLLPVLCQDHGLTPDQVVAIASHD
GGKQALETVQRLLPVLCQDHGLTPDQVVAIASNNG
GKQALETVQRLLPVLCQDHGLTPDQVVAIASHDGG
KOALETVQRLLPVLCQDHGLTPDQVVAIASNNGGK
QALETVQRLLPVLCQDHGLTPDQVVAIASHDGGKQ
ALETVQRLLPVLCQDHGLTPDQVVAIASNGGGKQA
LETVQRLLPVLCQDHGLTPDQVVAIASNGGGKQAL
ETVQRLLPVLCQDHGLTPDQVVAIASNNGGKQALE
TVQRLLPVLCQDHGLTPDQVVAIASHDGGKQALET
VQRLLPVLCQDHGLTPDQVVAIASHDGGKQALETV
QRLLPVLCQDHGLTPDQVVAIASHDGGKQALETVQ
RLLPVLCQDHGLTPDQVVAIASNGGGKQALETVQR
LLPVLCQDHGLTPDQVVAIASHDGGKQALETVQRL
LPVLCQDHGLTPDQVVAIASHDGGKQALETVQRLL
PVLCQDHGLTPDQVVAIASHDGGKQALESIVAQLS
RPDPALAALTNDHLVALACLGGRPALDAVKKGLPH
APALIKRTNRRIPERTSHRVAGSGGG (SEQ ID
NO: 67)

Nucleotide sequence of the corresponding
TALE binding site
5'-TCCCTTGCTGCCAAACTTT-3'
(SEQ ID NO: 68)

TALE BCL11A #17
MGKPIPNPLLGLDSTGGMAPKKKRKVDGGVDLRTL
GYSQQQQEKIKPKVRSTVAQHHEALVGHGFTHAHI
VALSQHPAALGTVAVKYQDMIAALPEATHEAIVGV
GKOWSGARALEALLTVAGELRGPPLQLDTGQLLKI
AKRGGVTAVEAVHAWRNALTGAPLNLTPDQVVAIA
SHDGGKQALETVQRLLPVLCQDHGLTPDQVVAIAS
HDGGKQALETVQRLLPVLCQDHGLTPDQVVAIASH
DGGKQALETVQRLLPVLCQDHGLTPDQVVAIASHD
GGKQALETVQRLLPVLCQDHGLTPDQVVAIASHDG
GKQALETVQRLLPVLCQDHGLTPDQVVAIASNNGG

TABLE 7-continued

KQALETVQRLLPVLCQDHGLTPDQVVAIASNNGGK
QALETVQRLLPVLCQDHGLTPDQVVAIASHDGGKQ
ALETVQRLLPVLCQDHGLTPDQVVAIASHDGGKQA
LETVQRLLPVLCQDHGLTPDQVVAIASHDGGKQAL
ETVQRLLPVLCQDHGLTPDQVVAIASNGGGKQALE
TVQRLLPVLCQDHGLTPDQVVAIASNIGGKQALET
VQRLLPVLCQDHGLTPDQVVAIASNNGGKQALETV
QRLLPVLCQDHGLTPDQVVAIASHDGGKQALETVQ
RLLPVLCQDHGLTPDQVVAIASNGGGKQALETVQR
LLPVLCQDHGLTPDQVVAIASHDGGKQALETVQRL
LPVLCQDHGLTPDQVVAIASHDGGKQALETVQRLL
PVLCQDHGLTPDQVVAIASNGGGKQALESIVAQLS
RPDPALAALTNDHLVALACLGGRPALDAVKKGLPH
APALIKRINRRIPERTSHRVAGSGGG (SEQ ID
NO: 69)

Nucleotide sequence of the corresponding
TALE binding site
5'-TGGGCCCTCACGCCTTTCT-3'
(SEQ ID NO: 70)

All publications mentioned in the above specification are herein incorporated by reference. Various modifications and variations of the described products, uses, methods and kits of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method comprising administering to a subject in need thereof a combination of artificial transcription repressors (ATRs) selected from the group consisting of: (a) and (b), and (a) and (c), or polynucleotides encoding therefor, wherein:

(a) is an ATR comprising a DNA-binding domain operably linked to a Kruppel-associated box (KRAB) domain or homologue thereof;

(b) is an ATR comprising a DNA-binding domain operably linked to a DNA methyltransferase 3A (DNMT3A), or homologue thereof; and (c) is an ATR comprising a DNA-binding domain operably linked to a DNA (cytosine-5)-methyltransferase 3-like (DNMT3L) domain or homologue thereof.

2. The method of claim 1, wherein:

(i) the KRAB domain or homologue thereof comprises an amino acid sequence that has at least 60% identity to any one of SEQ ID NOs: 1-7;

(ii) the DNMT3A domain or homologue thereof comprises an amino acid sequence that has at least 60% identity to SEQ ID NO: 8;

(iii) the DNMT3L domain or homologue thereof comprises an amino acid sequence that has at least 60% identity to SEQ ID NO: 11; and/or (iv) the DNA-binding domain of (a), (b), or (c) comprises a domain independently selected from a transcription-activator like effector (TALE) DNA-binding domain, a zinc finger domain, a tetracycline-controlled repressor (tetR) DNA-binding domain, a meganuclease or a Clustered Regularly Interspaced Short Palindromic Repeats (CRISPR)/Cas system.

3. The method of claim 1, wherein the polynucleotides encoding the ATRs are in the form of a single vector or are comprised within separate vectors.

4. The method of claim 1, further comprising administering a separate effector protein that is not operably linked to a DNA-binding domain, or polynucleotide encoding therefor, wherein the separate effector protein that is not operably linked to a DNA-binding domain comprises a domain selected from groups (a), (b), (c) or (d):

(a) a KRAB domain or homologue thereof;

(b) a DNMT3A, DNMT3B or DNMT1 domain or homologue thereof;

(c) a DNMT3L domain or homologue thereof; and (d) a SETDB1 domain or homologue thereof.

5. The method of claim 1 in which the combination of artificial transcription repressors (ATRs) is in the form of a pharmaceutical composition further comprising a pharmaceutically acceptable carrier, diluent or excipient.

6. A method comprising administering to a subject in need thereof a cell comprising the ATRs as defined in claim 1.

7. A method comprising administering to a subject in need thereof a cell wherein said cell is a descendant of the cell of the method of claim 6.

8. The method of claim 1 comprising administering an artificial transcription repressor (ATR) comprising a DNA-binding domain operably linked to a KRAB domain or homologue thereof, an ATR comprising a DNA-binding domain operably linked to a DNMT3L domain or homologue thereof, and an ATR comprising a DNA-binding domain operably linked to a DNMT3A domain or homologue thereof, or polynucleotides encoding therefor.

9. The method of claim 1 comprising administering an artificial transcription repressor (ATR) comprising a DNA-binding domain operably linked to a KRAB domain or homologue thereof, and an ATR comprising a DNA-binding domain operably linked to a DNMT3L domain or homologue thereof, or polynucleotides encoding therefor.

10. The method of claim 1 comprising administering an artificial transcription repressor (ATR) comprising a DNA-binding domain operably linked to a KRAB domain or homologue thereof, and an ATR comprising a DNA-binding domain operably linked to a DNMT3A domain or homologue thereof, or polynucleotides encoding therefor.

11. A method comprising administering to a subject in need thereof an artificial transcription repressor (ATR) comprising a DNA-binding domain operably linked to two or more domains selected from groups (a), (b), or (c); wherein the two or more domains comprise: (a) and (b), or (a) and (c); wherein:

(a) is a Kruppel-associated box (KRAB) domain or homologue thereof;

(b) is a DNA methyltransferase 3A (DNMT3A), or homologue thereof; and (c) is a DNA (cytosine-5)-methyltransferase 3-like (DNMT3L) domain or homologue thereof;

optionally wherein the DNA-binding domain comprises a transcription-activator like effector (TALE) DNA-binding domain, a zinc finger domain, a tetracycline-controlled repressor (tetR) DNA-binding domain, a meganuclease, or a Clustered Regularly Interspaced Short Palindromic Repeats (CRISPR)/Cas system.

12. A method comprising administering to a subject in need thereof a polynucleotide encoding the ATR of the method of claim 11.

13. A method comprising administering to a subject in need thereof a cell comprising the ATR as defined in claim 11.

14. A method comprising administering to a subject in need thereof a cell wherein said cell is a descendant of the cell of the method of claim 13.

15. A method comprising administering to a subject in need thereof the ATR of the method of claim 11, wherein the ATR comprises a DNA-binding domain operably linked to a KRAB domain or homologue thereof, a DNTM3A domain or homologue thereof, and a DNMT3L domain or homologue thereof.

16. A method comprising administering to a subject in need thereof the ATR of the method of claim 11, wherein the ATR comprises a DNA-binding domain operably linked to a KRAB domain or homologue thereof, and a DNMT3L domain or homologue thereof.

17. A method comprising administering to a subject in need thereof the ATR of the method of claim 11, wherein the ATR comprises a DNA-binding domain operably linked to a KRAB domain or homologue thereof, and a DNTM3A domain or homologue thereof.

18. A method comprising administering to a subject in need thereof two or more different artificial transcription repressors (ATRs), or polynucleotides encoding therefor, wherein the two or more different ATRs individually comprise a DNA-binding domain operably linked to two or more domains selected from groups (a), (b), or (c); wherein the two or more domains comprise: (a) and (b), or (a) and (c); wherein:

(a) is a Kruppel-associated box (KRAB) domain or homologue thereof;

(b) is a DNA methyltransferase 3A (DNMT3A), or homologue thereof; and (c) is a DNA (cytosine-5)-methyltransferase 3-like (DNMT3L) domain or homologue thereof;

optionally wherein the DNA-binding domains of the two or more different ATRs are individually selected from the group consisting of a transcription-activator like effector (TALE) DNA-binding domain, a zinc finger domain, a tetracycline-controlled repressor (tetR) DNA-binding domain, a meganuclease, and a Clustered Regularly Interspaced Short Palindromic Repeats (CRISPR)/Cas system.

19. A method comprising administering to a subject in need thereof a cell comprising the ATR as defined in claim 18.

20. A method comprising administering to a subject in need thereof a cell wherein said cell is a descendant of the cell of the method of claim 19.

* * * * *

SEQUENCE LISTING

```
Sequence total quantity: 175
SEQ ID NO: 1            moltype = AA  length = 117
FEATURE                 Location/Qualifiers
source                  1..117
                        mol_type = protein
                        organism = Homo sapiens
SEQUENCE: 1
ALSPQHSAVT QGSIIKNKEG MDAKSLTAWS RTLVTFKDVF VDFTREEWKL LDTAQQIVYR  60
NVMLENYKNL VSLGYQLTKP DVILRLEKGE EPWLVEREIH QETHPDSETA FEIKSSV     117

SEQ ID NO: 2            moltype = AA  length = 72
FEATURE                 Location/Qualifiers
source                  1..72
                        mol_type = protein
                        organism = Homo sapiens
SEQUENCE: 2
ITLEDVAVDF TWEEWQLLGA AQKDLYRDVM LENYSNLVAV GYQASKPDAL FKLEQGEQLW  60
TIEDGIHSGA CS                                                      72

SEQ ID NO: 3            moltype = AA  length = 73
FEATURE                 Location/Qualifiers
source                  1..73
                        mol_type = protein
                        organism = Homo sapiens
SEQUENCE: 3
VMFEEVSVCF TSEEWACLGP IQRALYWDVM LENYGNVTSL EWETMTENEE VTSKPSSSQR  60
ADSHKGTSKR LQG                                                     73

SEQ ID NO: 4            moltype = AA  length = 72
FEATURE                 Location/Qualifiers
source                  1..72
                        mol_type = protein
                        organism = Homo sapiens
SEQUENCE: 4
VSFKDVAVDF TQEEWQQLDP DEKITYRDVM LENYSHLVSV GYDTTKPNVI IKLEQGEEPW  60
IMGGEFPCQH SP                                                      72
```

```
SEQ ID NO: 5            moltype = AA  length = 74
FEATURE                 Location/Qualifiers
source                  1..74
                        mol_type = protein
                        organism = Homo sapiens
SEQUENCE: 5
VKIEDMAVSL ILEEWGCQNL ARRNLSRDNR QENYGSAFPQ GGENRNENEE STSKAETSED  60
SASRGETTGR SQKE                                                    74

SEQ ID NO: 6            moltype = AA  length = 72
FEATURE                 Location/Qualifiers
source                  1..72
                        mol_type = protein
                        organism = Homo sapiens
SEQUENCE: 6
LTFKDVFVDF TLEEWQQLDS AQKNLYRDVM LENYSHLVSV GYLVAKPDVI FRLGPGEESW  60
MADGGTPVRT CA                                                      72

SEQ ID NO: 7            moltype = AA  length = 72
FEATURE                 Location/Qualifiers
source                  1..72
                        mol_type = protein
                        organism = Homo sapiens
SEQUENCE: 7
VTFEDVTLGF TPEEWGLLDL KQKSLYREVM LENYRNLVSV EHQLSKPDVV SQLEEAEDFW  60
PVERGIPQDT IP                                                      72

SEQ ID NO: 8            moltype = AA  length = 322
FEATURE                 Location/Qualifiers
source                  1..322
                        mol_type = protein
                        organism = Homo sapiens
SEQUENCE: 8
TYGLLRRRED WPSRLQMFFA NNHDQEFDPP KVYPPVPAEK RKPIRVLSLF DGIATGLLVL  60
KDLGIQVDRY IASEVCEDSI TVGMVRHQGK IMYVGDVRSV TQKHIQEWGP FDLVIGGSPC  120
NDLSIVNPAR KGLYEGTGRL FFEFYRLLHD ARPKEGDDRP FFWLFENVVA MGVSDKRDIS  180
RFLESNPVMI DAKEVSAAHR ARYFWGNLPG MNRPLASTVN DKLELQECLE HGRIAKFSKV  240
RTITTRSNSI KQGKDQHFPV FMNEKEDILW CTEMERVFGF PVHYTDVSNM SRLARQRLLG  300
RSWSVPVIRH LFAPLKEYFA CV                                           322

SEQ ID NO: 9            moltype = AA  length = 322
FEATURE                 Location/Qualifiers
source                  1..322
                        mol_type = protein
                        organism = Homo sapiens
SEQUENCE: 9
CHGVLRRRKD WNVRLQAFFT SDTGLEYEAP KLYPAIPAAR RRPIRVLSLF DGIATGYLVL  60
KELGIKVGKY VASEVCEESI AVGTVKHEGN IKYVNDVRNI TKKNIEEWGP FDLVIGGSPC  120
NDLSNVNPAR KGLYEGTGRL FFEFYHLLNY SRPKEGDDRP FFWMFENVVA MKVGDKRDIS  180
RFLECNPVMI DAIKVSAAHR ARYFWGNLPG MNRPVIASKN DKLELQDCLE YNRIAKLKKV  240
QTITTKSNSI KQGKNQLFPV VMNGKEDVLW CTELERIFGF PVHYTDVSNM GRGARQKLLG  300
RSWSVPVIRH LFAPLKDYFA CE                                           322

SEQ ID NO: 10           moltype = AA  length = 478
FEATURE                 Location/Qualifiers
source                  1..478
                        mol_type = protein
                        organism = Homo sapiens
SEQUENCE: 10
LRTLDVFSGC GGLSEGFHQA GISDTLWAIE MWDPAAQAFR LNNPGSTVFT EDCNILLKLV  60
MAGETTNSRG QRLPQKGDVE MLCGGPPCQG FSGMNRFNSR TYSKFKNSLV VSFLSYCDYY  120
RPRFFLLENV RNFVSFKRSM VLKLTLRCLV RMGYQCTFGV LQAGQYGVAQ TRRRAIILAA  180
APGEKLPLFP EPLHVFAPRA CQLSVVVDDK KFVSNITRLS SGPFRTITVR DTMSDLPEVR  240
NGASALEISY NGEPQSWFQR QLRGAQYQPI LRDHICKDMS ALVAARMRHI PLAPGSDWRD  300
LPNIEVRLSD GTMARKLRYT HHDRKNGRSS SGALRGVCSC VEAGKACDPA ARQFNTLIPW  360
CLPHTGNRHN HWAGLYGRLE WDGFFSTTVT NPEPMGKQGR VLHPEQHRVV SVRECARSQG  420
FPDTYRLFGN ILDKHRQVGN AVPPPLAKAI GLEIKLCMLA KARESASAKI KEEEAAKD    478

SEQ ID NO: 11           moltype = AA  length = 386
FEATURE                 Location/Qualifiers
source                  1..386
                        mol_type = protein
                        organism = Homo sapiens
SEQUENCE: 11
MAAIPALDPE AEPSMDVILV GSSELSSSVS PGTGRDLIAY EVKANQRNIE DICICCGSLQ  60
VHTQHPLFEG GICAPCKDKF LDALFLYDDD GYQSYCSICC SGETLLICGN PDCTRCYCFE  120
CVDSLVGPGT SGKVHAMSNW VCYLCLPSSR SGLLQRRRKW RSQLKAFYDR ESENPLEMFE  180
TVPVWRRQPV RVLSLFEDIK KELTSLGFLE SGSDPGQLKH VVDVTDTVRK DVEEWGPFDL  240
```

```
VYGATPPLGH TCDRPPSWYL FQFHRLLQYA RPKPGSPRPF FWMFVDNLVL NKEDLDVASR  300
FLEMEPVTIP DVHGGSLQNA VRVWSNIPAI RSRHWALVSE EELSLLAQNK QSSKLAAKWP  360
TKLVKNCFLP LREYFKYFST ELTSSL                                      386

SEQ ID NO: 12           moltype = AA  length = 1291
FEATURE                 Location/Qualifiers
source                  1..1291
                        mol_type = protein
                        organism = Homo sapiens
SEQUENCE: 12
MSSLPGCIGL DAATATVESE EIAELQQAVV EELGISMEEL RHFIDEELEK MDCVQQRKKQ  60
LAELETWVIQ KESEVAHVDQ LFDDASRAVT NCESLVKDFY SKLGLQYRDS SSEDESSRPT  120
EIIEIPDEDD DVLSIDSGDA GSRTPKDQKL REAMAALRKS AQDVQKFMDA VNKKSSSQDL  180
HKGTLSQMSG ELSKDGDLIV SMRILGKKRT KTWHKGTLIA IQTVGPGKKY KVKFDNKGKS  240
LLSGNHIAYD YHPPADKLYV GSRVVAKYKD GNQVWLYAGI VAETPNVKNK LRFLIFFDDG  300
YASYVTQSEL YPICRPLKKT WEDIEDISCR DFIEEYVTAY PNRPMVLLKS GQLIKTEWEG  360
TWWKSRVEEV DGSLVRILFL DDKRCEWIYR GSTRLEPMFS MKTSSASALE KKQGQLRTRP  420
NMGAVRSKGP VVQYTQDLTG TGTQFKPVEP PQPTAPPAPP FPPAPPLSPQ AGDSDLESQL  480
AQSRKQVAKK STSFRPGSVG SGHSSPTSPA LSENVSGGKP GINQTYRSPL GSTASAPAPS  540
ALPAPPAPPV FHGMLERAPA EPSYRAPMEK LFYLPHVCSY TCLSRVRPMR NEQYRGKNPL  600
LVPLLYDFRR MTARRRVNRK MGFHVIYKTP CGLCLRTMQE IERYLFETGC DFLFLEMFCL  660
DPYVLVDRKF QPYKPFYYIL DITYGKEDVP LSCVNEIDTT PPPQVAYSKE RIPGKGVFIN  720
TGPEFLVGCD CKDGCRDKSK CACHQLTIQA TACTPGGQIN PNSGYQYKRL EECLPTGVYE  780
CNKRCKCDPN MCTNRLVQHG LQVRLQLFKT QNKGWGIRCL DDIAKGSFVC IYAGKILTDD  840
FADKEGLEMG DEYFANLDHI ESVENFKEGY ESDAPCSSDS SGVDLKDQED GNSGTEDPEE  900
SNDDSSDDNF CKDEDFSTSS VWRSYATRRQ TRGQKENGLS ETTSKDSHPP DLGPPHIPVP  960
PSIPVGGCNP PSSEETPKNK VASWLSCNSV SEGGFADSDS HSSFKTNEGG EGRAGGSRME  1020
AEKASTSGLG IKDEGDIKQA KKEDTDDRNK MSVVTESSRN YGYNPSPVKP EGLRRPPSKT  1080
SMHQSRRLMA SAQSNPDDVL TLSSSTESEG ESGTSRKPTA GQTSATAVDS DDIQTISSGS  1140
EGDDFEDKKN MTGPMKRQVA VKSTRGFALK STHGIAIKST NMASVDKGES APVRKNTRQF  1200
YDGEESCYII DAKLEGNLGR YLNHSCSPNL FVQNVFVDTH DLRFPWVAFF ASKRIRAGTE  1260
LTWDYNYEVG SVEGKELLCC CGAIECRGRL L                                1291

SEQ ID NO: 13           moltype = AA  length = 565
FEATURE                 Location/Qualifiers
source                  1..565
                        mol_type = protein
                        organism = Homo sapiens
SEQUENCE: 13
VGCDCKDGCR DKSKCACHQL TIQATACTPG GQINPNSGYQ YKRLEECLPT GVYECNKRCK  60
CDPNMCTNRL VQHGLQVRLQ LFKTQNKGWG IRCLDDIAKG SFVCIYAGKI LTDDFADKEG  120
LEMGDEYFAN LDHIESVENF KEGYESDAPC SSDSSGVDLK DQEDGNSGTE DPEESNDDSS  180
DDNFCKDEDF STSSVWRSYA TRRQTRGQKE NGLSETTSKD SHPPDLGPPH IPVPPSIPVG  240
GCNPPSSEET PKNKVASWLS CNSVSEGGFA DSDSHSSFKT NEGGEGRAGG SRMEAEKAST  300
SGLGIKDEGD IKQAKKEDTD DRNKMSVVTE SSRNYGYNPS PVKPEGLRRP PSKTSMHQSR  360
RLMASAQSNP DDVLTLSSST ESEGESGTSR KPTAGQTSAT AVDSDDIQTI SSGSEGDDFE  420
DKKNMTGPMK RQVAVKSTRG FALKSTHGIA IKSTNMASVD KGESAPVRKN TRQFYDGEES  480
CYIIDAKLEG NLGRYLNHSC SPNLFVQNVF VDTHDLRFPW VAFFASKRIR AGTELTWDYN  540
YEVGSVEGKE LLCCCGAIEC RGRLL                                       565

SEQ ID NO: 14           moltype = AA  length = 826
FEATURE                 Location/Qualifiers
source                  1..826
                        mol_type = protein
                        note = Transcription-activator like effector (TALE) domain
                        organism = synthetic construct
SEQUENCE: 14
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPEQ VVAIASNIGG  180
KQALETVQRL LPVLCQAHGL TPEQVVAIAS HDGGKQALET VQRLLPVLCQ AHGLTPEQVV  240
AIASHDGGKQ ALETVQRLLP VLCQAHGLTP EQVVAIASHD GGKQALETVQ RLLPVLCQAH  300
GLTPEQVVAI ASNIGGKQAL ETVQRLLPVL CQAHGLTPEQ VVAIASNNGG KQALETVQRL  360
LPVLCQAHGL TPEQVVAIAS NIGGKQALET VQRLLPVLCQ AHGLTPEQVV AIASNGGGKQ  420
ALETVQRLLP VLCQAHGLTP EQVVAIASNG GGKQALETVQ RLLPVLCQAH GLTPEQVVAI  480
ASNNGGKQAL ETVQRLLPVL CQAHGLTPEQ VVAIASNNGG KQALETVQRL LPVLCQAHGL  540
TPEQVVAIAS HDGGKQALET VQRLLPVLCQ AHGLTPEQVV AIASHDGGKQ ALETVQRLLP  600
VLCQAHGLTP EQVVAIASHD GGKQALETVQ RLLPVLCQAH GLTPEQVVAI ASHDGGKQAL  660
ETVQRLLPVL CQAHGLTPEQ VVAIASNIGG KQALETVQRL LPVLCQAHGL TPEQVVAIAS  720
HDGGKQALET VQRLLPVLCQ AHGLTPQQVV AIASNGGGRP ALESIVAQLS RPDPALAALT  780
NDHLVALACL GGRPALDAVK KGLPHAPALI KRTNRRIPER TSHRVA                826

SEQ ID NO: 15           moltype = AA  length = 826
FEATURE                 Location/Qualifiers
source                  1..826
                        mol_type = protein
                        note = TALE domain
                        organism = synthetic construct
SEQUENCE: 15
```

```
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPEQ VVAIASNIGG  180
KQALETVQRL LPVLCQAHGL TPEQVVAIAS HDGGKQALET VQRLLPVLCQ AHGLTPEQVV  240
AIASHDGGKQ ALETVQRLLP VLCQAHGLTP EQVVAIASNG GGKQALETVQ RLLPVLCQAH  300
GLTPEQVVAI ASNIGGKQAL ETVQRLLPVL CQAHGLTPEQ VVAIASNNGG KQALETVQRL  360
LPVLCQAHGL TPEQVVAIAS NIGGKQALET VQRLLPVLCQ AHGLTPEQVV AIASNNGGKQ  420
ALETVQRLLP VLCQAHGLTP EQVVAIASNN GGKQALETVQ RLLPVLCQAH GLTPEQVVAI  480
ASNIGGKQAL ETVQRLLPVL CQAHGLTPEQ VVAIASNNGG KQALETVQRL LPVLCQAHGL  540
TPEQVVAIAS NIGGKQALET VQRLLPVLCQ AHGLTPEQVV AIASNIGGKQ ALETVQRLLP  600
VLCQAHGLTP EQVVAIASNI GGKQALETVQ RLLPVLCQAH GLTPEQVVAI ASNNGGKQAL  660
ETVQRLLPVL CQAHGLTPEQ VVAIASNNGG KQALETVQRL LPVLCQAHGL TPEQVVAIAS  720
NGGGKQALET VQRLLPVLCQ AHGLTPQQVV AIASNGGGRP ALESIVAQLS RPDPALAALT  780
NDHLVALACL GGRPALDAVK KGLPHAPALI KRTNRRIPER TSHRVA                826

SEQ ID NO: 16           moltype = AA  length = 831
FEATURE                 Location/Qualifiers
source                  1..831
                        mol_type = protein
                        note = TALE domain
                        organism = synthetic construct
SEQUENCE: 16
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS NGGGKQALET VQRLLPVLCQ DHGLTPDQVV  240
AIASHDGGKQ ALETVQRLLP VLCQDHGLTP DQVVAIASNG GGKQALETVQ RLLPVLCQDH  300
GLTPDQVVAI ASHDGGKQAL ETVQRLLPVL CQDHGLTPDQ VVAIASHDGG KQALETVQRL  360
LPVLCQDHGL TPDQVVAIAS NGGGKQALET VQRLLPVLCQ DHGLTPDQVV AIASNIGGKQ  420
ALETVQRLLP VLCQDHGLTP DQVVAIASHD GGKQALETVQ RLLPVLCQDH GLTPDQVVAI  480
ASHDGGKQAL ETVQRLLPVL CQDHGLTPDQ VVAIASHDGG KQALETVQRL LPVLCQDHGL  540
TPDQVVAIAS NGGGKQALET VQRLLPVLCQ DHGLTPDQVV AIASHDGGKQ ALETVQRLLP  600
VLCQDHGLTP DQVVAIASHD GGKQALETVQ RLLPVLCQDH GLTPDQVVAI ASHDGGKQAL  660
ETVQRLLPVL CQDHGLTPDQ VVAIASNHGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G          831

SEQ ID NO: 17           moltype = DNA  length = 19
FEATURE                 Location/Qualifiers
source                  1..19
                        mol_type = other DNA
                        note = Binding site
                        organism = synthetic construct
SEQUENCE: 17
tctctcctac cctcccgct                                             19

SEQ ID NO: 18           moltype = AA  length = 831
FEATURE                 Location/Qualifiers
source                  1..831
                        mol_type = protein
                        note = TALE domain
                        organism = synthetic construct
SEQUENCE: 18
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNNGG  180
KQALETVQRL LPVLCQDHGL TPDQVVAIAS NNGGKQALET VQRLLPVLCQ DHGLTPDQVV  240
AIASNGGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASNGGG KQALETVQRL  360
LPVLCQDHGL TPDQVVAIAS NGGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASNGGGKQAL ETVQRLLPVL CQDHGLTPDQ VVAIASHDGG KQALETVQRL LPVLCQDHGL  540
TPDQVVAIAS NGGGKQALET VQRLLPVLCQ DHGLTPDQVV AIASHDGGKQ ALETVQRLLP  600
VLCQDHGLTP DQVVAIASHD GGKQALETVQ RLLPVLCQDH GLTPDQVVAI ASHDGGKQAL  660
ETVQRLLPVL CQDHGLTPDQ VVAIASNGGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G          831

SEQ ID NO: 19           moltype = DNA  length = 19
FEATURE                 Location/Qualifiers
source                  1..19
                        mol_type = other DNA
                        note = Binding site
                        organism = synthetic construct
SEQUENCE: 19
tggtccttcc tctcccgct                                             19

SEQ ID NO: 20           moltype = AA  length = 831
FEATURE                 Location/Qualifiers
```

```
source                  1..831
                        mol_type = protein
                        note = TALE domain
                        organism = synthetic construct
SEQUENCE: 20
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS NNGGKQALET VQRLLPVLCQ DHGLTPDQVV  240
AIASHDGGKQ ALETVQRLLP VLCQDHGLTP DQVVAIASNG GGKQALETVQ RLLPVLCQDH  300
GLTPDQVVAI ASHDGGKQAL ETVQRLLPVL CQDHGLTPDQ VVAIASHDGG KQALETVQRL  360
LPVLCQDHGL TPDQVVAIAS NNGGKQALET VQRLLPVLCQ DHGLTPDQVV AIASNGGGKQ  420
ALETVQRLLP VLCQDHGLTP DQVVAIASNN GGKQALETVQ RLLPVLCQDH GLTPDQVVAI  480
ASNIGGKQAL ETVQRLLPVL CQDHGLTPDQ VVAIASHDGG KQALETVQRL LPVLCQDHGL  540
TPDQVVAIAS NGGGKQALET VQRLLPVLCQ DHGLTPDQVV AIASNGGGKQ ALETVQRLLP  600
VLCQDHGLTP DQVVAIASHD GGKQALETVQ RLLPVLCQDH GLTPDQVVAI ASHDGGKQAL  660
ETVQRLLPVL CQDHGLTPDQ VVAIASHDGG KQALETVQRL LPVLCQDHGL TPDQVVAIAS  720
NGGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 21           moltype = DNA  length = 19
FEATURE                 Location/Qualifiers
source                  1..19
                        mol_type = other DNA
                        note = Binding site
                        organism = synthetic construct
SEQUENCE: 21
tcgctccgtg acttccctt                                               19

SEQ ID NO: 22           moltype = AA  length = 1441
FEATURE                 Location/Qualifiers
source                  1..1441
                        mol_type = protein
                        note = Artificial transcription repressor (ATR) sequence,
                         catalytically inactive Cas9
                        organism = synthetic construct
SEQUENCE: 22
MGGRRVRWEV YISRALWLTR EPTAYWLIEI NTTHYRETQA TGATMYPYDV PDYASPKKKR  60
KVEASDKKYS IGLAIGTNSV GWAVITDEYK VPSKKFKVLG NTDRHSIKKN LIGALLFDSG  120
ETAEATRLKR TARRRYTRRK NRICYLQEIF SNEMAKVDDS FFHRLEESFL VEEDKKHERH  180
PIFGNIVDEV AYHEKYPTIY HLRKKLVDST DKADLRLIYL ALAHMIKFRG HFLIEGDLNP  240
DNSDVDKLFI QLVQTYNQLF EENPINASGV DAKAILSARL SKSRRLENLI AQLPGEKKNG  300
LFGNLIALSL GLTPNFKSNF DLAEDAKLQL SKDTYDDDLD NLLAQIGDQY ADLFLAAKNL  360
SDAILLSDIL RVNTEITKAP LSASMIKRYD EHHQDLTLLK ALVRQQLPEK YKEIFFDQSK  420
NGYAGYIDGG ASQEEFYKFI KPILEKMDGT EELLVKLNRE DLLRKQRTFD NGSIPHQIHL  480
GELHAILRRQ EDFYPFLKDN REKIEKILTF RIPYYVGPLA RGNSRFAWMT RKSEETITPW  540
NFEEVVDKGA SAQSFIERMT NFDKNLPNEK VLPKHSLLYE YFTVYNELTK VKYVTEGMRK  600
PAFLSGEQKK AIVDLLFKTN RKVTVKQLKE DYFKKIECFD SVEISGVEDR FNASLGTYHD  660
LLKIIKDKDF LDNEENEDIL EDIVLTLTLF EDREMIEERL KTYAHLFDDK VMKQLKRRRY  720
TGWGRLSRKL INGIRDKQSG KTILDFLKSD GFANRNFMQL IHDDSLTFKE DIQKAQVSGQ  780
GDSLHEHIAN LAGSPAIKKG ILQTVKVVDE LVKVMGRHKP ENIVIEMARE NQTTQKGQKN  840
SRERMKRIEE GIKELGSQIL KEHPVENTQL QNEKLYLYYL QNGRDMYVDQ ELDINRLSDY  900
DVDAIVPQSF LKDDSIDNKV LTRSDKNRGK SDNVPSEEVV KKMKNYWRQL LNAKLITQRK  960
FDNLTKAERG GLSELDKAGF IKRQLVETRQ ITKHVAQILD SRMNTKYDEN DKLIREVKVI  1020
TLKSKLVSDF RKDFQFYKVR EINNYHHAHD AYLNAVVGTA LIKKYPKLES EFVYGDYKVY  1080
DVRKMIAKSE QEIGKATAKY FFYSNIMNFF KTEITLANGE IRKRPLIETN GETGEIVWDK  1140
GRDFATVRKV LSMPQVNIVK KTEVQTGGFS KESILPKRNS DKLIARKKDW DPKKYGGFDS  1200
PTVAYSVLVV AKVEKGKSKK LKSVKELLGI TIMERSSFEK NPIDFLEAKG YKEVKKDLII  1260
KLPKYSLFEL ENGRKRMLAS AGELQKGNEL ALPSKYVNFL YLASHYEKLK GSPEDNEQKQ  1320
LFVEQHKHYL DEIIEQISEF SKRVILADAN LDKVLSAYNK HRDKPIREQA ENIIHLFTLT  1380
NLGAPAAFKY FDTTIDRKRY TSTKEVLDAT LIHQSITGLY ETRIDLSQLG GDSPKKKRKV  1440
G                                                                  1441

SEQ ID NO: 23           moltype = DNA  length = 20
FEATURE                 Location/Qualifiers
source                  1..20
                        mol_type = other DNA
                        note = Genomic target site for guide RNA (gRNA) #1 for
                         beta2-microglobulin gene
                        organism = synthetic construct
SEQUENCE: 23
tataagtgga ggcgtcgcgc                                              20

SEQ ID NO: 24           moltype = DNA  length = 20
FEATURE                 Location/Qualifiers
source                  1..20
                        mol_type = other DNA
                        note = Genomic target site for gRNA #2 for
                         beta2-microglobulin gene
```

```
                        organism = synthetic construct
SEQUENCE: 24
gcccgaatgc tgtcagcttc                                              20

SEQ ID NO: 25           moltype = DNA  length = 20
FEATURE                 Location/Qualifiers
source                  1..20
                        mol_type = other DNA
                        note = Genomic target site for gRNA #3 for
                         beta2-microglobulin gene
                        organism = synthetic construct
SEQUENCE: 25
tgcgtcgctg gcttggagac                                              20

SEQ ID NO: 26           moltype = DNA  length = 20
FEATURE                 Location/Qualifiers
source                  1..20
                        mol_type = other DNA
                        note = Genomic target site for gRNA #4 for
                         beta2-microglobulin gene
                        organism = synthetic construct
SEQUENCE: 26
ccaatcagga caaggcccgc                                              20

SEQ ID NO: 27           moltype = DNA  length = 20
FEATURE                 Location/Qualifiers
source                  1..20
                        mol_type = other DNA
                        note = Genomic target site for gRNA #5 for
                         beta2-microglobulin gene
                        organism = synthetic construct
SEQUENCE: 27
agggtaggag agactcacgc                                              20

SEQ ID NO: 28           moltype = DNA  length = 20
FEATURE                 Location/Qualifiers
source                  1..20
                        mol_type = other DNA
                        note = Genomic target site for gRNA #6 for
                         beta2-microglobulin gene
                        organism = synthetic construct
SEQUENCE: 28
gcgggccacc aaggagaact                                              20

SEQ ID NO: 29           moltype = DNA  length = 20
FEATURE                 Location/Qualifiers
source                  1..20
                        mol_type = other DNA
                        note = Genomic target site for gRNA #7 for
                         beta2-microglobulin gene
                        organism = synthetic construct
SEQUENCE: 29
gctactctct ctttctggcc                                              20

SEQ ID NO: 30           moltype = DNA  length = 20
FEATURE                 Location/Qualifiers
source                  1..20
                        mol_type = other DNA
                        note = Genomic target site for gRNA #8 for
                         beta2-microglobulin gene
                        organism = synthetic construct
SEQUENCE: 30
ctcccgctct gcaccctctg                                              20

SEQ ID NO: 31           moltype = DNA  length = 20
FEATURE                 Location/Qualifiers
source                  1..20
                        mol_type = other DNA
                        note = Genomic target site for gRNA #9 for
                         beta2-microglobulin gene
                        organism = synthetic construct
SEQUENCE: 31
tttggcctac ggcgacggga                                              20

SEQ ID NO: 32           moltype = DNA  length = 20
FEATURE                 Location/Qualifiers
source                  1..20
                        mol_type = other DNA
                        note = Genomic target site for gRNA #10 for
```

```
                        beta2-microglobulin gene
                       organism = synthetic construct
SEQUENCE: 32
ggggcaagta gcgcgcgtcc                                              20

SEQ ID NO: 33          moltype = DNA  length = 20
FEATURE                Location/Qualifiers
source                 1..20
                       mol_type = other DNA
                       note = Genomic target site for gRNA #11 for
                        beta2-microglobulin gene
                       organism = synthetic construct
SEQUENCE: 33
tagtccaggg ctggatctcg                                              20

SEQ ID NO: 34          moltype = DNA  length = 19
FEATURE                Location/Qualifiers
source                 1..19
                       mol_type = other DNA
                       note = Binding site
                       organism = synthetic construct
SEQUENCE: 34
tacccagatt ggccccact                                               19

SEQ ID NO: 35          moltype = DNA  length = 19
FEATURE                Location/Qualifiers
source                 1..19
                       mol_type = other DNA
                       note = Binding site
                       organism = synthetic construct
SEQUENCE: 35
tacctagagg agaaaggtt                                               19

SEQ ID NO: 36          moltype = AA  length = 846
FEATURE                Location/Qualifiers
source                 1..846
                       mol_type = protein
                       organism = Homo sapiens
SEQUENCE: 36
MVAELISEED LEFMKGDTRH LNGEEDAGGR EDSILVNGAC SDQSSDSPPI LEAIRTPEIR  60
GRRSSSRLSK REVSSLLSYT QDLTGDGDGE DGDGSDTPVM PKLFRETRTR SESPAVRTRN  120
NNSVSSRERH RPSPRSTRGR QGRNHVDESP VEFPATRSLR RRATASAGTP WPSPPSSYLT  180
IDLTDDTEDT HGTPQSSSTP YARLAQDSQQ GGMESPQVEA DSGDGDSSEY QDGKEFGIGD  240
LVWGKIKGFS WWPAMVVSWK ATSKRQAMSG MRWVQWFGDG KFSEVSADKL VALGLFSQHF  300
NLATFNKLVS YRKAMYHALE KARVRAGKTF PSSPGDSLED QLKPMLEWAH GGFKPTGIEG  360
LKPNNTQPEN KTRRRTADDS ATSDYCPAPK RLKTNCYNNG KDRGDEDQSR EQMASDVANN  420
KSSLEDGCLS CGRKNPVSFH PLFEGGLCQT CRDRFLELFY MYDDDGYQSY CTVCCEGREL  480
LLCSNTSCCR CFCVECLEVL VGTGTAAEAK LQEPWSCYMC LPQRCHGVLR RRKDWNVRLQ  540
AFFTSDTGLE YEAPKLYPAI PAARRRPIRV LSLFDGIATG YLVLKELGIK VGKYVASEVC  600
EESIAVGTVK HEGNIKYVND VRNITKKNIE EWGPFDLVIG GSPCNDLSNV NPARKGLYEG  660
TGRLFFEFYH LLNYSRPKEG DDRPFFWMFE NVVAMKVGDK RDISRFLECN PVMIDAIKVS  720
AAHRARYFWG NLPGMNRPVI ASKNDKLELQ DCLEYNRIAK LKKVQTITTK SNSIKQGKNQ  780
LFPVVMNGKE DVLWCTELER IFGFPVHYTD VSNMGRGARQ KLLGRSWSVP VIRHLFAPLK  840
DYFACE                                                             846

SEQ ID NO: 37          moltype = AA  length = 831
FEATURE                Location/Qualifiers
source                 1..831
                       mol_type = protein
                       note = TALE domain BCL11A #1
                       organism = synthetic construct
SEQUENCE: 37
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASNGGGKQ ALETVQRLLP VLCQDHGLTP DQVVAIASNN GGKQALETVQ RLLPVLCQDH  300
GLTPDQVVAI ASNNGGKQAL ETVQRLLPVL CQDHGLTPDQ VVAIASNGGG KQALETVQRL  360
LPVLCQDHGL TPDQVVAIAS HDGGKQALET VQRLLPVLCQ DHGLTPDQVV AIASHDGGKQ  420
ALETVQRLLP VLCQDHGLTP DQVVAIASNN GGKQALETVQ RLLPVLCQDH GLTPDQVVAI  480
ASHDGGKQAL ETVQRLLPVL CQDHGLTPDQ VVAIASHDGG KQALETVQRL LPVLCQDHGL  540
TPDQVVAIAS HDGGKQALET VQRLLPVLCQ DHGLTPDQVV AIASHDGGKQ ALETVQRLLP  600
VLCQDHGLTP DQVVAIASHD GGKQALETVQ RLLPVLCQDH GLTPDQVVAI ASNIGGKQAL  660
ETVQRLLPVL CQDHGLTPDQ VVAIASNNGG KQALETVQRL LPVLCQDHGL TPDQVVAIAS  720
HDGGKQALET VQRLLPVLCQ DHGLTPDQVV AIASNIGGKQ ALESIVAQLS RPDPALAALT  780
NDHLVALACL GGRPALDAVK KGLPHAPALI KRTNRRIPER TSHRVAGSGG G           831

SEQ ID NO: 38          moltype = DNA  length = 19
FEATURE                Location/Qualifiers
```

```
source                  1..19
                        mol_type = other DNA
                        note = BCL11A gene binding site
                        organism = synthetic construct
SEQUENCE: 38
tccaaaagcc agtctcacc                                            19

SEQ ID NO: 39           moltype = AA  length = 831
FEATURE                 Location/Qualifiers
source                  1..831
                        mol_type = protein
                        note = TALE domain BCL11A #2
                        organism = synthetic construct
SEQUENCE: 39
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNNGG  180
KQALETVQRL LPVLCQDHGL TPDQVVAIAS HDGGKQALET VQRLLPVLCQ DHGLTPDQVV  240
AIASHDGGKQ ALETVQRLLP VLCQDHGLTP DQVVAIASNN GGKQALETVQ RLLPVLCQDH  300
GLTPDQVVAI ASNIGGKQAL ETVQRLLPVL CQDHGLTPDQ VVAIASNNGG KQALETVQRL  360
LPVLCQDHGL TPDQVVAIAS NIGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASNGGGKQAL ETVQRLLPVL CQDHGLTPDQ VVAIASHDGG KQALETVQRL LPVLCQDHGL  540
TPDQVVAIAS NGGGKQALET VQRLLPVLCQ DHGLTPDQVV AIASNGGGKQ ALETVQRLLP  600
VLCQDHGLTP DQVVAIASHD GGKQALETVQ RLLPVLCQDH GLTPDQVVAI ASNGGGKQAL  660
ETVQRLLPVL CQDHGLTPDQ VVAIASHDGG KQALETVQRL LPVLCQDHGL TPDQVVAIAS  720
NNGGKQALET VQRLLPVLCQ DHGLTPDQVV AIASNIGGKQ ALESIVAQLS RPDPALAALT  780
NDHLVALACL GGRPALDAVK KGLPHAPALI KRTNRRIPER TSHRVAGSGG G           831

SEQ ID NO: 40           moltype = DNA  length = 19
FEATURE                 Location/Qualifiers
source                  1..19
                        mol_type = other DNA
                        note = BCL11A gene binding site
                        organism = synthetic construct
SEQUENCE: 40
tctccccggg aatcgtttt                                            19

SEQ ID NO: 41           moltype = AA  length = 831
FEATURE                 Location/Qualifiers
source                  1..831
                        mol_type = protein
                        note = TALE domain BCL11A #3
                        organism = synthetic construct
SEQUENCE: 41
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS NNGGKQALET VQRLLPVLCQ DHGLTPDQVV  240
AIASNNGGKQ ALETVQRLLP VLCQDHGLTP DQVVAIASHD GGKQALETVQ RLLPVLCQDH  300
GLTPDQVVAI ASNGGGKQAL ETVQRLLPVL CQDHGLTPDQ VVAIASNGGG KQALETVQRL  360
LPVLCQDHGL TPDQVVAIAS NGGGKQALET VQRLLPVLCQ DHGLTPDQVV AIASNNGGKQ  420
ALETVQRLLP VLCQDHGLTP DQVVAIASHD GGKQALETVQ RLLPVLCQDH GLTPDQVVAI  480
ASNIGGKQAL ETVQRLLPVL CQDHGLTPDQ VVAIASNIGG KQALETVQRL LPVLCQDHGL  540
TPDQVVAIAS NIGGKQALET VQRLLPVLCQ DHGLTPDQVV AIASNHGGKQ ALETVQRLLP  600
VLCQDHGLTP DQVVAIASHD GGKQALETVQ RLLPVLCQDH GLTPDQVVAI ASNIGGKQAL  660
ETVQRLLPVL CQDHGLTPDQ VVAIASNGGG KQALETVQRL LPVLCQDHGL TPDQVVAIAS  720
NGGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 42           moltype = DNA  length = 19
FEATURE                 Location/Qualifiers
source                  1..19
                        mol_type = other DNA
                        note = BCL11A gene binding site
                        organism = synthetic construct
SEQUENCE: 42
tcctcccgct gcacacttg                                            19

SEQ ID NO: 43           moltype = AA  length = 831
FEATURE                 Location/Qualifiers
source                  1..831
                        mol_type = protein
                        note = TALE domain BCL11A #4
                        organism = synthetic construct
SEQUENCE: 43
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNNGG  180
```

```
KQALETVQRL LPVLCQDHGL TPDQVVAIAS HDGGKQALET VQRLLPVLCQ DHGLTPDQVV  240
AIASNIGGKQ ALETVQRLLP VLCQDHGLTP DQVVAIASNI GGKQALETVQ RLLPVLCQDH  300
GLTPDQVVAI ASNIGGKQAL ETVQRLLPVL CQDHGLTPDQ VVAIASNNGG KQALETVQRL  360
LPVLCQDHGL TPDQVVAIAS HDGGKQALET VQRLLPVLCQ DHGLTPDQVV AIASHDGGKQ  420
ALETVQRLLP VLCQDHGLTP DQVVAIASNN GGKQALETVQ RLLPVLCQDH GLTPDQVVAI  480
ASNIGGKQAL ETVQRLLPVL CQDHGLTPDQ VVAIASNNGG KQALETVQRL LPVLCQDHGL  540
TPDQVVAIAS NGGGKQALET VQRLLPVLCQ DHGLTPDQVV AIASNGGGKQ ALETVQRLLP  600
VLCQDHGLTP DQVVAIASNG GGKQALETVQ RLLPVLCQDH GLTPDQVVAI ASHDGGKQAL  660
ETVQRLLPVL CQDHGLTPDQ VVAIASNIGG KQALETVQRL LPVLCQDHGL TPDQVVAIAS  720
HDGGKQALET VQRLLPVLCQ DHGLTPDQVV AIASHDGGKQ ALESIVAQLS RPDPALAALT  780
NDHLVALACL GGRPALDAVK KGLPHAPALI KRTNRRIPER TSHRVAGSGG G           831

SEQ ID NO: 44          moltype = DNA  length = 19
FEATURE                Location/Qualifiers
source                 1..19
                       mol_type = other DNA
                       note = BCL11A gene binding site
                       organism = synthetic construct
SEQUENCE: 44
tagtcatccc cacaatagt                                                19

SEQ ID NO: 45          moltype = AA  length = 831
FEATURE                Location/Qualifiers
source                 1..831
                       mol_type = protein
                       note = TALE domain BCL11A #5
                       organism = synthetic construct
SEQUENCE: 45
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNIGG  180
KQALETVQRL LPVLCQDHGL TPDQVVAIAS HDGGKQALET VQRLLPVLCQ DHGLTPDQVV  240
AIASNIGGKQ ALETVQRLLP VLCQDHGLTP DQVVAIASNN GGKQALETVQ RLLPVLCQDH  300
GLTPDQVVAI ASNGGGKQAL ETVQRLLPVL CQDHGLTPDQ VVAIASNGGG KQALETVQRL  360
LPVLCQDHGL TPDQVVAIAS NNGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASHDGGKQAL ETVQRLLPVL CQDHGLTPDQ VVAIASNGGG KQALETVQRL LPVLCQDHGL  540
TPDQVVAIAS NNGGKQALET VQRLLPVLCQ DHGLTPDQVV AIASHDGGKQ ALETVQRLLP  600
VLCQDHGLTP DQVVAIASNI GGKQALETVQ RLLPVLCQDH GLTPDQVVAI ASNIGGKQAL  660
ETVQRLLPVL CQDHGLTPDQ VVAIASNIGG KQALETVQRL LPVLCQDHGL TPDQVVAIAS  720
NIGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 46          moltype = DNA  length = 19
FEATURE                Location/Qualifiers
source                 1..19
                       mol_type = other DNA
                       note = BCL11A gene binding site
                       organism = synthetic construct
SEQUENCE: 46
tcccgctgcc ttttgtgcc                                                19

SEQ ID NO: 47          moltype = AA  length = 831
FEATURE                Location/Qualifiers
source                 1..831
                       mol_type = protein
                       note = TALE domain BCL11A #6
                       organism = synthetic construct
SEQUENCE: 47
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASNNGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASHDGG KQALETVQRL  360
LPVLCQDHGL TPDQVVAIAS NGGGKQALET VQRLLPVLCQ DHGLTPDQVV AIASNNGGKQ  420
ALETVQRLLP VLCQDHGLTP DQVVAIASNN GGKQALETVQ RLLPVLCQDH GLTPDQVVAI  480
ASNNGGKQAL ETVQRLLPVL CQDHGLTPDQ VVAIASNGGG KQALETVQRL LPVLCQDHGL  540
TPDQVVAIAS NIGGKQALET VQRLLPVLCQ DHGLTPDQVV AIASHDGGKQ ALETVQRLLP  600
VLCQDHGLTP DQVVAIASNG GGKQALETVQ RLLPVLCQDH GLTPDQVVAI ASNGGGKQAL  660
ETVQRLLPVL CQDHGLTPDQ VVAIASNGGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 48          moltype = DNA  length = 19
FEATURE                Location/Qualifiers
source                 1..19
                       mol_type = other DNA
                       note = BCL11A gene binding site
```

```
                         organism = synthetic construct
SEQUENCE: 48
tcctcgcgct tgccctccc                                            19

SEQ ID NO: 49            moltype = AA  length = 831
FEATURE                  Location/Qualifiers
source                   1..831
                         mol_type = protein
                         note = TALE domain BCL11A #7
                         organism = synthetic construct
SEQUENCE: 49
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS NGGGKQALET VQRLLPVLCQ DHGLTPDQVV  240
AIASHDGGKQ ALETVQRLLP VLCQDHGLTP DQVVAIASNG GGKQALETVQ RLLPVLCQDH  300
GLTPDQVVAI ASNGGGKQAL ETVQRLLPVL CQDHGLTPDQ VVAIASNNGG KQALETVQRL  360
LPVLCQDHGL TPDQVVAIAS NGGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASNIGGKQAL ETVQRLLPVL CQDHGLTPDQ VVAIASHDGG KQALETVQRL LPVLCQDHGL  540
TPDQVVAIAS NIGGKQALET VQRLLPVLCQ DHGLTPDQVV AIASNHGGKQ ALETVQRLLP  600
VLCQDHGLTP DQVVAIASHD GGKQALETVQ RLLPVLCQDH GLTPDQVVAI ASNGGGKQAL  660
ETVQRLLPVL CQDHGLTPDQ VVAIASHDGG KQALETVQRL LPVLCQDHGL TPDQVVAIAS  720
NNGGKQALET VQRLLPVLCQ DHGLTPDQVV AIASNNGGKQ ALESIVAQLS RPDPALAALT  780
NDHLVALACL GGRPALDAVK KGLPHAPALI KRTNRRIPER TSHRVAGSGG G           831

SEQ ID NO: 50            moltype = DNA  length = 19
FEATURE                  Location/Qualifiers
source                   1..19
                         mol_type = other DNA
                         note = BCL11A gene binding site
                         organism = synthetic construct
SEQUENCE: 50
tcccccggcc ctagctcct                                            19

SEQ ID NO: 51            moltype = AA  length = 831
FEATURE                  Location/Qualifiers
source                   1..831
                         mol_type = protein
                         note = TALE domain BCL11A #8
                         organism = synthetic construct
SEQUENCE: 51
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS NGGGKQALET VQRLLPVLCQ DHGLTPDQVV  240
AIASHDGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASNNGG KQALETVQRL  360
LPVLCQDHGL TPDQVVAIAS HDGGKQALET VQRLLPVLCQ DHGLTPDQVV AIASNGGGKQ  420
ALETVQRLLP VLCQDHGLTP DQVVAIASNN GGKQALETVQ RLLPVLCQDH GLTPDQVVAI  480
ASNIGGKQAL ETVQRLLPVL CQDHGLTPDQ VVAIASHDGG KQALETVQRL LPVLCQDHGL  540
TPDQVVAIAS NGGGKQALET VQRLLPVLCQ DHGLTPDQVV AIASNHGGKQ ALETVQRLLP  600
VLCQDHGLTP DQVVAIASHD GGKQALETVQ RLLPVLCQDH GLTPDQVVAI ASNHGGKQAL  660
ETVQRLLPVL CQDHGLTPDQ VVAIASHDGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 52            moltype = DNA  length = 19
FEATURE                  Location/Qualifiers
source                   1..19
                         mol_type = other DNA
                         note = BCL11A gene binding site
                         organism = synthetic construct
SEQUENCE: 52
tcctggtccg cccccagca                                            19

SEQ ID NO: 53            moltype = AA  length = 831
FEATURE                  Location/Qualifiers
source                   1..831
                         mol_type = protein
                         note = TALE domain BCL11A #9
                         organism = synthetic construct
SEQUENCE: 53
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASHDGGKQ ALETVQRLLP VLCQDHGLTP DQVVAIASNG GGKQALETVQ RLLPVLCQDH  300
GLTPDQVVAI ASNGGGKQAL ETVQRLLPVL CQDHGLTPDQ VVAIASNNGG KQALETVQRL  360
```

```
LPVLCQDHGL TPDQVVAIAS HDGGKQALET VQRLLPVLCQ DHGLTPDQVV AIASNGGGKQ  420
ALETVQRLLP VLCQDHGLTP DQVVAIASNN GGKQALETVQ RLLPVLCQDH GLTPDQVVAI  480
ASHDGGKQAL ETVQRLLPVL CQDHGLTPDQ VVAIASHDGG KQALETVQRL LPVLCQDHGL  540
TPDQVVAIAS NIGGKQALET VQRLLPVLCQ DHGLTPDQVV AIASNIGGKQ ALETVQRLLP  600
VLCQDHGLTP DQVVAIASNI GGKQALETVQ RLLPVLCQDH GLTPDQVVAI ASHDGGKQAL  660
ETVQRLLPVL CQDHGLTPDQ VVAIASNGGG KQALETVQRL LPVLCQDHGL TPDQVVAIAS  720
NGGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 54          moltype = DNA  length = 19
FEATURE                Location/Qualifiers
source                 1..19
                       mol_type = other DNA
                       note = BCL11A gene binding site
                       organism = synthetic construct
SEQUENCE: 54
tgccgagacc tcttctcga                                               19

SEQ ID NO: 55          moltype = AA  length = 831
FEATURE                Location/Qualifiers
source                 1..831
                       mol_type = protein
                       note = TALE domain BCL11A #10
                       organism = synthetic construct
SEQUENCE: 55
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNNGG  180
KQALETVKRL LPVLCQDHGL TPDQVVAIAS NNGGKQALET VQRLLPVLCQ DHGLTPDQVV  240
AIASNNGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASHDGG KQALETVQRL  360
LPVLCQDHGL TPDQVVAIAS NGGGKQALET VQRLLPVLCQ DHGLTPDQVV AIASHDGGKQ  420
ALETVQRLLP VLCQDHGLTP DQVVAIASNI GGKQALETVQ RLLPVLCQDH GLTPDQVVAI  480
ASHDGGKQAL ETVQRLLPVL CQDHGLTPDQ VVAIASNNGG KQALETVQRL LPVLCQDHGL  540
TPDQVVAIAS HDGGKQALET VQRLLPVLCQ DHGLTPDQVV AIASHDGGKQ ALETVQRLLP  600
VLCQDHGLTP DQVVAIASNG GGKQALETVQ RLLPVLCQDH GLTPDQVVAI ASNGGGKQAL  660
ETVQRLLPVL CQDHGLTPDQ VVAIASNGGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 56          moltype = DNA  length = 19
FEATURE                Location/Qualifiers
source                 1..19
                       mol_type = other DNA
                       note = BCL11A gene binding site
                       organism = synthetic construct
SEQUENCE: 56
tcggctttgc aaagcattt                                               19

SEQ ID NO: 57          moltype = AA  length = 831
FEATURE                Location/Qualifiers
source                 1..831
                       mol_type = protein
                       note = TALE domain BCL11A #11
                       organism = synthetic construct
SEQUENCE: 57
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS NGGGKQALET VQRLLPVLCQ DHGLTPDQVV  240
AIASHDGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASHDGG KQALETVQRL  360
LPVLCQDHGL TPDQVVAIAS NNGGKQALET VQRLLPVLCQ DHGLTPDQVV AIASNNGGKQ  420
ALETVQRLLP VLCQDHGLTP DQVVAIASNN GGKQALETVQ RLLPVLCQDH GLTPDQVVAI  480
ASNIGGKQAL ETVQRLLPVL CQDHGLTPDQ VVAIASNIGG KQALETVQRL LPVLCQDHGL  540
TPDQVVAIAS NGGGKQALET VQRLLPVLCQ DHGLTPDQVV AIASHDGGKQ ALETVQRLLP  600
VLCQDHGLTP DQVVAIASNN GGKQALETVQ RLLPVLCQDH GLTPDQVVAI ASNGGGKQAL  660
ETVQRLLPVL CQDHGLTPDQ VVAIASNGGG KQALETVQRL LPVLCQDHGL TPDQVVAIAS  720
NGGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 58          moltype = DNA  length = 19
FEATURE                Location/Qualifiers
source                 1..19
                       mol_type = other DNA
                       note = BCL11A gene binding site
                       organism = synthetic construct
SEQUENCE: 58
tgcaaagccg agtttcacc                                               19
```

```
SEQ ID NO: 59          moltype = AA  length = 831
FEATURE                Location/Qualifiers
source                 1..831
                       mol_type = protein
                       note = TALE domain BCL11A #12
                       organism = synthetic construct
SEQUENCE: 59
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASNIGGKQ ALETVQRLLP VLCQDHGLTP DQVVAIASNI GGKQALETVQ RLLPVLCQDH  300
GLTPDQVVAI ASNIGGKQAL ETVQRLLPVL CQDHGLTPDQ VVAIASNIGG KQALETVQRL  360
LPVLCQDHGL TPDQVVAIAS NHGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASNIGGKQAL ETVQRLLPVL CQDHGLTPDQ VVAIASNNGG KQALETVQRL LPVLCQDHGL  540
TPDQVVAIAS NGGGKQALET VQRLLPVLCQ DHGLTPDQVV AIASHDGGKQ ALETVQRLLP  600
VLCQDHGLTP DQVVAIASNG GGKQALETVQ RLLPVLCQDH GLTPDQVVAI ASHDGGKQAL  660
ETVQRLLPVL CQDHGLTPDQ VVAIASNIGG KQALETVQRL LPVLCQDHGL TPDQVVAIAS  720
HDGGKQALET VQRLLPVLCQ DHGLTPDQVV AIASHDGGKQ ALESIVAQLS RPDPALAALT  780
NDHLVALACL GGRPALDAVK KGLPHAPALI KRTNRRIPER TSHRVAGSGG G           831

SEQ ID NO: 60          moltype = DNA  length = 19
FEATURE                Location/Qualifiers
source                 1..19
                       mol_type = other DNA
                       note = BCL11A gene binding site
                       organism = synthetic construct
SEQUENCE: 60
tacagttgcc ctgcaaaat                                               19

SEQ ID NO: 61          moltype = AA  length = 831
FEATURE                Location/Qualifiers
source                 1..831
                       mol_type = protein
                       note = TALE domain BCL11A #13
                       organism = synthetic construct
SEQUENCE: 61
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASNGGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASHDGG KQALETVQRL  360
LPVLCQDHGL TPDQVVAIAS NNGGKQALET VQRLLPVLCQ DHGLTPDQVV AIASHDGGKQ  420
ALETVQRLLP VLCQDHGLTP DQVVAIASNG GGKQALETVQ RLLPVLCQDH GLTPDQVVAI  480
ASNNGGKQAL ETVQRLLPVL CQDHGLTPDQ VVAIASHDGG KQALETVQRL LPVLCQDHGL  540
TPDQVVAIAS NIGGKQALET VQRLLPVLCQ DHGLTPDQVV AIASHDGGKQ ALETVQRLLP  600
VLCQDHGLTP DQVVAIASNI GGKQALETVQ RLLPVLCQDH GLTPDQVVAI ASHDGGKQAL  660
ETVQRLLPVL CQDHGLTPDQ VVAIASNGGG KQALETVQRL LPVLCQDHGL TPDQVVAIAS  720
NGGGKQALET VQRLLPVLCQ DHGLTPDQVV AIASNNGGKQ ALESIVAQLS RPDPALAALT  780
NDHLVALACL GGRPALDAVK KGLPHAPALI KRTNRRIPER TSHRVAGSGG G           831

SEQ ID NO: 62          moltype = DNA  length = 19
FEATURE                Location/Qualifiers
source                 1..19
                       mol_type = other DNA
                       note = BCL11A gene binding site
                       organism = synthetic construct
SEQUENCE: 62
tccgccctgg gtactttct                                               19

SEQ ID NO: 63          moltype = AA  length = 831
FEATURE                Location/Qualifiers
source                 1..831
                       mol_type = protein
                       note = TALE domain BCL11A #14
                       organism = synthetic construct
SEQUENCE: 63
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNIGG  180
KQALETVQRL LPVLCQDHGL TPDQVVAIAS NNGGKQALET VQRLLPVLCQ DHGLTPDQVV  240
AIASNGGGKQ ALETVQRLLP VLCQDHGLTP DQVVAIASHD GGKQALETVQ RLLPVLCQDH  300
GLTPDQVVAI ASNIGGKQAL ETVQRLLPVL CQDHGLTPDQ VVAIASNGGG KQALETVQRL  360
LPVLCQDHGL TPDQVVAIAS HDGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASHDGGKQAL ETVQRLLPVL CQDHGLTPDQ VVAIASNIGG KQALETVQRL LPVLCQDHGL  540
```

```
TPDQVVAIAS HDGGKQALET VQRLLPVLCQ DHGLTPDQVV AIASNIGGKQ ALETVQRLLP  600
VLCQDHGLTP DQVVAIASNI GGKQALETVQ RLLPVLCQDH GLTPDQVVAI ASNGGGKQAL  660
ETVQRLLPVL CQDHGLTPDQ VVAIASNIGG KQALETVQRL LPVLCQDHGL TPDQVVAIAS  720
NNGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 64          moltype = DNA  length = 19
FEATURE                Location/Qualifiers
source                 1..19
                       mol_type = other DNA
                       note = BCL11A gene binding site
                       organism = synthetic construct
SEQUENCE: 64
tctcttgtcc acagctcgg                                               19

SEQ ID NO: 65          moltype = AA  length = 831
FEATURE                Location/Qualifiers
source                 1..831
                       mol_type = protein
                       note = TALE domain BCL11A #15
                       organism = synthetic construct
SEQUENCE: 65
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASHDGGKQ ALETVQRLLP VLCQDHGLTP DQVVAIASNN GGKQALETVQ RLLPVLCQDH  300
GLTPDQVVAI ASHDGGKQAL ETVQRLLPVL CQDHGLTPDQ VVAIASNGGG KQALETVQRL  360
LPVLCQDHGL TPDQVVAIAS NNGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASNGGGKQAL ETVQRLLPVL CQDHGLTPDQ VVAIASNGGG KQALETVQRL LPVLCQDHGL  540
TPDQVVAIAS NGGGKQALET VQRLLPVLCQ DHGLTPDQVV AIASNGGGKQ ALETVQRLLP  600
VLCQDHGLTP DQVVAIASNN GGKQALETVQ RLLPVLCQDH GLTPDQVVAI ASNGGGKQAL  660
ETVQRLLPVL CQDHGLTPDQ VVAIASNNGG KQALETVQRL LPVLCQDHGL TPDQVVAIAS  720
HDGGKQALET VQRLLPVLCQ DHGLTPDQVV AIASHDGGKQ ALESIVAQLS RPDPALAALT  780
NDHLVALACL GGRPALDAVK KGLPHAPALI KRTNRRIPER TSHRVAGSGG G           831

SEQ ID NO: 66          moltype = DNA  length = 19
FEATURE                Location/Qualifiers
source                 1..19
                       mol_type = other DNA
                       note = BCL11A gene binding site
                       organism = synthetic construct
SEQUENCE: 66
tctcccgctg actgcgcct                                               19

SEQ ID NO: 67          moltype = AA  length = 831
FEATURE                Location/Qualifiers
source                 1..831
                       mol_type = protein
                       note = TALE domain BCL11A #16
                       organism = synthetic construct
SEQUENCE: 67
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASNGGGKQ ALETVQRLLP VLCQDHGLTP DQVVAIASHD GGKQALETVQ RLLPVLCQDH  300
GLTPDQVVAI ASNNGGKQAL ETVQRLLPVL CQDHGLTPDQ VVAIASHDGG KQALETVQRL  360
LPVLCQDHGL TPDQVVAIAS NNGGKQALET VQRLLPVLCQ DHGLTPDQVV AIASHDGGKQ  420
ALETVQRLLP VLCQDHGLTP DQVVAIASNG GGKQALETVQ RLLPVLCQDH GLTPDQVVAI  480
ASNGGGKQAL ETVQRLLPVL CQDHGLTPDQ VVAIASNNGG KQALETVQRL LPVLCQDHGL  540
TPDQVVAIAS HDGGKQALET VQRLLPVLCQ DHGLTPDQVV AIASHDGGKQ ALETVQRLLP  600
VLCQDHGLTP DQVVAIASHD GGKQALETVQ RLLPVLCQDH GLTPDQVVAI ASNGGGKQAL  660
ETVQRLLPVL CQDHGLTPDQ VVAIASHDGG KQALETVQRL LPVLCQDHGL TPDQVVAIAS  720
HDGGKQALET VQRLLPVLCQ DHGLTPDQVV AIASHDGGKQ ALESIVAQLS RPDPALAALT  780
NDHLVALACL GGRPALDAVK KGLPHAPALI KRTNRRIPER TSHRVAGSGG G           831

SEQ ID NO: 68          moltype = DNA  length = 19
FEATURE                Location/Qualifiers
source                 1..19
                       mol_type = other DNA
                       note = BCL11A gene binding site
                       organism = synthetic construct
SEQUENCE: 68
tcccttgctg ccaaacttt                                               19

SEQ ID NO: 69          moltype = AA  length = 831
FEATURE                Location/Qualifiers
```

```
source                  1..831
                        mol_type = protein
                        note = TALE domain BCL11A #17
                        organism = synthetic construct
SEQUENCE: 69
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASHDGG  180
KQALETVQRL LPVLCQDHGL TPDQVVAIAS HDGGKQALET VQRLLPVLCQ DHGLTPDQVV  240
AIASHDGGKQ ALETVQRLLP VLCQDHGLTP DQVVAIASHD GGKQALETVQ RLLPVLCQDH  300
GLTPDQVVAI ASHDGGKQAL ETVQRLLPVL CQDHGLTPDQ VVAIASNNGG KQALETVQRL  360
LPVLCQDHGL TPDQVVAIAS NNGGKQALET VQRLLPVLCQ DHGLTPDQVV AIASHDGGKQ  420
ALETVQRLLP VLCQDHGLTP DQVVAIASHD GGKQALETVQ RLLPVLCQDH GLTPDQVVAI  480
ASHDGGKQAL ETVQRLLPVL CQDHGLTPDQ VVAIASNGGG KQALETVQRL LPVLCQDHGL  540
TPDQVVAIAS NIGGKQALET VQRLLPVLCQ DHGLTPDQVV AIASNNGGKQ ALETVQRLLP  600
VLCQDHGLTP DQVVAIASHD GGKQALETVQ RLLPVLCQDH GLTPDQVVAI ASNGGGKQAL  660
ETVQRLLPVL CQDHGLTPDQ VVAIASHDGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 70           moltype = DNA  length = 19
FEATURE                 Location/Qualifiers
source                  1..19
                        mol_type = other DNA
                        note = BCL11A gene binding site
                        organism = synthetic construct
SEQUENCE: 70
tgggccctca cgcctttct                                               19

SEQ ID NO: 71           moltype = RNA  length = 20
FEATURE                 Location/Qualifiers
source                  1..20
                        mol_type = other RNA
                        note = gRNA #1 against CpG 105, BCL11A gene
                        organism = synthetic construct
SEQUENCE: 71
gcctttctgc agacgttccc                                              20

SEQ ID NO: 72           moltype = RNA  length = 20
FEATURE                 Location/Qualifiers
source                  1..20
                        mol_type = other RNA
                        note = gRNA #2 against CpG 105, BCL11A gene
                        organism = synthetic construct
SEQUENCE: 72
tgggtgtgcg ccttggccgg                                              20

SEQ ID NO: 73           moltype = RNA  length = 20
FEATURE                 Location/Qualifiers
source                  1..20
                        mol_type = other RNA
                        note = gRNA #3 against CpG 105, BCL11A gene
                        organism = synthetic construct
SEQUENCE: 73
cggtggtgag atgaccgcct                                              20

SEQ ID NO: 74           moltype = RNA  length = 20
FEATURE                 Location/Qualifiers
source                  1..20
                        mol_type = other RNA
                        note = gRNA #4 against CpG 105, BCL11A gene
                        organism = synthetic construct
SEQUENCE: 74
ggaatgtgct cacggcgccg                                              20

SEQ ID NO: 75           moltype = RNA  length = 20
FEATURE                 Location/Qualifiers
source                  1..20
                        mol_type = other RNA
                        note = gRNA #5 against CpG 105, BCL11A gene
                        organism = synthetic construct
SEQUENCE: 75
gactgcccgc gctttgtcct                                              20

SEQ ID NO: 76           moltype = RNA  length = 20
FEATURE                 Location/Qualifiers
source                  1..20
                        mol_type = other RNA
                        note = gRNA #6 against CpG 105, BCL11A gene
```

```
                        organism = synthetic construct
SEQUENCE: 76
ccagagtctg gcccccggag                                            20

SEQ ID NO: 77           moltype = RNA  length = 20
FEATURE                 Location/Qualifiers
source                  1..20
                        mol_type = other RNA
                        note = gRNA #7 against CpG 105, BCL11A gene
                        organism = synthetic construct
SEQUENCE: 77
tctgcgaccc ttaggagccg                                            20

SEQ ID NO: 78           moltype = RNA  length = 20
FEATURE                 Location/Qualifiers
source                  1..20
                        mol_type = other RNA
                        note = gRNA #8 against CpG 105, BCL11A gene
                        organism = synthetic construct
SEQUENCE: 78
gagcgccccg ccaagcgact                                            20

SEQ ID NO: 79           moltype = RNA  length = 20
FEATURE                 Location/Qualifiers
source                  1..20
                        mol_type = other RNA
                        note = gRNA #9 against CpG 105, BCL11A gene
                        organism = synthetic construct
SEQUENCE: 79
caagtctcca ggagcccgcg                                            20

SEQ ID NO: 80           moltype = RNA  length = 20
FEATURE                 Location/Qualifiers
source                  1..20
                        mol_type = other RNA
                        note = gRNA #10 against CpG 105, BCL11A gene
                        organism = synthetic construct
SEQUENCE: 80
cgcggaatcc agcctaagtt                                            20

SEQ ID NO: 81           moltype = RNA  length = 20
FEATURE                 Location/Qualifiers
source                  1..20
                        mol_type = other RNA
                        note = gRNA #11 against CpG 105, BCL11A gene
                        organism = synthetic construct
SEQUENCE: 81
cccgctgcgg agctgtaact                                            20

SEQ ID NO: 82           moltype = RNA  length = 20
FEATURE                 Location/Qualifiers
source                  1..20
                        mol_type = other RNA
                        note = gRNA #1 against CpG 31, BCL11A gene
                        organism = synthetic construct
SEQUENCE: 82
cgctcctgag tccgcggagt                                            20

SEQ ID NO: 83           moltype = RNA  length = 20
FEATURE                 Location/Qualifiers
source                  1..20
                        mol_type = other RNA
                        note = gRNA #2 against CpG 31, BCL11A gene
                        organism = synthetic construct
SEQUENCE: 83
cacggctctc cccgtcgccg                                            20

SEQ ID NO: 84           moltype = RNA  length = 20
FEATURE                 Location/Qualifiers
source                  1..20
                        mol_type = other RNA
                        note = gRNA #3 against CpG 31, BCL11A gene
                        organism = synthetic construct
SEQUENCE: 84
ccgcctttg ttccggccag                                             20

SEQ ID NO: 85           moltype = RNA  length = 20
FEATURE                 Location/Qualifiers
source                  1..20
```

```
                        mol_type = other RNA
                        note = gRNA #4 against CpG 31, BCL11A gene
                        organism = synthetic construct
SEQUENCE: 85
gcgcgaggag ccggcacaaa                                                20

SEQ ID NO: 86           moltype = RNA  length = 20
FEATURE                 Location/Qualifiers
source                  1..20
                        mol_type = other RNA
                        note = gRNA #5 against CpG 31, BCL11A gene
                        organism = synthetic construct
SEQUENCE: 86
gccactttct cactattgtg                                                20

SEQ ID NO: 87           moltype = RNA  length = 20
FEATURE                 Location/Qualifiers
source                  1..20
                        mol_type = other RNA
                        note = gRNA #6 against CpG 31, BCL11A gene
                        organism = synthetic construct
SEQUENCE: 87
gctgcctctg aggttcggtc                                                20

SEQ ID NO: 88           moltype = RNA  length = 20
FEATURE                 Location/Qualifiers
source                  1..20
                        mol_type = other RNA
                        note = gRNA #7 against CpG 31, BCL11A gene
                        organism = synthetic construct
SEQUENCE: 88
aagggcagga gctagggccg                                                20

SEQ ID NO: 89           moltype = RNA  length = 20
FEATURE                 Location/Qualifiers
source                  1..20
                        mol_type = other RNA
                        note = gRNA #8 against CpG 31, BCL11A gene
                        organism = synthetic construct
SEQUENCE: 89
gagcccggac tgctgcctcc                                                20

SEQ ID NO: 90           moltype = RNA  length = 20
FEATURE                 Location/Qualifiers
source                  1..20
                        mol_type = other RNA
                        note = gRNA #1 against CpG 38, BCL11A gene
                        organism = synthetic construct
SEQUENCE: 90
gtttacaagc accgcgtgtg                                                20

SEQ ID NO: 91           moltype = RNA  length = 20
FEATURE                 Location/Qualifiers
source                  1..20
                        mol_type = other RNA
                        note = gRNA #2 against CpG 38, BCL11A gene
                        organism = synthetic construct
SEQUENCE: 91
aacagacaga ggaccgagcg                                                20

SEQ ID NO: 92           moltype = RNA  length = 20
FEATURE                 Location/Qualifiers
source                  1..20
                        mol_type = other RNA
                        note = gRNA #3 against CpG 38, BCL11A gene
                        organism = synthetic construct
SEQUENCE: 92
ggcgccgggt gggcgatccg                                                20

SEQ ID NO: 93           moltype = RNA  length = 20
FEATURE                 Location/Qualifiers
source                  1..20
                        mol_type = other RNA
                        note = gRNA #4 against CpG 38, BCL11A gene
                        organism = synthetic construct
SEQUENCE: 93
ggtcgggcaa ggcccgggcg                                                20

SEQ ID NO: 94           moltype = RNA  length = 20
```

```
FEATURE                 Location/Qualifiers
source                  1..20
                        mol_type = other RNA
                        note = gRNA #5 against CpG 38, BCL11A gene
                        organism = synthetic construct
SEQUENCE: 94
aagaggtctc ggcattgtgc                                                20

SEQ ID NO: 95           moltype = RNA  length = 22
FEATURE                 Location/Qualifiers
source                  1..22
                        mol_type = other RNA
                        note = gRNA #6 against CpG 38, BCL11A gene
                        organism = synthetic construct
SEQUENCE: 95
gttccacagc ttcgggaccg cg                                             22

SEQ ID NO: 96           moltype = RNA  length = 20
FEATURE                 Location/Qualifiers
source                  1..20
                        mol_type = other RNA
                        note = gRNA #7 against CpG 38, BCL11A gene
                        organism = synthetic construct
SEQUENCE: 96
gaaatcggct gggtgaaact                                                20

SEQ ID NO: 97           moltype = RNA  length = 20
FEATURE                 Location/Qualifiers
source                  1..20
                        mol_type = other RNA
                        note = gRNA #8 against CpG 38, BCL11A gene
                        organism = synthetic construct
SEQUENCE: 97
gcagtgtctc cgcgccagcc                                                20

SEQ ID NO: 98           moltype = RNA  length = 23
FEATURE                 Location/Qualifiers
source                  1..23
                        mol_type = other RNA
                        note = gRNA #9 against CpG 38, BCL11A gene
                        organism = synthetic construct
SEQUENCE: 98
cctcccctcc cctccgccct ggg                                            23

SEQ ID NO: 99           moltype = RNA  length = 23
FEATURE                 Location/Qualifiers
source                  1..23
                        mol_type = other RNA
                        note = gRNA #1 against CpG 115, BCL11A gene
                        organism = synthetic construct
SEQUENCE: 99
tcctcctgtc ccggggttaa agg                                            23

SEQ ID NO: 100          moltype = RNA  length = 25
FEATURE                 Location/Qualifiers
source                  1..25
                        mol_type = other RNA
                        note = gRNA #2 against CpG 115, BCL11A gene
                        organism = synthetic construct
SEQUENCE: 100
catcttttgg gacactctag gctgg                                          25

SEQ ID NO: 101          moltype = RNA  length = 23
FEATURE                 Location/Qualifiers
source                  1..23
                        mol_type = other RNA
                        note = gRNA #3 against CpG 115, BCL11A gene
                        organism = synthetic construct
SEQUENCE: 101
aagtcaggcc cttcttcgga agg                                            23

SEQ ID NO: 102          moltype = RNA  length = 23
FEATURE                 Location/Qualifiers
source                  1..23
                        mol_type = other RNA
                        note = gRNA #4 against CpG 115, BCL11A gene
                        organism = synthetic construct
SEQUENCE: 102
gcagcctgga ctgcgcgccc cgg                                            23
```

```
SEQ ID NO: 103          moltype = RNA  length = 20
FEATURE                 Location/Qualifiers
source                  1..20
                        mol_type = other RNA
                        note = gRNA #5 against CpG 115, BCL11A gene
                        organism = synthetic construct
SEQUENCE: 103
tgcccggcga ttctcgtccg                                                20

SEQ ID NO: 104          moltype = RNA  length = 20
FEATURE                 Location/Qualifiers
source                  1..20
                        mol_type = other RNA
                        note = gRNA #6 against CpG 115, BCL11A gene
                        organism = synthetic construct
SEQUENCE: 104
tgagccattc ggtcgctagg                                                20

SEQ ID NO: 105          moltype = RNA  length = 20
FEATURE                 Location/Qualifiers
source                  1..20
                        mol_type = other RNA
                        note = gRNA #7 against CpG 115, BCL11A gene
                        organism = synthetic construct
SEQUENCE: 105
ggtggtactg aggaccggga                                                20

SEQ ID NO: 106          moltype = RNA  length = 20
FEATURE                 Location/Qualifiers
source                  1..20
                        mol_type = other RNA
                        note = gRNA #1 for IFNAR1 gene
                        organism = synthetic construct
SEQUENCE: 106
aggaacggcg cgtgcgcgga                                                20

SEQ ID NO: 107          moltype = RNA  length = 20
FEATURE                 Location/Qualifiers
source                  1..20
                        mol_type = other RNA
                        note = gRNA #8 against CpG 115, BCL11A gene
                        organism = synthetic construct
SEQUENCE: 107
attttctggg tgctcagagg                                                20

SEQ ID NO: 108          moltype = RNA  length = 20
FEATURE                 Location/Qualifiers
source                  1..20
                        mol_type = other RNA
                        note = gRNA #9 against CpG 115, BCL11A gene
                        organism = synthetic construct
SEQUENCE: 108
tggtctcagc tcgcgcacgg                                                20

SEQ ID NO: 109          moltype = RNA  length = 20
FEATURE                 Location/Qualifiers
source                  1..20
                        mol_type = other RNA
                        note = gRNA #10 against CpG 115, BCL11A gene
                        organism = synthetic construct
SEQUENCE: 109
tggtctcagc tcgcgcacgg                                                20

SEQ ID NO: 110          moltype = DNA  length = 23
FEATURE                 Location/Qualifiers
source                  1..23
                        mol_type = other DNA
                        note = sequence of gRNA targeting exon 3
                        organism = synthetic construct
SEQUENCE: 110
ggagctctaa tccccacgcc tgg                                            23

SEQ ID NO: 111          moltype = DNA  length = 23
FEATURE                 Location/Qualifiers
source                  1..23
                        mol_type = other DNA
                        note = sequence of gRNA for B2M
                        organism = synthetic construct
```

```
SEQUENCE: 111
aggctactag ccccatcaag agg                                         23

SEQ ID NO: 112          moltype = DNA  length = 23
FEATURE                 Location/Qualifiers
source                  1..23
                        mol_type = other DNA
                        note = Primer BIS B2M #1 F
                        organism = synthetic construct
SEQUENCE: 112
gttgtgtttt ttggggaagt tag                                         23

SEQ ID NO: 113          moltype = DNA  length = 22
FEATURE                 Location/Qualifiers
source                  1..22
                        mol_type = other DNA
                        note = Primer BIS B2M #1 R
                        organism = synthetic construct
SEQUENCE: 113
aaaattcctc cctatatcct ta                                          22

SEQ ID NO: 114          moltype = DNA  length = 27
FEATURE                 Location/Qualifiers
source                  1..27
                        mol_type = other DNA
                        note = Primer BIS B2M #2 F
                        organism = synthetic construct
SEQUENCE: 114
aagaatggag aaattttgta gggaatt                                     27

SEQ ID NO: 115          moltype = DNA  length = 25
FEATURE                 Location/Qualifiers
source                  1..25
                        mol_type = other DNA
                        note = Primer BIS B2M #2 R
                        organism = synthetic construct
SEQUENCE: 115
accaccaaaa aaaacttaaa aaaaa                                       25

SEQ ID NO: 116          moltype = DNA  length = 25
FEATURE                 Location/Qualifiers
source                  1..25
                        mol_type = other DNA
                        note = Primer BIS B2M #3 F
                        organism = synthetic construct
SEQUENCE: 116
tttttttggt ttggaggtta tttag                                       25

SEQ ID NO: 117          moltype = DNA  length = 25
FEATURE                 Location/Qualifiers
source                  1..25
                        mol_type = other DNA
                        note = Primer BIS B2M #3 R
                        organism = synthetic construct
SEQUENCE: 117
caaaacacat aaaatcctta acaca                                       25

SEQ ID NO: 118          moltype = DNA  length = 25
FEATURE                 Location/Qualifiers
source                  1..25
                        mol_type = other DNA
                        note = Primer BIS B2M #4 F
                        organism = synthetic construct
SEQUENCE: 118
ttttagattg gagagttgtg gattt                                       25

SEQ ID NO: 119          moltype = DNA  length = 25
FEATURE                 Location/Qualifiers
source                  1..25
                        mol_type = other DNA
                        note = Primer BIS B2M #4 R
                        organism = synthetic construct
SEQUENCE: 119
aattttacaa ctcccctaac taaca                                       25

SEQ ID NO: 120          moltype = DNA  length = 23
FEATURE                 Location/Qualifiers
source                  1..23
                        mol_type = other DNA
```

```
                      note = Primer B2M -241 F
                      organism = synthetic construct
SEQUENCE: 120
gcaagtcact tagcatctct ggg                                   23

SEQ ID NO: 121        moltype = DNA  length = 20
FEATURE               Location/Qualifiers
source                1..20
                      mol_type = other DNA
                      note = Primer B2M -241 R
                      organism = synthetic construct
SEQUENCE: 121
ttgctgtctg tacatcggcg                                       20

SEQ ID NO: 122        moltype = DNA  length = 20
FEATURE               Location/Qualifiers
source                1..20
                      mol_type = other DNA
                      note = Primer B2M +158 F
                      organism = synthetic construct
SEQUENCE: 122
tctctcgctc cgtgacttcc                                       20

SEQ ID NO: 123        moltype = DNA  length = 21
FEATURE               Location/Qualifiers
source                1..21
                      mol_type = other DNA
                      note = Primer B2M +158 R
                      organism = synthetic construct
SEQUENCE: 123
cgcttccccg agatccagcc c                                     21

SEQ ID NO: 124        moltype = DNA  length = 20
FEATURE               Location/Qualifiers
source                1..20
                      mol_type = other DNA
                      note = Primer B2M +315 F
                      organism = synthetic construct
SEQUENCE: 124
aggggagacc tttggcctac                                       20

SEQ ID NO: 125        moltype = DNA  length = 20
FEATURE               Location/Qualifiers
source                1..20
                      mol_type = other DNA
                      note = Primer B2M +315 R
                      organism = synthetic construct
SEQUENCE: 125
ctctgacgct tatcgacgcc                                       20

SEQ ID NO: 126        moltype = DNA  length = 23
FEATURE               Location/Qualifiers
source                1..23
                      mol_type = other DNA
                      note = Primer B2M +580 F
                      organism = synthetic construct
SEQUENCE: 126
agactggaga gctgtggact tcg                                   23

SEQ ID NO: 127        moltype = DNA  length = 22
FEATURE               Location/Qualifiers
source                1..22
                      mol_type = other DNA
                      note = Primer B2M +580 R
                      organism = synthetic construct
SEQUENCE: 127
gccaagcatt ctacaaacgt cg                                    22

SEQ ID NO: 128        moltype = DNA  length = 22
FEATURE               Location/Qualifiers
source                1..22
                      mol_type = other DNA
                      note = Primer B2M +1529 F
                      organism = synthetic construct
SEQUENCE: 128
cagtcagggg agctgtaaaa cc                                    22

SEQ ID NO: 129        moltype = DNA  length = 22
FEATURE               Location/Qualifiers
```

```
source                1..22
                      mol_type = other DNA
                      note = Primer B2M +1529 R
                      organism = synthetic construct
SEQUENCE: 129
ttgccaggta cttagaaagt gc                                          22

SEQ ID NO: 130        moltype = DNA  length = 21
FEATURE               Location/Qualifiers
source                1..21
                      mol_type = other DNA
                      note = Primer B2M +3307 F
                      organism = synthetic construct
SEQUENCE: 130
ccttgggttg atccacttag g                                           21

SEQ ID NO: 131        moltype = DNA  length = 23
FEATURE               Location/Qualifiers
source                1..23
                      mol_type = other DNA
                      note = Primer B2M +3307 r
                      organism = synthetic construct
SEQUENCE: 131
tagtagagtg cctgggacat agc                                         23

SEQ ID NO: 132        moltype = DNA  length = 22
FEATURE               Location/Qualifiers
source                1..22
                      mol_type = other DNA
                      note = Primer B2M +3969 F
                      organism = synthetic construct
SEQUENCE: 132
gtgtctgggt ttcatccatc cg                                          22

SEQ ID NO: 133        moltype = DNA  length = 22
FEATURE               Location/Qualifiers
source                1..22
                      mol_type = other DNA
                      note = Primer B2M +3969 R
                      organism = synthetic construct
SEQUENCE: 133
gctgaaagac aagtctgaat gc                                          22

SEQ ID NO: 134        moltype = DNA  length = 22
FEATURE               Location/Qualifiers
source                1..22
                      mol_type = other DNA
                      note = Primer B2M +5082 F
                      organism = synthetic construct
SEQUENCE: 134
aggataaagg caggtggtta cc                                          22

SEQ ID NO: 135        moltype = DNA  length = 22
FEATURE               Location/Qualifiers
source                1..22
                      mol_type = other DNA
                      note = Primer B2M +5082 R
                      organism = synthetic construct
SEQUENCE: 135
agatgtccaa tgtggaaatg gc                                          22

SEQ ID NO: 136        moltype = DNA  length = 23
FEATURE               Location/Qualifiers
source                1..23
                      mol_type = other DNA
                      note = Primer CCR5 -305 F
                      organism = synthetic construct
SEQUENCE: 136
agtctgacta cagaggccac tgg                                         23

SEQ ID NO: 137        moltype = DNA  length = 23
FEATURE               Location/Qualifiers
source                1..23
                      mol_type = other DNA
                      note = Primer CCR5 R -255
                      organism = synthetic construct
SEQUENCE: 137
aggcaaatga gaccccaaac agc                                         23
```

```
SEQ ID NO: 138          moltype = DNA  length = 23
FEATURE                 Location/Qualifiers
source                  1..23
                        mol_type = other DNA
                        note = Primer PPP1R12C -861 F
                        organism = synthetic construct
SEQUENCE: 138
taagaaccga ggacaagtag tgc                                          23

SEQ ID NO: 139          moltype = DNA  length = 22
FEATURE                 Location/Qualifiers
source                  1..22
                        mol_type = other DNA
                        note = Primer PPP1R12C -768R
                        organism = synthetic construct
SEQUENCE: 139
tgctgggatg acgagcgtaa gc                                           22

SEQ ID NO: 140          moltype = AA  length = 149
FEATURE                 Location/Qualifiers
source                  1..149
                        mol_type = protein
                        organism = Homo sapiens
SEQUENCE: 140
NVSCKNCSIQ RGSKKHLLLA PSDVAGWGIF IKDPVQKNEF ISEYCGEIIS QDEADRRGKV  60
YDKYMCSFLF NLNNDFVVDA TRKGNKIRFA NHSVNPNCYA KVMMVNGDHR IGIFAKRAIQ  120
TGEELFFDYR YSQADALKYV GIEREMEIP                                    149

SEQ ID NO: 141          moltype = AA  length = 250
FEATURE                 Location/Qualifiers
source                  1..250
                        mol_type = protein
                        organism = Homo sapiens
SEQUENCE: 141
RLWAAHCRKI QLKKDGSSNH VYNYQPCDHP RQPCDSSCPC VIAQNFCEKF CQCSSECQNR  60
FPGCRCKAQC NTKQCPCYLA VRECDPDLCL TCGAADHWDS KNVSCKNCSI QRGSKKHLLL  120
APSDVAGWGI FIKDPVQKNE FISEYCGEII SQDEADRRGK VYDKYMCSFL FNLNNDFVVD  180
ATRKGNKIRF ANHSVNPNCY AKVMMVNGDH RIGIFAKRAI QTGEELFFDY RYSQADALKY  240
VGIEREMEIP                                                         250

SEQ ID NO: 142          moltype = AA  length = 136
FEATURE                 Location/Qualifiers
source                  1..136
                        mol_type = protein
                        organism = Homo sapiens
SEQUENCE: 142
MFPQSRHPTP HQAAGQPFKF TIPESLDRIK EEFQFLQAQY HSLKLECEKL ASEKTEMQRH  60
YVMYYEMSYG LNIEMHKQTE IAKRLNTICA QVIPFLSQEH QQQVAQAVER AKQVTMAELN  120
AIIGQQQLQA QHLSHG                                                  136

SEQ ID NO: 143          moltype = AA  length = 308
FEATURE                 Location/Qualifiers
source                  1..308
                        mol_type = protein
                        organism = Homo sapiens
SEQUENCE: 143
LNRKLRLGVG NRAIRTEKII CRDVARGYEN VPIPCVNGVD GEPCPEDYKY ISENCETSTM  60
NIDRNITHLQ HCTCVDDCSS SNCLCGQLSI RCWYDKDGRL LQEFNKIEPP LIFECNQACS  120
CWRNCKNRVV QSGIKVRLQL YRTAKMGWGV RALQTIPQGT FICEYVGELI SDAEADVRED  180
DSYLFDLDNK DGEVYCIDAR YYGNISRFIN HLCDPNIIPV RVFMLHQDLR FPRIAFFSSR  240
DIRTGEELGF DYGDRFWDIK SKYFTCQCGS EKCKHSAEAI ALEQSRLARL DPHPELLPEL  300
GSLPPVNT                                                           308

SEQ ID NO: 144          moltype = AA  length = 579
FEATURE                 Location/Qualifiers
source                  1..579
                        mol_type = protein
                        organism = Homo sapiens
SEQUENCE: 144
LEKALVIQES ERRKKLRFHP RQLYLSVKQG ELQKVILMLL DNLDPNFQSD QQSKRTPLHA  60
AAQKGSVEIC HVLLQAGANI NAVDKQQRTP LMEAVVNNHL EVARYMVQRG GCVYSKEEDG  120
STCLHHAAKI GNLEMVSLLL STGQVDVNAQ DSGGWTPIIW AAEHKHIEVI RMLLTRGADV  180
TLTDNEENIC LHWASFTGSA AIAEVLLNAR CDLHAVNYHG DTPLHIAARE SYHDCVLLFL  240
SRGANPELRN KEGDTAWDLT PERSDVWFAL QLNRKLRLGV GNRAIRTEKI ICRDVARGYE  300
NVPIPCVNGV DGEPCPEDYK YISENCETST MNIDRNITHL QHCTCVDDCS SSNCLCGQLS  360
IRCWYDKDGR LLQEFNKIEP PLIFECNQAC SCWRNCKNRV VQSGIKVRLQ LYRTAKMGWG  420
VRALQTIPQG TFICEYVGEL ISDAEADVRE DDSYLFDLDN KDGEVYCIDA RYYGNISRFI  480
NHLCDPNIIP VRVFMLHQDL RFPRIAFFSS RDIRTGEELG FDYGDRFWDI KSKYFTCQCG  540
SEKCKHSAEA IALEQSRLAR LDPHPELLPE LGSLPPVNT                         579
```

```
SEQ ID NO: 145         moltype = AA  length = 279
FEATURE                Location/Qualifiers
source                 1..279
                       mol_type = protein
                       organism = Homo sapiens
SEQUENCE: 145
MGPDRVTARE LCENDDLATS LVLDPYLGFR THKMNVSPVP PLRRQQHLRS ALETFLRQRD  60
LEAAYRALTL GGWTARYFQS RGPRQEAALK THVYRYLRAF LPESGFTILP CTRYSMETNG  120
AKIVSTRAWK KNEKLELLVG CIAELREADE GLLRAGENDF SIMYSTRKRS AQLWLGPAAF  180
INHDCKPNCK FVPADGNAAC VKVLRDIEPG DEVTCFYGEG FFGEKNEHCE CHTCERKGEG  240
AFRTRPREPA LPPRPLDKYQ LRETKRRLQQ GLDSGSRQG                         279

SEQ ID NO: 146         moltype = AA  length = 191
FEATURE                Location/Qualifiers
source                 1..191
                       mol_type = protein
                       organism = Homo sapiens
SEQUENCE: 146
MGKKTKRTAD SSSSEDEEEY VVEKVLDRRV VKGQVEYLLK WKGFSEEHNT WEPEKNLDCP  60
ELISEFMKKY KKMKEGENNK PREKSESNKR KSNFSNSADD IKSKKKREQS NDIARGFERG  120
LEPEKIIGAT DSCGDLMFLM KWKDTDEADL VLAKEANVKC PQIVIAFYEE RLTWHAYPED  180
AENKEKETAK S                                                       191

SEQ ID NO: 147         moltype = AA  length = 831
FEATURE                Location/Qualifiers
source                 1..831
                       mol_type = protein
                       note = TALE domain
                       organism = synthetic construct
SEQUENCE: 147
MGKPIPNPLL GLDSTGGMAP KKKRKVDGGV DLRTLGYSQQ QQEKIKPKVR STVAQHHEAL  60
VGHGFTHAHI VALSQHPAAL GTVAVKYQDM IAALPEATHE AIVGVGKQWS GARALEALLT  120
VAGELRGPPL QLDTGQLLKI AKRGGVTAVE AVHAWRNALT GAPLNLTPDQ VVAIASNNGG  180
KQALETVQRL LPVLCQDHGL TPDQVVAIAS HDGGKQALET VQRLLPVLCQ DHGLTPDQVV  240
AIASNGGGKQ ALETVQRLLP VLCQDHGLTP DQVVAIASHD GGKQALETVQ RLLPVLCQDH  300
GLTPDQVVAI ASNNGGKQAL ETVQRLLPVL CQDHGLTPDQ VVAIASHDGG KQALETVQRL  360
LPVLCQDHGL TPDQVVAIAS NNGGKQALET VQRLLPVLCQ DHGLTPDQVV AIASHDGGKQ  420
ALETVQRLLP VLCQDHGLTP DQVVAIASNG GGKQALETVQ RLLPVLCQDH GLTPDQVVAI  480
ASNIGGKQAL ETVQRLLPVL CQDHGLTPDQ VVAIASHDGG KQALETVQRL LPVLCQDHGL  540
TPDQVVAIAS NGGGKQALET VQRLLPVLCQ DHGLTPDQVV AIASHDGGKQ ALETVQRLLP  600
VLCQDHGLTP DQVVAIASNG GGKQALETVQ RLLPVLCQDH GLTPDQVVAI ASHDGGKQAL  660
ETVQRLLPVL CQDHGLTPDQ VVAIASNGGG KQALETVQRL LPVLCQDHGL TPDQVVAIAS  720
HDGGKQALET VQRLLPVLCQ DHGLTPDQVV AIASNGGGKQ ALESIVAQLS RPDPALAALT  780
NDHLVALACL GGRPALDAVK KGLPHAPALI KRTNRRIPER TSHRVAGSGG G           831

SEQ ID NO: 148         moltype = DNA  length = 19
FEATURE                Location/Qualifiers
source                 1..19
                       mol_type = other DNA
                       note = Binding site
                       organism = synthetic construct
SEQUENCE: 148
tgctcgcgct actctctct                                               19

SEQ ID NO: 149         moltype = RNA  length = 20
FEATURE                Location/Qualifiers
source                 1..20
                       mol_type = other RNA
                       note = guide RNA (gRNA) #1 for beta2-microglobulin gene
                       organism = synthetic construct
SEQUENCE: 149
tataagtgga ggcgtcgcgc                                              20

SEQ ID NO: 150         moltype = RNA  length = 20
FEATURE                Location/Qualifiers
source                 1..20
                       mol_type = other RNA
                       note = gRNA #2 for beta2-microglobulin gene
                       organism = synthetic construct
SEQUENCE: 150
gcccgaatgc tgtcagcttc                                              20

SEQ ID NO: 151         moltype = RNA  length = 20
FEATURE                Location/Qualifiers
source                 1..20
                       mol_type = other RNA
                       note = gRNA #3 for beta2-microglobulin gene
                       organism = synthetic construct
```

```
SEQUENCE: 151
tgcgtcgctg gcttggagac                                              20

SEQ ID NO: 152         moltype = RNA  length = 20
FEATURE                Location/Qualifiers
source                 1..20
                       mol_type = other RNA
                       note = gRNA #4 for beta2-microglobulin gene
                       organism = synthetic construct
SEQUENCE: 152
ccaatcagga caaggcccgc                                              20

SEQ ID NO: 153         moltype = RNA  length = 20
FEATURE                Location/Qualifiers
source                 1..20
                       mol_type = other RNA
                       note = gRNA #5 for beta2-microglobulin gene
                       organism = synthetic construct
SEQUENCE: 153
agggtaggag agactcacgc                                              20

SEQ ID NO: 154         moltype = RNA  length = 20
FEATURE                Location/Qualifiers
source                 1..20
                       mol_type = other RNA
                       note = gRNA #6 for beta2-microglobulin gene
                       organism = synthetic construct
SEQUENCE: 154
gcgggccacc aaggagaact                                              20

SEQ ID NO: 155         moltype = RNA  length = 20
FEATURE                Location/Qualifiers
source                 1..20
                       mol_type = other RNA
                       note = gRNA #7 for beta2-microglobulin gene
                       organism = synthetic construct
SEQUENCE: 155
gctactctct ctttctggcc                                              20

SEQ ID NO: 156         moltype = RNA  length = 20
FEATURE                Location/Qualifiers
source                 1..20
                       mol_type = other RNA
                       note = gRNA #8 for beta2-microglobulin gene
                       organism = synthetic construct
SEQUENCE: 156
ctcccgctct gcaccctctg                                              20

SEQ ID NO: 157         moltype = RNA  length = 20
FEATURE                Location/Qualifiers
source                 1..20
                       mol_type = other RNA
                       note = gRNA #9 for beta2-microglobulin gene
                       organism = synthetic construct
SEQUENCE: 157
tttggcctac ggcgacggga                                              20

SEQ ID NO: 158         moltype = RNA  length = 20
FEATURE                Location/Qualifiers
source                 1..20
                       mol_type = other RNA
                       note = gRNA #10 for beta2-microglobulin gene
                       organism = synthetic construct
SEQUENCE: 158
ggggcaagta gcgcgcgtcc                                              20

SEQ ID NO: 159         moltype = RNA  length = 20
FEATURE                Location/Qualifiers
source                 1..20
                       mol_type = other RNA
                       note = gRNA #11 for beta2-microglobulin gene
                       organism = synthetic construct
SEQUENCE: 159
tagtccaggg ctggatctcg                                              20

SEQ ID NO: 160         moltype = RNA  length = 88
FEATURE                Location/Qualifiers
source                 1..88
                       mol_type = other RNA
```

```
                         note = gRNA scaffold
                         organism = synthetic construct
SEQUENCE: 160
gtttaagagc tatgctggaa acagcatagc aagtttaaat aaggctagtc cgttattcaa  60
cttgaaaaag tggcaccgag tcggtgct                                     88

SEQ ID NO: 161           moltype = RNA  length = 20
FEATURE                  Location/Qualifiers
source                   1..20
                         mol_type = other RNA
                         note = gRNA #2 for IFNAR1 gene
                         organism = synthetic construct
SEQUENCE: 161
aagaggcggc gcgtgcgtag                                              20

SEQ ID NO: 162           moltype = RNA  length = 20
FEATURE                  Location/Qualifiers
source                   1..20
                         mol_type = other RNA
                         note = gRNA #3 for IFNAR1 gene
                         organism = synthetic construct
SEQUENCE: 162
gggcggtgtg acttaggacg                                              20

SEQ ID NO: 163           moltype = RNA  length = 20
FEATURE                  Location/Qualifiers
source                   1..20
                         mol_type = other RNA
                         note = gRNA #4 for IFNAR1 gene
                         organism = synthetic construct
SEQUENCE: 163
ccagatgatg gtcgtcctcc                                              20

SEQ ID NO: 164           moltype = RNA  length = 20
FEATURE                  Location/Qualifiers
source                   1..20
                         mol_type = other RNA
                         note = gRNA #5 for IFNAR1 gene
                         organism = synthetic construct
SEQUENCE: 164
gaccctagtg ctcgtcgccg                                              20

SEQ ID NO: 165           moltype = RNA  length = 20
FEATURE                  Location/Qualifiers
source                   1..20
                         mol_type = other RNA
                         note = gRNA #6 for IFNAR1 gene
                         organism = synthetic construct
SEQUENCE: 165
tgggtgttgt ccgcagccgc                                              20

SEQ ID NO: 166           moltype = RNA  length = 20
FEATURE                  Location/Qualifiers
source                   1..20
                         mol_type = other RNA
                         note = gRNA #7 for IFNAR1 gene
                         organism = synthetic construct
SEQUENCE: 166
acgggggcgg cgatgctgtt                                              20

SEQ ID NO: 167           moltype = RNA  length = 20
FEATURE                  Location/Qualifiers
source                   1..20
                         mol_type = other RNA
                         note = gRNA #8 for IFNAR1 gene
                         organism = synthetic construct
SEQUENCE: 167
gaccgaaggt ttcccagact                                              20

SEQ ID NO: 168           moltype = RNA  length = 20
FEATURE                  Location/Qualifiers
source                   1..20
                         mol_type = other RNA
                         note = gRNA #9 for IFNAR1 gene
                         organism = synthetic construct
SEQUENCE: 168
gtcgggttta atctttggcg                                              20

SEQ ID NO: 169           moltype = RNA  length = 20
```

-continued

```
FEATURE                 Location/Qualifiers
source                  1..20
                        mol_type = other RNA
                        note = gRNA #10 for IFNAR1 gene
                        organism = synthetic construct
SEQUENCE: 169
cgctcccgag gacccgtaca                                            20

SEQ ID NO: 170          moltype = RNA  length = 20
FEATURE                 Location/Qualifiers
source                  1..20
                        mol_type = other RNA
                        note = gRNA #11 for IFNAR1 gene
                        organism = synthetic construct
SEQUENCE: 170
cgggtcccac ccccgtgaaa                                            20

SEQ ID NO: 171          moltype = RNA  length = 20
FEATURE                 Location/Qualifiers
source                  1..20
                        mol_type = other RNA
                        note = gRNA #12 for IFNAR1 gene
                        organism = synthetic construct
SEQUENCE: 171
tcaaactcga cacaaagctc                                            20

SEQ ID NO: 172          moltype = RNA  length = 20
FEATURE                 Location/Qualifiers
source                  1..20
                        mol_type = other RNA
                        note = gRNA #13 for IFNAR1 gene
                        organism = synthetic construct
SEQUENCE: 172
gcggagccgc ggtactttcc                                            20

SEQ ID NO: 173          moltype = RNA  length = 20
FEATURE                 Location/Qualifiers
source                  1..20
                        mol_type = other RNA
                        note = gRNA #1 for VEGFA gene
                        organism = synthetic construct
SEQUENCE: 173
ggcgcgcgcg ctaggtggga                                            20

SEQ ID NO: 174          moltype = RNA  length = 20
FEATURE                 Location/Qualifiers
source                  1..20
                        mol_type = other RNA
                        note = gRNA #2 for VEGFA gene
                        organism = synthetic construct
SEQUENCE: 174
agagaggctc accgcccacg                                            20

SEQ ID NO: 175          moltype = RNA  length = 20
FEATURE                 Location/Qualifiers
source                  1..20
                        mol_type = other RNA
                        note = gRNA #3 for VEGFA gene
                        organism = synthetic construct
SEQUENCE: 175
gtacgtgcgg tgactccggt                                            20
```